United States Patent
Stojanovic et al.

(10) Patent No.: US 7,470,516 B2
(45) Date of Patent: Dec. 30, 2008

(54) CROSS REACTIVE ARRAYS OF THREE-WAY JUNCTION SENSORS FOR STEROID DETERMINATION

(75) Inventors: Milan N. Stojanovic, Fort Lee, NJ (US);
Donald Landry, New York, NY (US);
Dragan B. Nikic, Belgrade (YU)

(73) Assignee: The Trustees of Columbia University in the City of New York, New York, NY (US)

( * ) Notice: Subject to any disclaimer, the term of this patent is extended or adjusted under 35 U.S.C. 154(b) by 12 days.

(21) Appl. No.: 11/251,496

(22) Filed: Oct. 14, 2005

(65) Prior Publication Data

US 2006/0204977 A1  Sep. 14, 2006

Related U.S. Application Data

(63) Continuation of application No. PCT/US2004/011696, filed on Apr. 15, 2004, which is a continuation-in-part of application No. 10/824,158, filed on Apr. 14, 2004, now abandoned.

(60) Provisional application No. 60/462,706, filed on Apr. 14, 2003.

(51) Int. Cl.
*C12Q 1/68* (2006.01)
*C12P 19/34* (2006.01)
*C07H 21/02* (2006.01)
*C07H 21/00* (2006.01)

(52) U.S. Cl. .................. 435/6; 435/91.1; 536/23.1; 536/25.32

(58) Field of Classification Search .......... 435/6, 435/91, 91.1; 536/23.1, 24.2, 25.3
See application file for complete search history.

(56) References Cited

U.S. PATENT DOCUMENTS

| | | | |
|---|---|---|---|
| 5,270,163 | A | 12/1993 | Gold et al. |
| 5,561,071 | A | 10/1996 | Hollenberg et al. |
| 5,580,733 | A | 12/1996 | Levis et al. |
| 5,597,696 | A | 1/1997 | Linn et al. |
| 5,627,030 | A | 5/1997 | Pandian et al. |
| 5,789,219 | A * | 8/1998 | Bieniarz et al. ............ 435/188 |
| 5,955,322 | A | 9/1999 | Guarnieri et al. |
| 6,451,535 | B1 | 9/2002 | Jenne et al. |
| 6,472,153 | B1 | 10/2002 | Dempcy et al. |
| 6,706,474 | B1 | 3/2004 | Lu et al. |
| 7,115,369 | B2 | 10/2006 | Nilsen-Hamilton |
| 2003/0087239 | A1* | 5/2003 | Stanton et al. ................. 435/6 |
| 2003/0198966 | A1 | 10/2003 | Stojanovic et al. |
| 2003/0208061 | A1* | 11/2003 | Manoharan et al. ......... 536/25.3 |
| 2004/0070426 | A1 | 4/2004 | Stojanovic et al. |
| 2004/0203007 | A1 | 10/2004 | Stojanovic et al. |
| 2004/0219523 | A1* | 11/2004 | Stanton et al. ................. 435/6 |
| 2005/0019916 | A1 | 1/2005 | Stojanovic et al. |
| 2005/0130208 | A1 | 6/2005 | Stojanovic et al. |
| 2005/0202503 | A1 | 9/2005 | Stojanovic et al. |

FOREIGN PATENT DOCUMENTS

WO   2006025808   3/2006

OTHER PUBLICATIONS

"Molecular Recognition" Gellman, S. (Guest Edt.) Chem.Rev. 1997, 97, special thematic issue.
Adelman, Leonard M.—Molecular Computation of Solutions to Combinational Problems. Sciences, issued Nov. 11, 1994, vol. 266, pp. 1021-1024.
Albert, K.J.; Lewis, N.S.; Schauer, C.L.; Sotzing, G.A.; Stitzel, S. E.I., Vaid, T.P.; Walt D.R. Chem. Rev. 2000, 100, 2595.
Aoyagi, T.; Nakamura, A.; Ikeda, H.; Mihara, H.; Ueno, Anal. Chem. 1997, 69, 659-663.
Ariga, K.; Terasaka, Y.; Sakai, D.; Tsuiji, H.; Kikuchi, J.J. Am. Chem. Soc. 200, 122, 7835-7836.
Axel, R. "Molecular Logic of Smell" Sci. Am. 1995, 273, 154.
Ball (Nature (2000) vol. 406, pp. 118-120).
Bedner et al. (2001) "Caffeine Dissociates Complexes Between DNA and Intercalating Dyes: Application for Bleaching Fluorochrome-Stained Cells for Their Subsequent Restaining and Analysis by Laser Scanning Cytometry." Cytometry 43:38-45.
Beer, P.D.; Gale, P.A.; Angew. Chem. Int. Ed. 2001, 40, 486.
Breslow, R., Dong, D.S.; Chem. Rev. 1998, 98, 1997-2011.
Broady, E.N.; Gold, L. Rev. Mol. Biotechnol. 2000, 74, 5.
Cao, Y.W.; Jin, R.; Mirkin, C.; J. Am. Chem. Soc. 2001, 123, 7961.
Castellano, R.K.; Craig, S.L.; Nuckolls, C.; Rebek, J. Jr. J. Am. Chem. Soc. 2000, 122, 7876-7882.
Chin, J.; Lee, K.J.; Park, S.; Kim, D.H. Nature 1999, 401, 254.
Cogan, Derek A. and Ellman, Jonathan A.; J. Am. Chem. Soc. 1999, 121,268.
Collier et al. (Science (1999) vol. 285, pp. 391-394).
De Silva, A.P.; Gunaratne, H.Q.N.; Gunnlaugsson, T.; Huxley, A.J. M.; McCoy, C.P.; Rademacher J.T.; Rice, T.E. Chem. Rev. 1997, 97 (15), 1515-1566.
Elin, R.J. "Reference Intervals and Laboratory Values" in Cecil Textbook of Medicine (Eds. Bennett, J.C. and Plum, F.) 1996, 20th Ed.
Fidanza, J.A.; Ozaki, H.; McLaughlin, L.W.J. Am. Chem. Soc. 1992, 114, 5509.

(Continued)

*Primary Examiner*—Jane Zara
(74) *Attorney, Agent, or Firm*—John P. White; Cooper & Dunham LLP

(57) ABSTRACT

This invention provides analyte sensitive oligonucleotide compositions for detecting and analyzing analytes in solution, including complex solutions using cross reactive arrays of analyte sensitive oligonucleotide compositions.

8 Claims, 95 Drawing Sheets

OTHER PUBLICATIONS

Fitch, Walter M. Calculating the expected frequencies of potential secondary structure in nucleic acids as a function of stem length, loop size, base composition and nearest-neighbor frequencies. Nucleic Acids Research, issued 1983, vol. 11, No. 13, pp. 4655-4663.

Ikeda H; Nakamura, M.; Nobuyuki, I.; Oguma, N.; Nakamura, A.; Ikeda, T.; Toda, F.; Ueno, A. J. Am. Chem. Soc. 1996, 118, 10980-10988.

James, T.D.; Sandanayake, K.R. A.S.; Shinkai, S. Nature 1995, 374, 345.

Jhaveri, S.; Rajendran, M.; Ellington, A.D. Nat. Biotechnol. 2000, 18(12) 1293-1297.

Jhaveri, S.D. et al. J. Am. Chem. Soc. 2000, 122, 2469.

Joachim et al. (Nature (2000) vol. 408, pp. 541-548).

Kato, T.; Takemura, T.; Yano, K.; Ikebukuro, K.; Karube, I. Biochim. Biophys. Acta 2000, 1493 (1-2), 12.

Kato, T.; Yano, K.; Ikebukuro, K.; Karube, I. Nucleic Acids Res. 2000, 28, 1963.

Knemeyer, J.P.; Marne, N.; Sauer, M. Anal. Chem. 2000, 72, 3717-3724.

Krey et al. (Biochemistry (1975) 14(23): 5061-5067).

Lavigne, J.J.; Anslyn, E.V. Angew. Chem. Int. Ed. 2001, 40(17), 3118.

Lu, M.; Guo, Q.; Mueller, J.E.; Kemper, B.; Studier, F.W.; Seeman, N.C.; Kallenbach, N.R. J. Biol. Chem. 1990, 265, 16778.

Miyaji, H.; Sessler, J.L. Angew. Chem. Int. Ed. 2001, 40, 154.

Osborne, Scott E.; Ellington, Andrew D.; Nucleic Acid Selection and the Challenge of Cominatorial Chemistry; Chem. Rev. 1997, 97 349-370.

Pal et al., (1995) "Spectroscopic Probe of the Competitive Binding of Ethidium Bromide and Neomycin to DNA." Spectrochimica Acta 51A(3): 489-498.

Patel, D.J.; Suri, A.K, J. Biotechnol. Mar. 2000; 74(1):39-60.

Perry, M.J. in Monoclonal Antibodies: Principles and Application, Birch, J.R.; Lennox, E.S.; Ess.; Willey-Liss: New York, 1995, pp. 107-120.

Rakow, N.A.; Suslick, K.S. Nature 2000, 406, 710.

Schauer, C.L., Steemers, F.J.; Walt, D.R. J.Am. Chem. Soc. 2001, 123, 9443. Journal of Medicine 344: 1750-1757.

Stojanovic, M.N.; Landry, D.W.J. Am. Chem. Soc. 2002, 124, 9673.

Stojanovic, Milan N.; Prada Paloma de & Landry, Donald W. Aptamer-Based Folding Fluorescent Sensor Based on Aptamer Self-Assembly; Am. Chem. Soc. (2000), 122:11547-11548.

Stojanovic, Milan N.; Prada Paloma de & Landry, Donald W. Aptamer-Based Folding Fluorescent Sensor for Cocaine J. Am. Chem. Soc. 2001, 4928-4931.

Tuite, E. Kelly, J.M. Biopolymers 1995, 35, 419.

Ulrich, Henning; Joseph E. Ippolito; Pagan, One R.; Eterovic, Vesna A.; Hann, Richard M.; Shi Hua; Lis, John T.; Eldefrawi, Mohyee E.; & Hess, George P. In vitro selection of RNA molecules that displace cocaine from the membrane-bound nicotinic acetycholine receptor. Proc. Nat'l. Acad. Sci. USA 95:14056. Nov. 1998 Biochemistry.

Wemmer, D. Biopolymers 2001, 52, 197.

Wiskur, S.L.; Ait-Haddou, H.; Lavigne, J.J.; Anslyn, E.V. Acc. Chem. Res. 2001, 34, 963-972.

Wu et al. (Nucleic Acids Research (1999) 27(6): 1512-1516).

Yang, Q.; Goldstein, I.J.; Mei, H.Y.; Engelke, D.R. Proc. Natl. Acad. Sci. U.S.A. 1998, 95, 5462.

Boger et al. (2001), A Simple, High-Resolution Method for Establishing DNA Binding Affinity and Sequence Selectivity, *J. Am. Chem. Soc.* 123:5878-5891.

Notice of Allowability issued Jan. 24, 2008 in connection with U.S. Appl. No. 11/123,648.

Office Action issued Oct. 29, 2007 in connection with related U.S. Appl. No. 10/371,550.

Office Action issued Aug. 6, 2007 in connection with U.S. Appl. No. 10/413,357.

Final Office Action issued Oct. 1, 2007 in connection with U.S. Appl. No. 10/990,187.

Notification of Transmittal of the International Search Report and the Written Opinion of the International Searching Authority issued Jun. 26, 2008 in connection with PCT International Application No. PCT/US04/11696.

Office Action issued Jul. 21, 2008 in connection with U.S. Appl. No. 10/990,187.

* cited by examiner

MNS4.81+T 32GF33G GGGAGACTAAGGATAAATCCTTCCAGAAAGTGG*GTCGACA

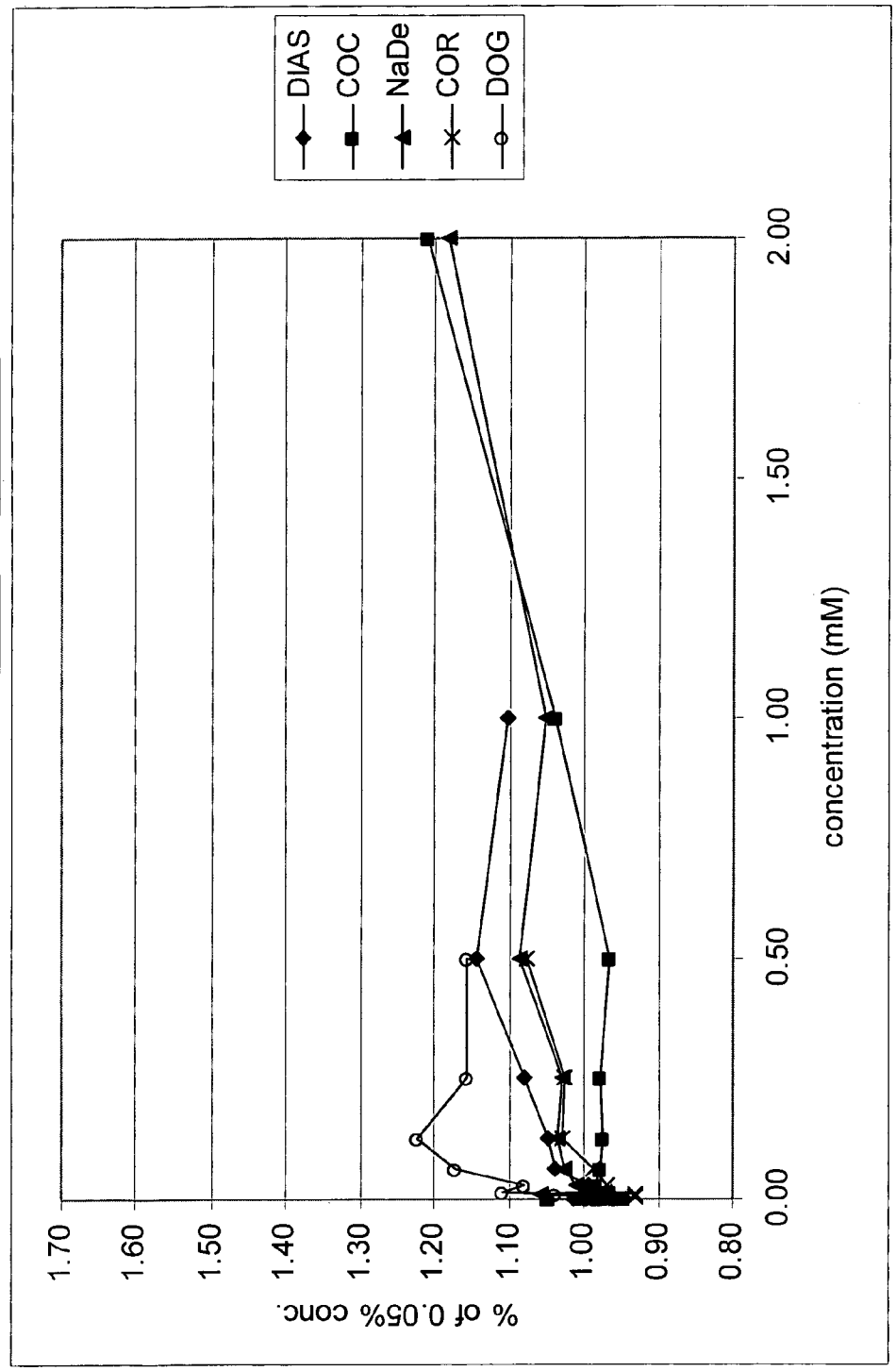

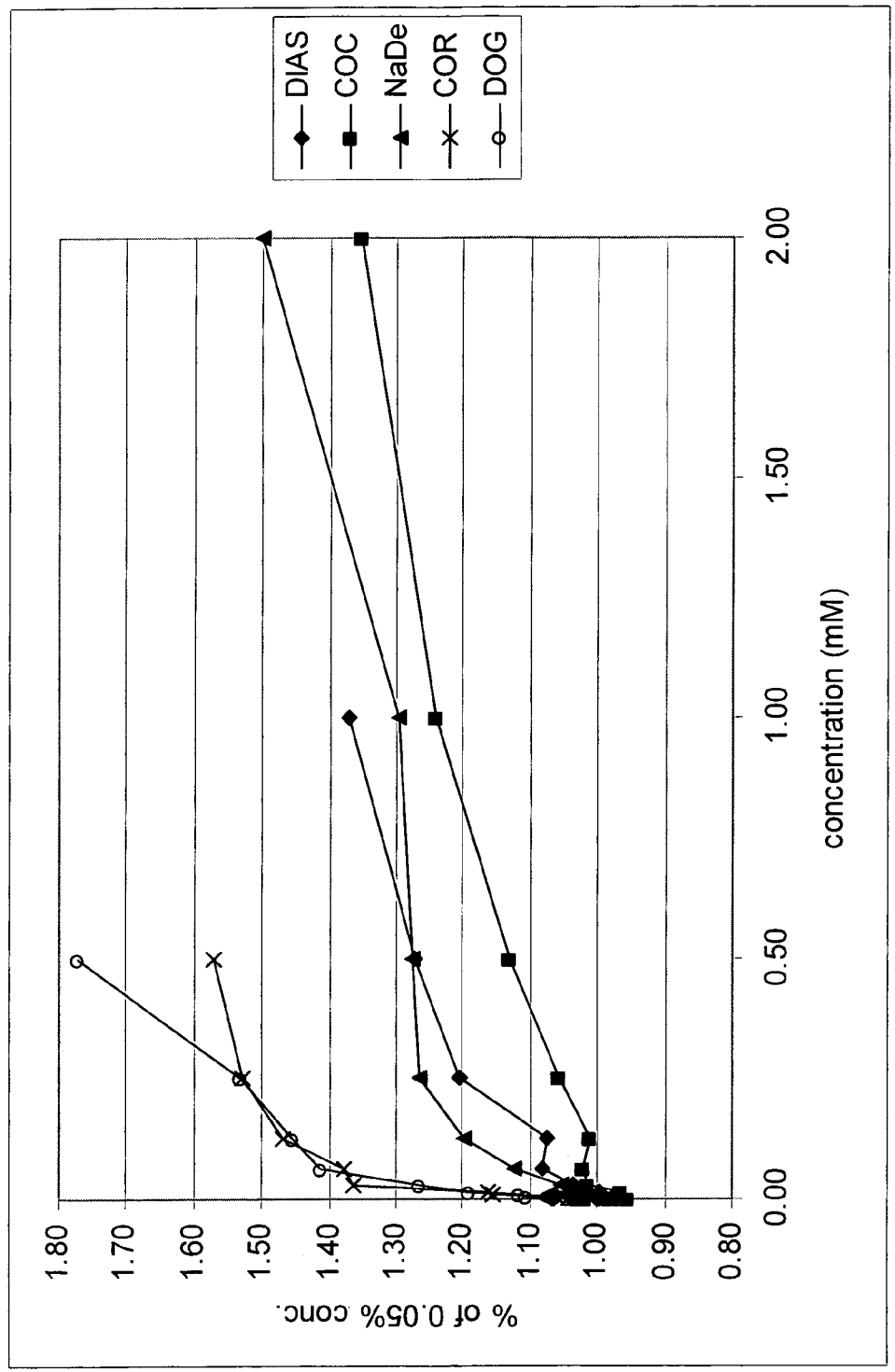

MNS4.1-19FT GGGAGACAGGATAAATCCfTCAATGAAGTGGGTCGACA

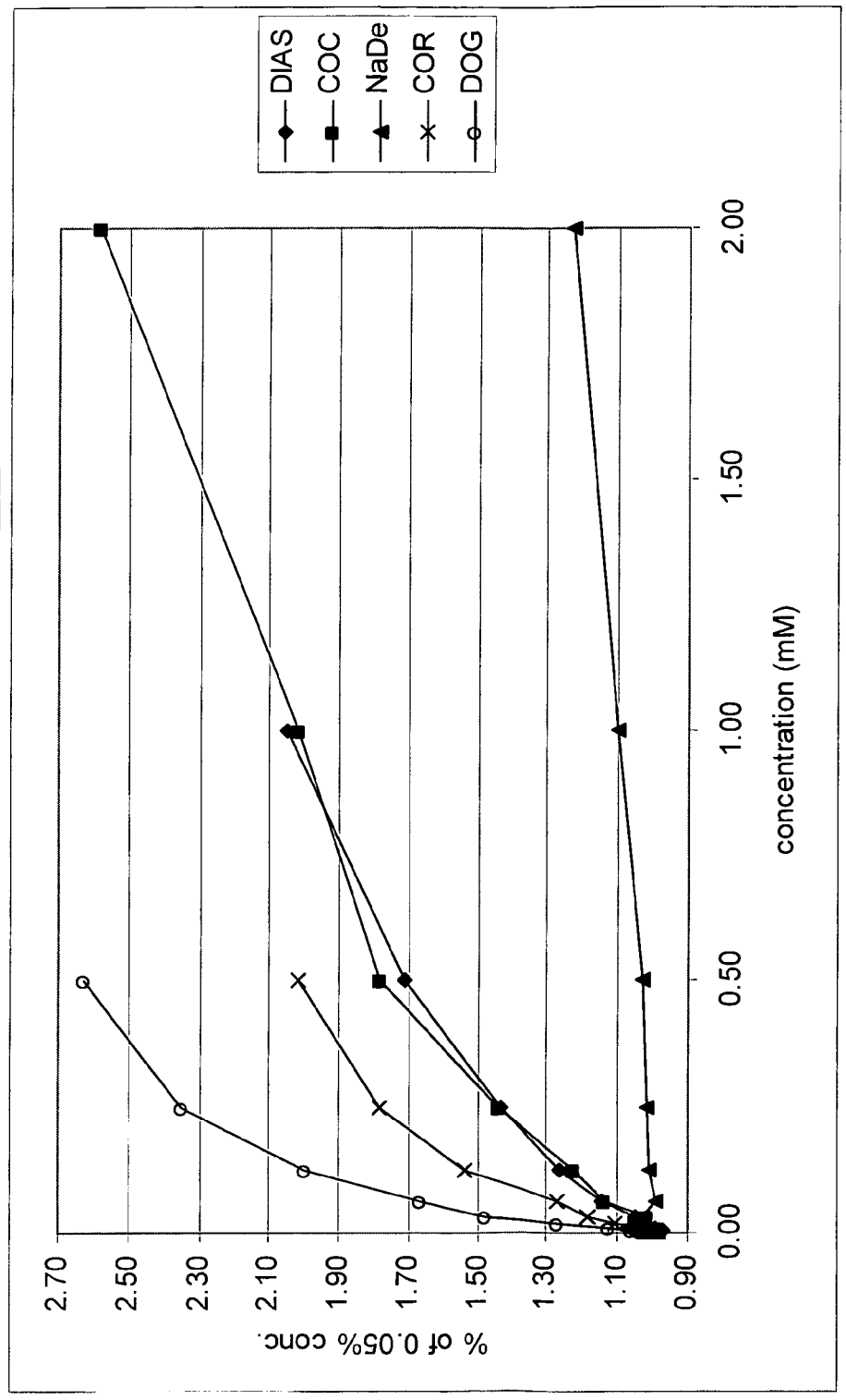

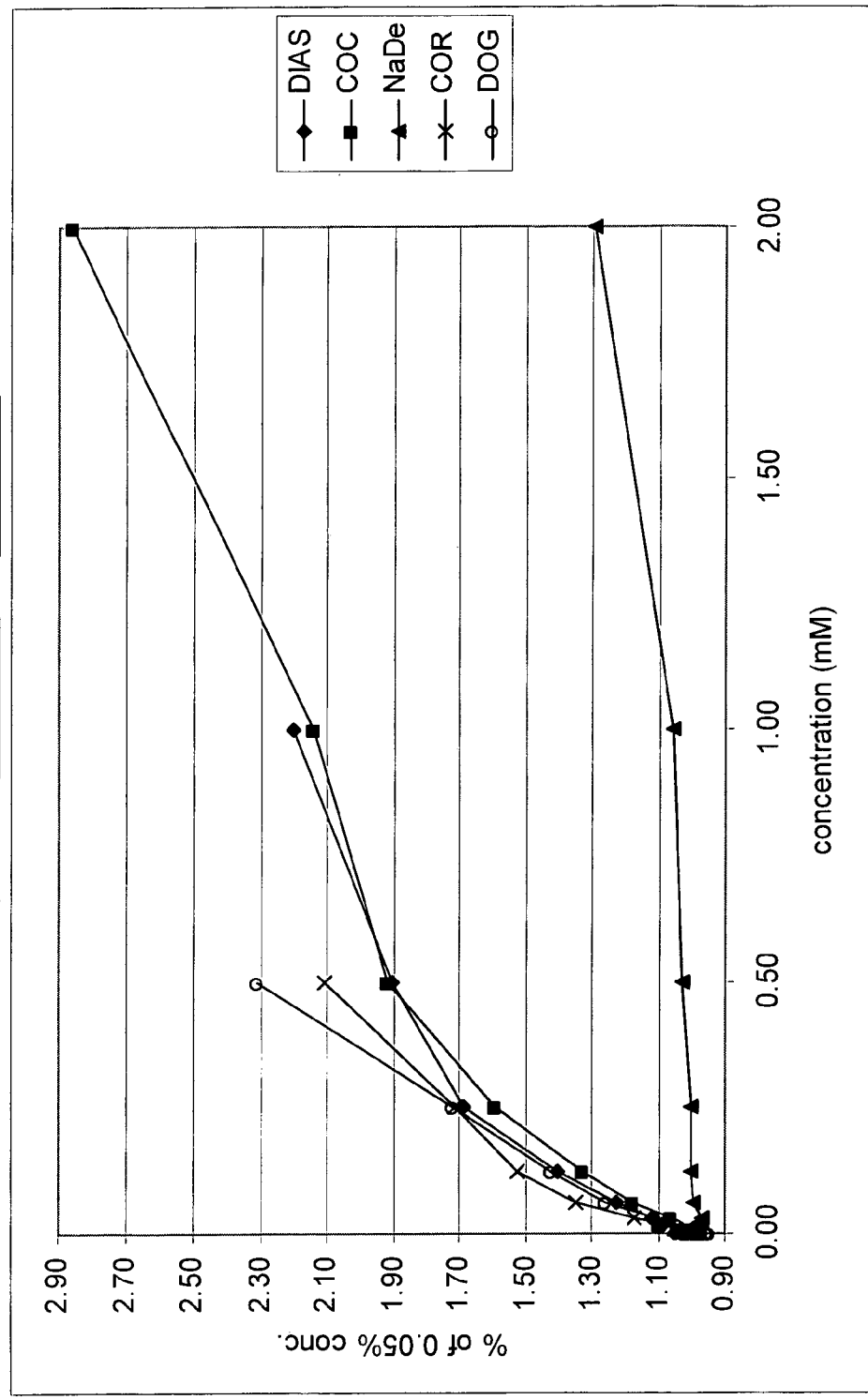

MNS4.1-19-35FU GGGAGACAGGATAAATCCTCAATGAAGTGGGfTCGACA

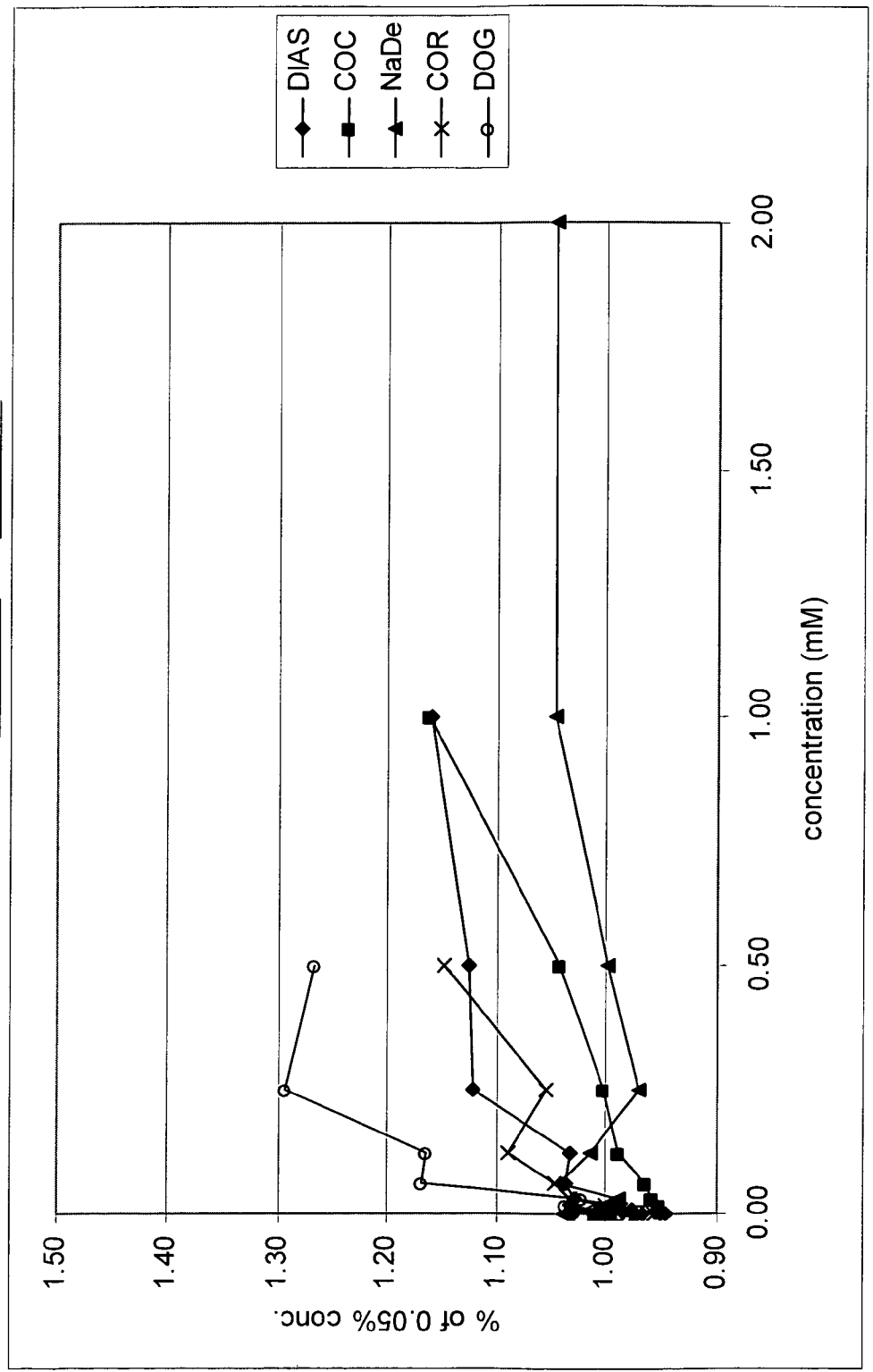

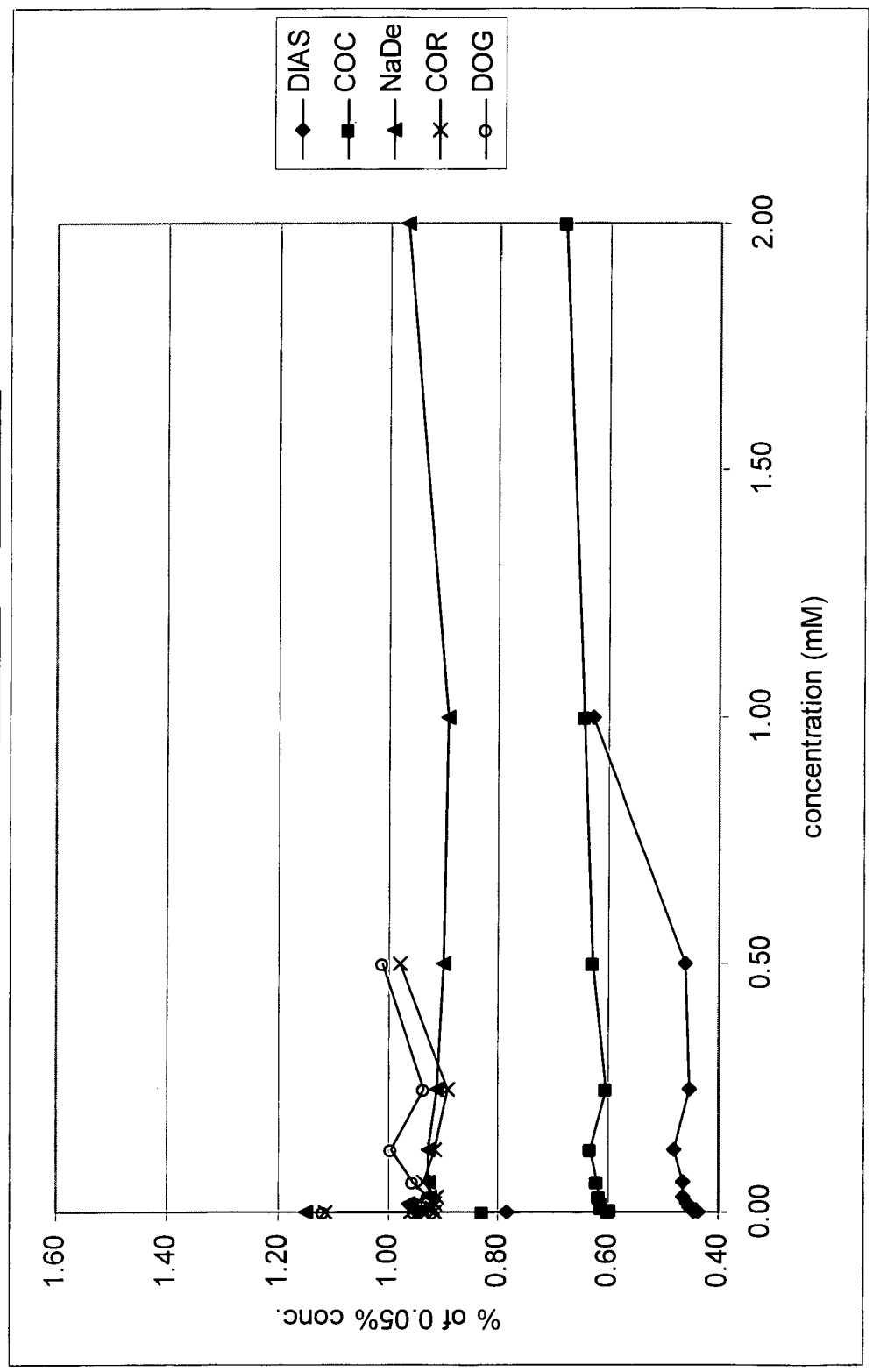

MNSF.19GAm 31GF32G  GGGAGACGAGGATAAATCCTGCGGCGAAGGGG*GTCGACA

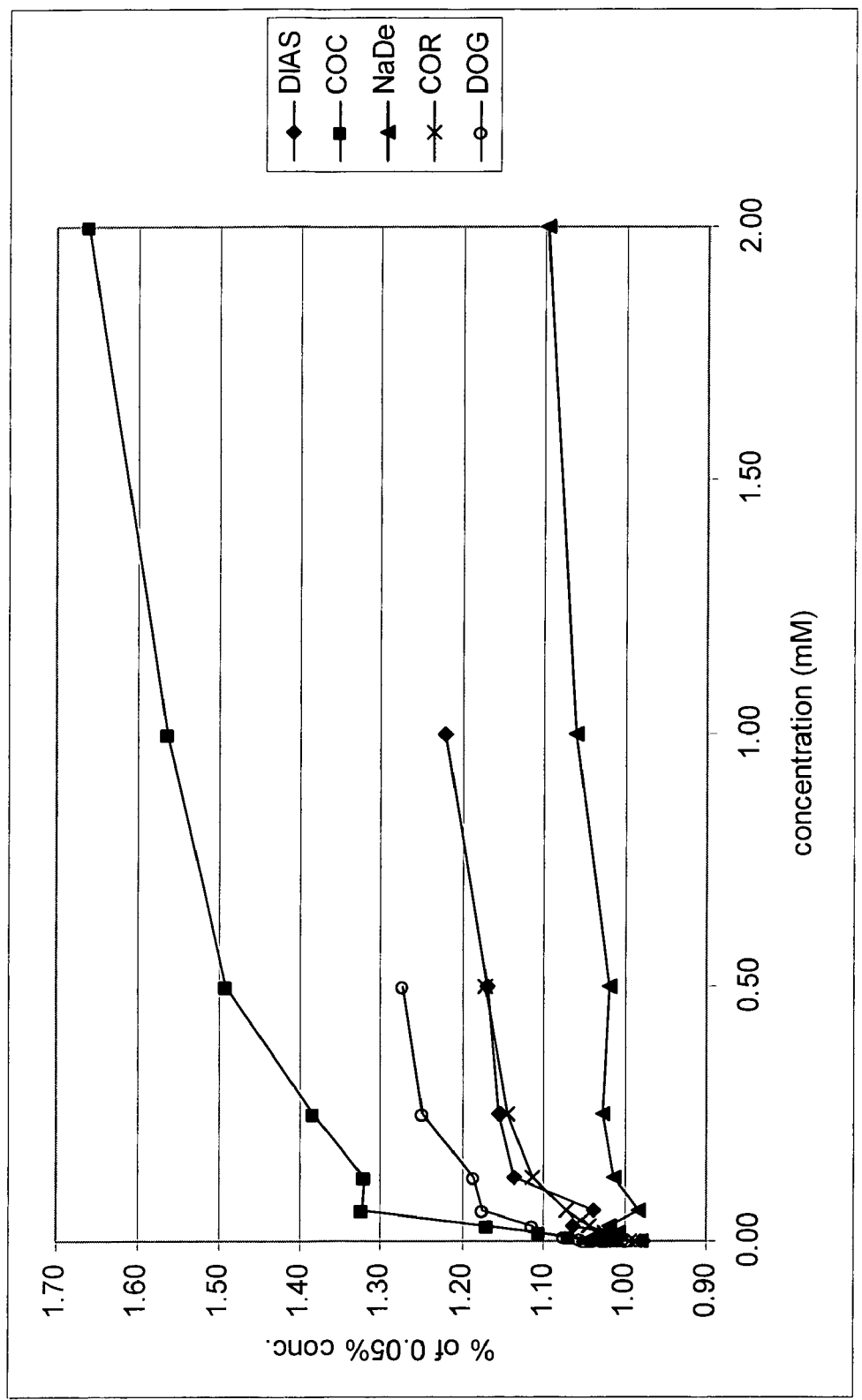

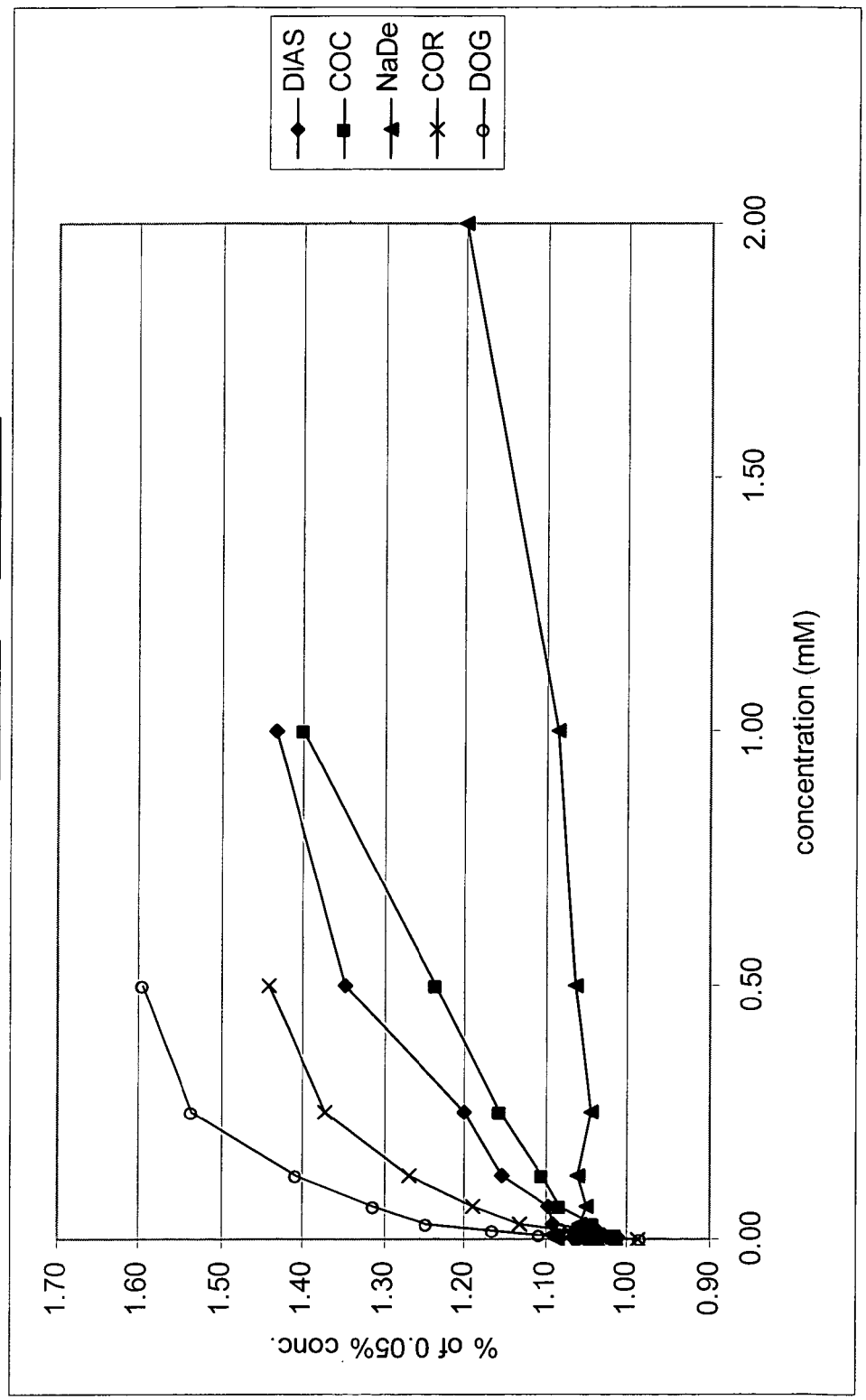

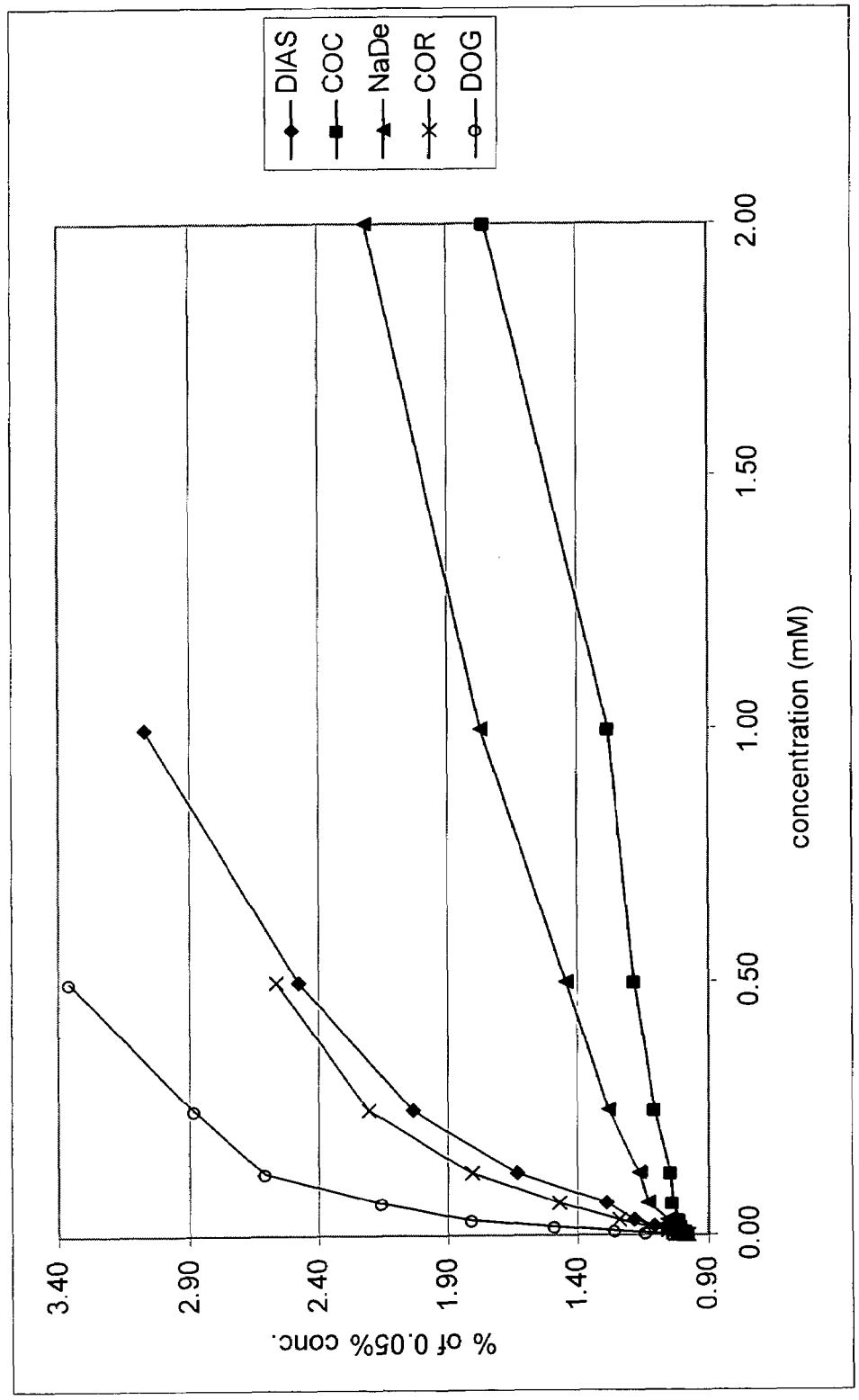

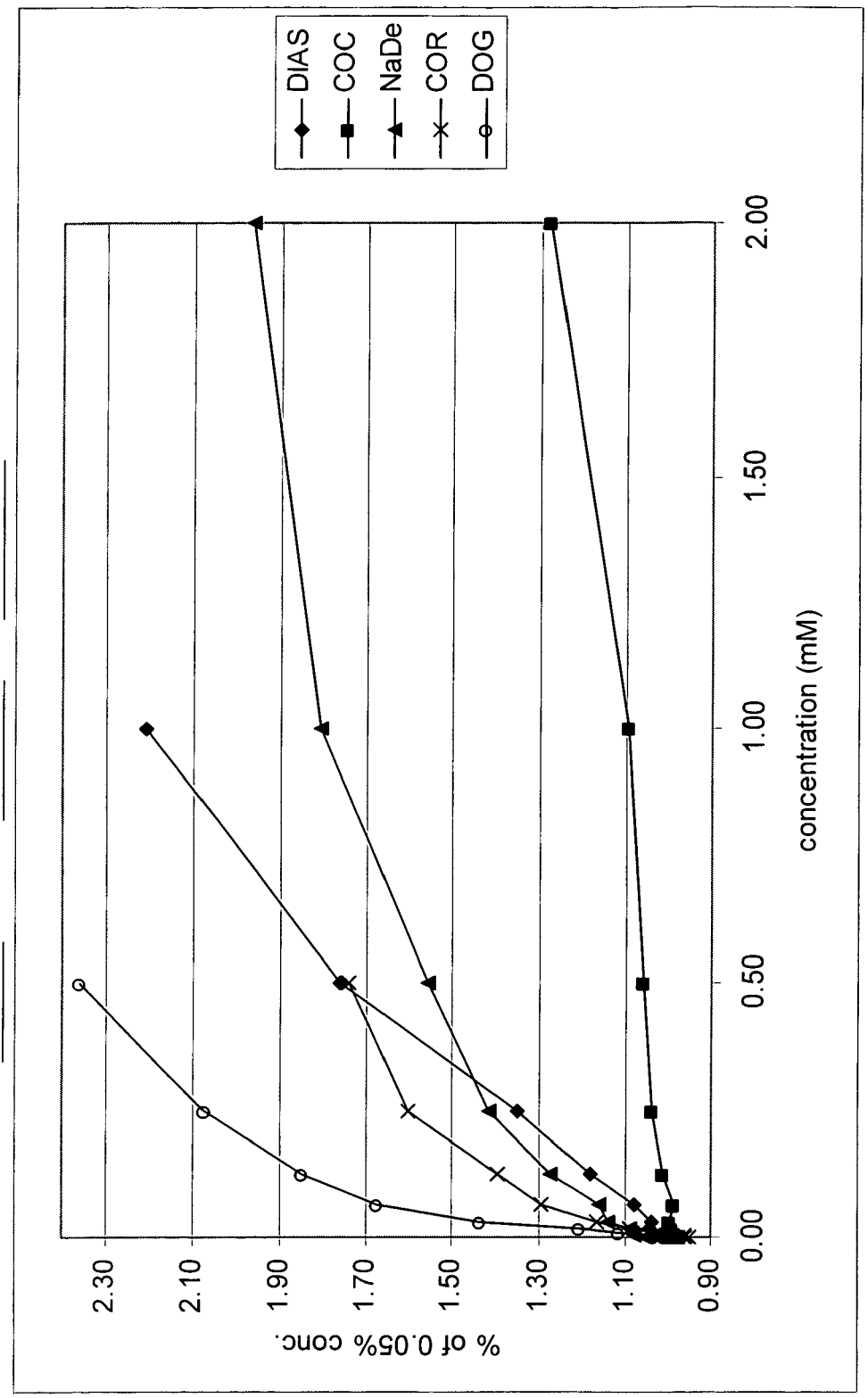

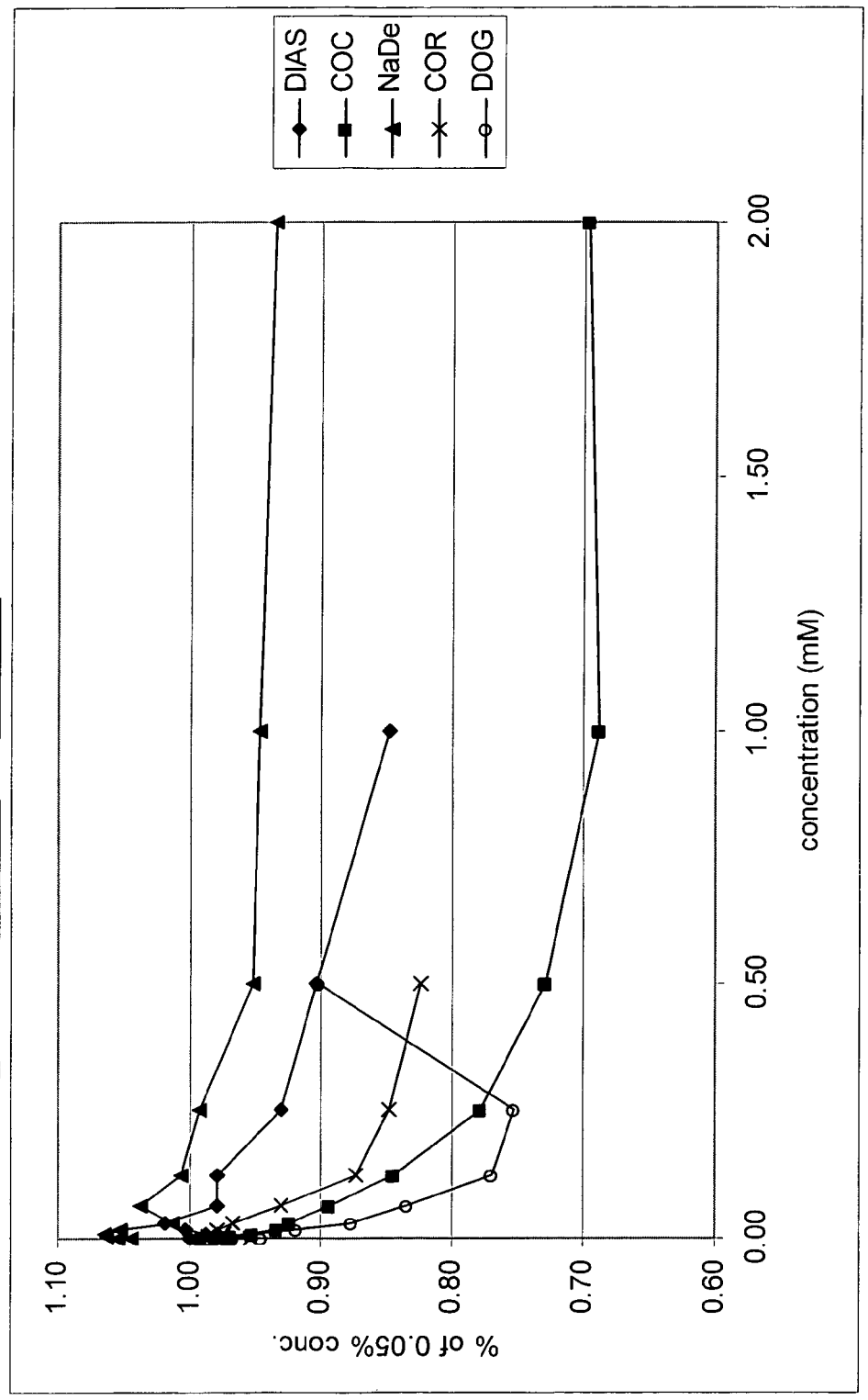

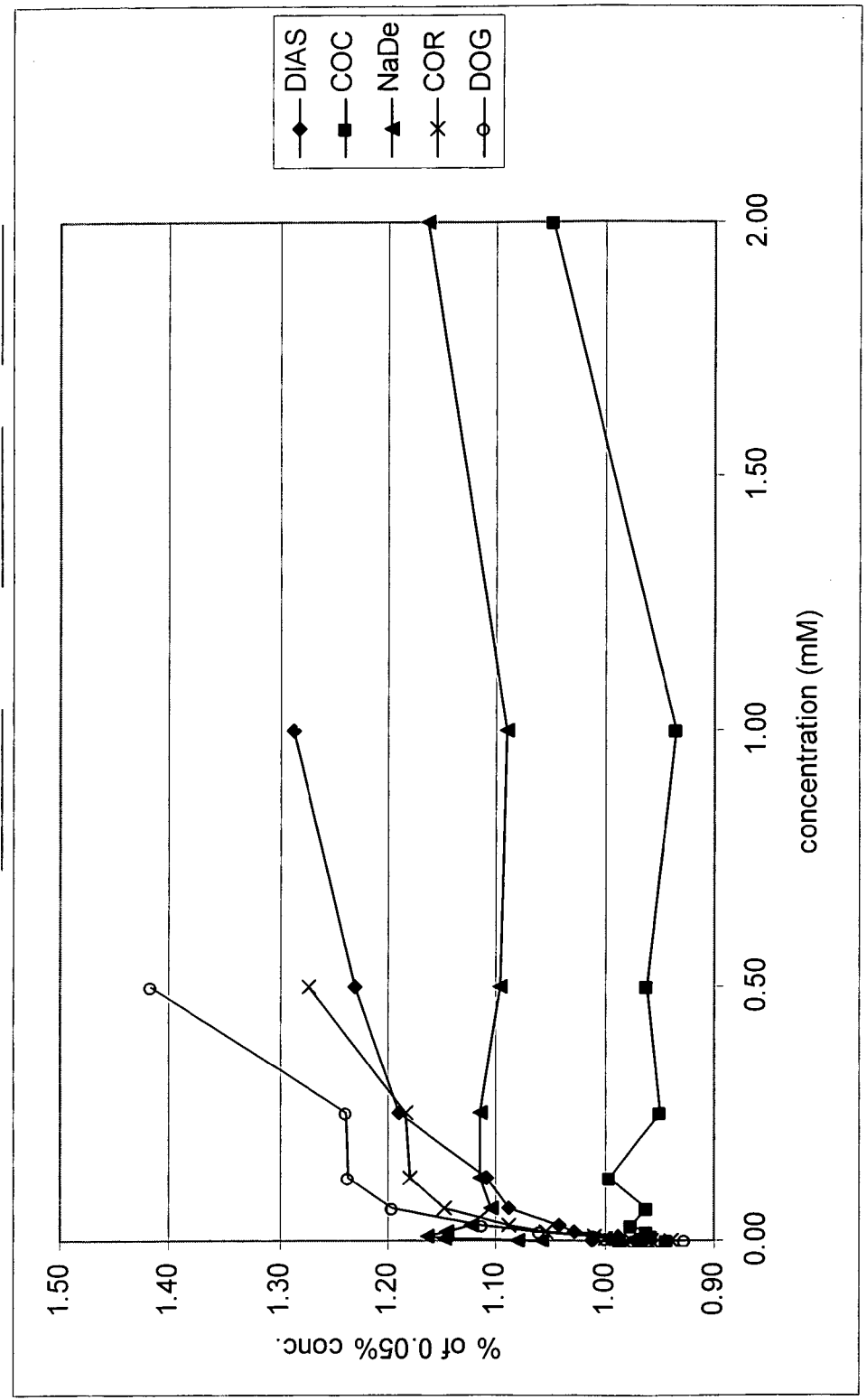

FIG. 31F

MNS4.61-FUBUIge-8FU ATATAGTC<u>f</u>TGGGATAAATCCCCACGAAGTGGGACTATAT

FMTCH-35FU GGGAGACAGGATAAATCCTCCACGAAGTGGGfTCGACA

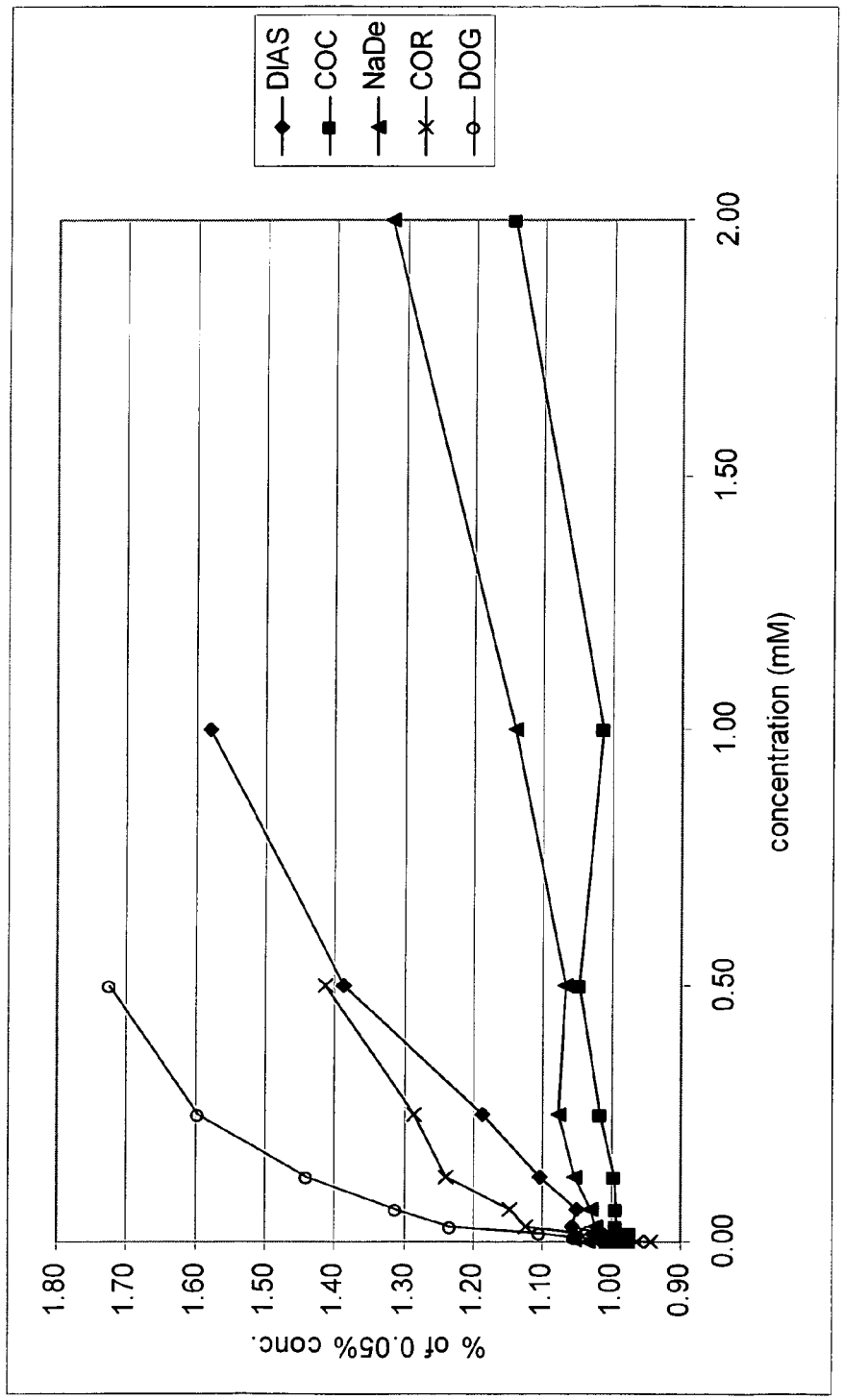

FMTCHMM-33FU ATATGACCGGATAAATCCGCCACGAAGTGGGfTCATAT

MNSan4.16-35FU ATATGTCCGGATAAATCCGCCACGAAGTGGGfTCATAT

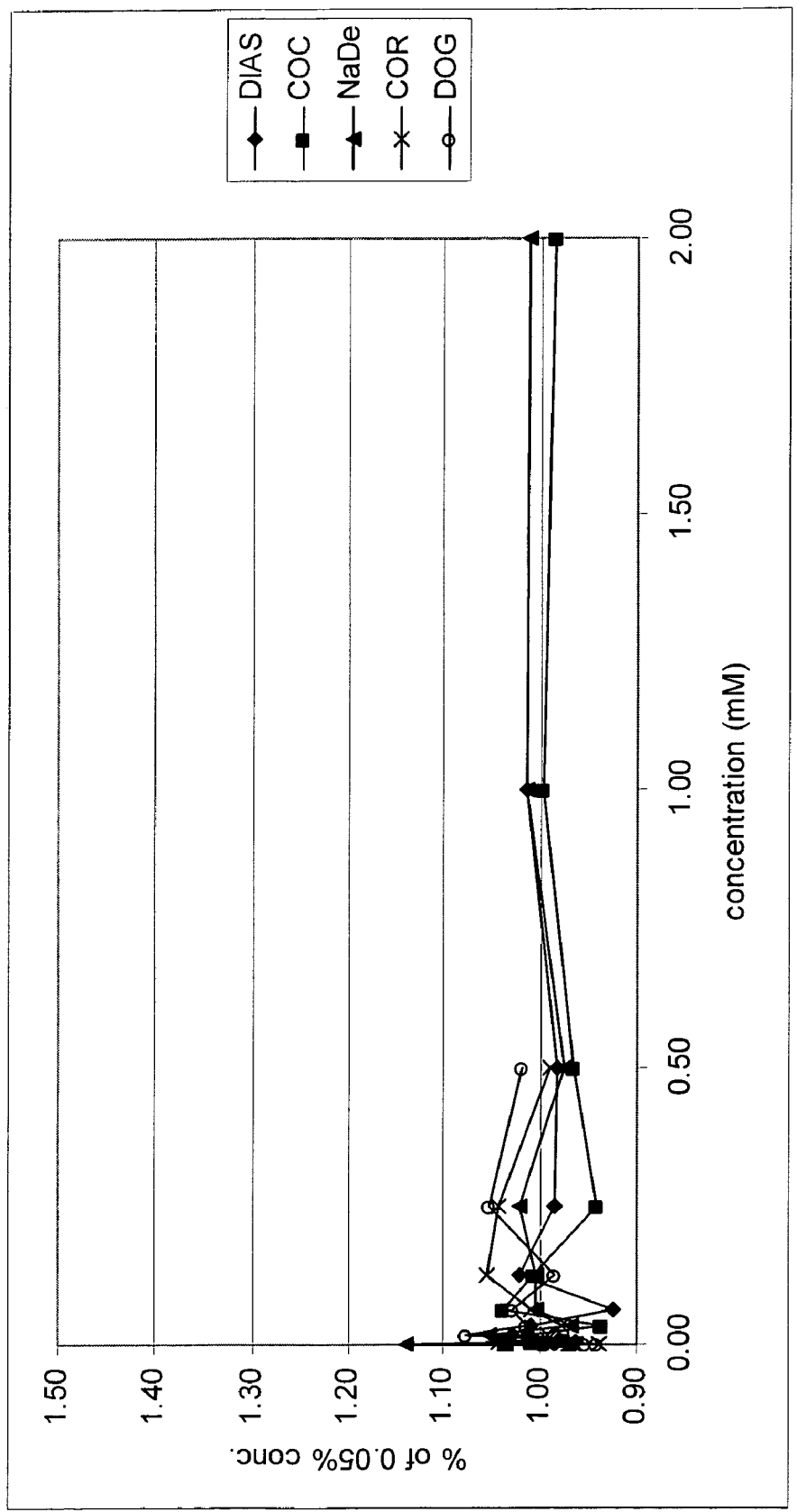

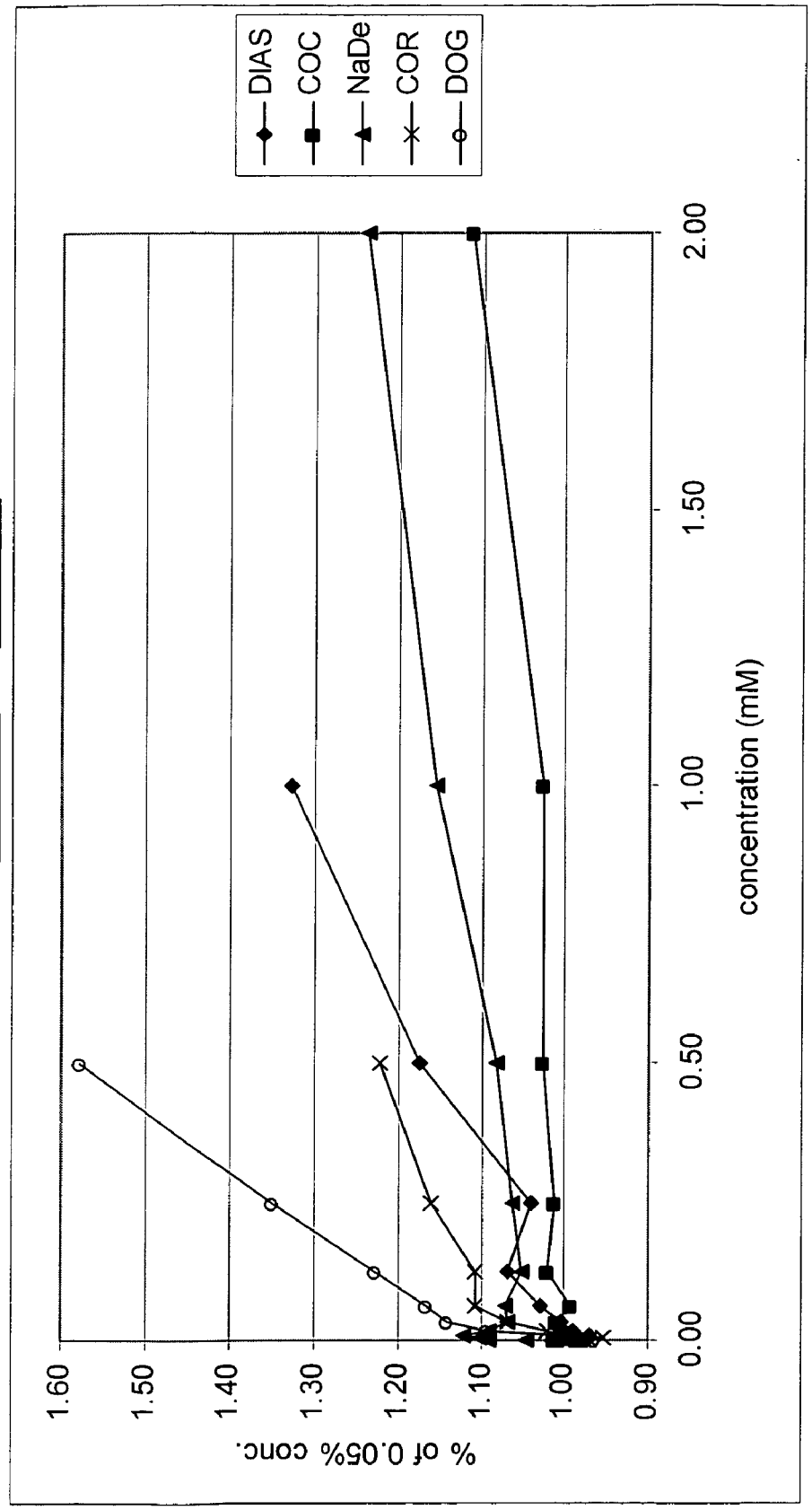

MNS4.1CTACGGGG.21FU GGGAGACAGGATAAATCCTCfTACGAAGGGGTCGACA

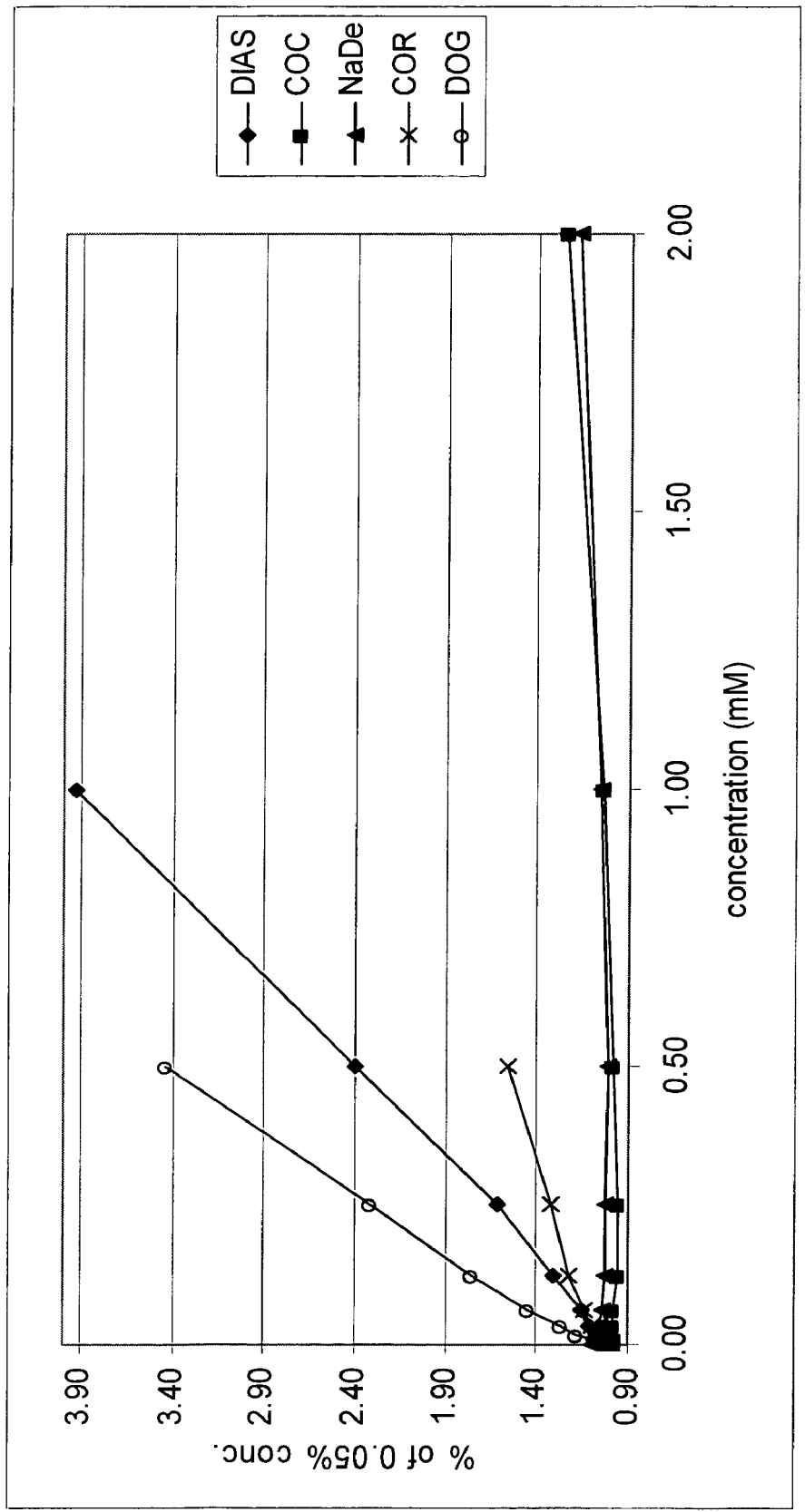

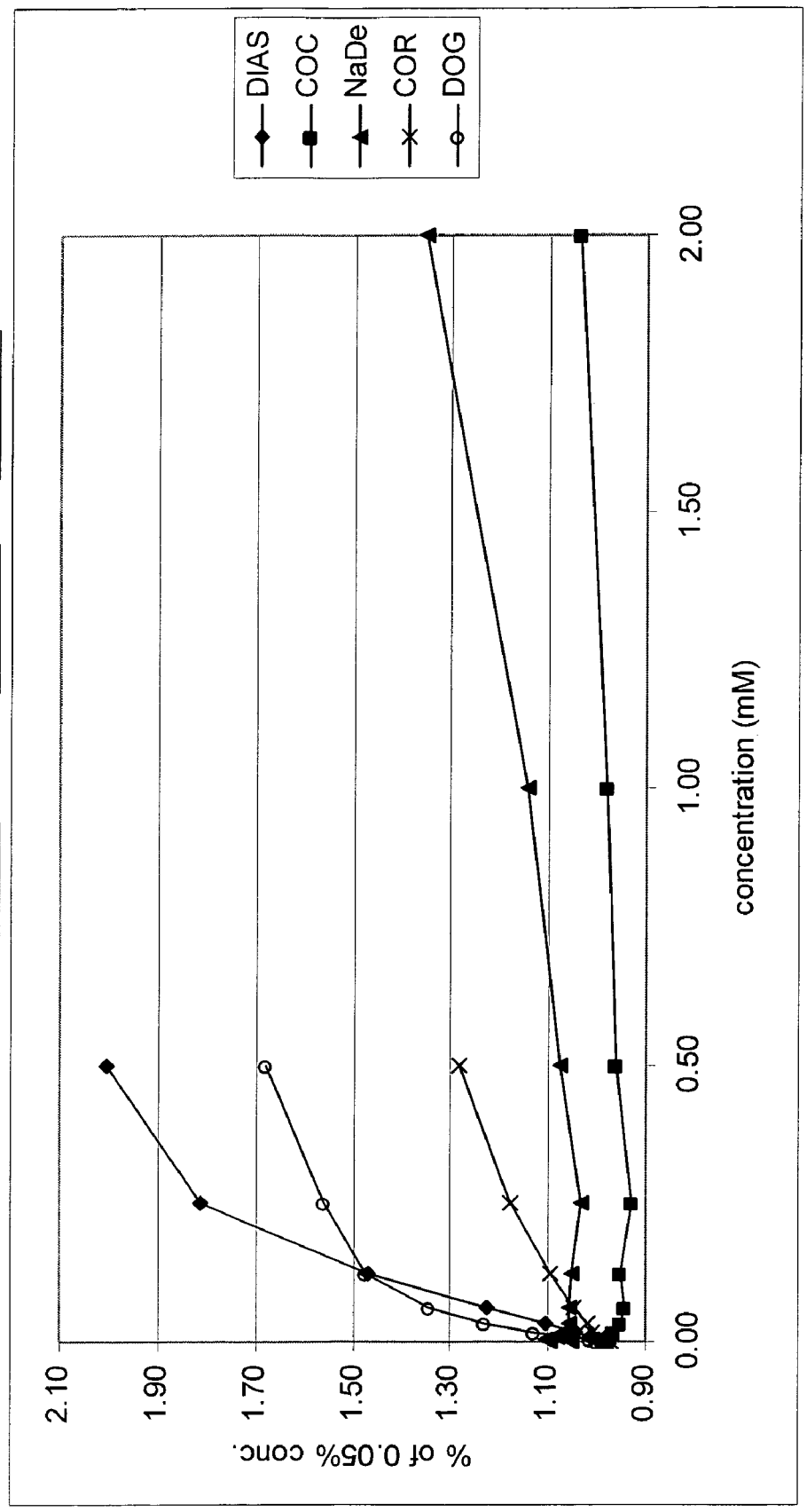

MNS4.120-7FUCCACGAGG ATATGAfTCGGATAAATCCGCCACGAAGAGGGTCATAT

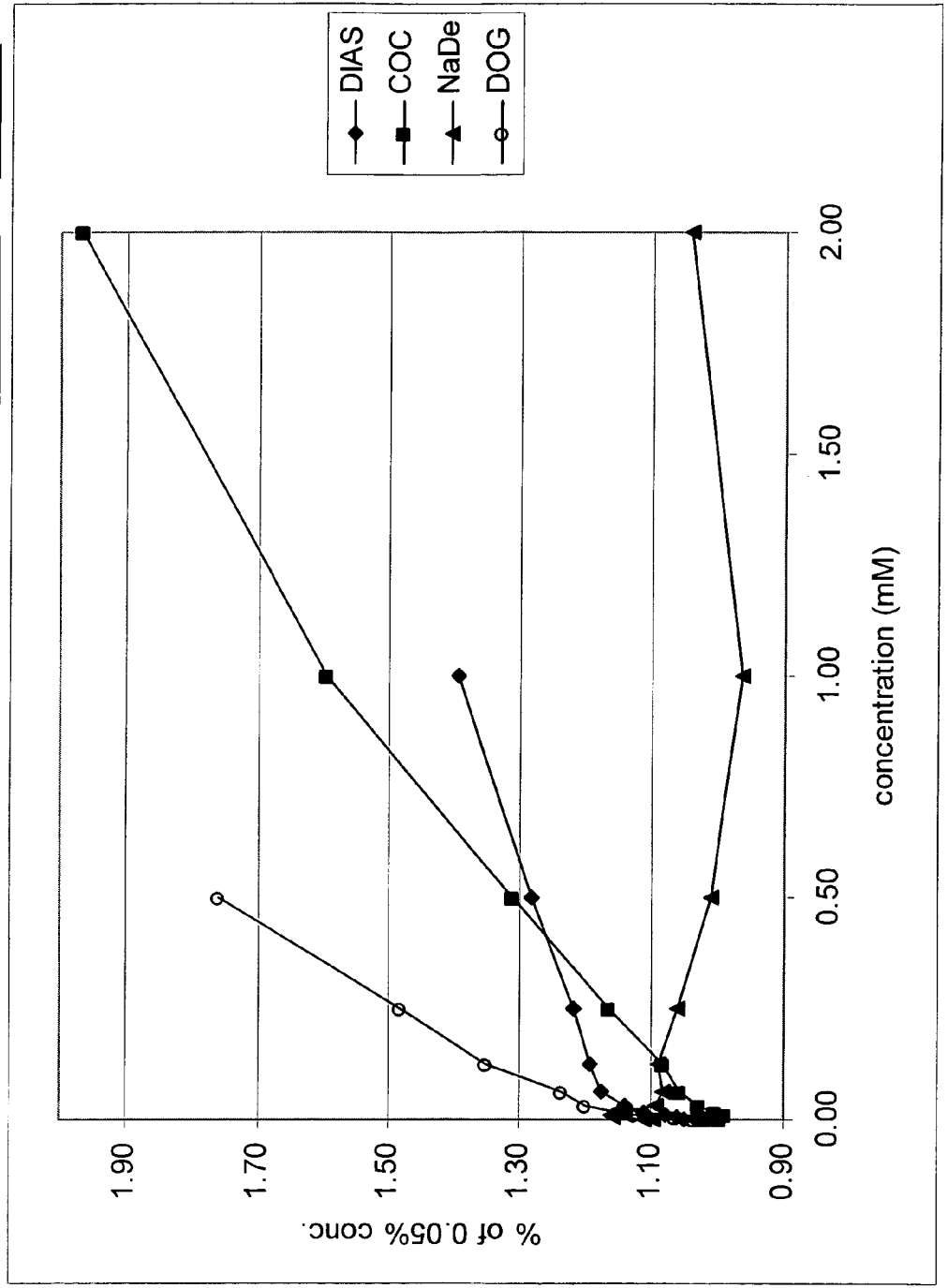

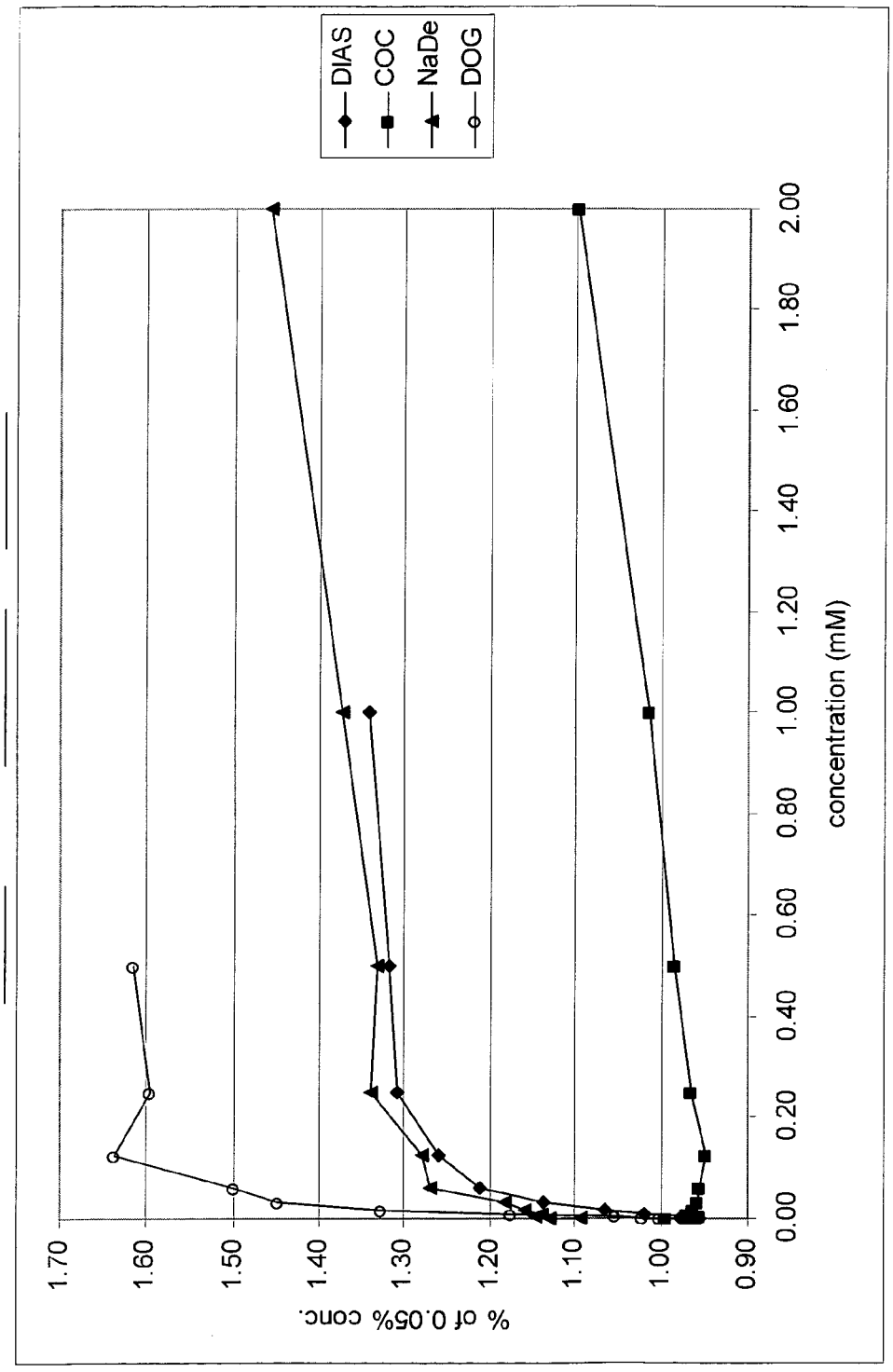

CROSS REACTIVE ARRAYS OF THREE-WAY JUNCTION SENSORS FOR STEROID DETERMINATION

This application is a continuation-in-part of U.S. Ser. No. 10/824,158, filed Apr. 14, 2004 now abandoned, which claims the benefit of U.S. Provisional Application No. 60/462,206, filed Apr. 14, 2003; and a continuation of PCT International Application No. PCT/US2004/011696, filed Apr. 15, 2004, the contents of all of which are hereby incorporated by reference.

At least some of the subject matter disclosed herein was supported by grants from NASA (NAS2-02039) and NIH (N1B1B, R01 EB000675-1). The United States Government may have rights to subject matter disclosed herein.

BACKGROUND OF THE INVENTION

Throughout this application, various publications are referenced to as footnotes or within parentheses. Disclosures of these publications in their entireties are hereby incorporated by reference into this application to more fully describe the state of the art to which this invention pertains. Full bibliographic citations for these references may be found within or at the end of this application, preceding the claims.

The mammalian olfactory system consists of approximately one thousand unique receptors (1). The distinctive characteristic of this system is cross-reactivity, i.e. one receptor may react with many odorants, and one odorant may react with many receptors. Thus, an odorant is not characterized by a single and specific interaction, but rather through a pattern of massively parallel responses yielding fingerprints characteristic for that specific odorant. Attempts to mimic the mammalian olfactory system have led to the development of "electronic noses", or arrays of cross-reactive sensors (2). In cross-reactive arrays, instead of standard dose-response curves, analytical samples are matched through their characteristic fingerprints to available standards. However, the frameworks suitable for the incremental variations of structure necessary to achieve differential cross-reactivity are currently limited. It would be useful to provide biomolecular receptors based on nucleic-acid three-way junctions that can be adapted to yield cross-reacting arrays for fingerprinting of solutions containing hydrophobic molecules.

SUMMARY OF THE INVENTION

The present invention recognizes and provides using biomolecules productively in cross-reacting arrays. The present invention provides an array based on nucleic-acids capable of fingerprinting hydrophobic molecules in solutions. With the recognition of a class of DNA-based molecular sensors for hydrophobic molecules as a starting point, the present invention provides for construction of an array from a large number of unique sensors. Such an array will be able to fingerprint instantaneously hydrophobic surfaces in urine belonging to steroids, alkaloids or any other hydrophobic drugs and correlate these fingerprints with disease states. This approach can be expanded to other biologically relevant molecules. Construction of large arrays on microchips that will incorporate different types of cross-reactive molecular sensors will lead to the rapid, one step procedures for diagnostic purposes.

Incorporation of hydrophobic molecules into various nucleic acid junctions has been noticed during early footprinting studies on these structures. These observations have been confirmed by the isolation of anti-steroid aptamers that were based on fully matched junctions. Also, one can isolate and characterize the first cocaine-binding junctions with mismatched stems. Unstacked base pairs at the ends of double helixes that form these junctions define the hydrophobic pocket. The shapes and sizes of junctions could be varied through changes in primary structure, and junctions can easily be turned into fluorescent sensors. These receptors are conceptually similar to various cyclodextrins, cyclophanes, calixarenes and other synthetic lipophylic cavities, which were earlier used to construct fluorescent sensors. Differences between nucleic acid-based sensors and other structures include the straightforward synthetic approach and, perhaps most importantly, rational construction of a large number of incrementally different structures.

The significance of the subject matter of the present invention is multifold. First, one can expand the scope of molecules and matrices where arrays could be applied to biologically relevant analytes. Accordingly, one can first expand on initial results and construct arrays that could report steroids in urine. Second, one can come closer to mimicking the resolution power of mammalian olfactory sense by incorporating in these arrays large number of closely related, yet distinct, sensors. This will become especially significant when one uses large arrays to characterize urine, which contains numerous structurally related molecules that are traditionally challenging to analyze. Third, from the practical point of view, the ability to rapidly determine hydrophobic content of urine will lead to immediate routine applications in general health monitoring and diagnosis. Namely, any gross deviation from the normal pattern of steroid excretion will be immediately detectable and will be correlated to the clinical conditions (e.g. endocrinopathy of steroid-based hormones or positive toxicology screens). Fourth, the successful development of the first nucleic acid-based cross-reacting arrays for hydrophobic fingerprinting will provide an impetus for other cross-reactive nucleic acid-based arrays, for which no comparable methods exist (e.g., for monitoring of blood and urinary oligosacharides and glycoprotein glycoforms), which will result in the construction of advanced arrayed labs-on-chips. Fifth, the screening of a large number of hydrophobic receptors for transduction of recognition into optical readout will likely yield some members that will be highly specific in the context of certain applications (for example ultra-high throughput screening applications).

The present invention provides a composition comprising an oligonucleotide which comprises consecutive nucleotides having the sequences set forth in SEQ ID NO:1 and SEQ ID NO:2, wherein SEQ ID NO:1 is located 5' to SEQ ID NO:2.

The present invention further provides the instant oligonucleotide, wherein the oligonucleotide folds so that the sequences set forth in SEQ ID NO:1 and SEQ ID NO:1 contained in the oligonucleotide are arranged as set forth in the following structure, wherein SEQ ID NO:1 is the left hand sequence and SEQ ID NO:2 is the right hand sequence:

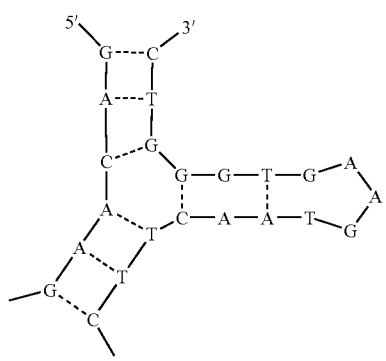

The present invention further provides the instant oligonucleotide, wherein the oligonucleotide comprises consecutive nucleotides having the sequence set forth in SEQ ID NO:152, wherein SEQ ID NO:152 is located 3' to SEQ ID NO:1 and 5' to SEQ ID NO:2.

The present invention also provides composition comprising an oligonucleotide which comprises consecutive nucleotides having the sequences set forth in SEQ ID NO:101 and SEQ ID NO:102, wherein SEQ ID NO:101 is located 5' to SEQ ID NO:102.

The present invention further provides the instant oligonucleotide, wherein the oligonucleotide folds so that the sequences set forth in SEQ ID NO:101 and SEQ ID NO:102 contained in the oligonucleotide are arranged as set forth in the following structure, wherein SEQ ID NO:1-1 is the left hand sequence and SEQ ID NO:102 is the right hand sequence:

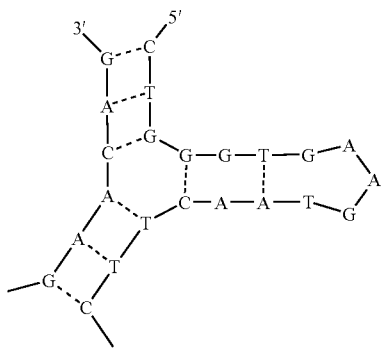

The present invention further provides the instant compositions, wherein the oligonucleotide comprises consecutive nucleotides having the sequence set forth in SEQ ID NO:153, wherein SEQ ID NO:153 is located 3' to SEQ ID NO:101 and 5' to SEQ ID NO:102.

This invention also provides a method of detecting an analyte in a solution comprising:
(a) providing a composition comprising an oligonucleotide and a fluorescent moiety attached to the oligonucleotide, wherein the oligonucleotide undergoes a conformational change upon contact with the analyte and the fluorescent moiety undergoes a change of fluorescence upon the conformational change;
(b) quantitating the fluorescence of the fluorescent moiety of the composition in the absence of the analyte;
(c) subsequently contacting the composition with the solution containing the analyte;
(d) quantitating the fluorescence of the fluorescent moiety of the composition in contact with the solution containing the analyte; and
(e) comparing the fluorescence quantitated in step (b) with that quantitated in step (d),
wherein a change in the fluorescence quantitated in step (d) as compared with the fluorescence quantitated in step (b) indicates that the analyte is present in the solution.

This invention also provides a method of determining whether an amount of an analyte in a first solution is different to that of an amount of the analyte in a second solution comprising:
(a) providing a composition comprising an oligonucleotide and a fluorescent moiety attached to the oligonucleotide, wherein the oligonucleotide undergoes a conformational change upon contact with the analyte and the fluorescent moiety undergoes a change of fluorescence upon the conformational change;
(b) contacting the composition with the first solution containing the analyte;
(c) quantitating the fluorescence of the fluorescent moiety of the composition;
(d) washing the composition to remove the first solution;
(e) contacting the composition with the second solution containing the analyte;
(f) quantitating the fluorescence of the fluorescent moiety of the composition; and
(g) comparing the fluorescence quantitated in step (f) with that quantitated in step (c),
wherein a change in the fluorescence quantitated in step (f) as compared with the fluorescence quantitated in step (c) indicates that the amount of the analyte in the first solution is different to the amount of the analyte in the second solution.

This invention also provides a method of quantitating an analyte in a solution comprising:
(a) providing a composition comprising an oligonucleotide and a fluorescent moiety attached to the oligonucleotide, wherein the oligonucleotide undergoes a conformational change upon contact with the analyte and the fluorescent moiety undergoes a change of fluorescence upon the conformational change;
(b) providing a predetermined relationship between the fluorescent moiety fluorescence and the analyte concentration;
(c) contacting the composition with the solution containing the analyte;
(d) quantitating the fluorescence of the fluorescent moiety of the composition in contact with the solution containing the analyte;
(e) quantitating the analyte in the solution from the fluorescence quantitated in step (d) and the predetermined relationship provided in step (b).

This invention also provides the instant methods, wherein two or more compositions are present.

This invention also provides a method of determining whether a first solution comprising a first analyte has an analyte composition different to that of a second solution comprising a second analyte comprising:
(a) providing a first composition comprising a first oligonucleotide and a first fluorescent moiety attached to the first oligonucleotide, and a second composition comprising a second oligonucleotide and a second fluorescent moiety attached to the second oligonucleotide, wherein each of the first and second oligonucleotides undergoes a conformational change upon contact with the first analyte and upon contact with the second analyte, and each of the fluorescent moieties undergoes a change of fluorescence upon the conformational change of the oligonucleotides upon contact with the first analyte and upon contact with the second analyte;
(b) contacting the first composition and second composition with the first solution containing the first analyte;
(c) quantitating the fluorescence of each of the fluorescent moieties;
(d) washing to remove the first solution;
(e) contacting the first composition and second composition with the second solution containing the second analyte;
(f) quantitating the fluorescence of each of the fluorescent moieties; and
(g) comparing the fluorescence quantitated in step (f) with that quantitated in step (c),
wherein a change in the fluorescence quantitated in step (f) as compared with the fluorescence quantitated in step (c)

indicates that the first solution containing the first analyte has an analyte composition different to that of the second solution containing the second analyte.

Figure 17:
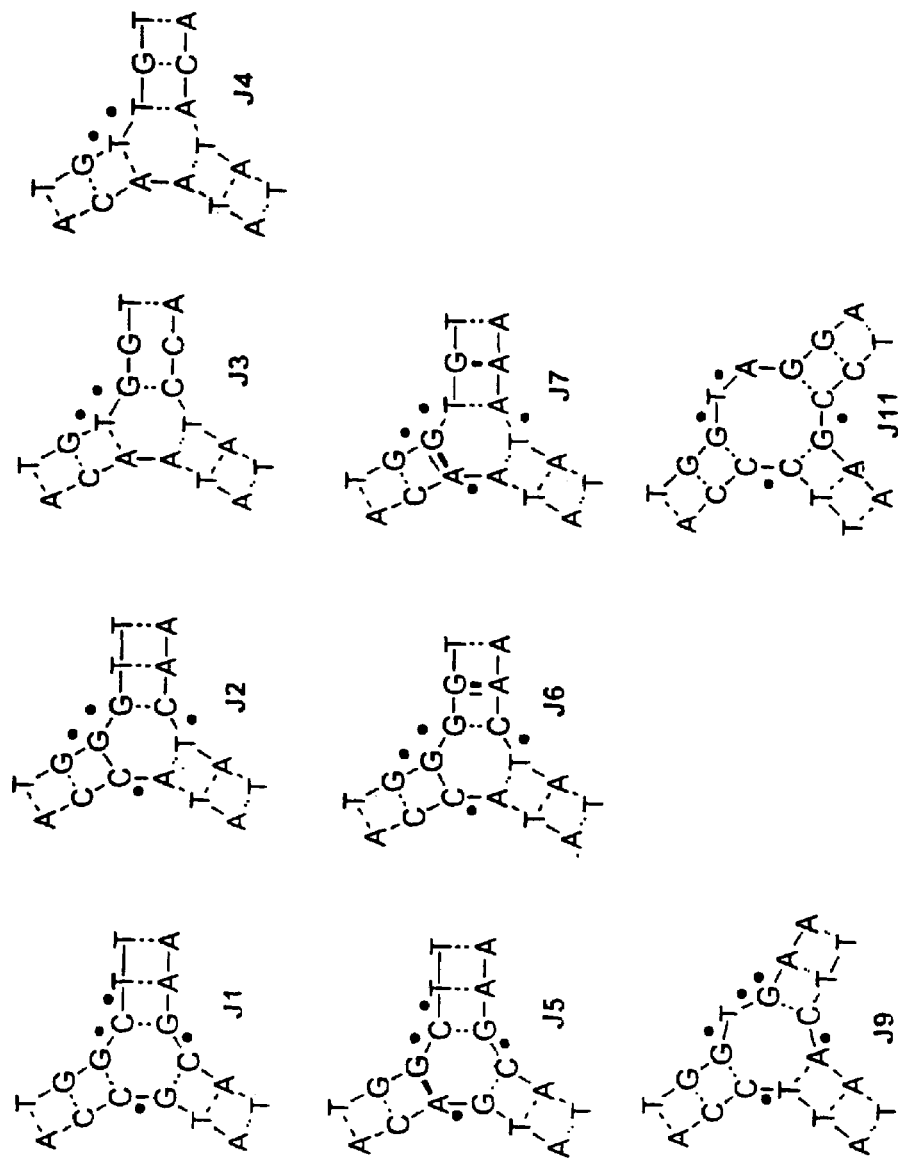

FIG. 17: Representative three-way junctions (9 illustrative examples, for brevity only three base pairs in each stem, and no loops are shown) which may be custom made and derivatized with fluorophores to yield sensors. The black dots mark positions of individual phosphorothioate bonds, lines mismatched base pairs. SEQ ID NOs. for each three-way junction, in a counter-clockwise fashion starting with the leftmost sequence, are SEQ ID NOs. 168, 169, 170 (J1); 171, 172, 170 (J2); 173, 174, 175 (J3); 173, 176, 177 (J4); 178, 179, 180 (J5); 181, 182, 183 (J6); 184, 185, 186 (J7); 187, 188, 189 (J9); and 190, 191, 192 (J11).

Figure 18:
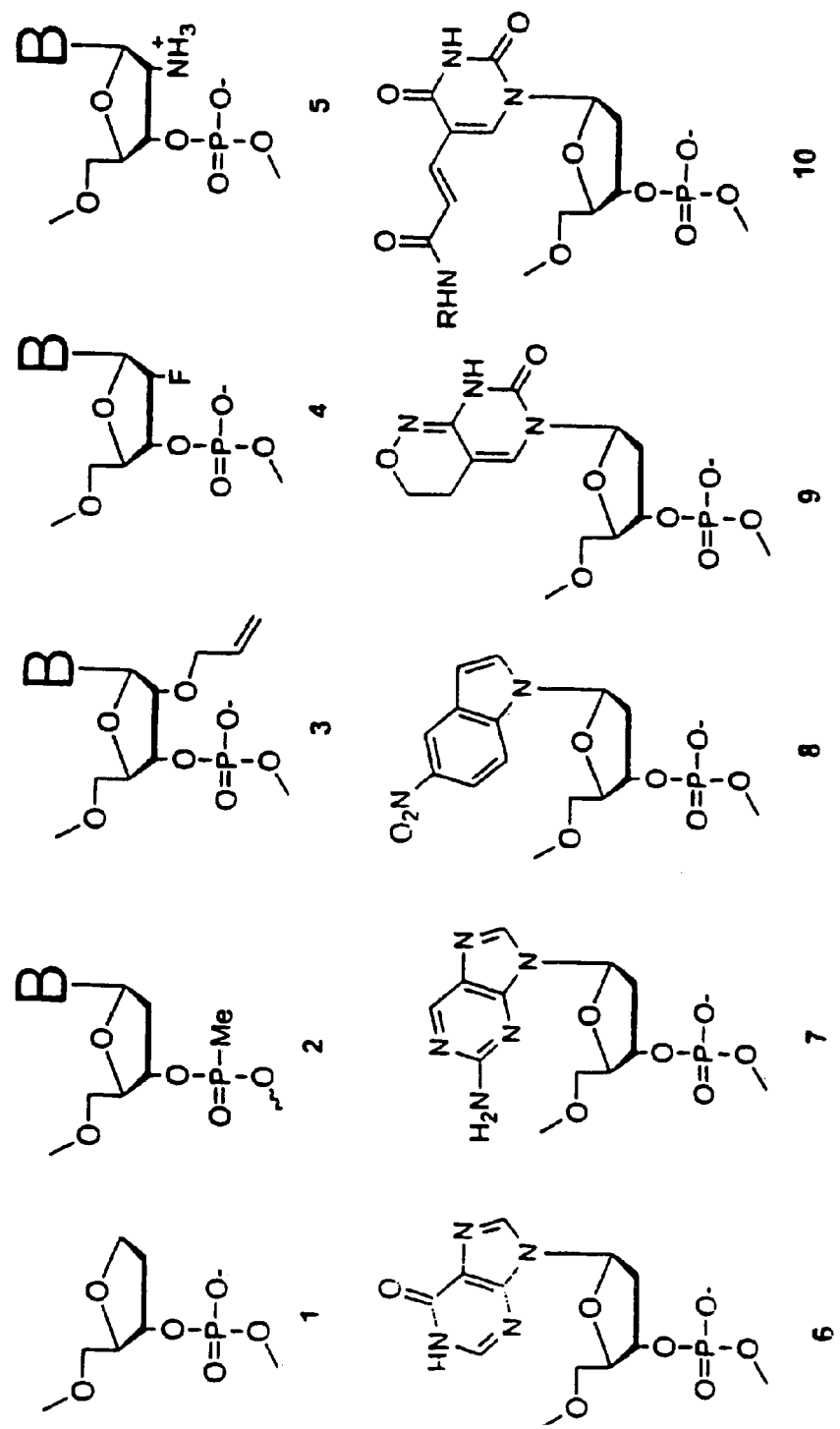

FIG. 18: Representative modified nucleotides that may be incorporated in junctions and tested. Note, methyl phosphonate will give electroneutral junction, while 2'-amino derivative will give junction with additional one positive charge. 2'-amine can be also directly modified with a fluorophore, without phosphorothioate.

Figure 19:
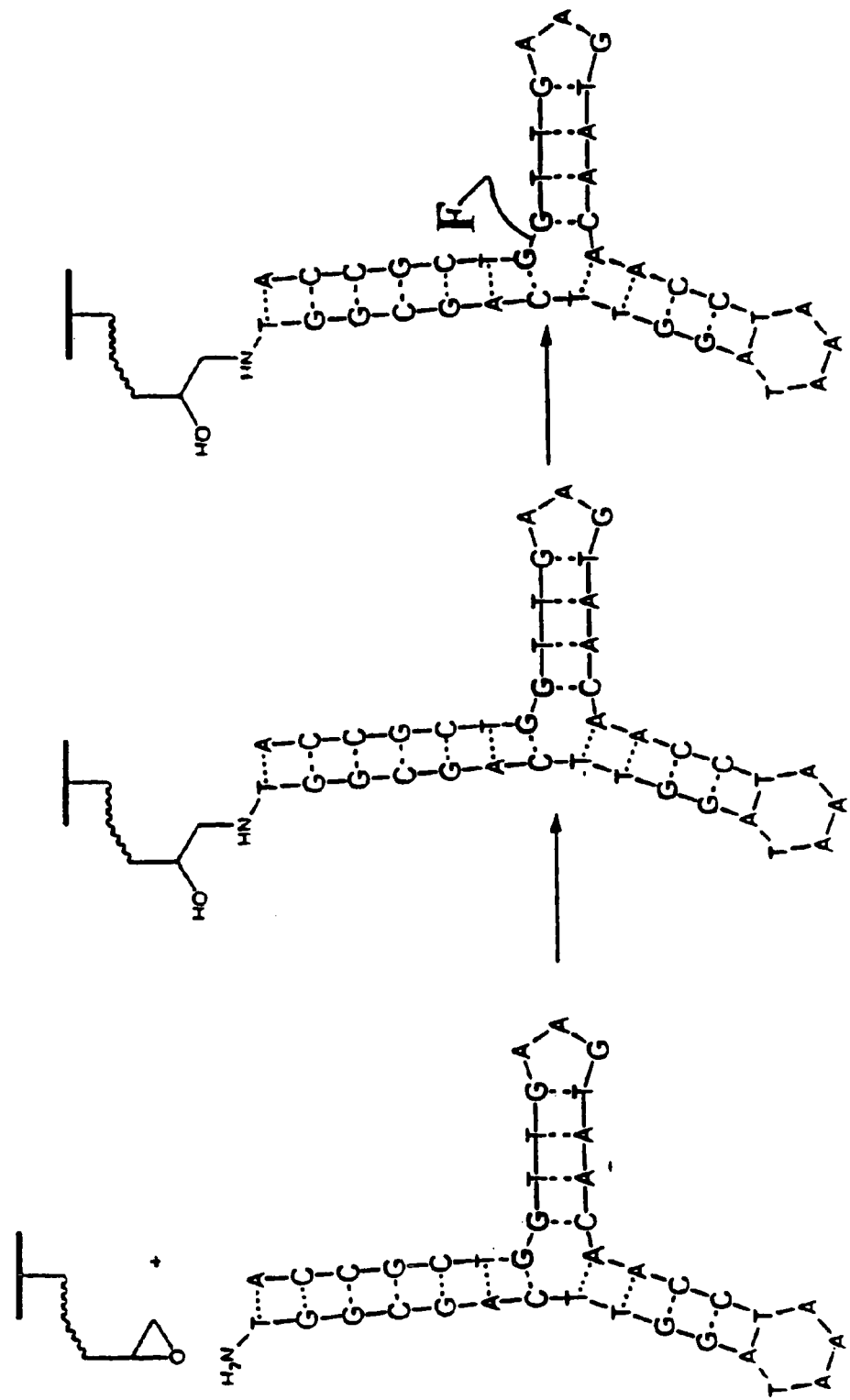

FIG. 19: An example of the synthesis of molecular sensors on solid support. 5'-amine modified junction is attached to the solid support through reaction with epoxide, followed by derivatization of junction with fluorophore.

Figure 20:
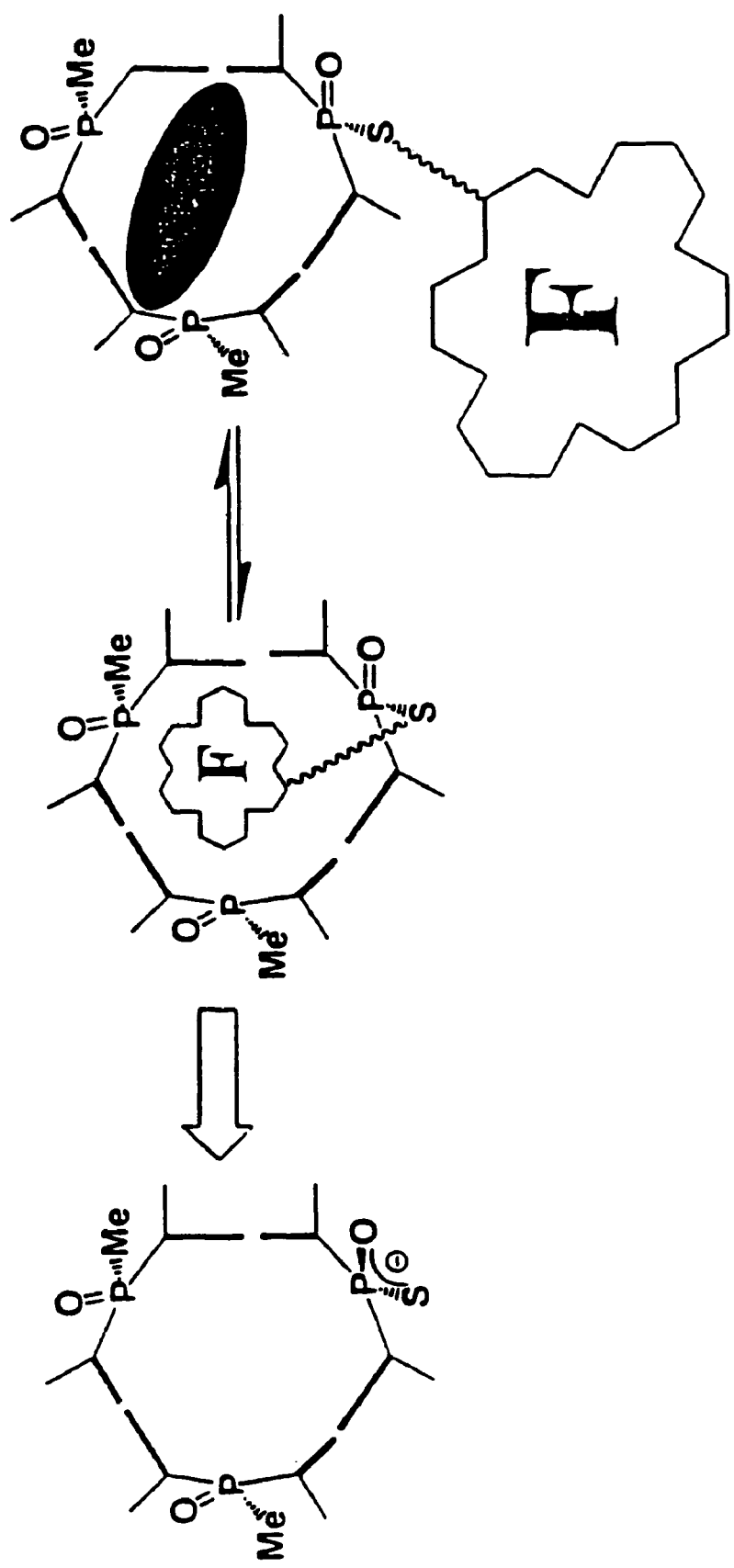

FIG. 20: A schematic representation of sensors based on neutral junctions. Black ellipsoid represents hydrophobic molecule that upon binding displaces fluorophore, causing an increase in fluorescence. Only one isomer is shown.

Figure 21:
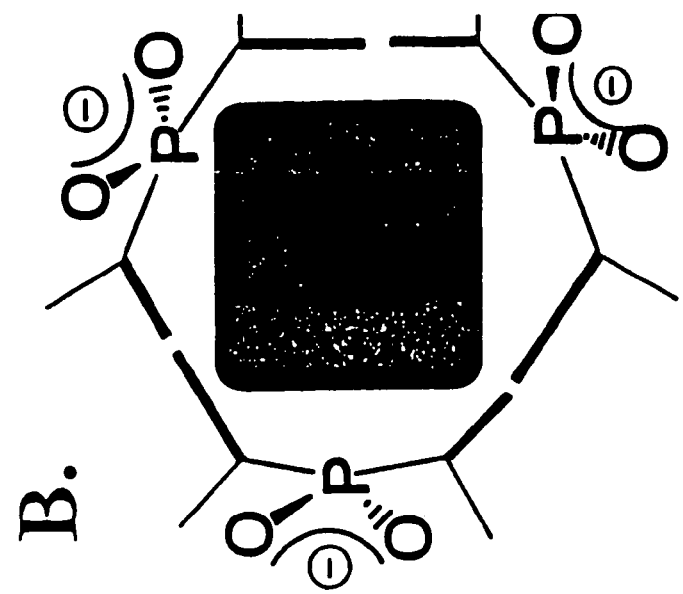
Figure 21:
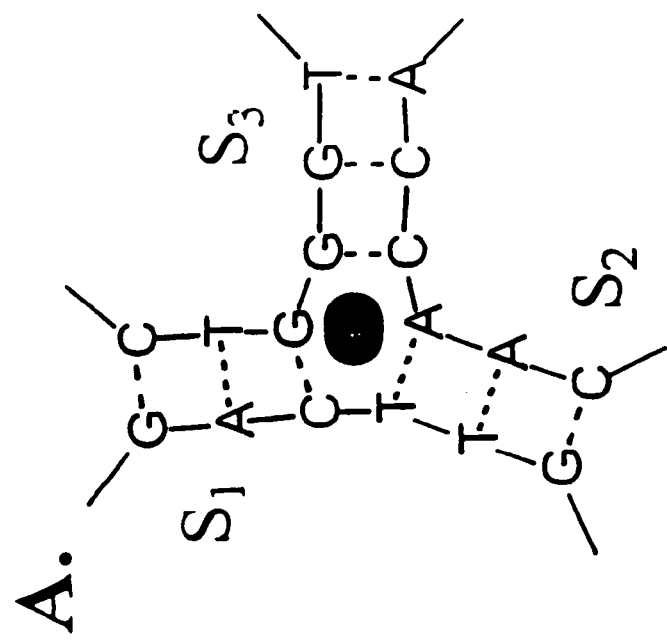

FIG. 21: The generic structure of the three-way junction region of a nucleic acids-based receptor with a ligand guest (black circle). Further variations in junction structure could be introduced by mismatches and bulges (unpaired bases). B. A schematic representation of junctions, with guest molecules (black square) shows the three aromatic unstacked surfaces separated by phosphodiester groups forming a hydrophobic binding pocket.

Figure 22:
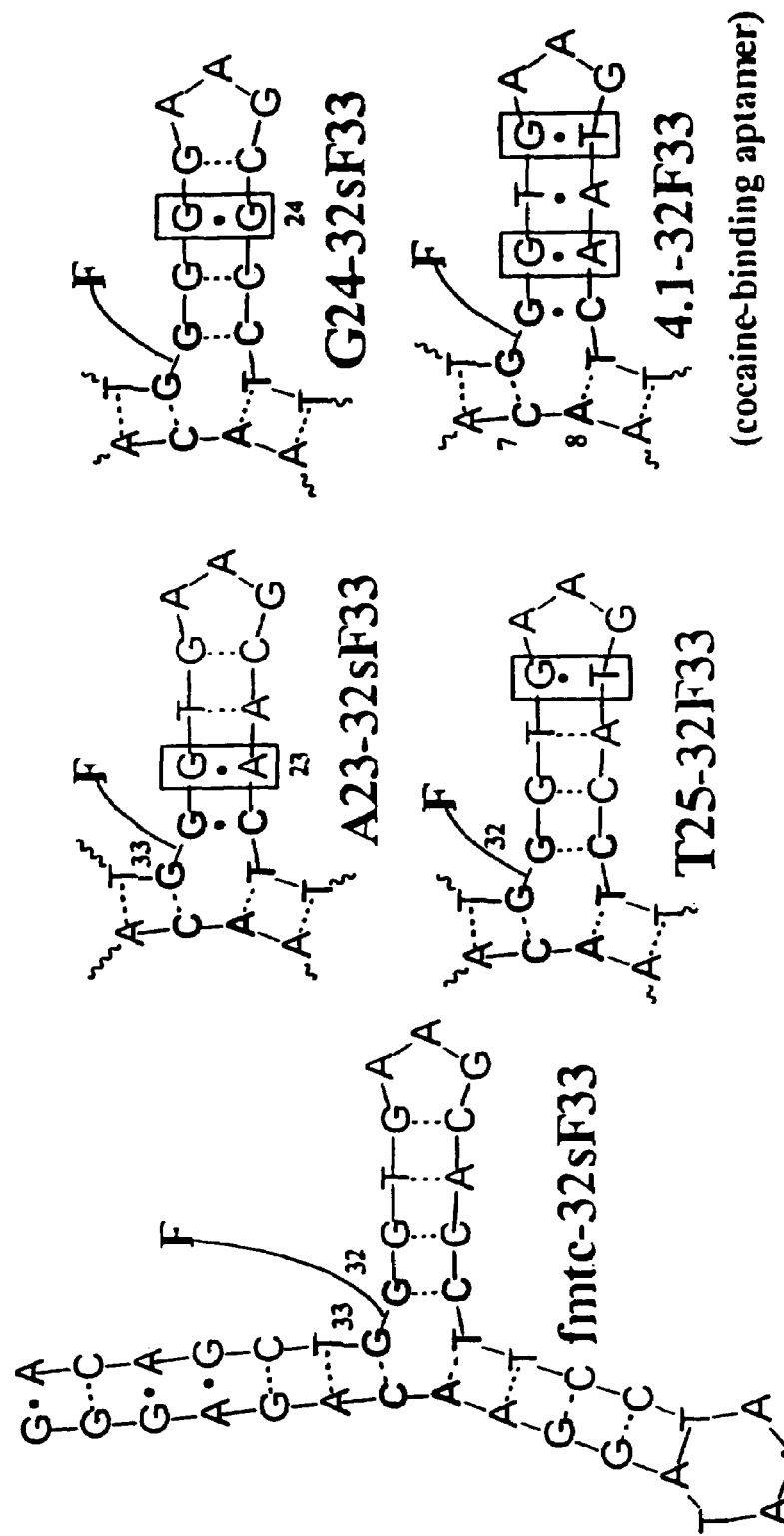

FIG. 22: The junctional structures of each sensor, with the position of fluorophore attachment indicated (F—fluorescein). These five junctions differ in the position of mismatches (boxed) in the $S_3$ stem. SEQ ID NOs. 193 (fmtc-32sF33); 194 and 195 (left and right sequences, A23-32sF33); 194 and 196 (left and right sequences, G24-32sF33); 194 and 197 (left and right sequences, T25-32F33); and 194 and 198 (left and right sequences, 4.1-32F33).

Figure 23:
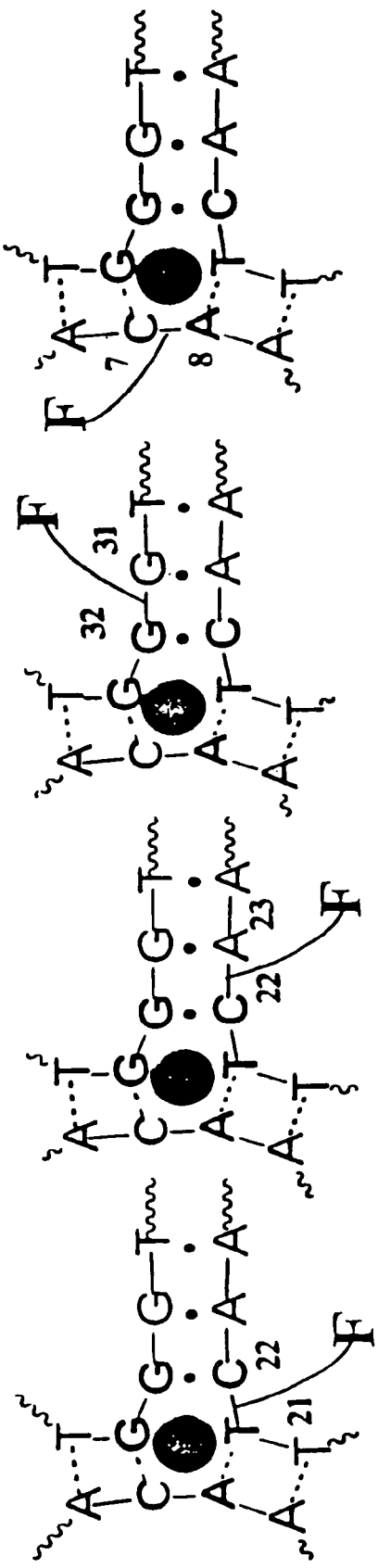

FIG. 23: The five isomeric sensors, based on the junction MNS4.1, with varying positions of fluorophore, as shown. $G_{26}AA$ loop in $S_3$ stem not shown. SEQ ID NOs. for each structure are 104, 199 and 200, starting with the leftmost sequence.

Figure 24:
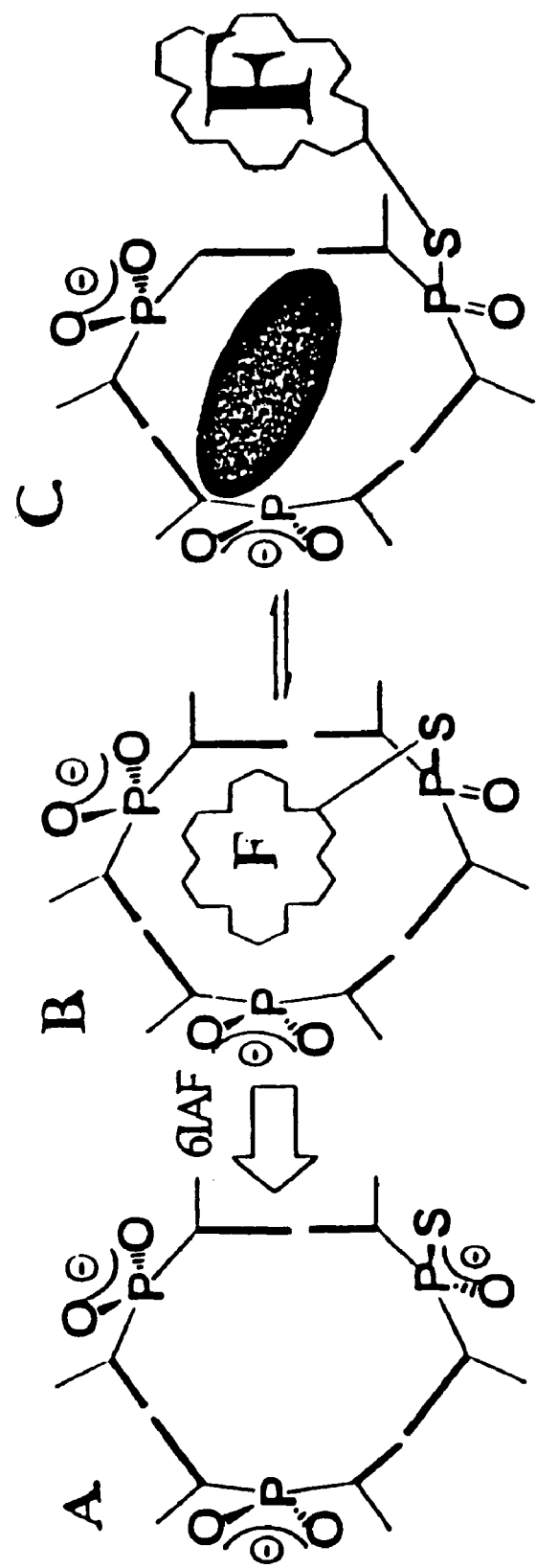

FIG. 24: Schematic representation of the core structures of a three-way junction with: A. One out of three junctional phosphodiester groups substituted with a phosphorothioate group; B. Fluorescein (F) attached to the reactive sulfur through reaction with 6-IAF (one diastereomer shown); C. Fluorophore internally displaced from the cavity of the three-way junction by hydrophobic molecule (black ellipse).

Figure 25:
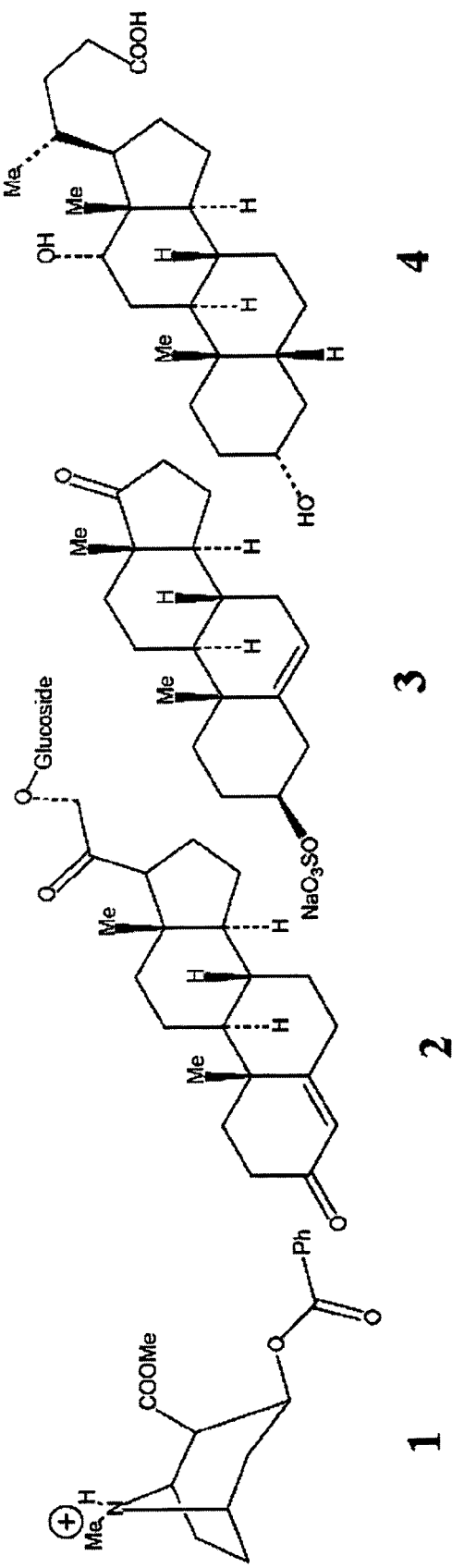

FIG. 25: The structures of four ligands: cocaine (1), deoxycorticosterone 21-glucoside (2), dehydroisoandrosterone 3-sulfate (3) and deoxycholic acid (4).

Figure 26:
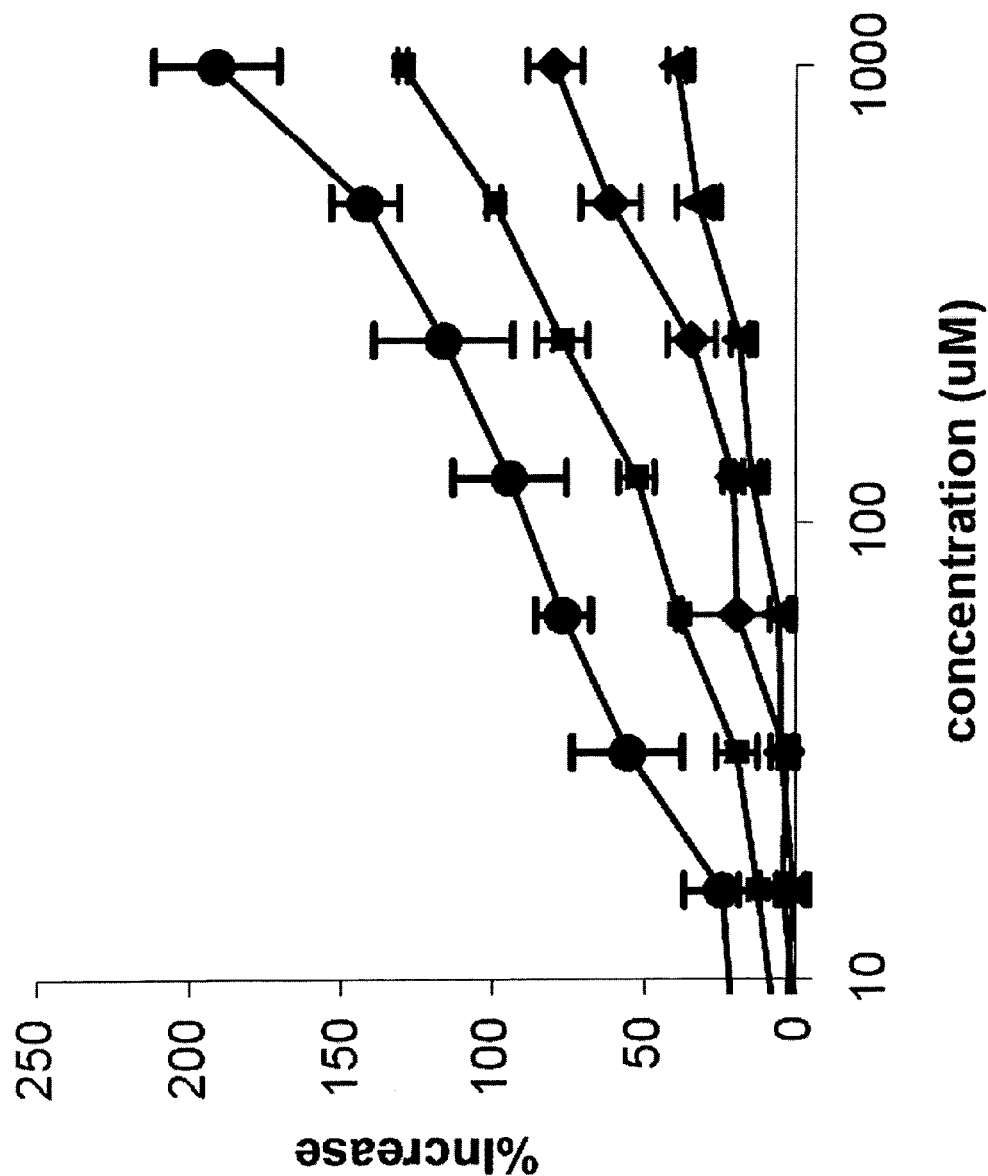

FIG. 26: Increase in fluorescence intensity (%) vs. ligand concentration (μM) for 4.1-32sF33. Ligands: cocaine hydrochloride 1 (diamonds), deoxycorticosterone 21-glucoside 2 (circles), dehydroisoandrosterone 3-sulfate sodium 3 (squares) and sodium deoxycholate 4 (triangles). All measurement were taken in triplicates and standard deviation is shown.

Figure 27:

FIG. 27: Fingerprints based on an array of eight sensors: cocaine 1 (500 μM) deoxycorticosterone 21-glucoside 2 (32 μM), dehydroisoandrosterone 3-sulfate 3 (125 μM) and deoxycholic acid 4 (2 mM). (first bar in each group: fmtch-32F33; (second bar): A23-32F33; (third bar): G24-32F33; (fourth bar):T25-32F33; (fifth bar): 4.1-32F33; (six bar): 4.1-7F8; ($7^{th}$ bar): 4.122F23; (eighth bar): 4.1-31F32. Response from 4.1-32F33 (fifth bar) was nearly identical to four ligands, and was used as a reference point to choose concentrations.

Figure 28:
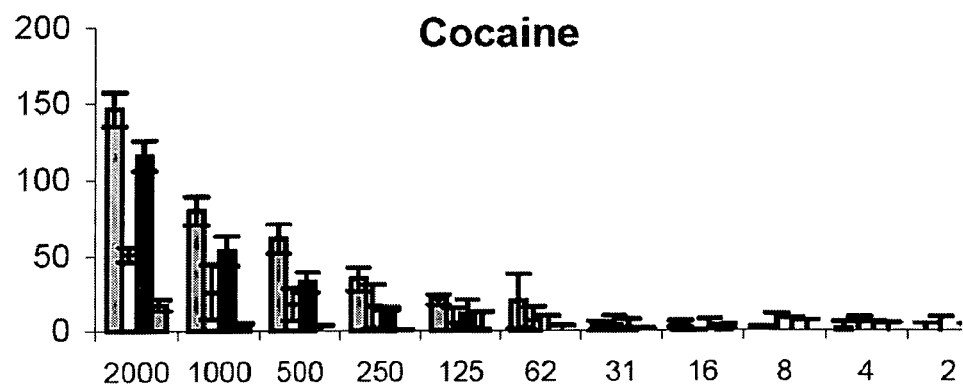
Figure 28:
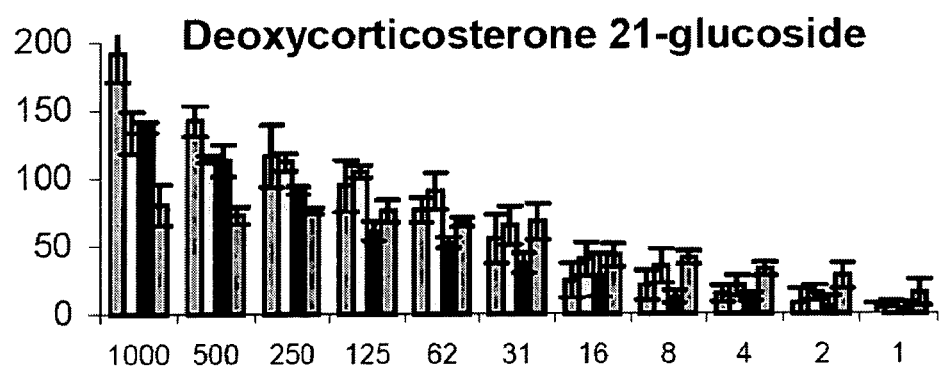
Figure 28:
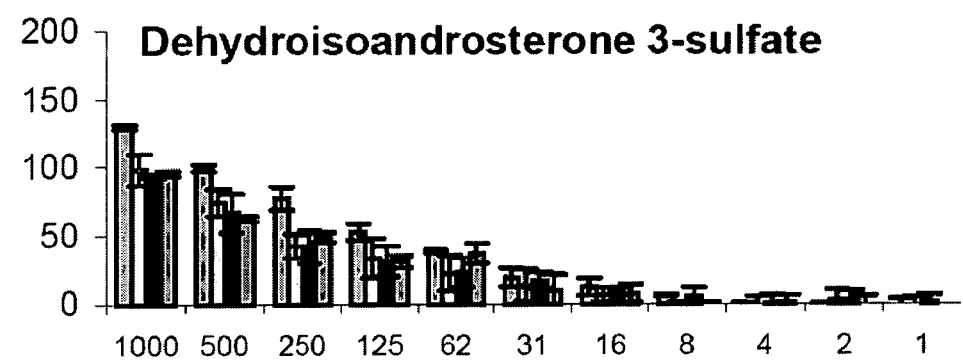
Figure 28:
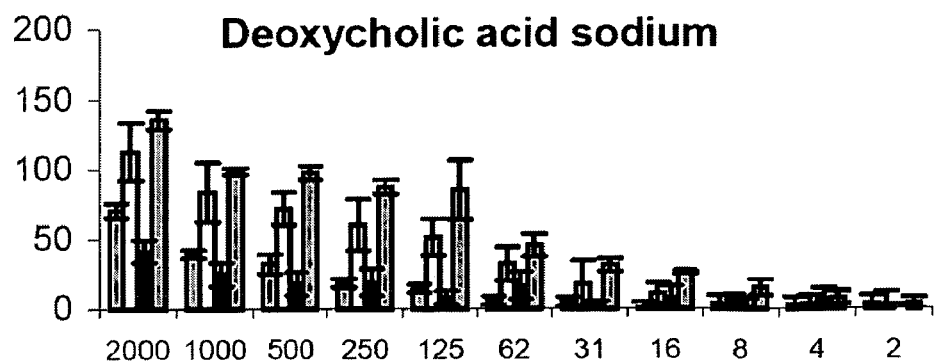

FIG. 28: The fingerprints (% Increase in fluorescence vs. concentration in μM) based on an array of seven sensors of cocaine 1, deoxycorticosterone 21-glucoside 2, dehydroisoandrosterone 3-sulfate 3 and deoxycholic acid 4; (first bar in each group): 4.1-32F33; (second bar): G24-32sF33; (third bar): 4.1-7F8; (fourth bar): fmtch-32S33. All measurements are in triplicates, with standard deviations shown.

Figure 29:
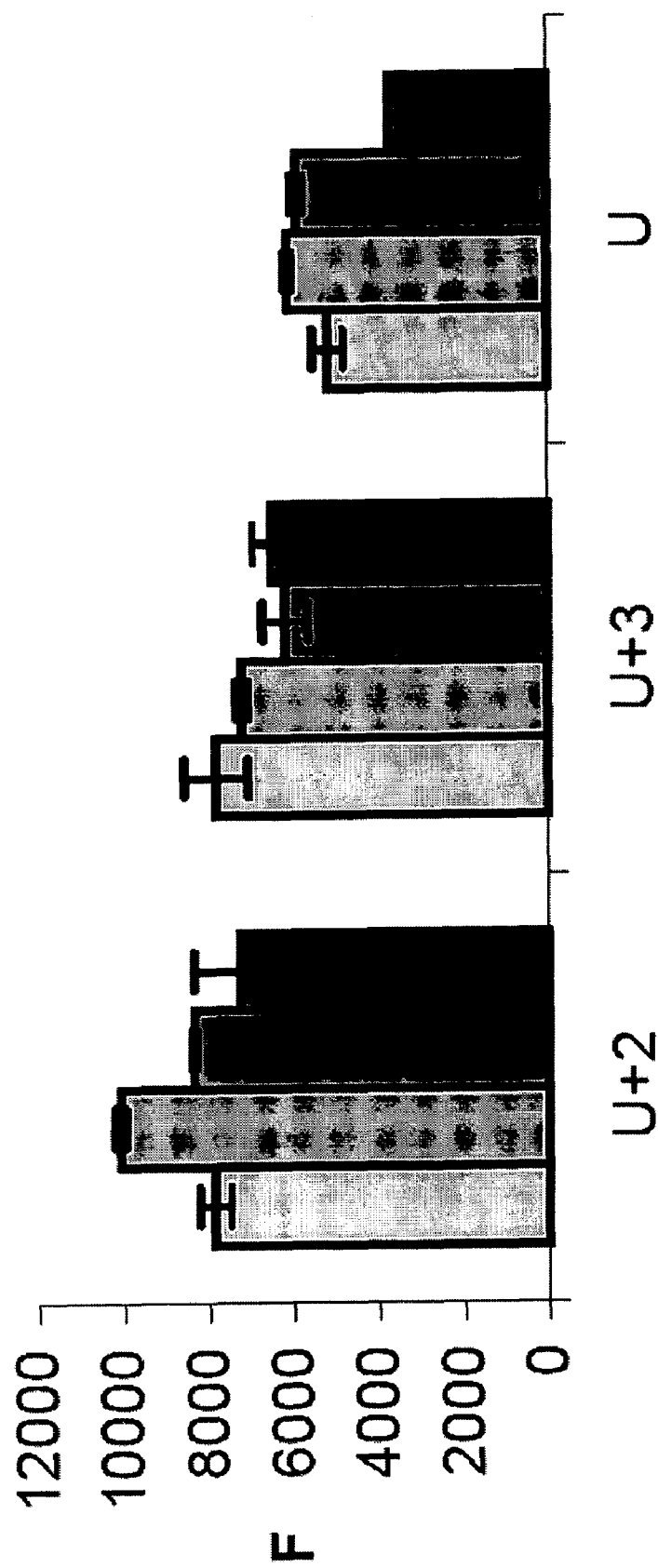
Figure 30A:
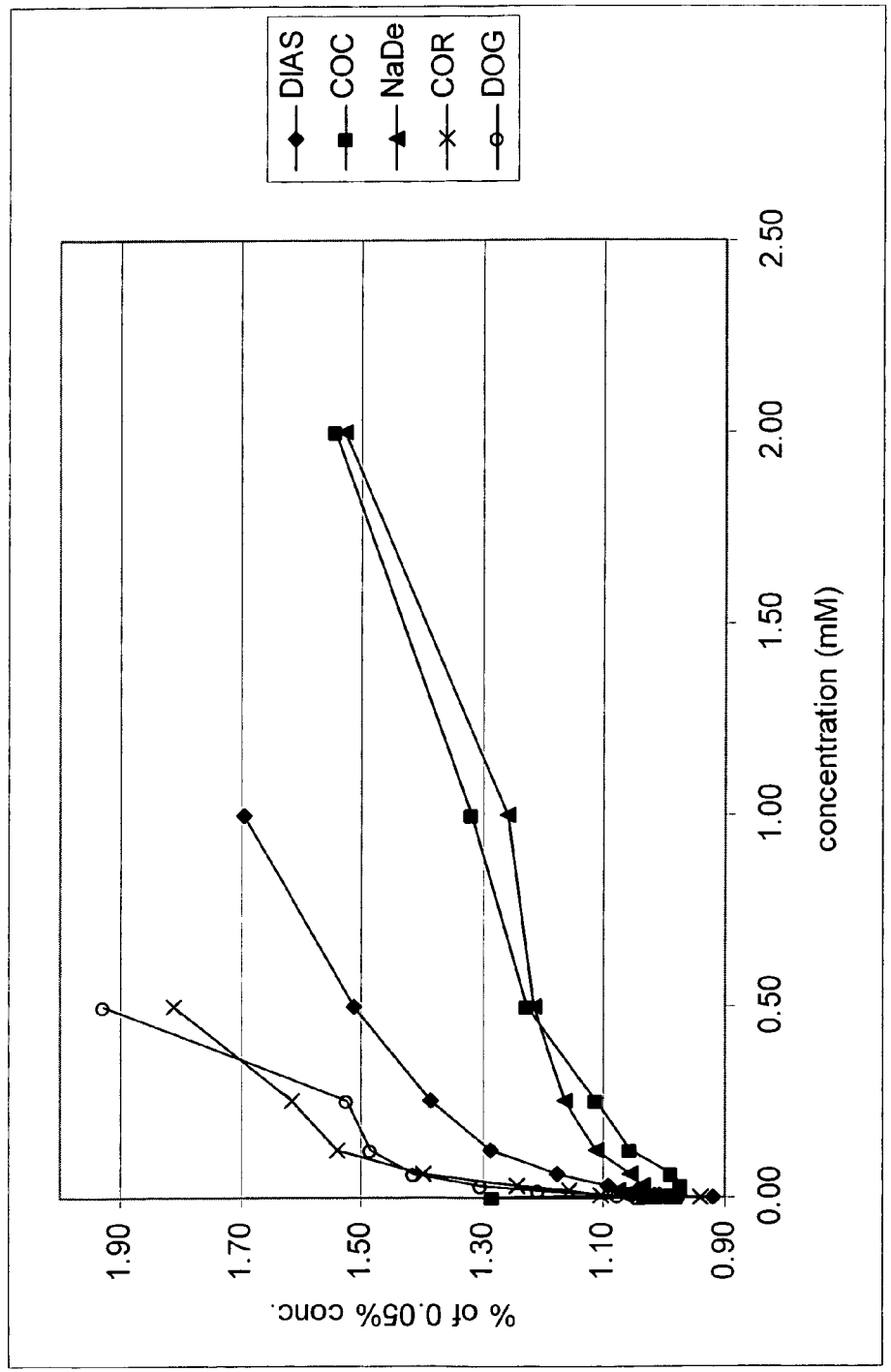
Figure 30B:
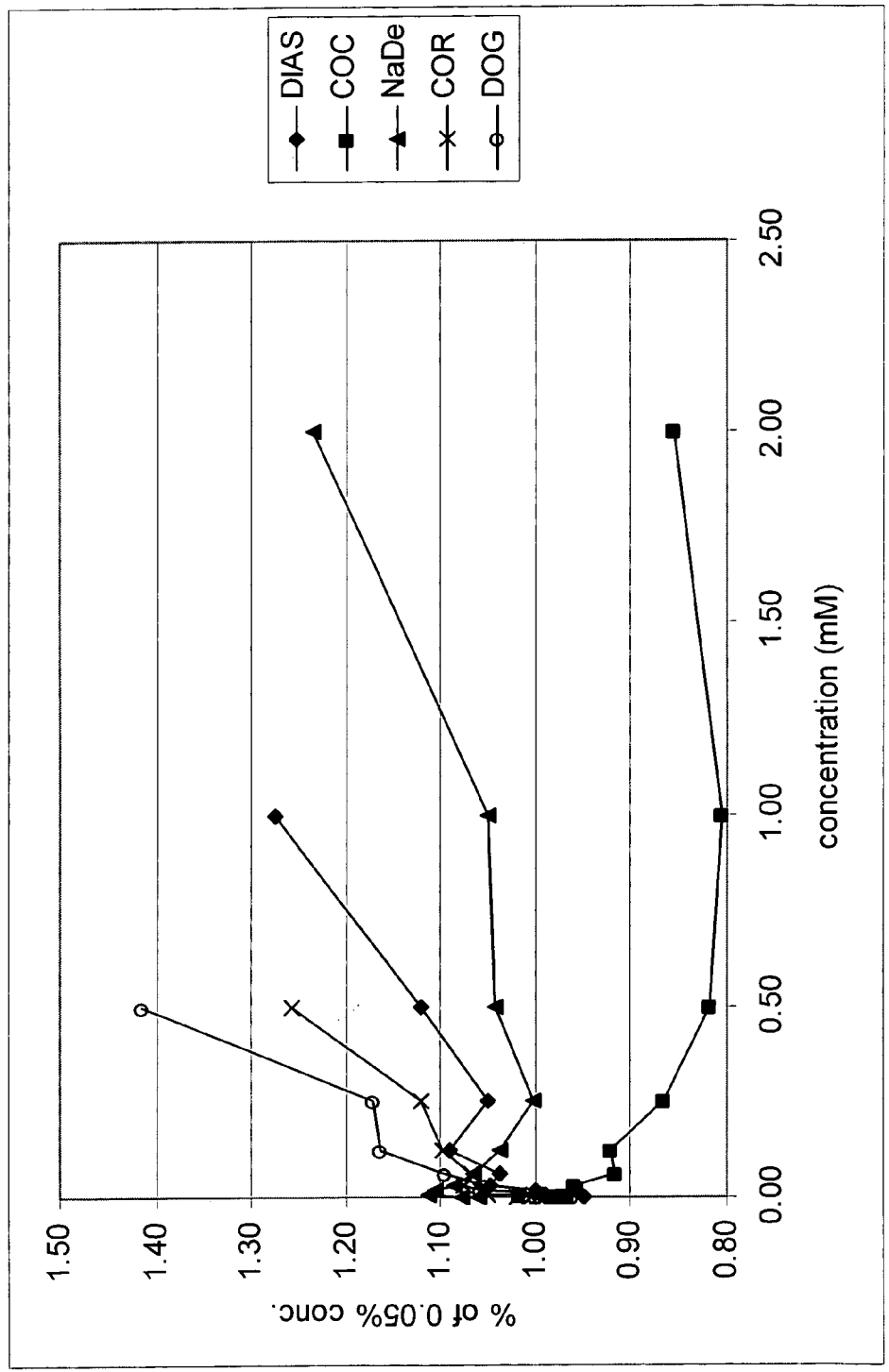
Figure 30C:
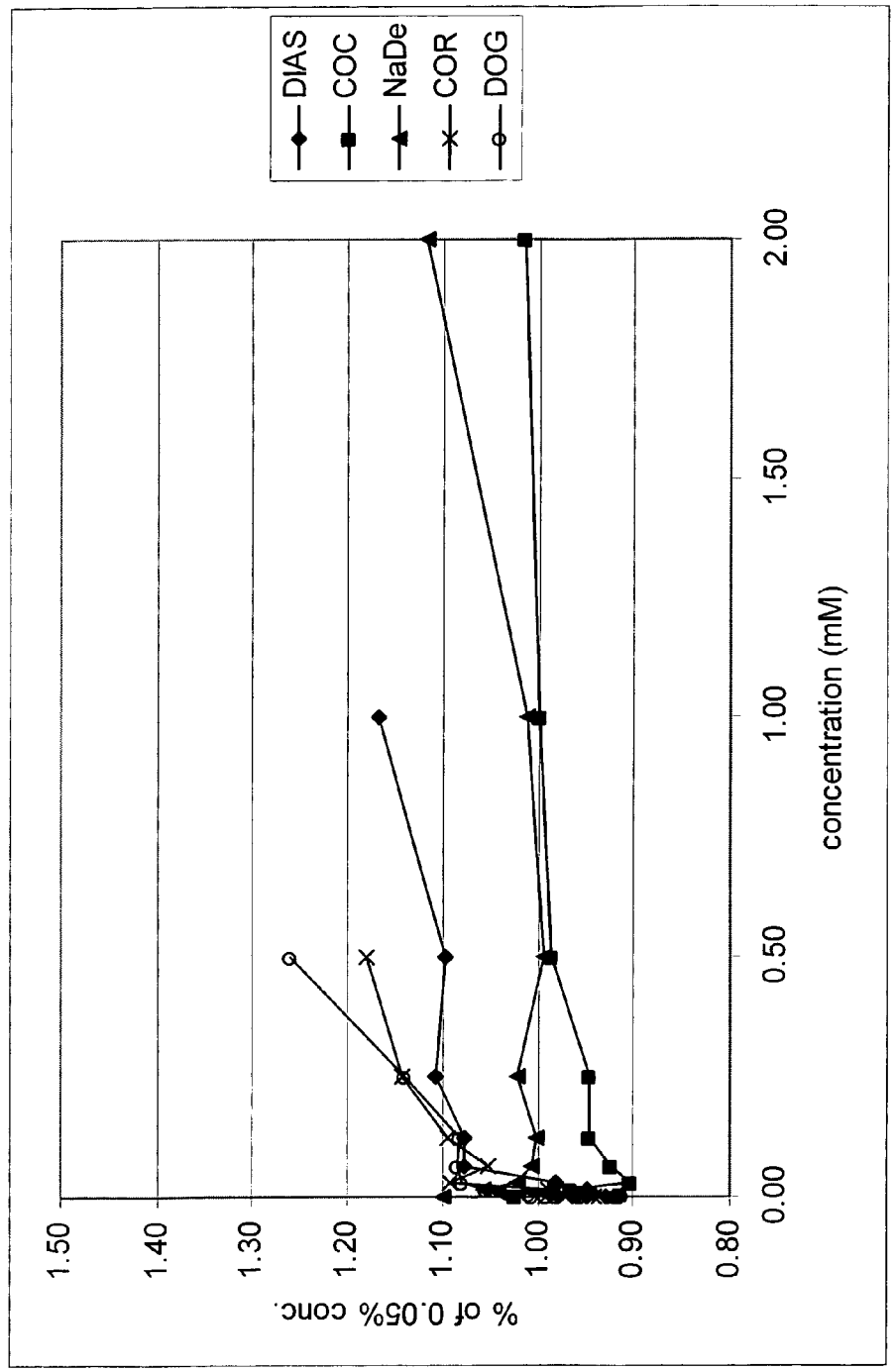
Figure 30D:
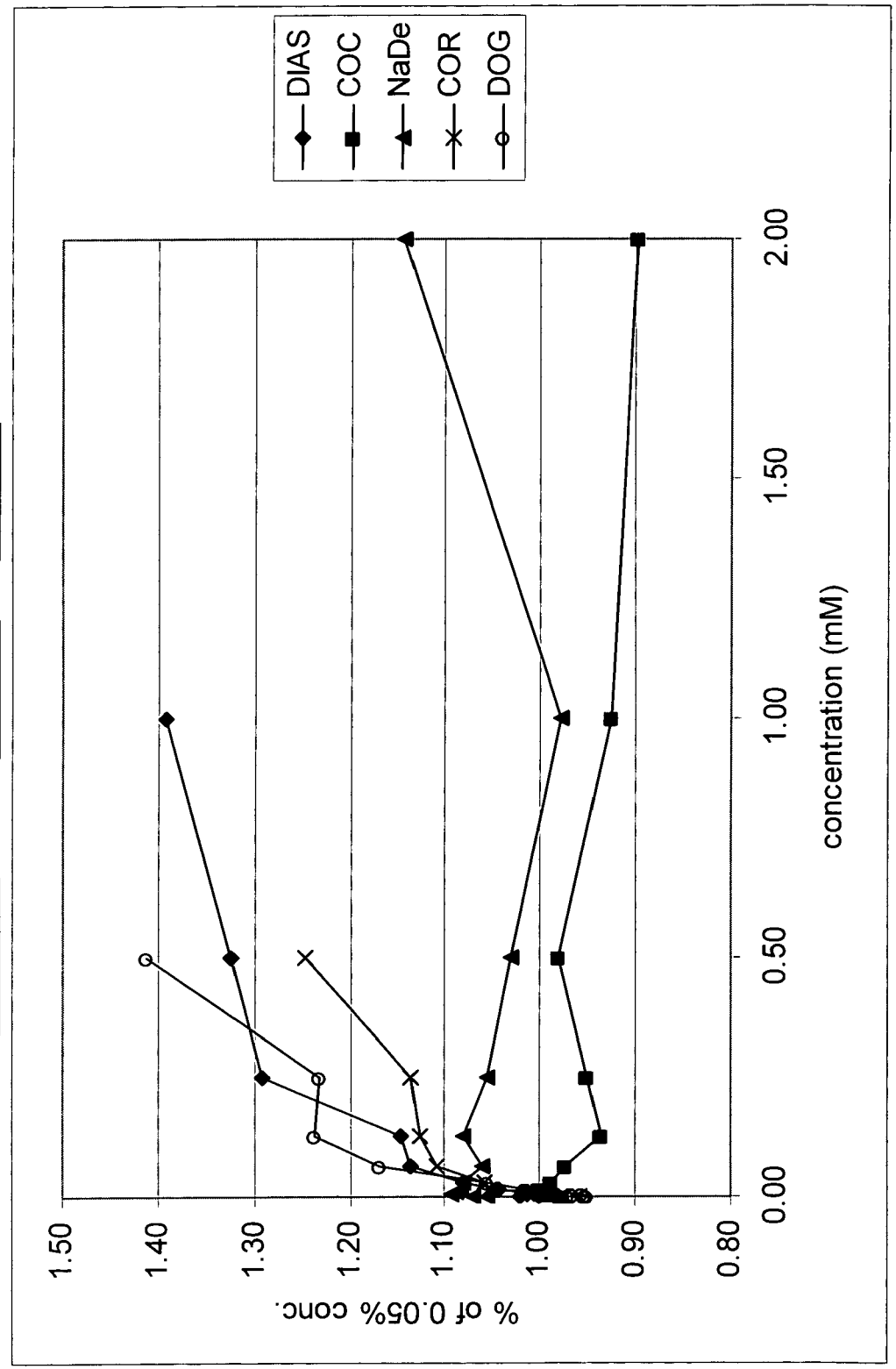
Figure 30E:
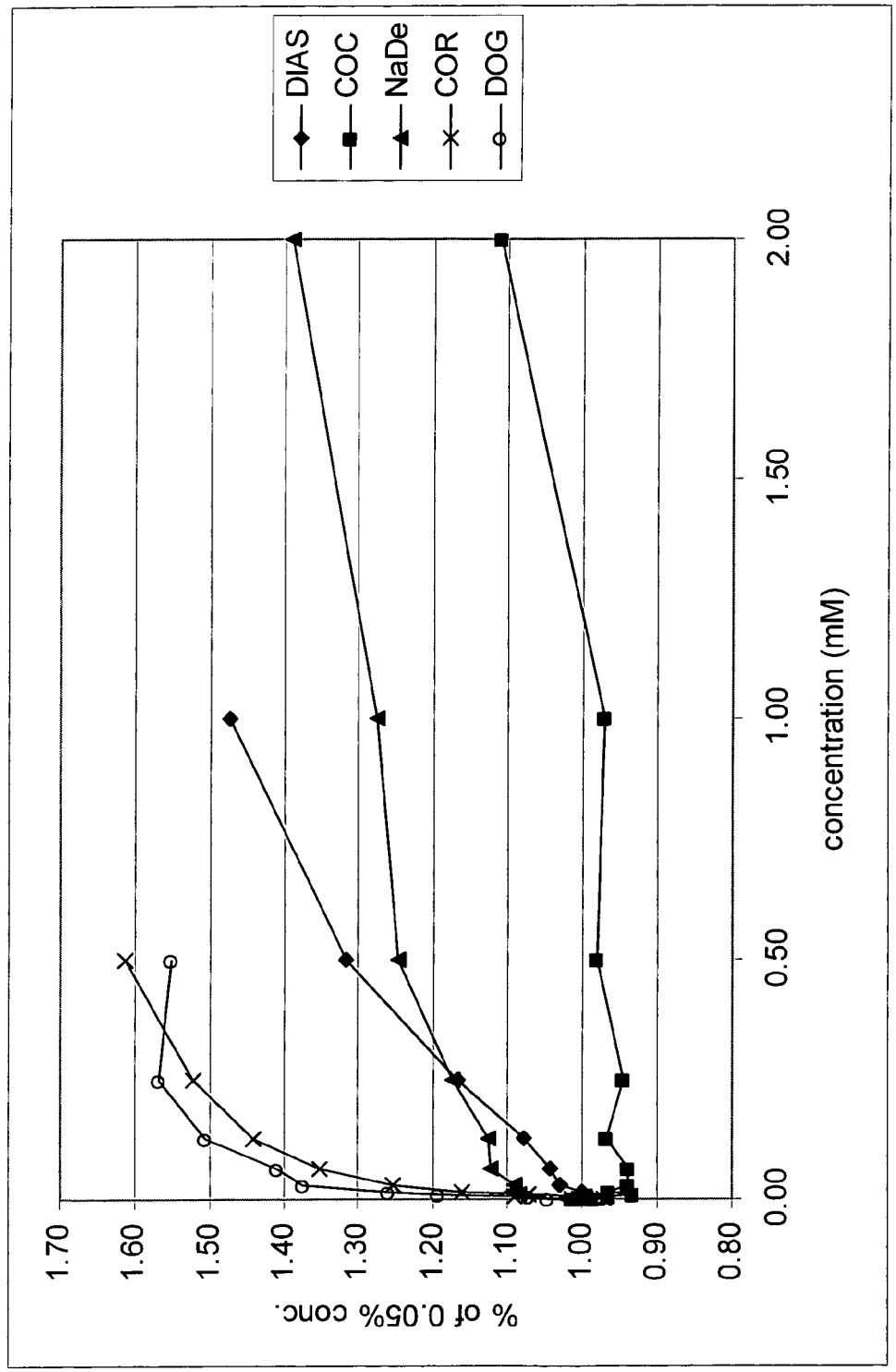
Figure 30F:
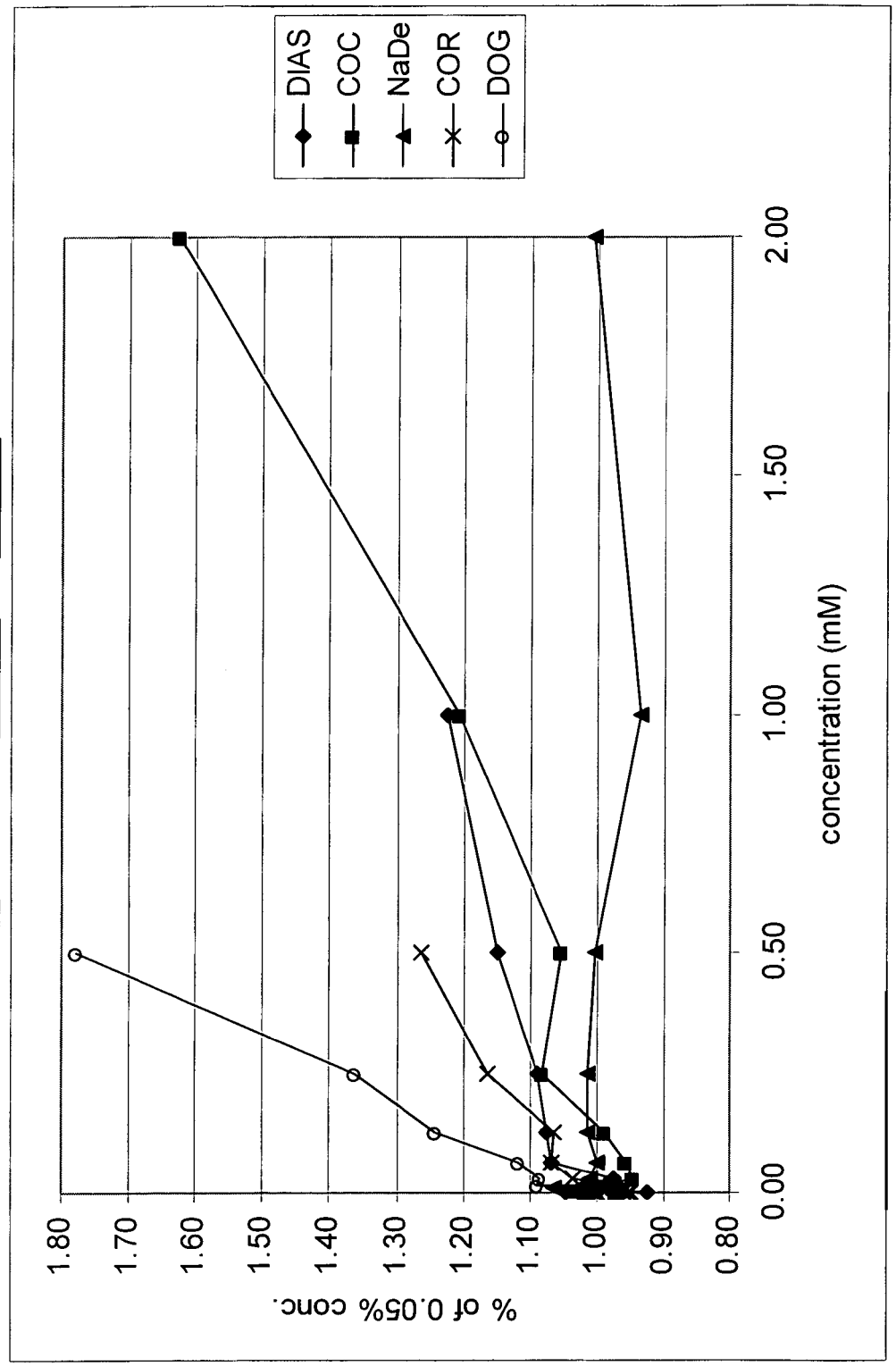
Figure 30G:
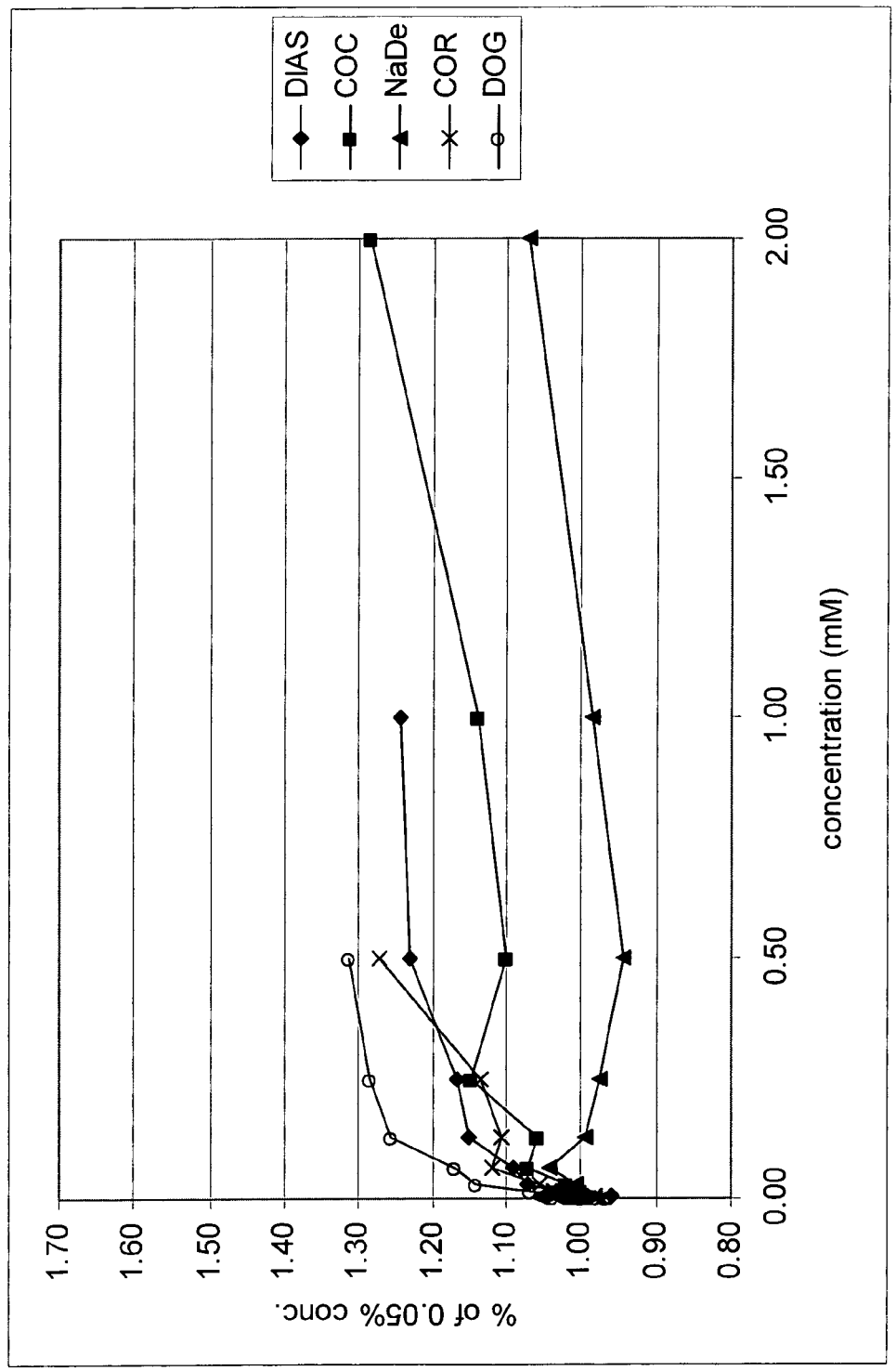
Figure 30J:
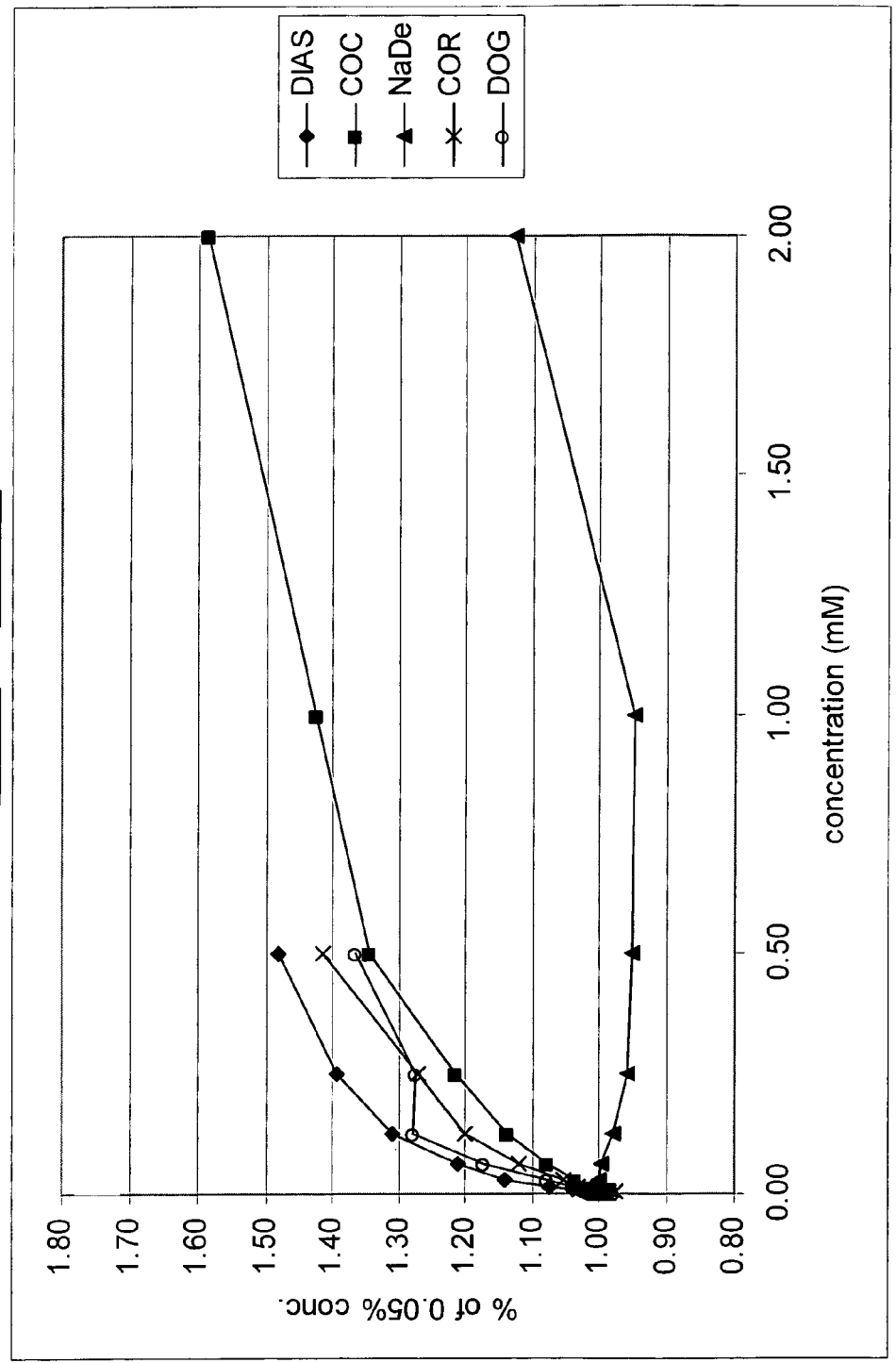
Figure 30K:
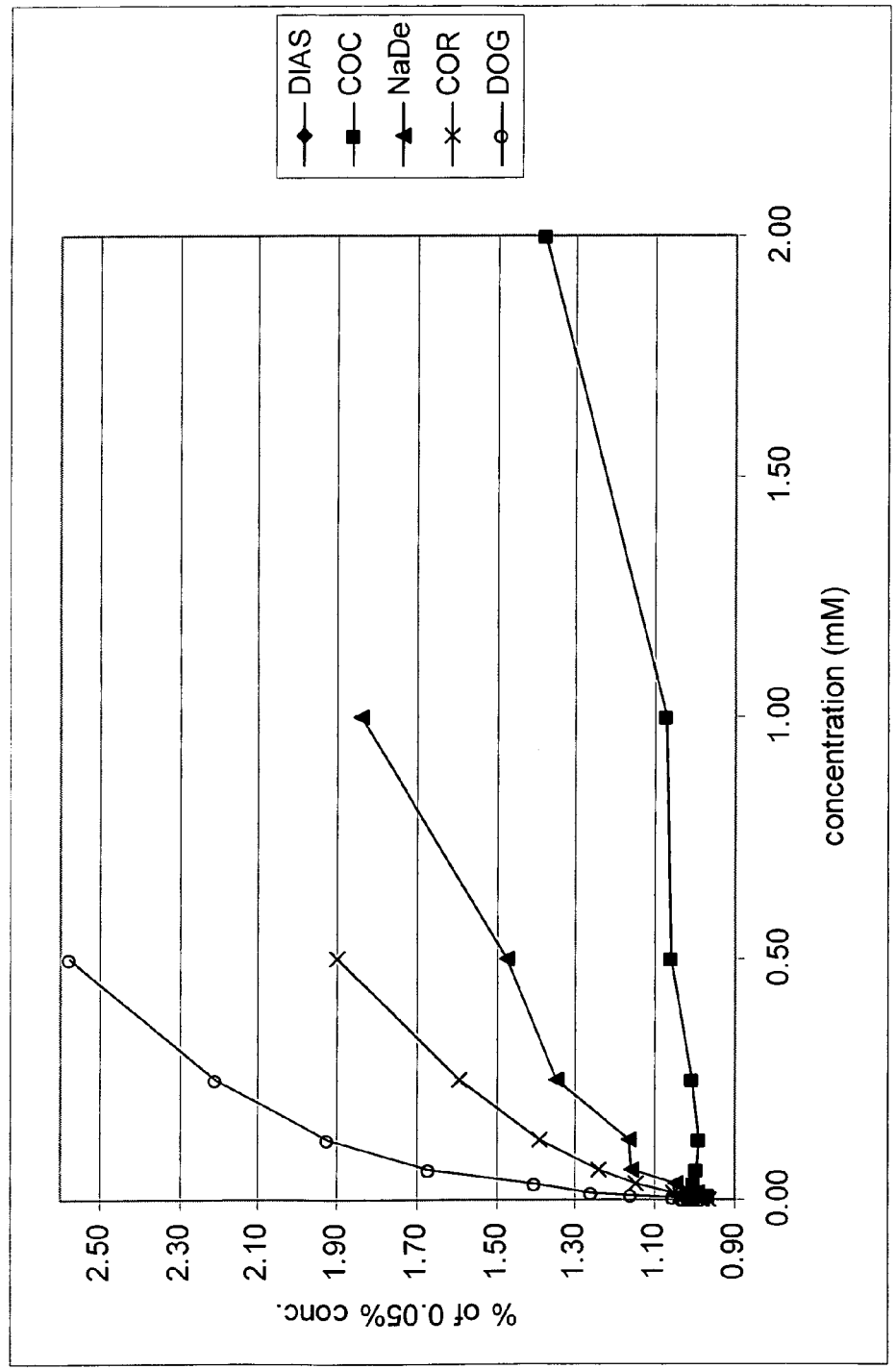
Figure 30L:
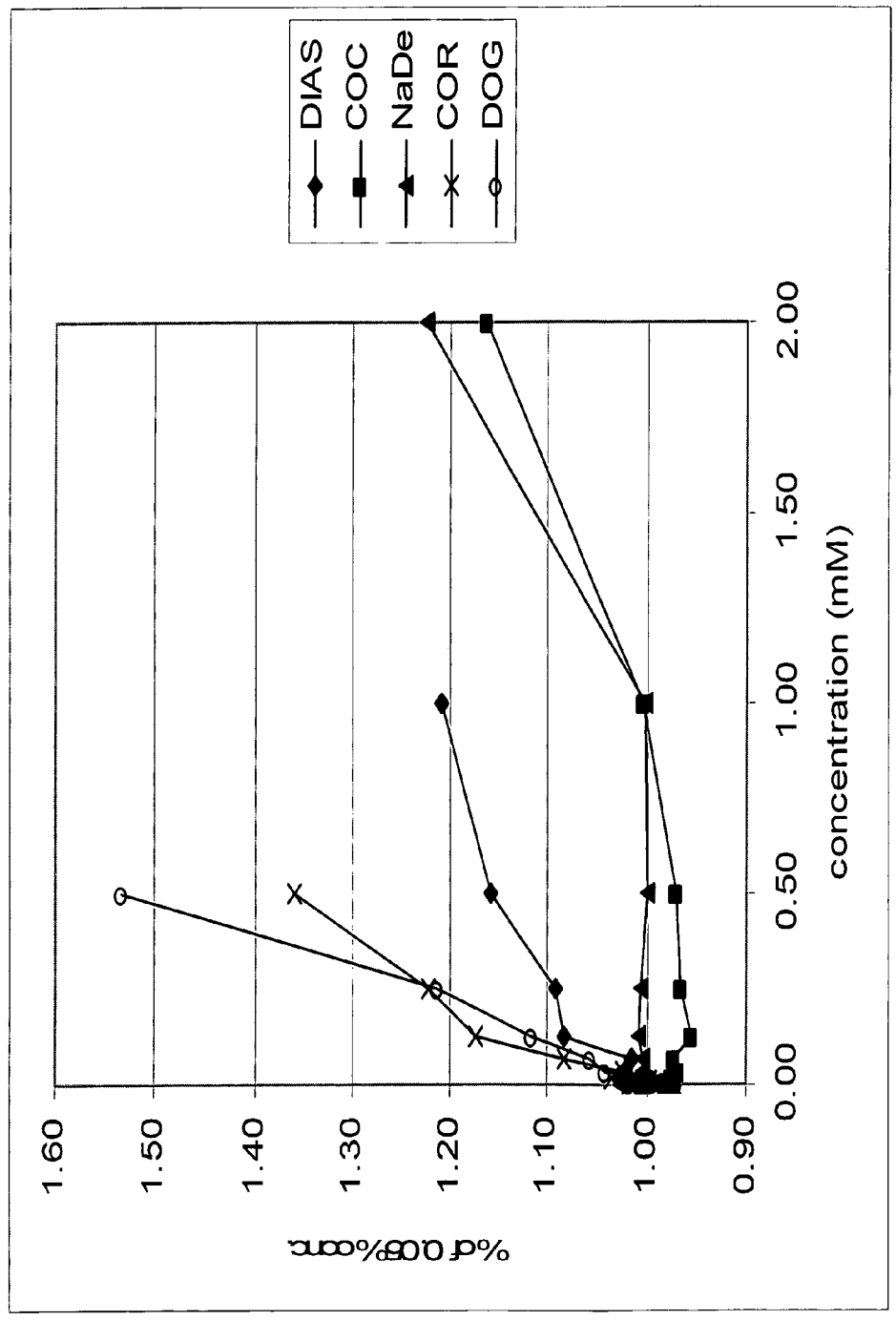
Figure 30M:
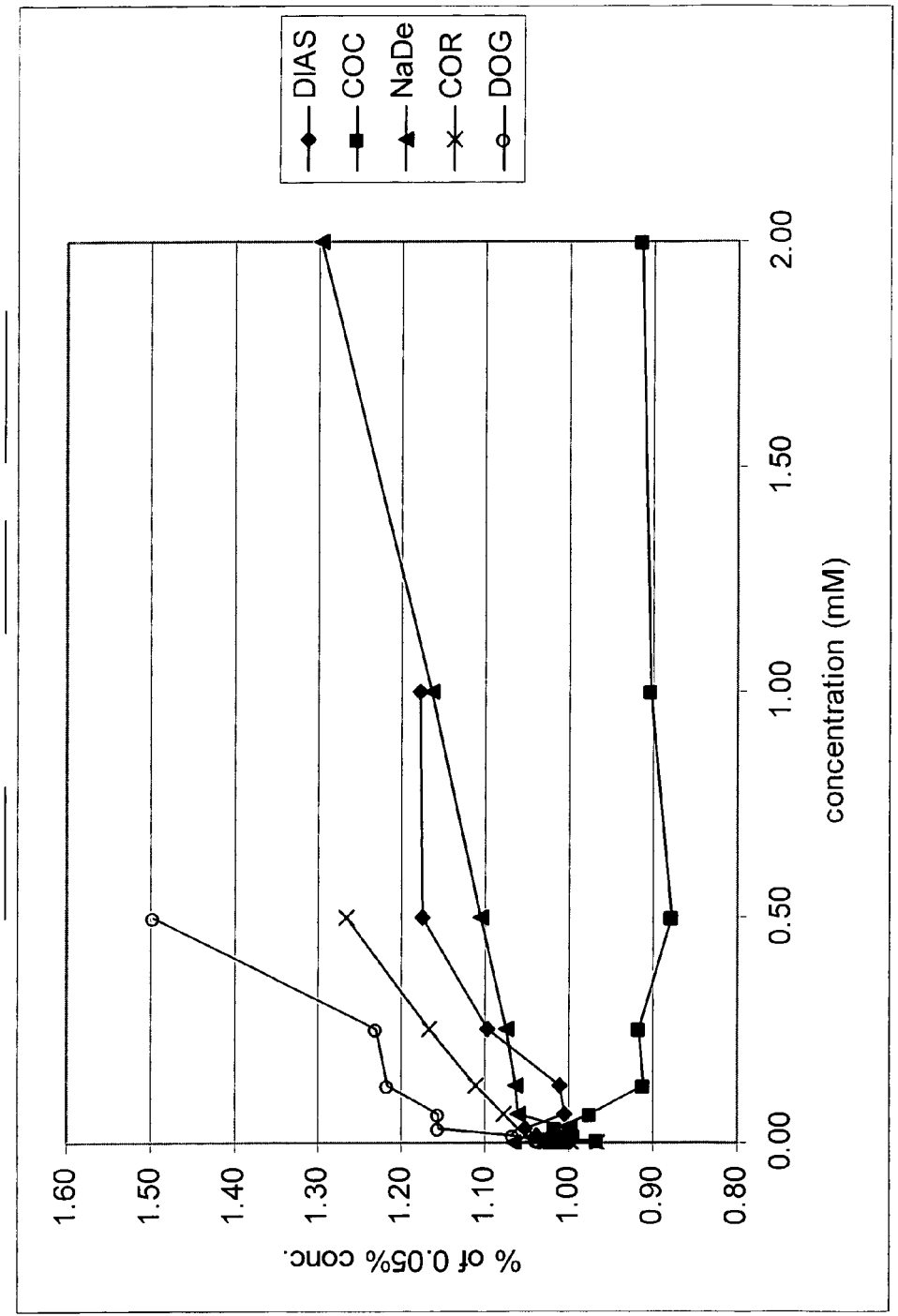
Figure 30O:
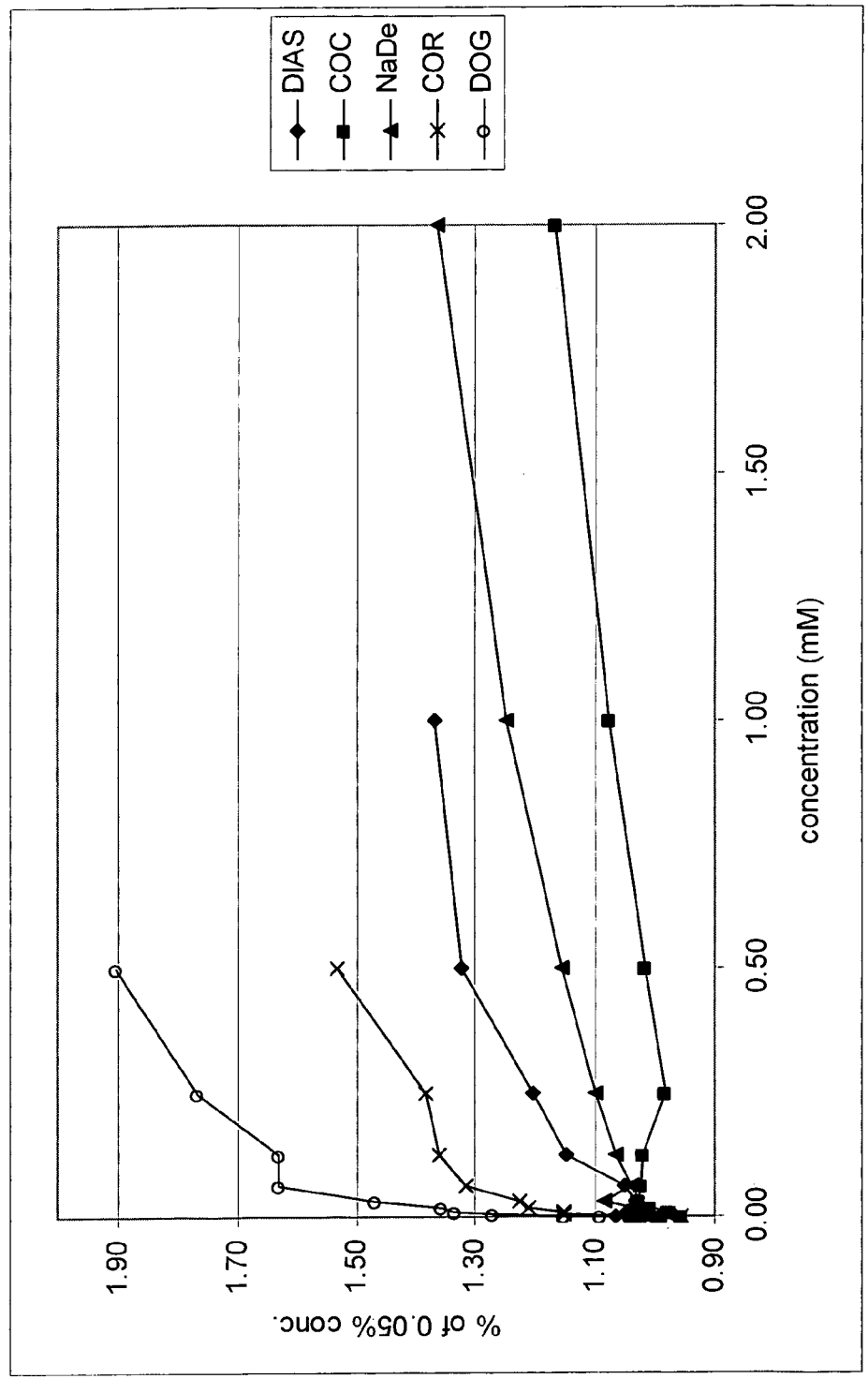
Figure 30P:
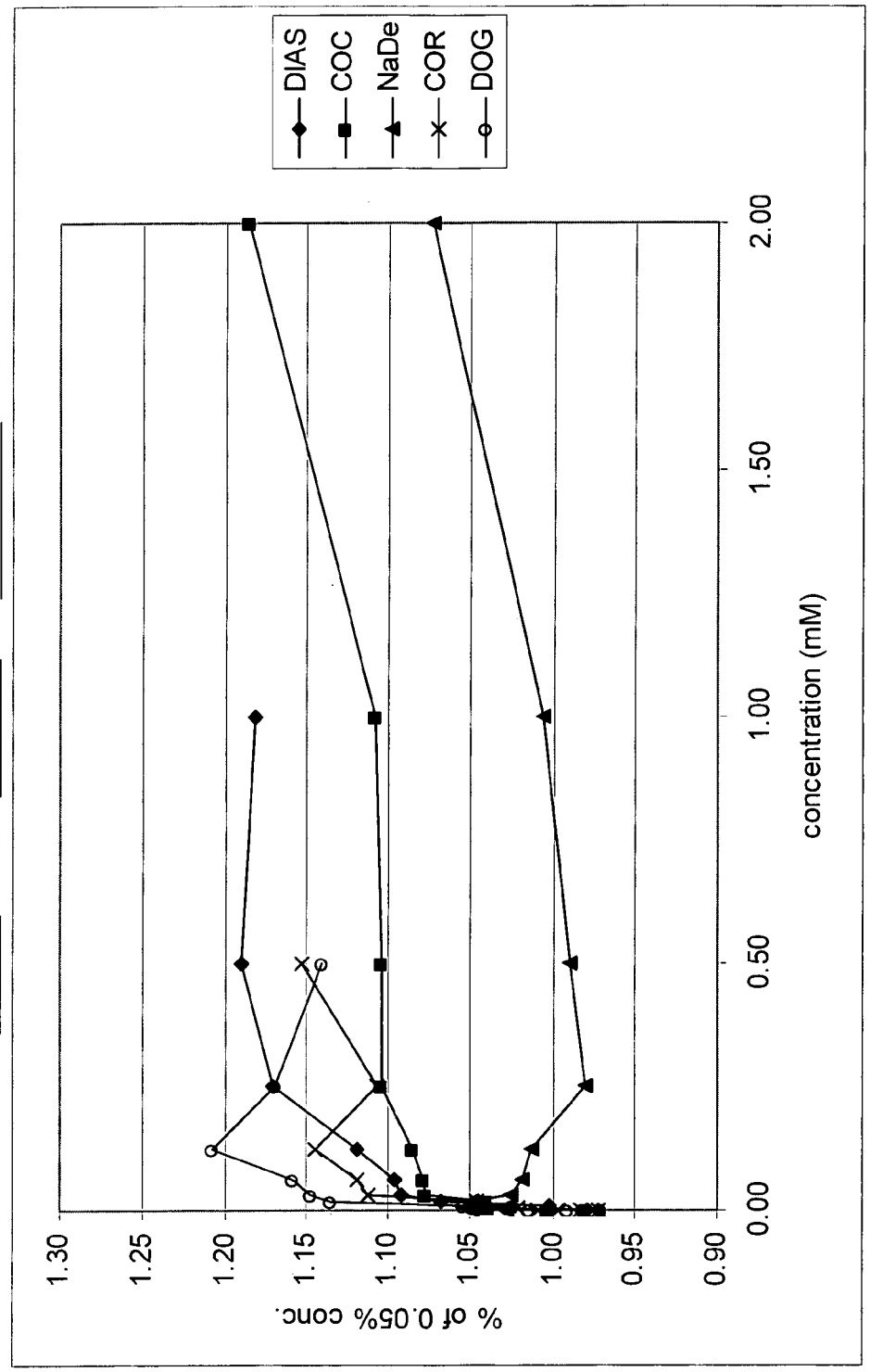
Figure 30R:
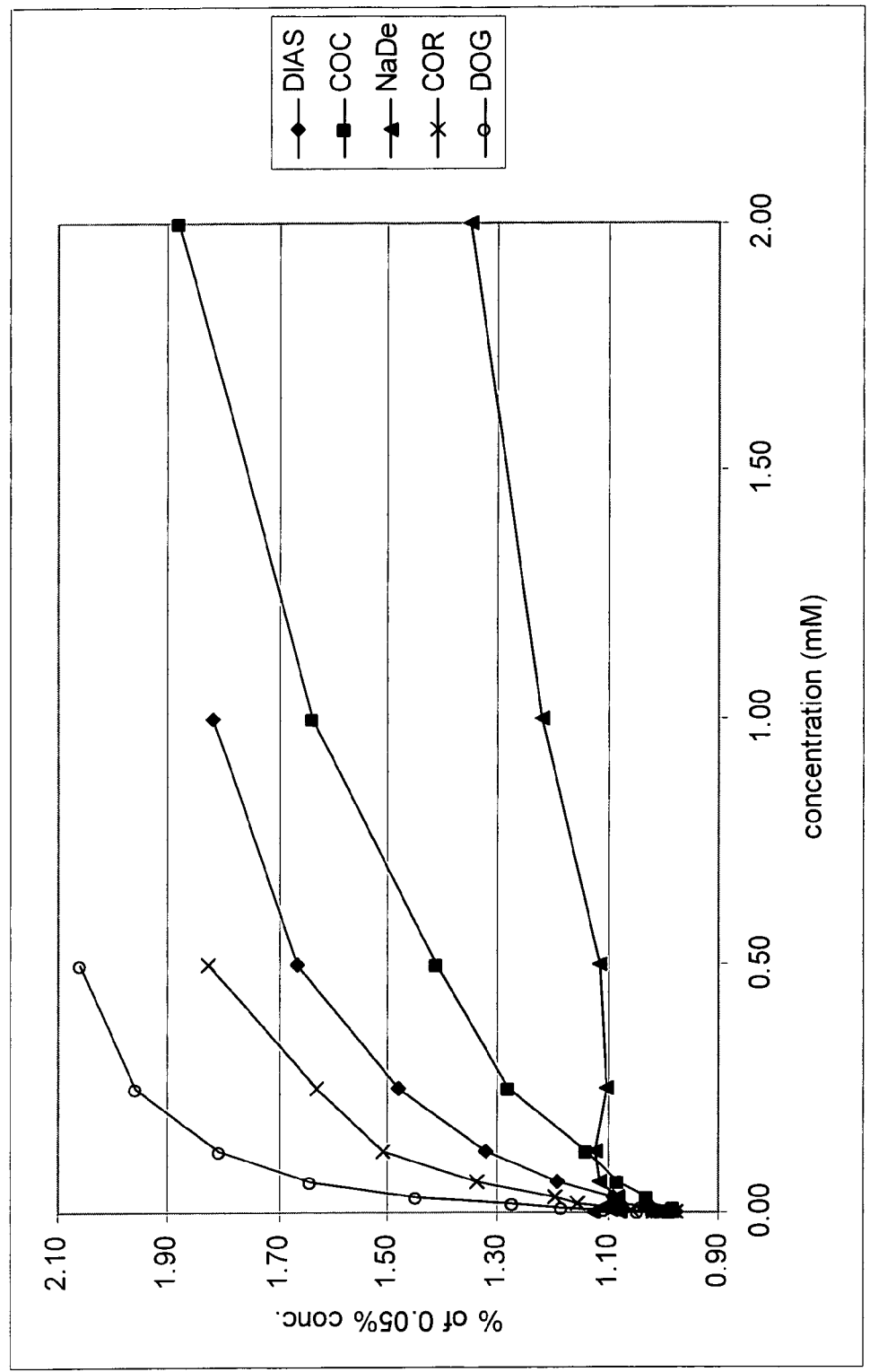
Figure 30T:
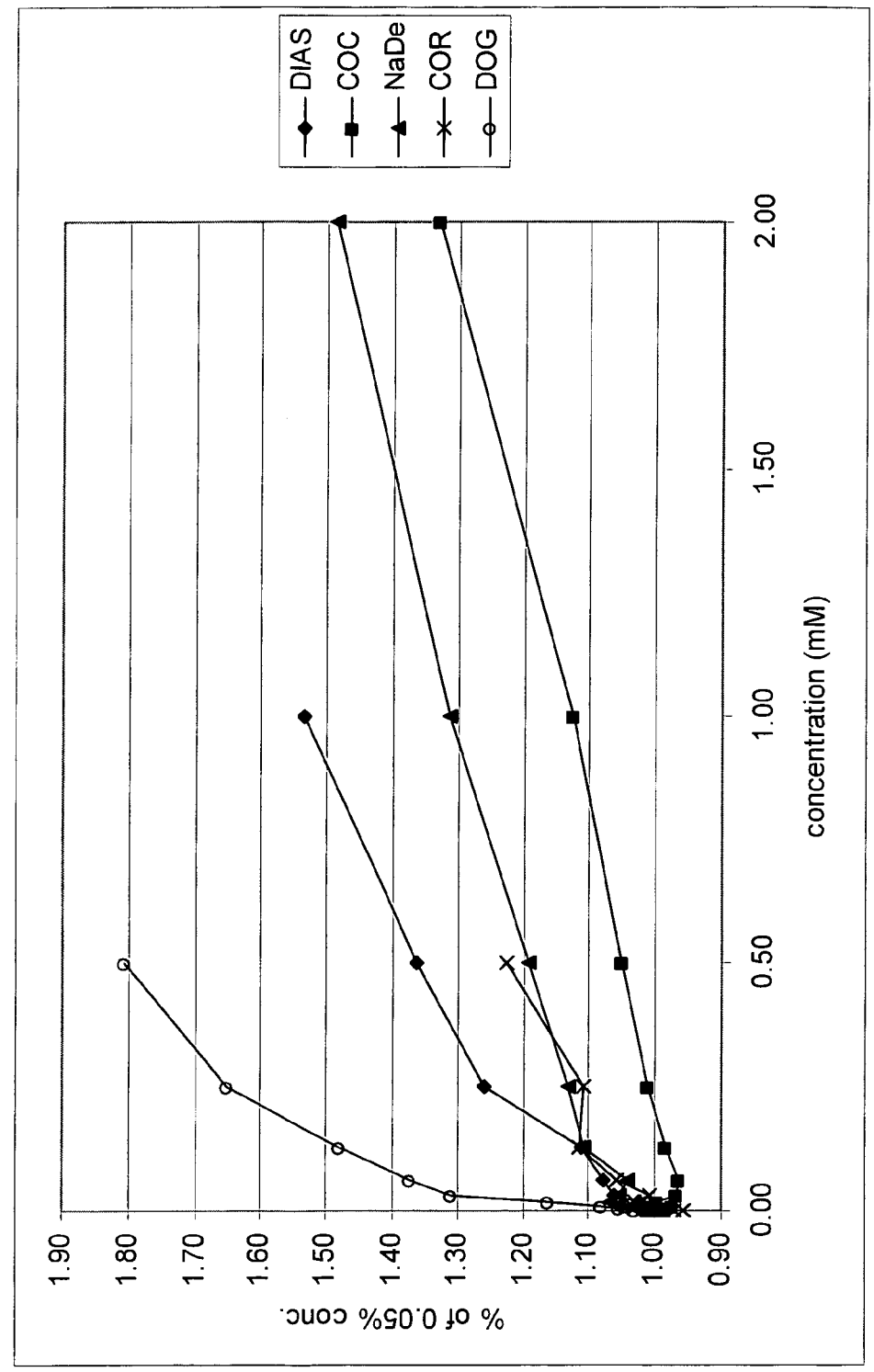
Figure 30U:
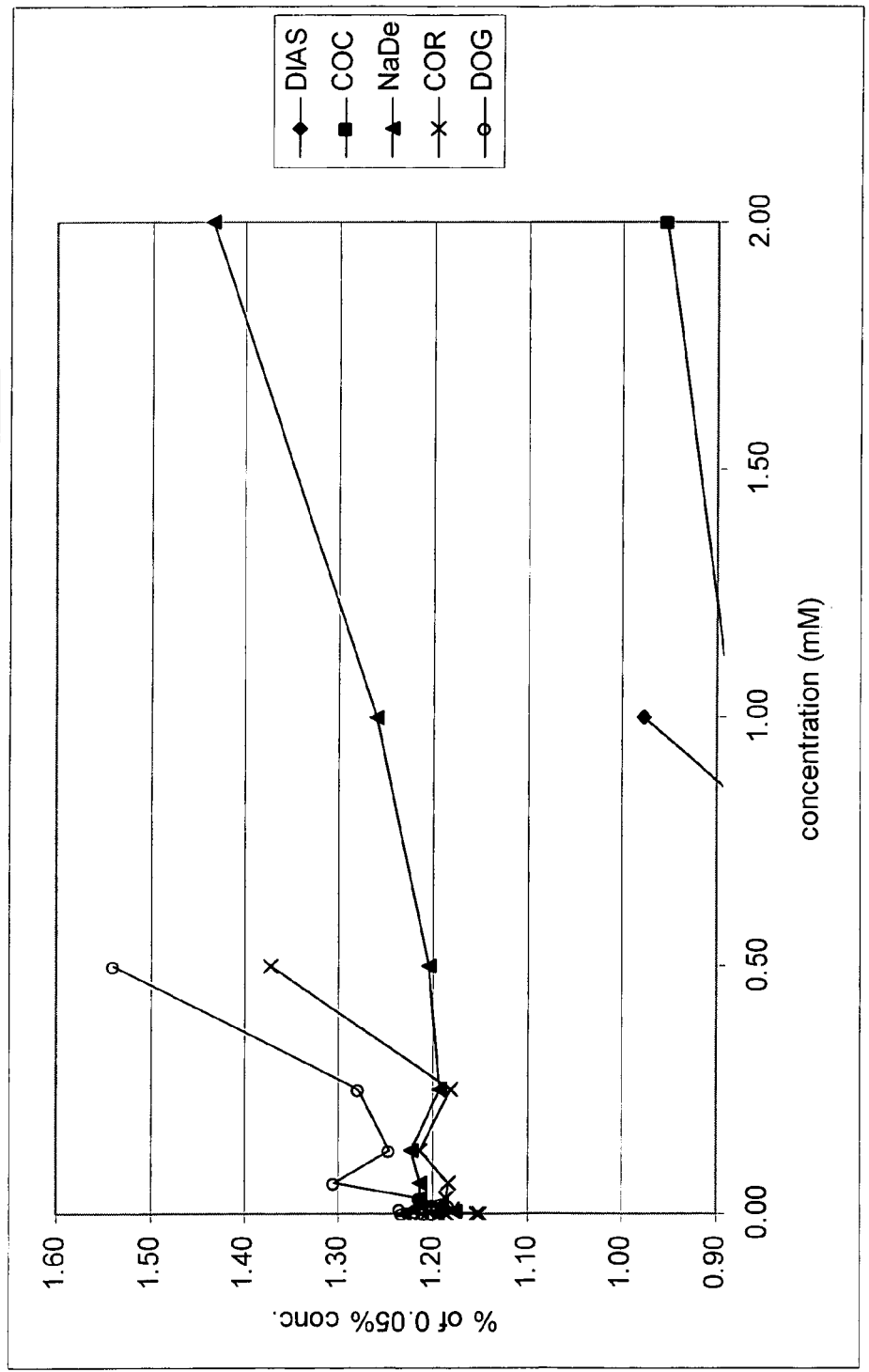
Figure 30W:
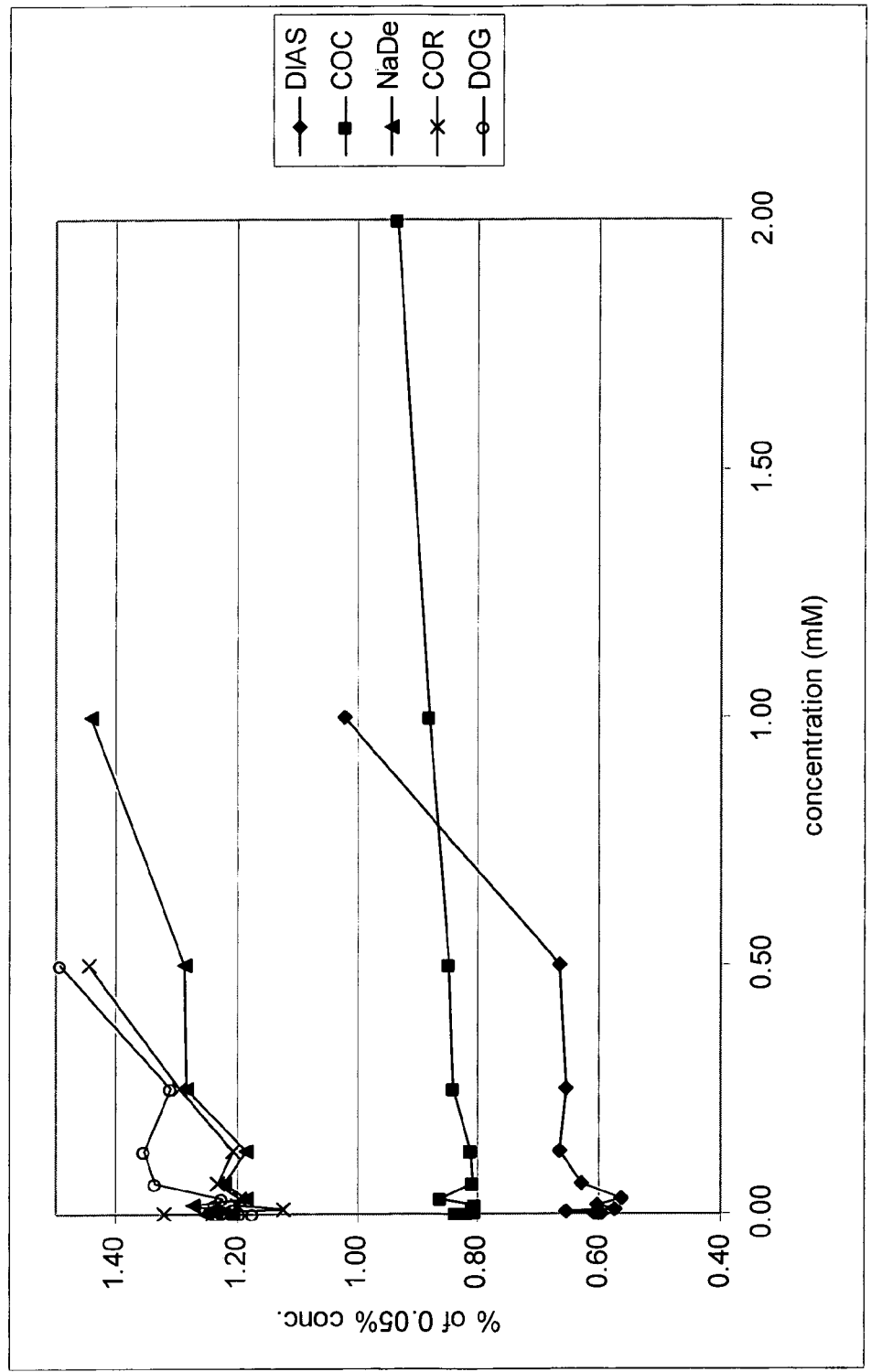
Figure 30X:
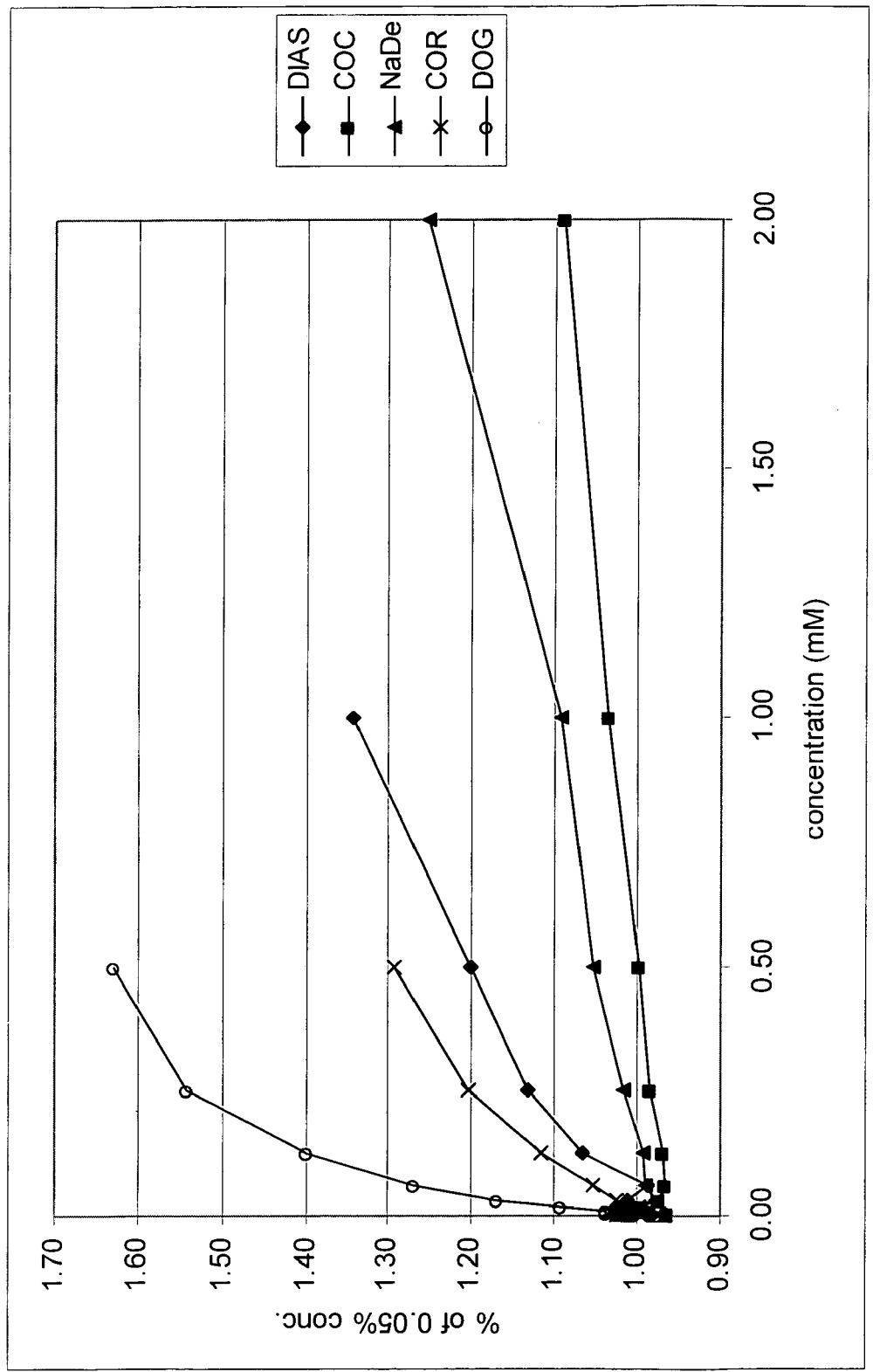
Figure 30Z:
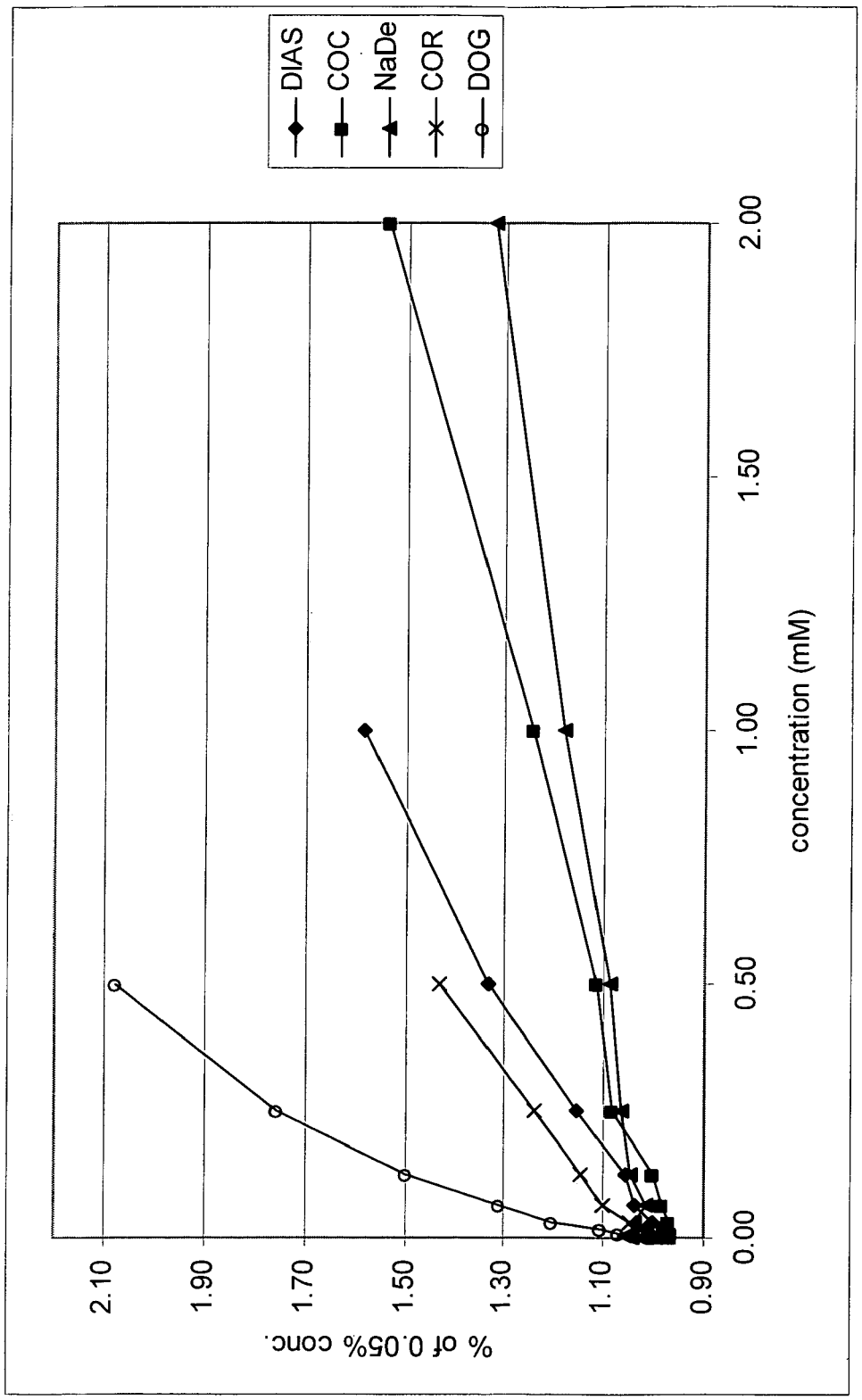
Figure 31G:
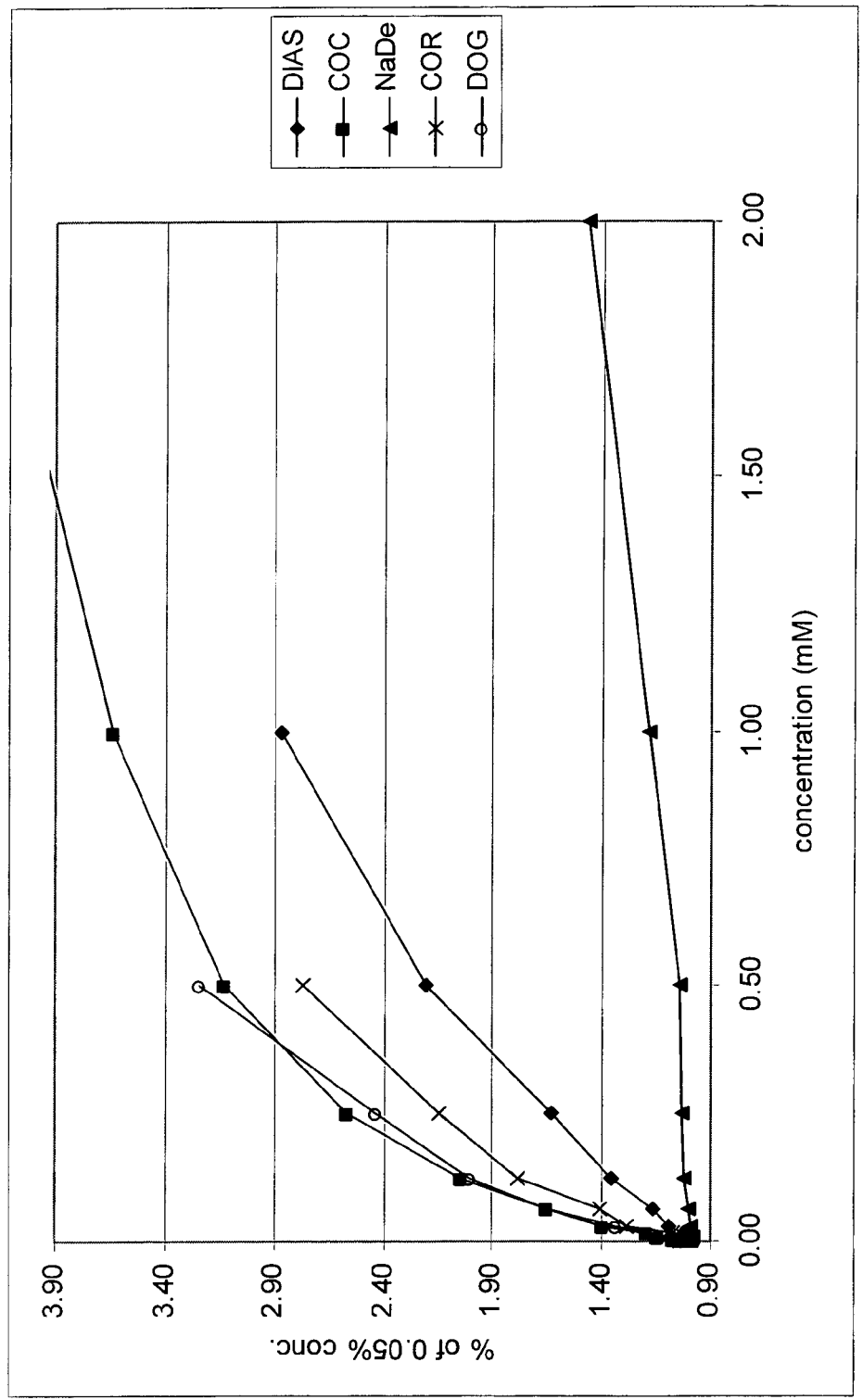
Figure 31H:
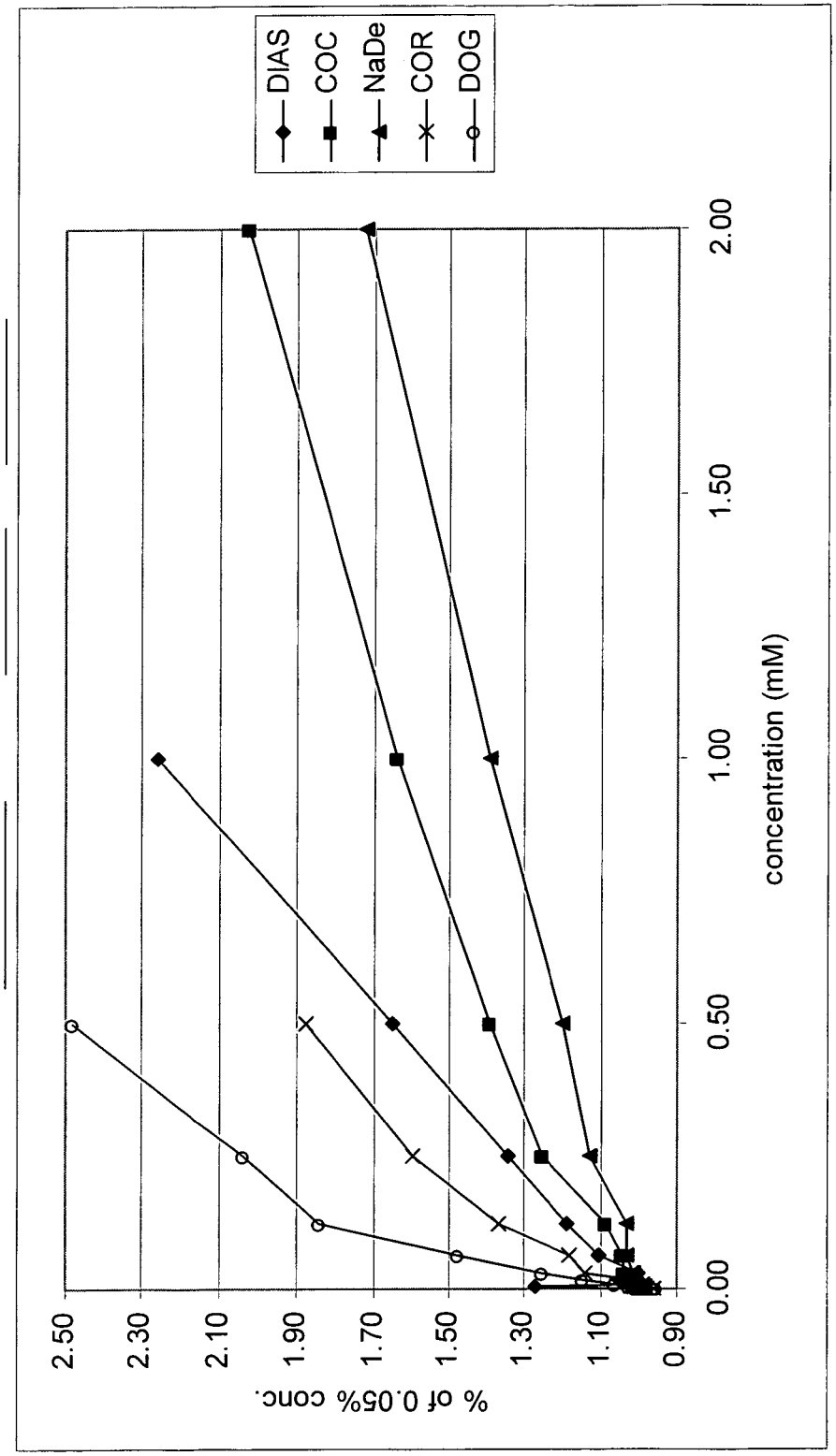
Figure 31I:
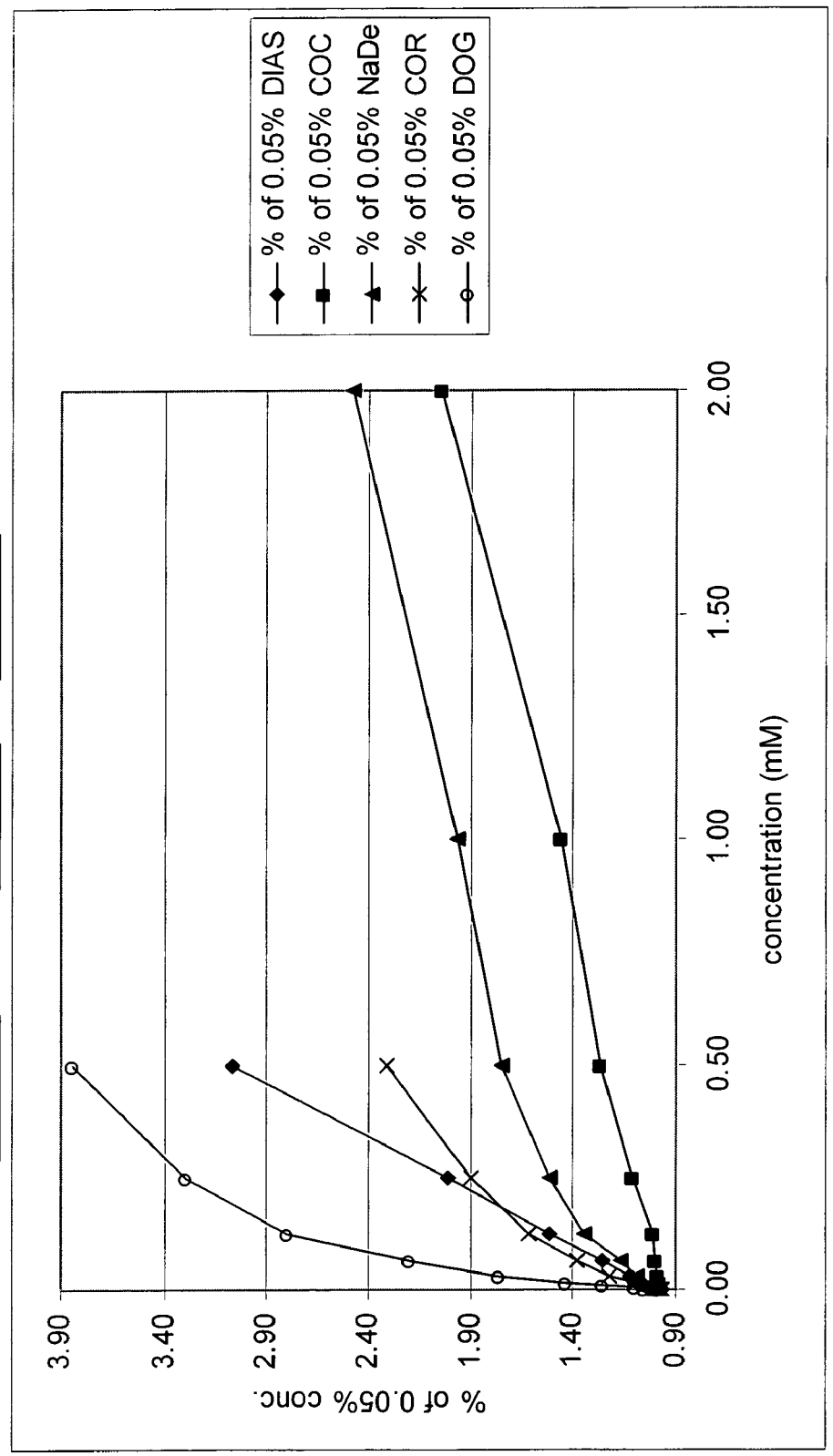
Figure 31J:
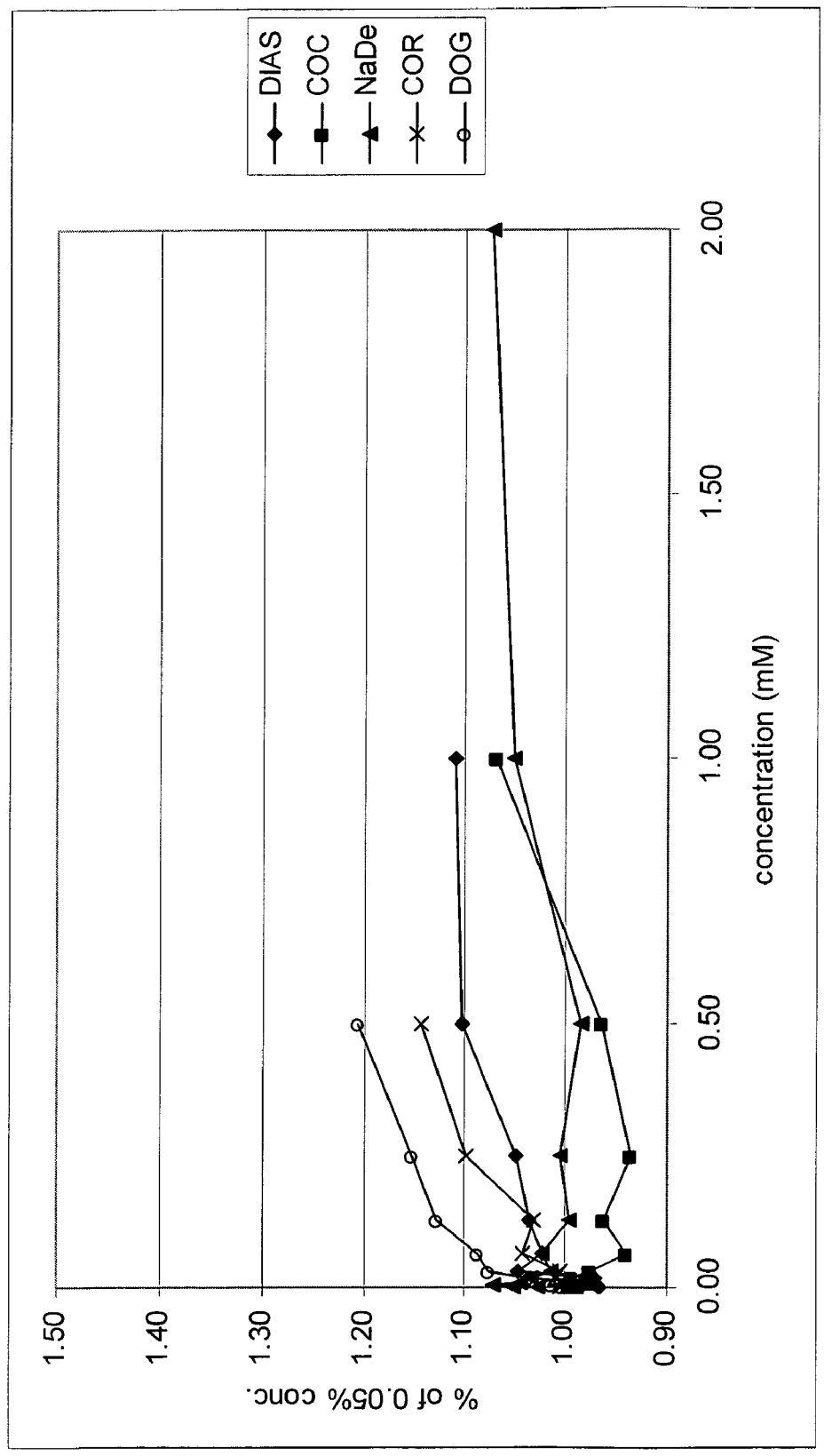
Figure 31K:
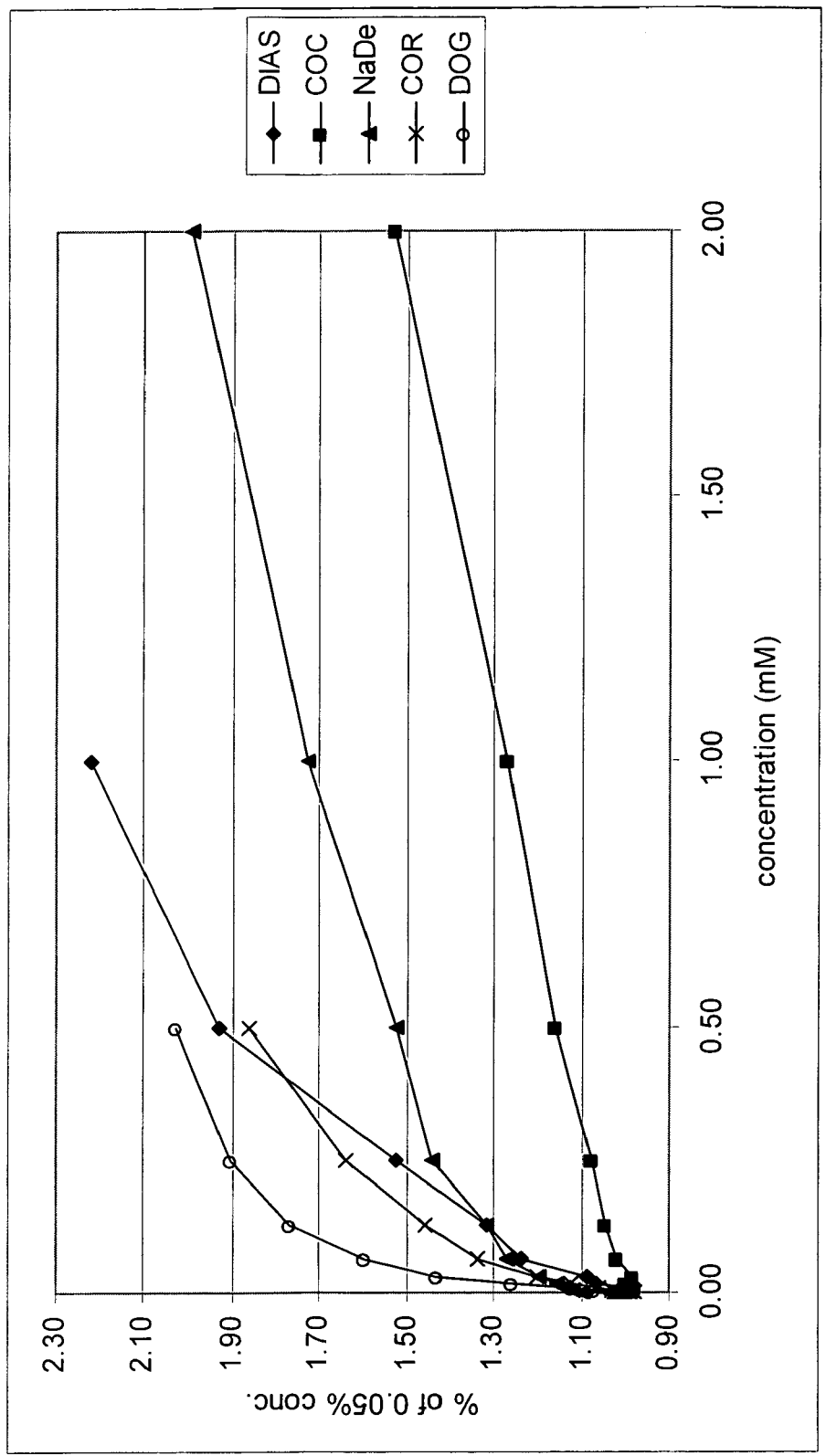
Figure 31L:
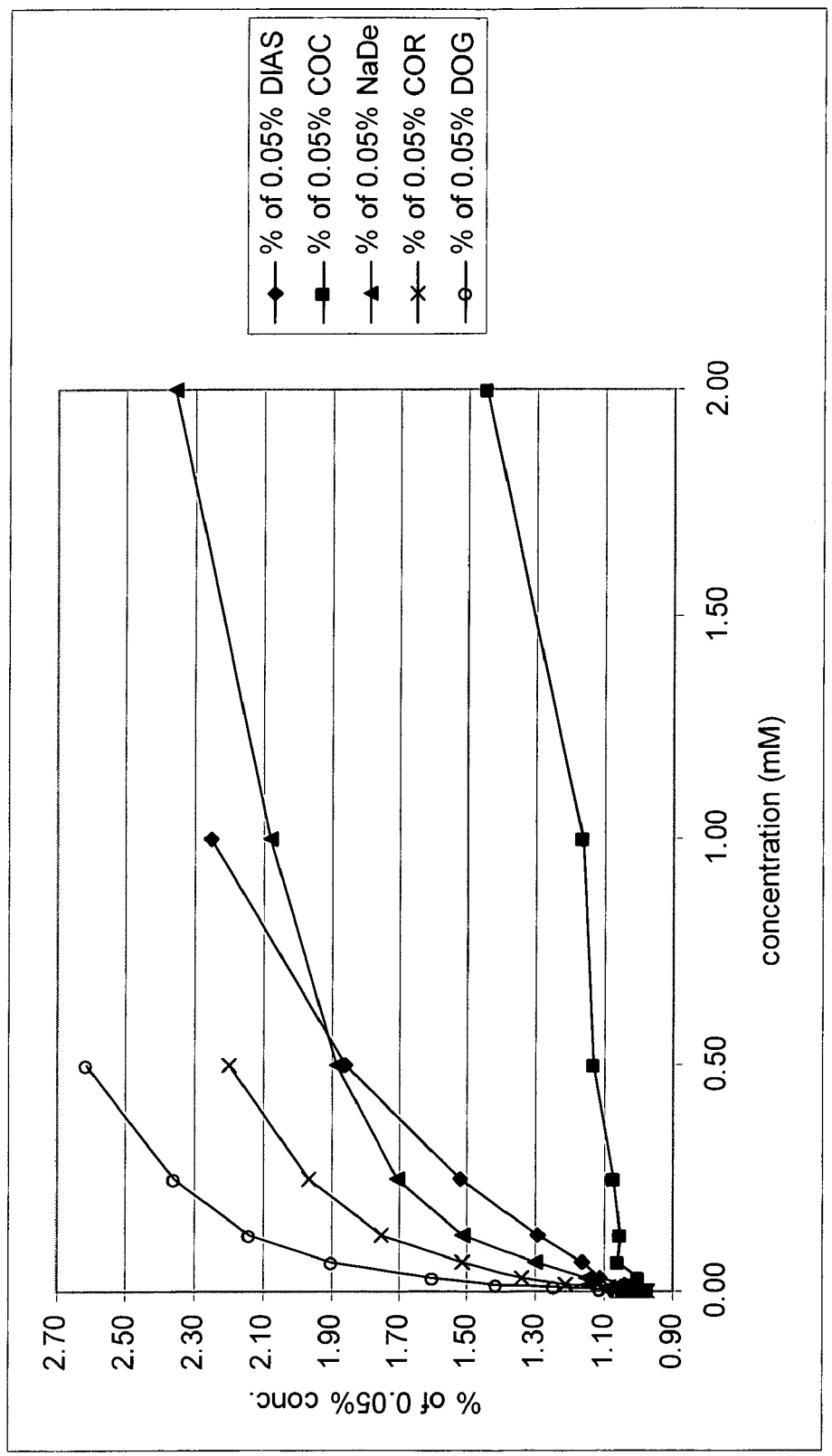
Figure 31N:
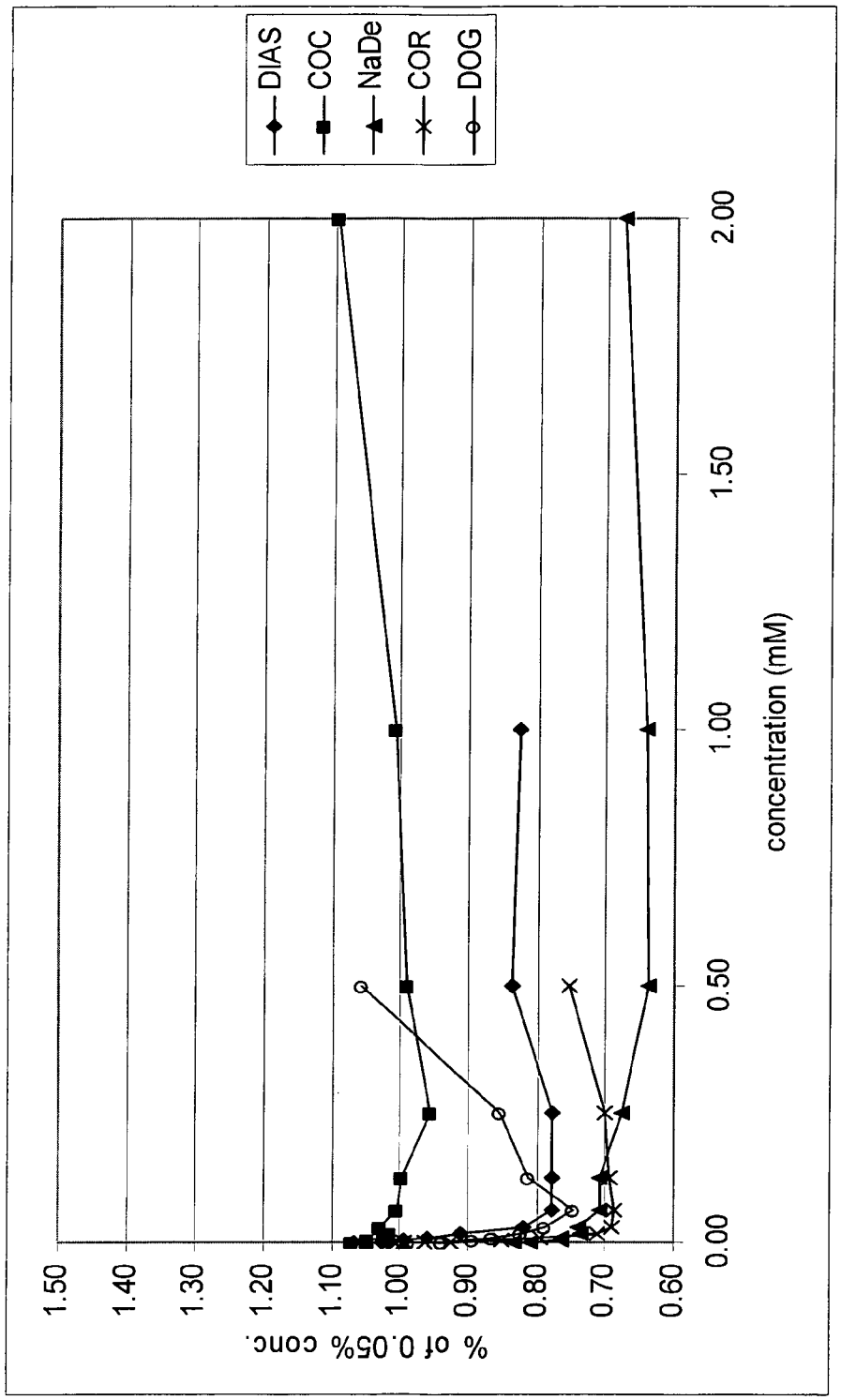
Figure 31O:
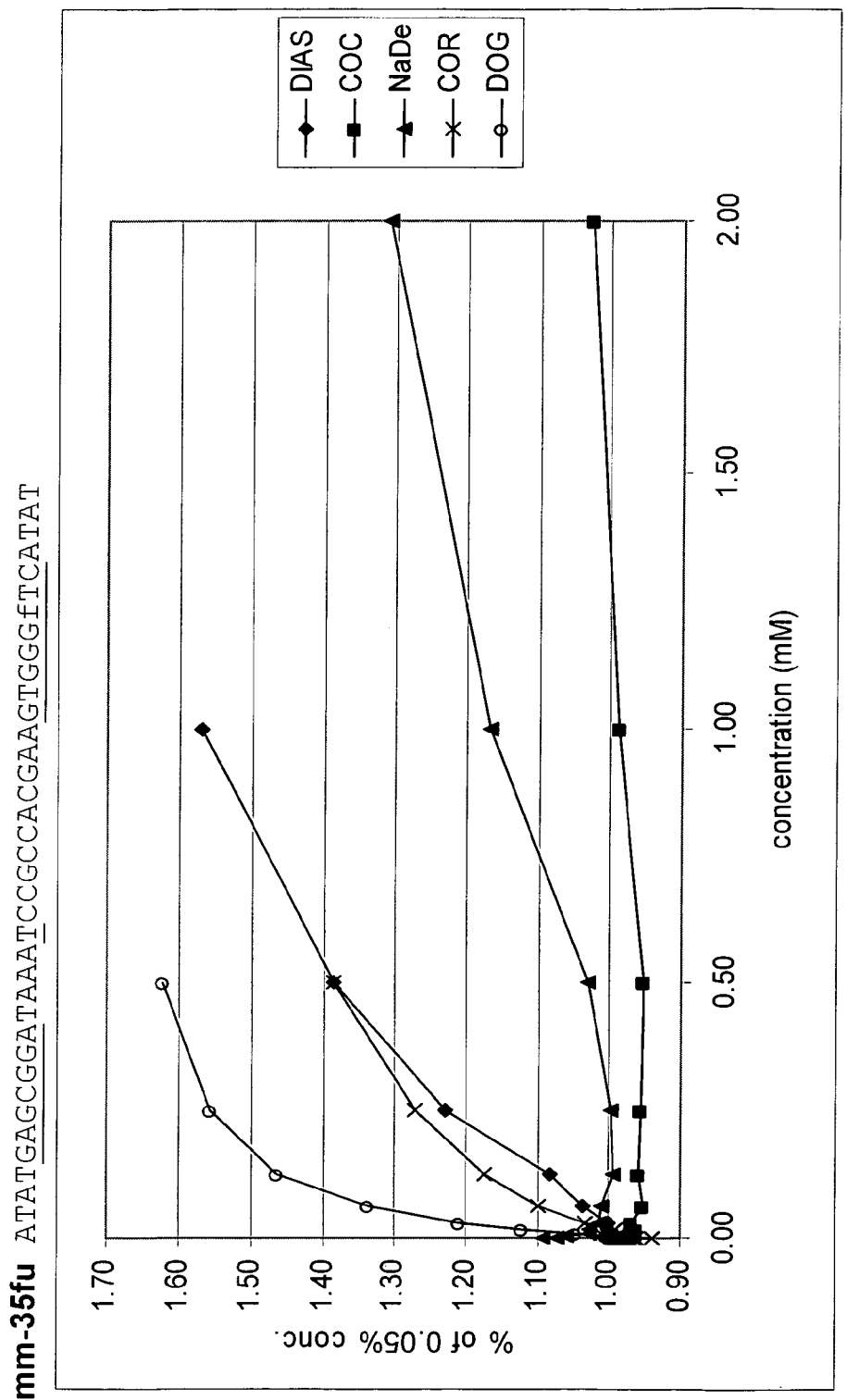
Figure 31P:
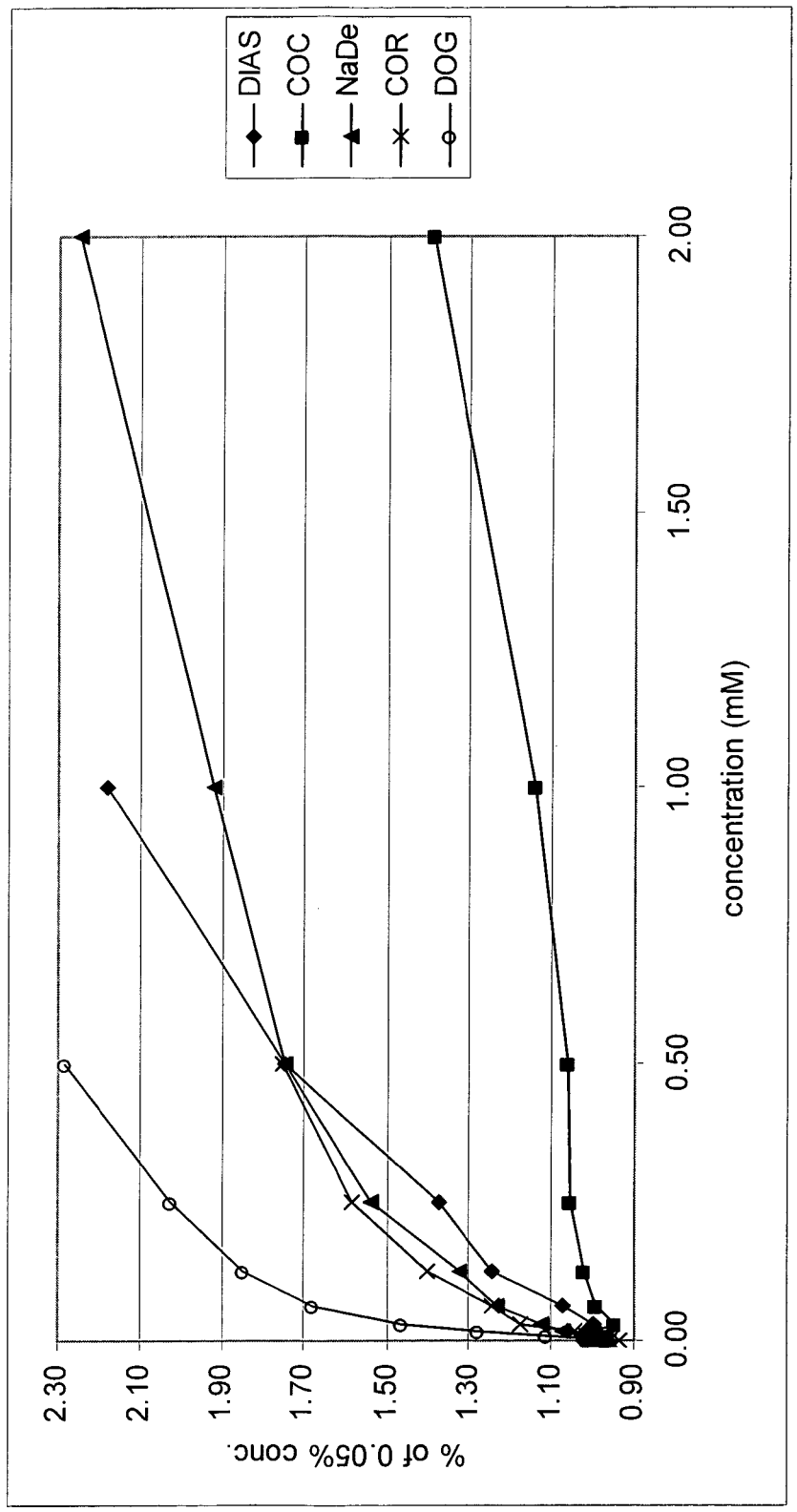
Figure 31Q:
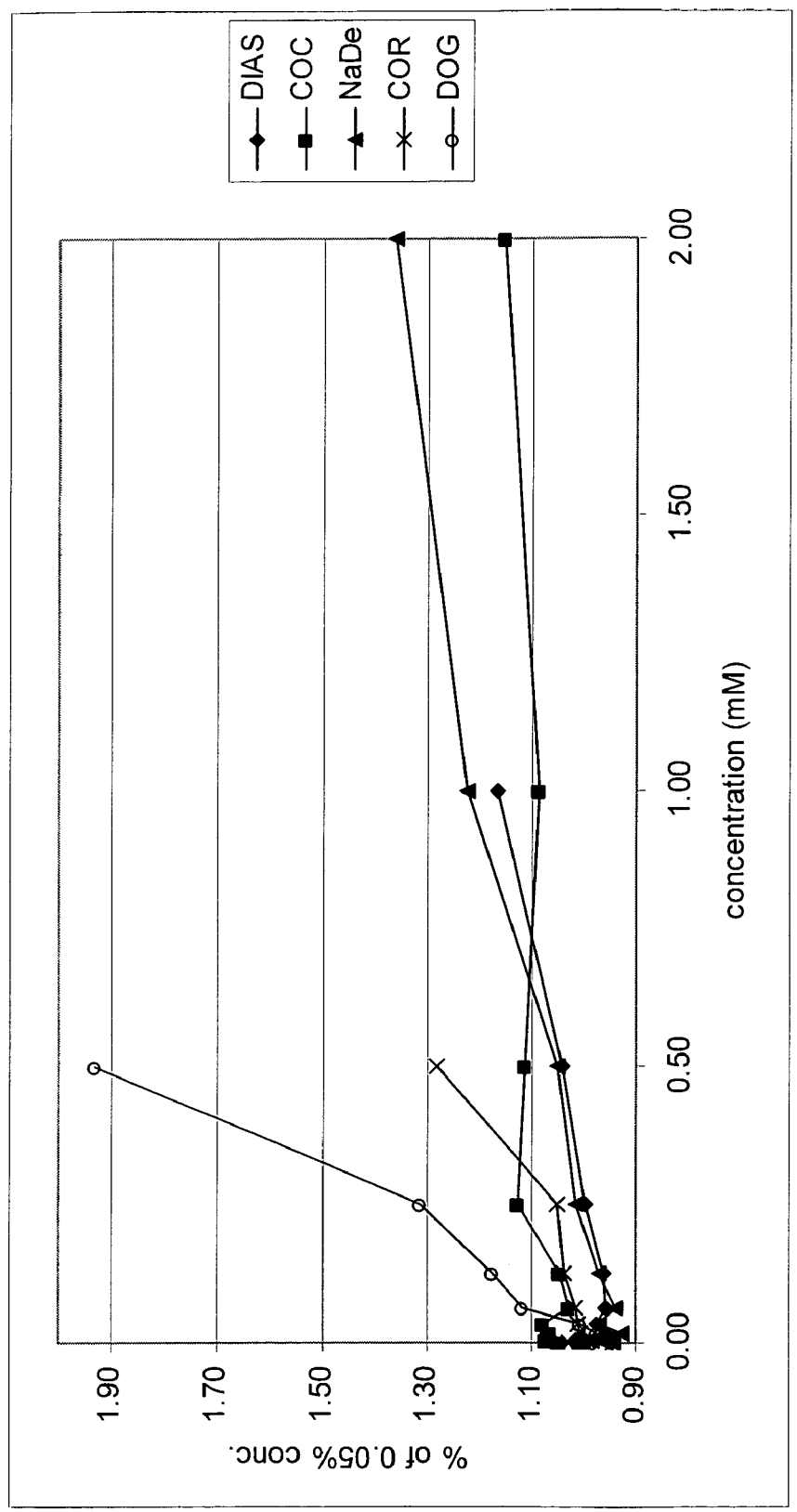
Figure 31S:
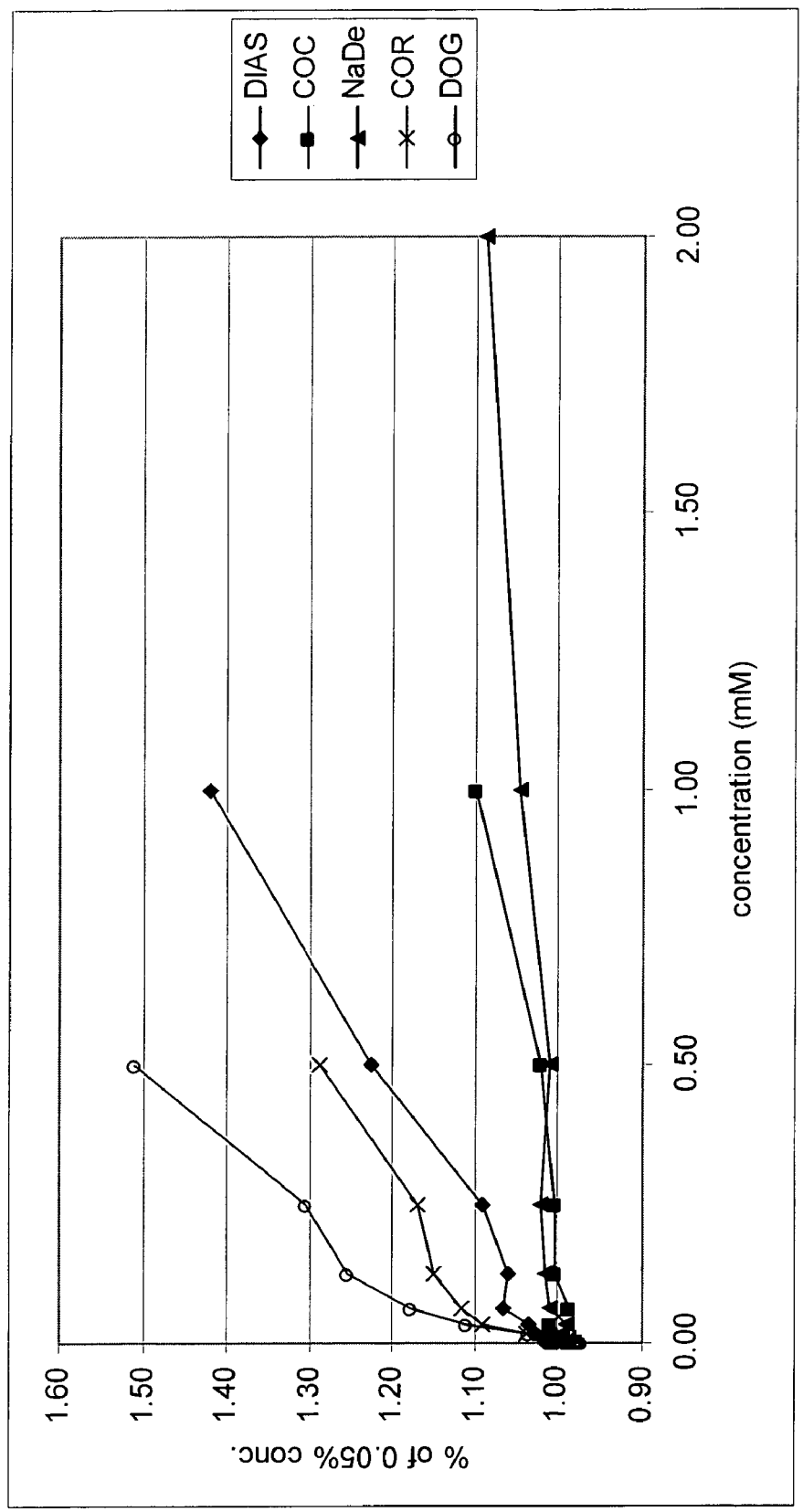
Figure 31U:
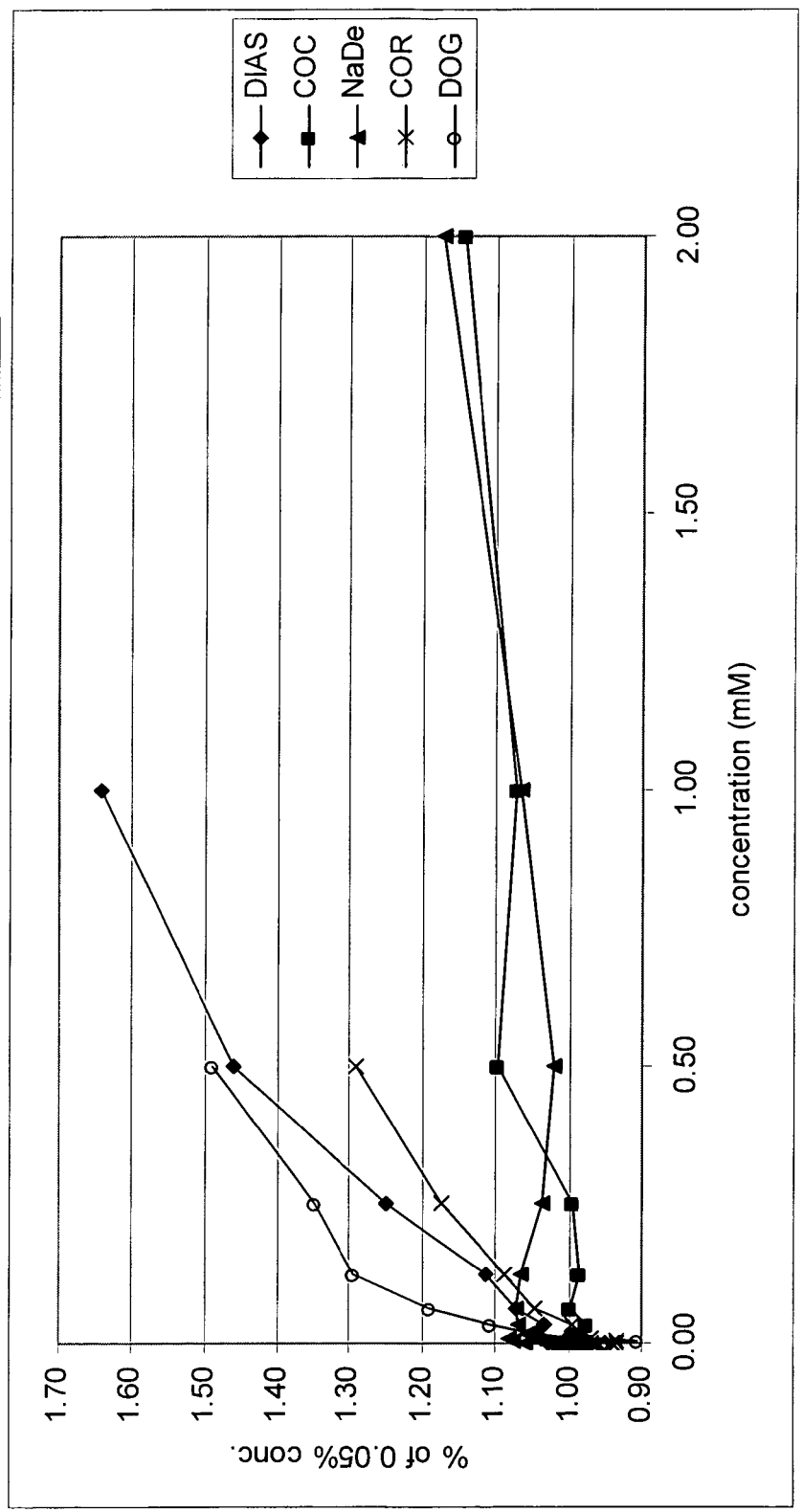
Figure 31V:
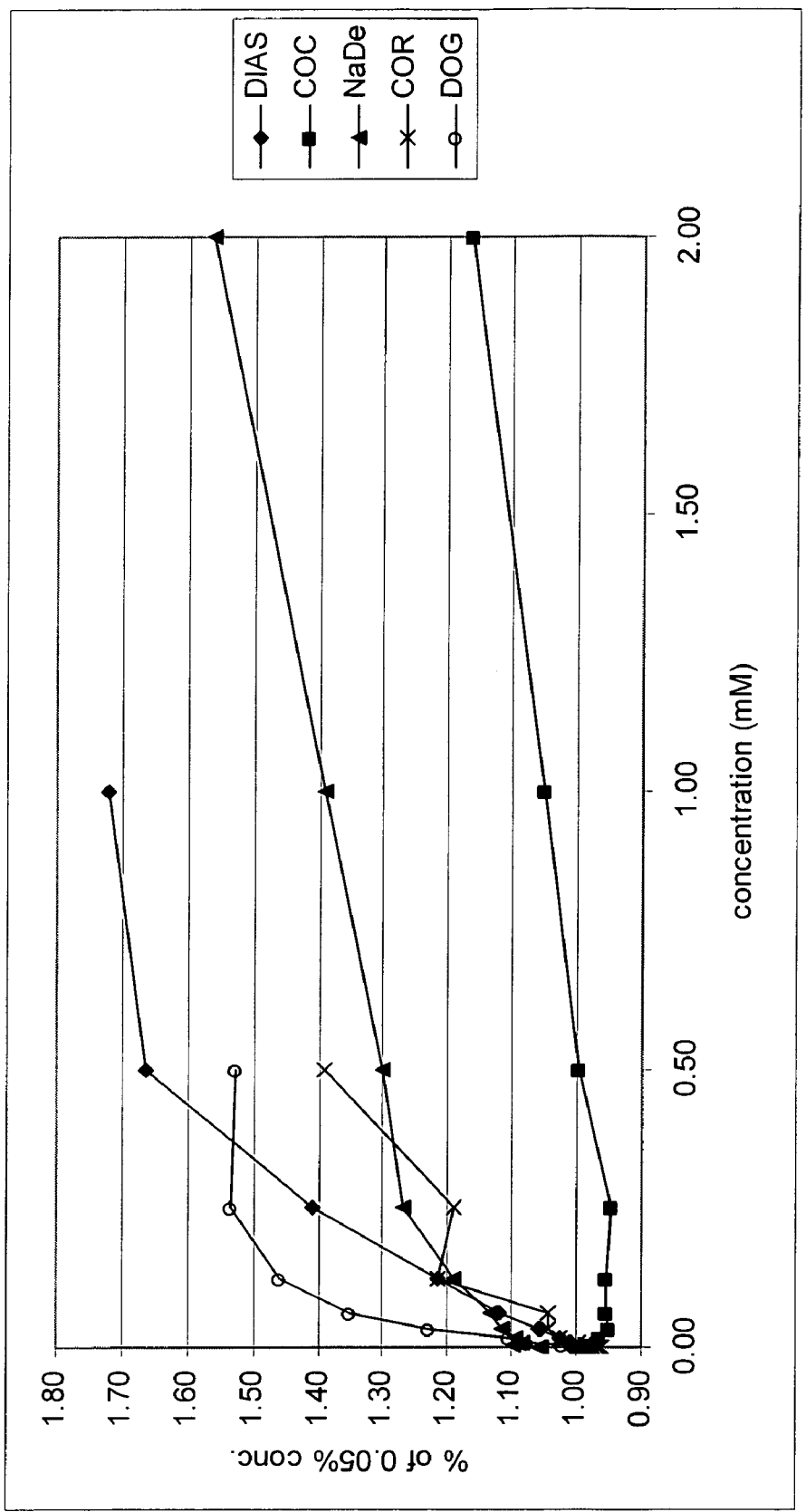
Figure 31X:
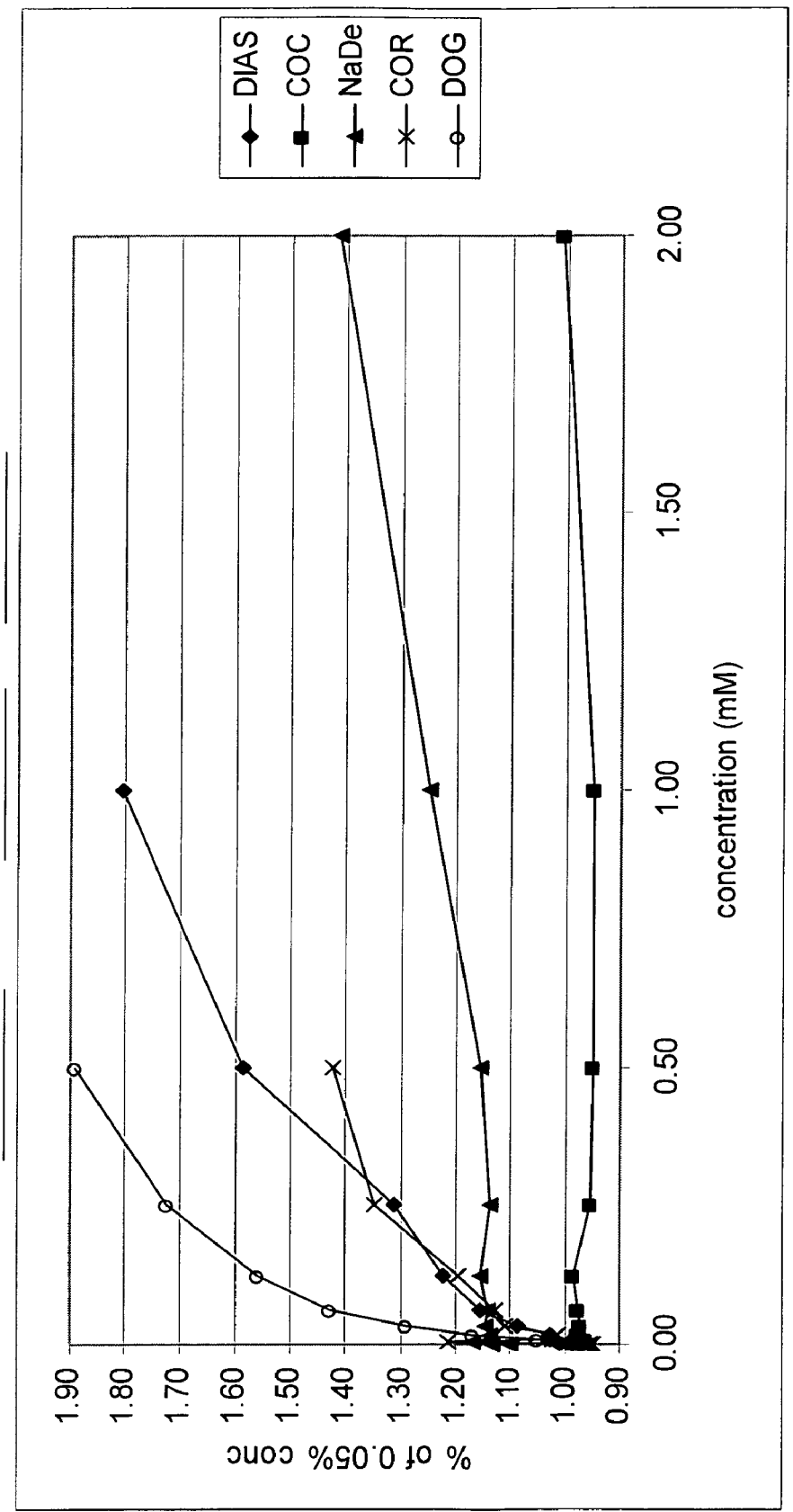
Figure 31Y:
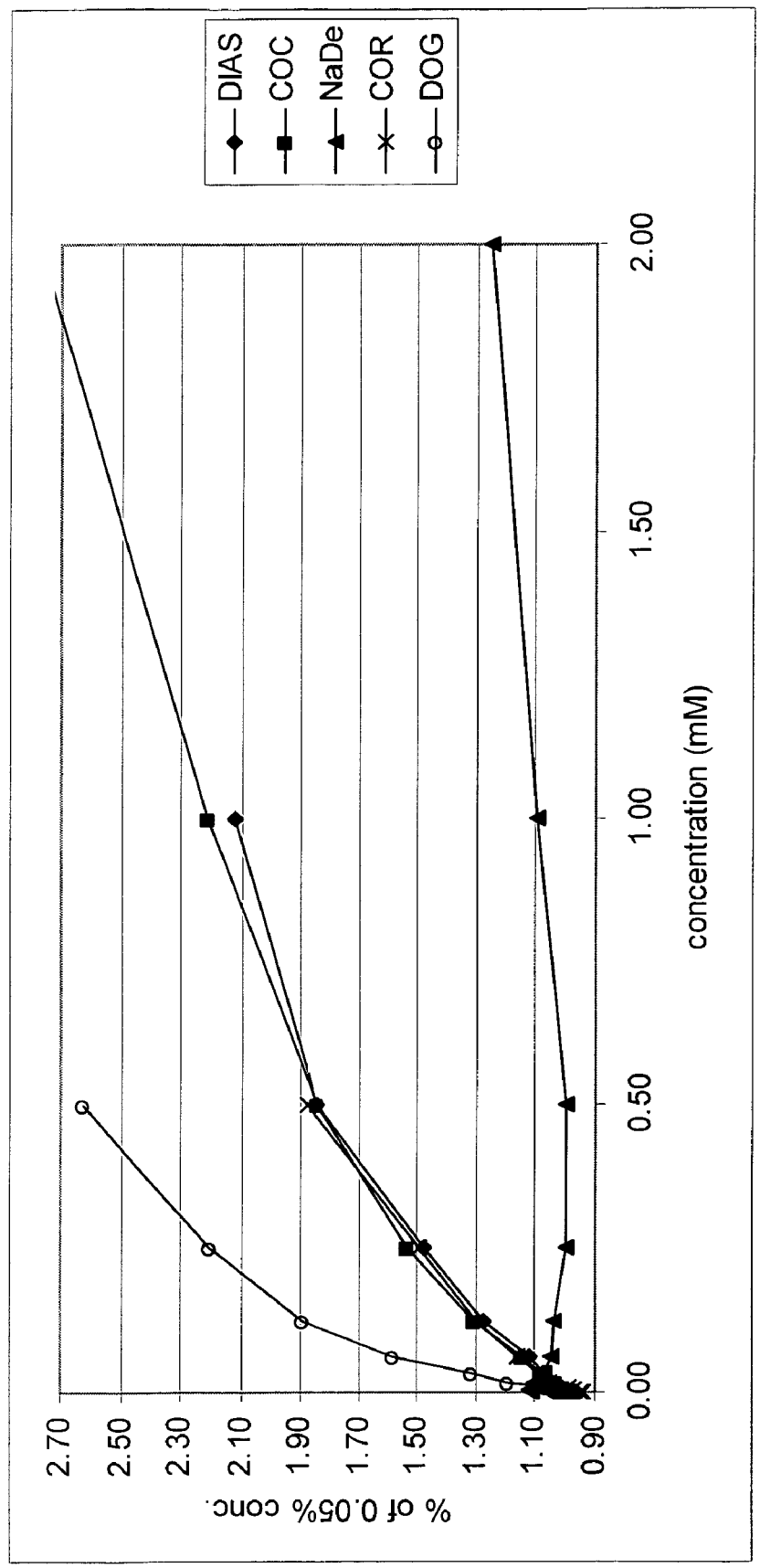
Figure 32A:
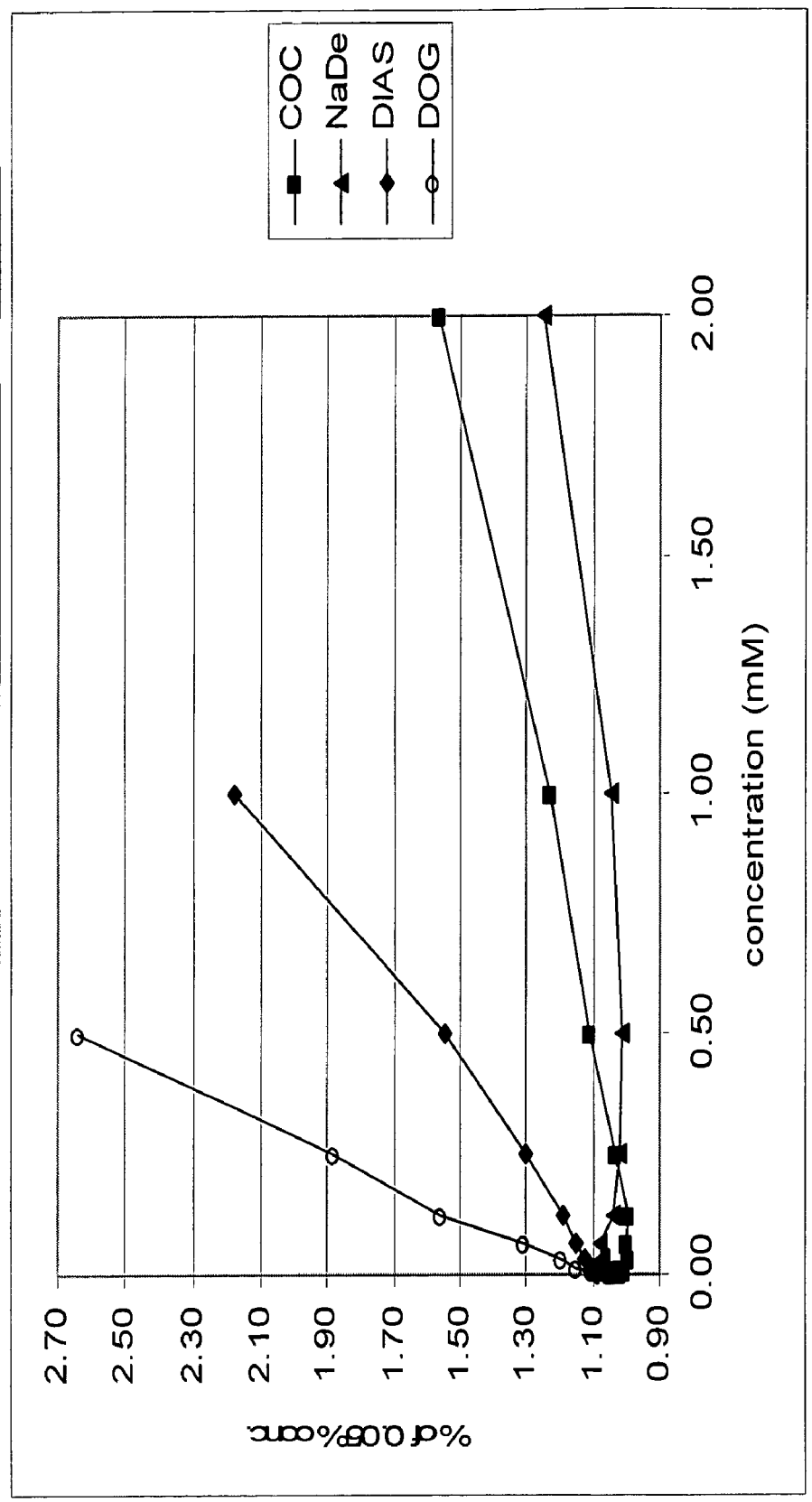
Figure 32B:
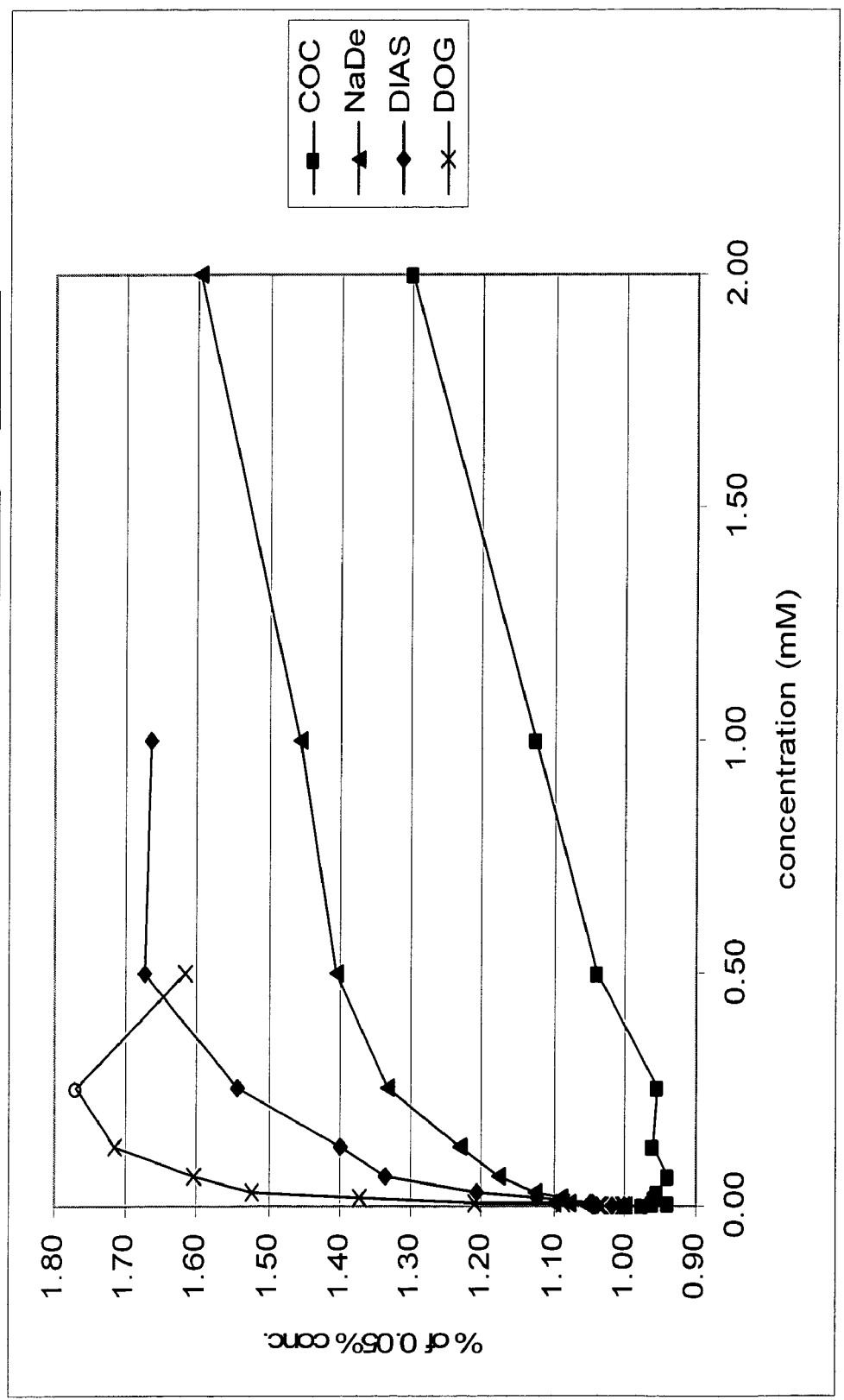
Figure 32D:
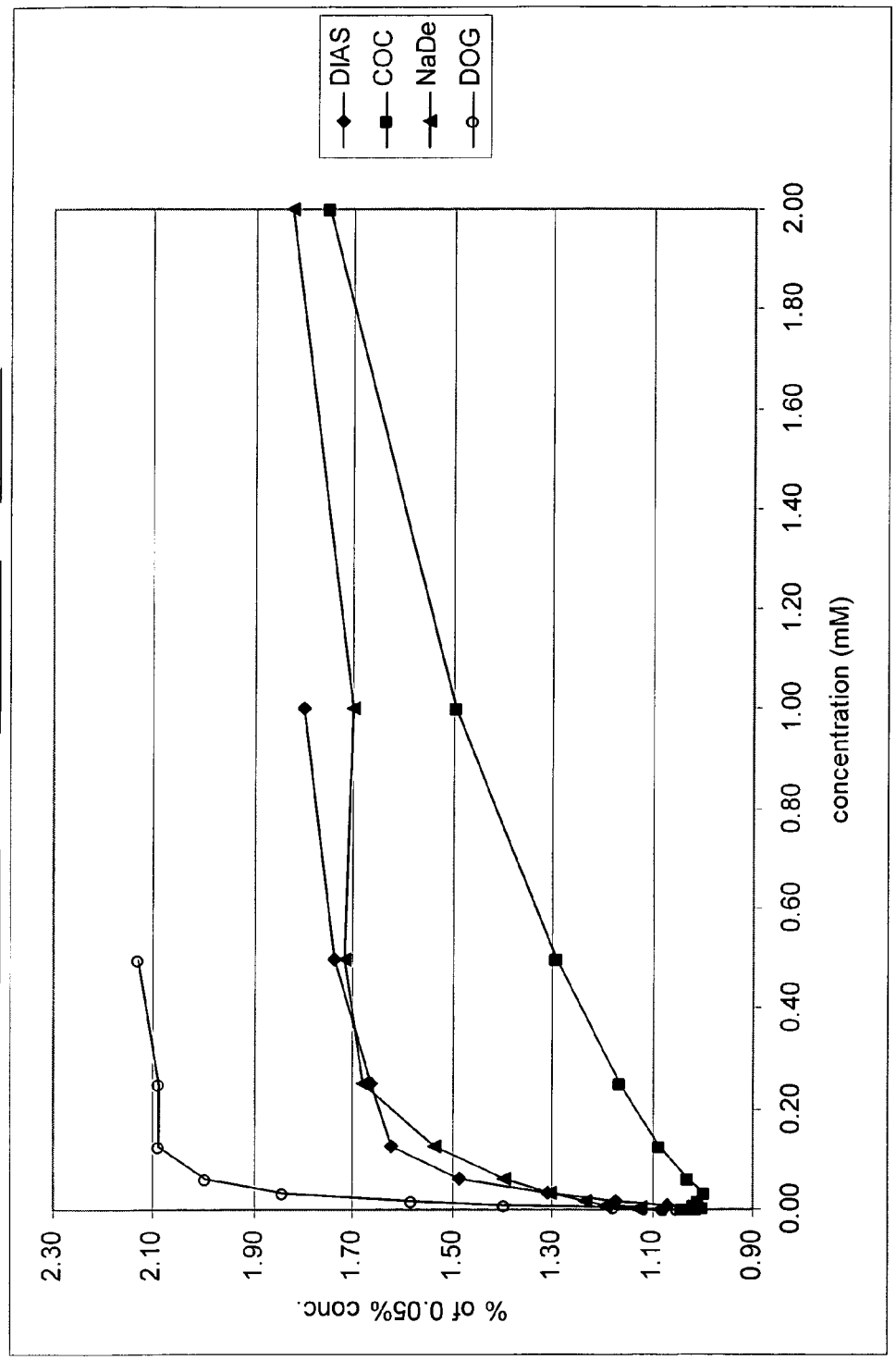
Figure 32E:
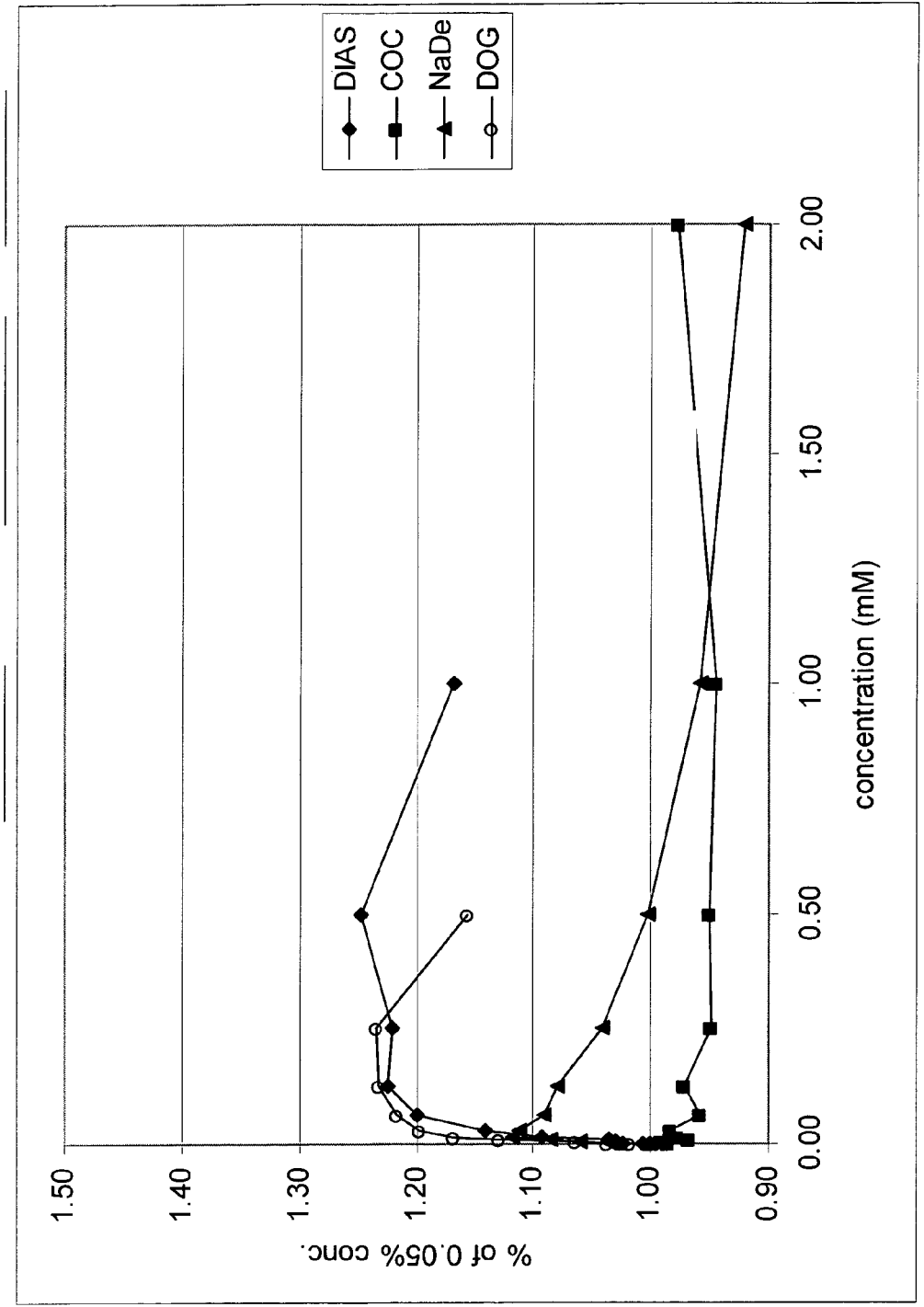
Figure 32F:
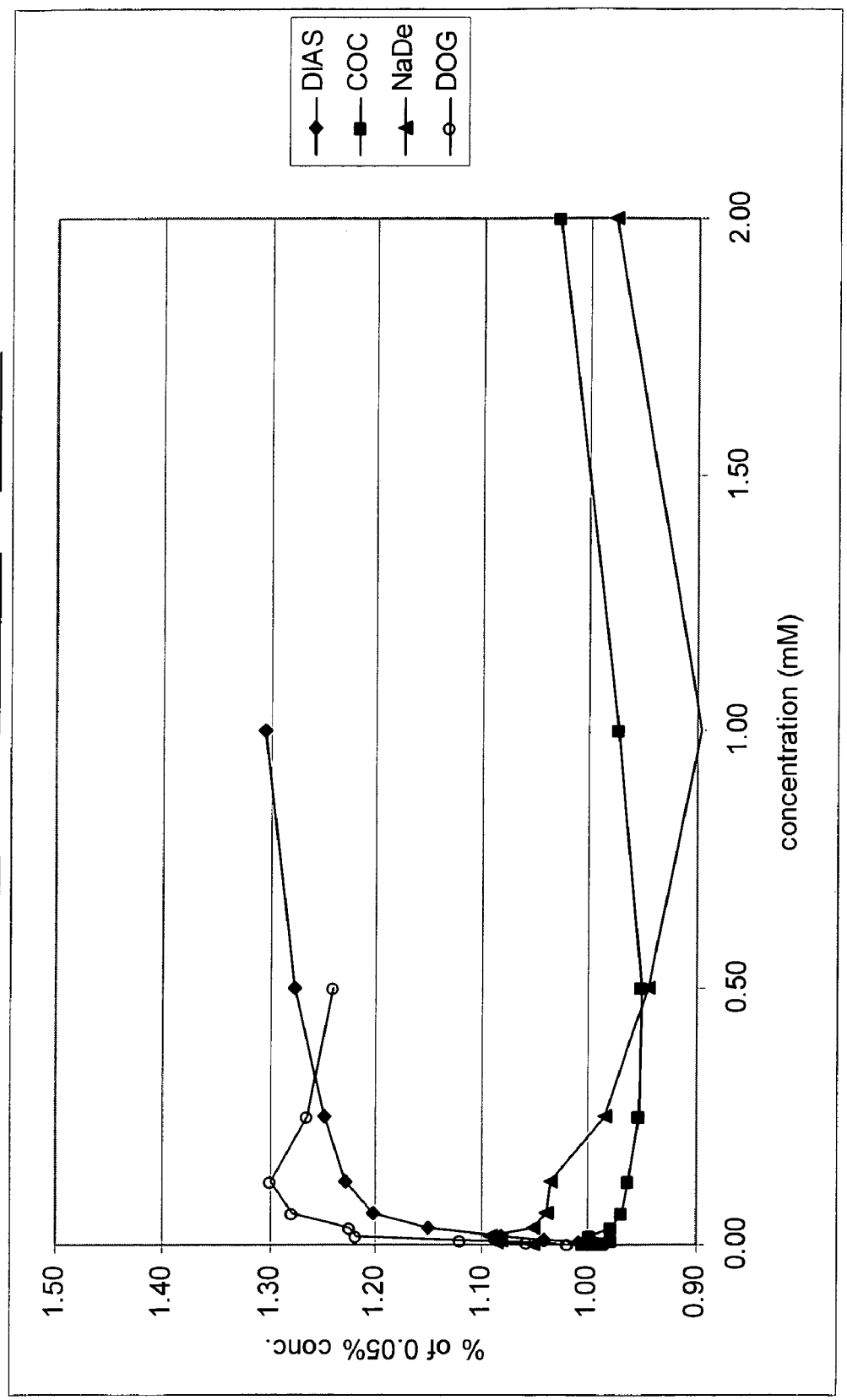
Figure 32G:
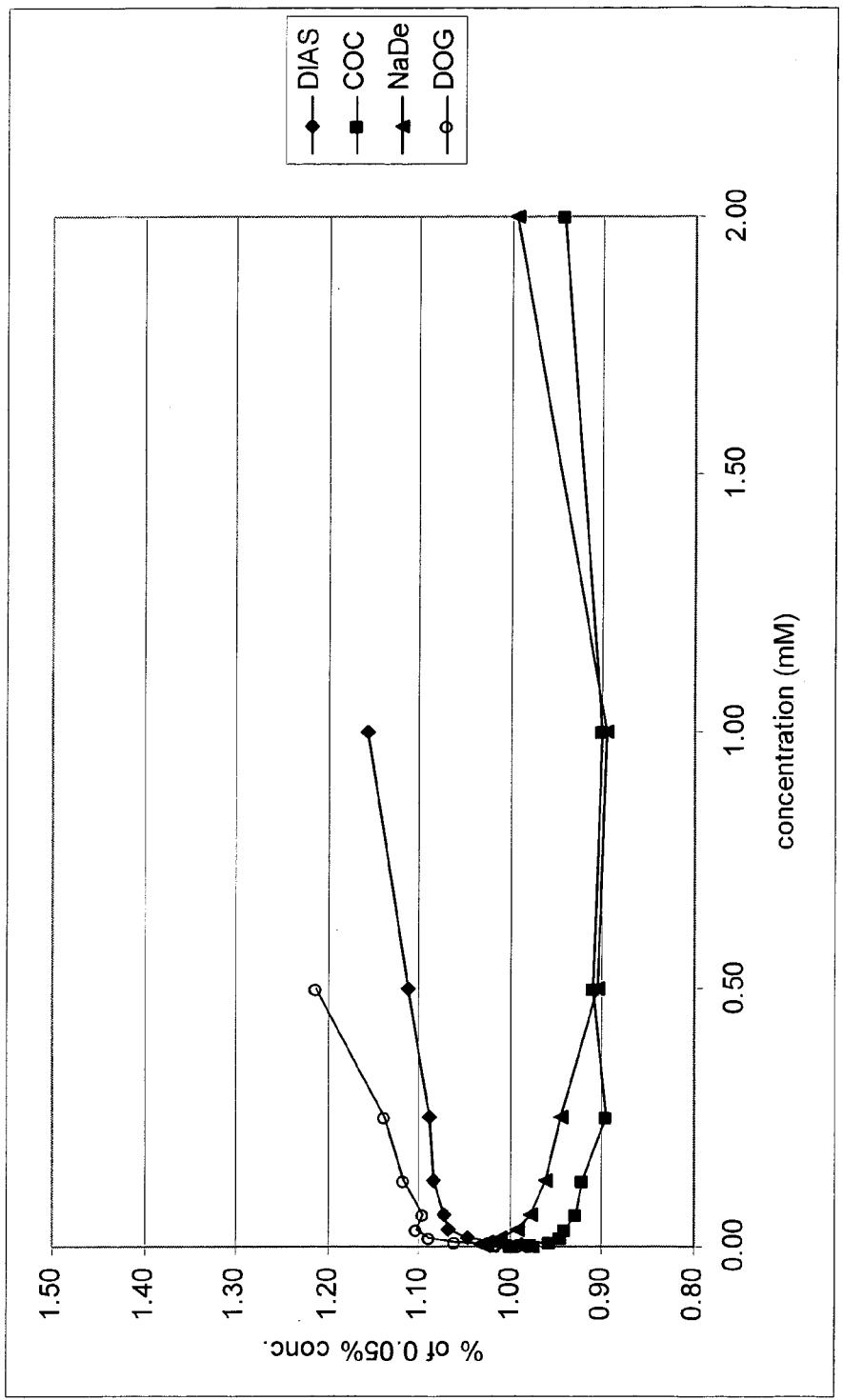
Figure 32H:
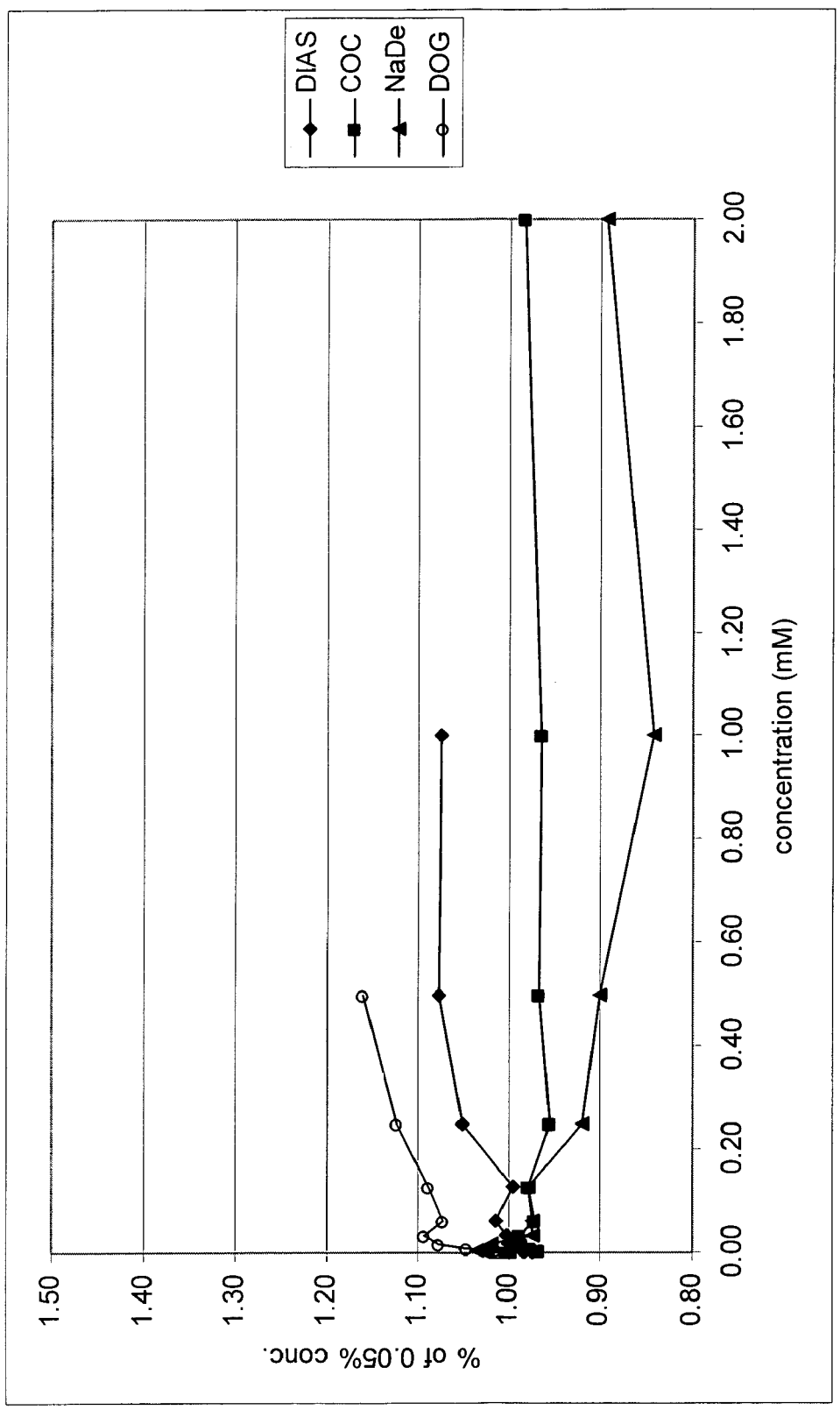
Figure 32I:
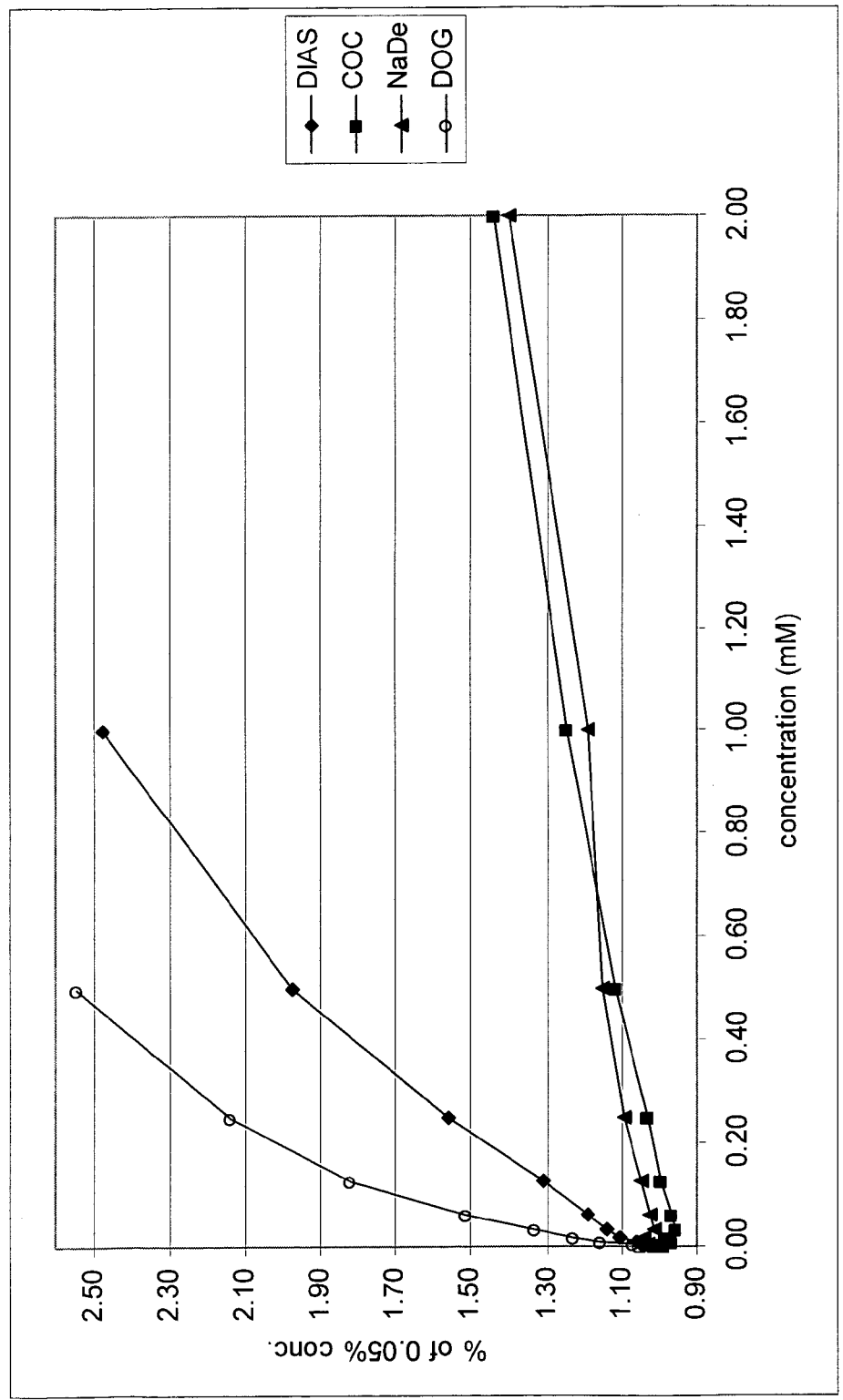
Figure 32J:
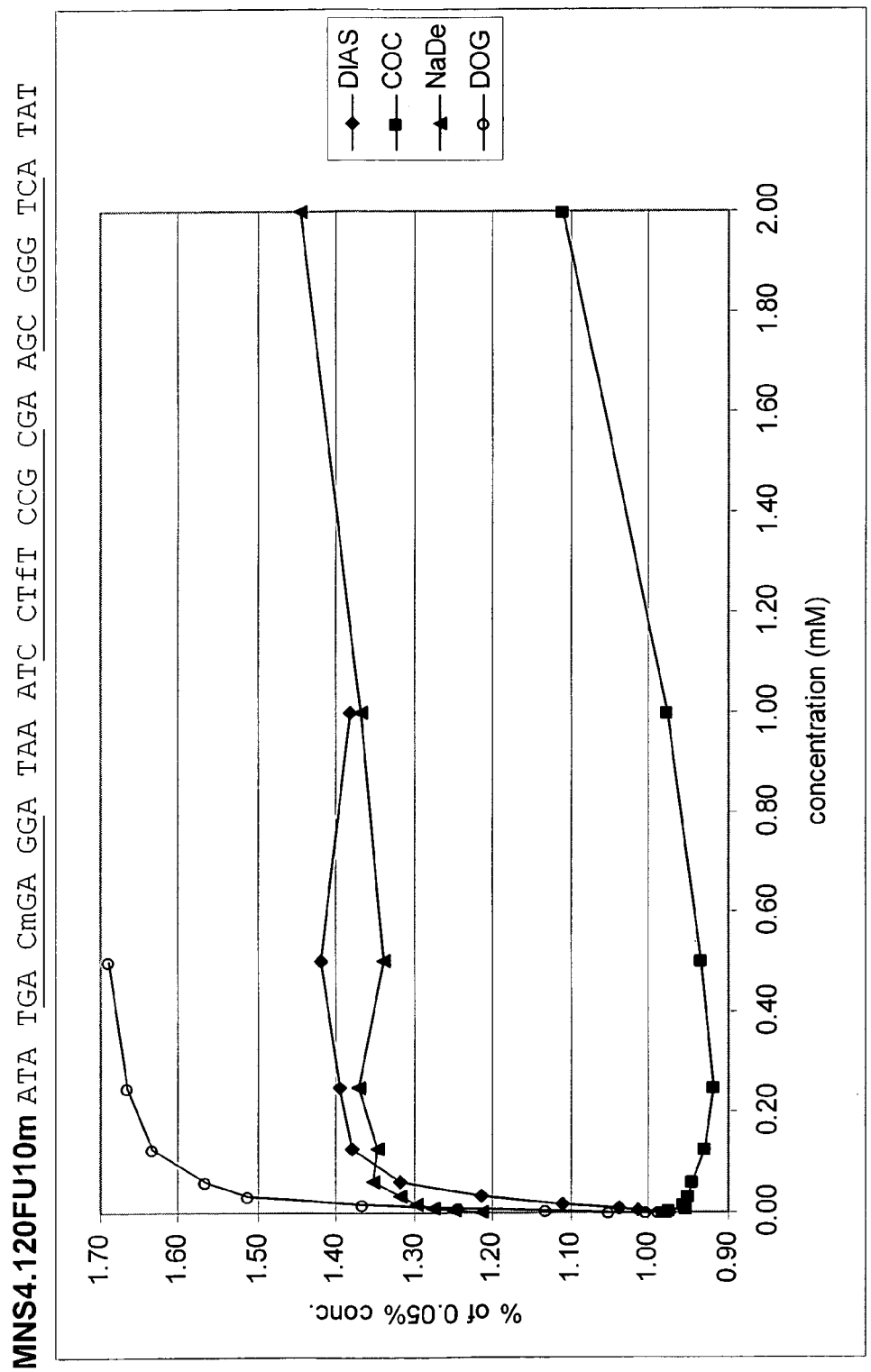
Figure 32K:
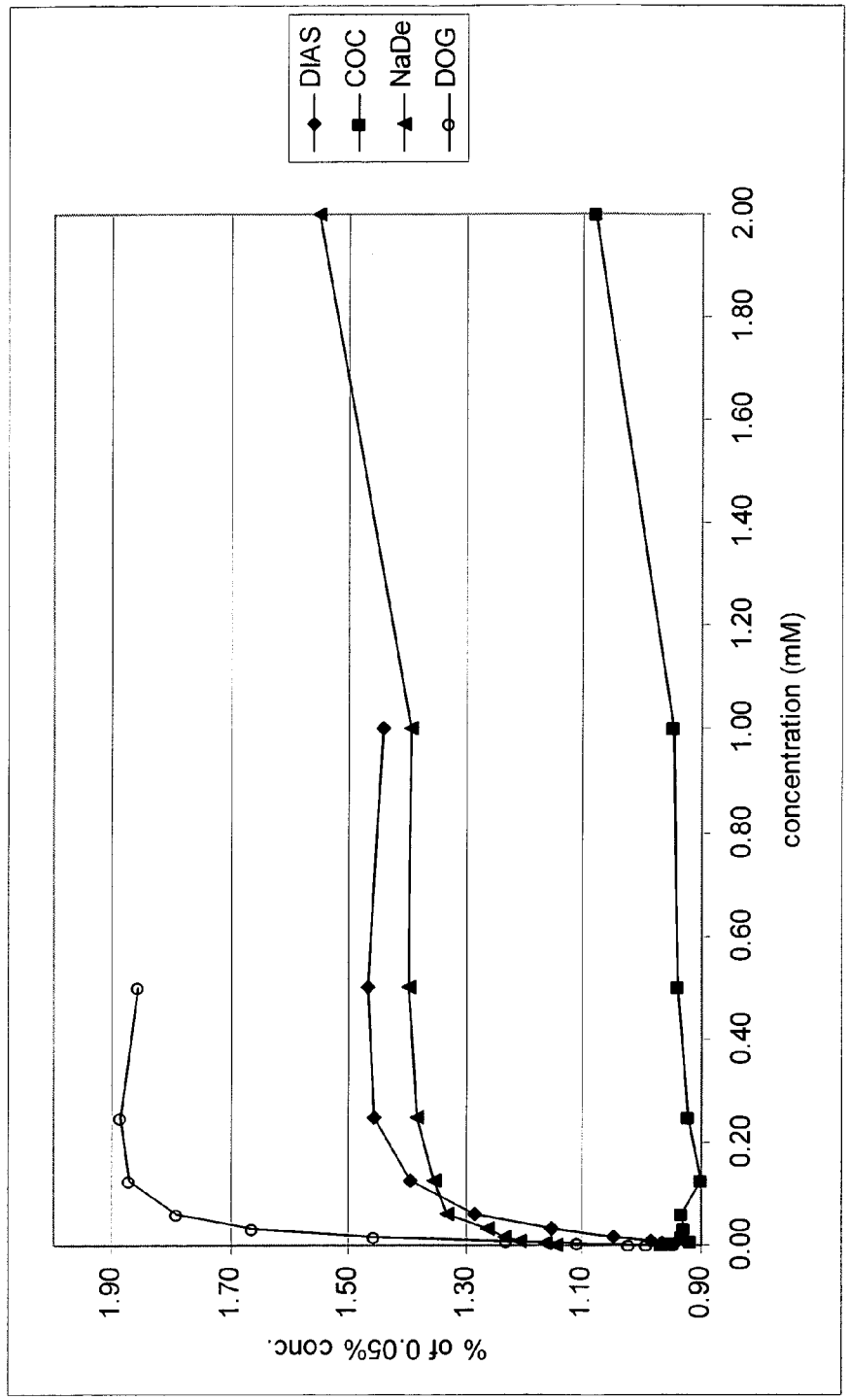
Figure 32L:
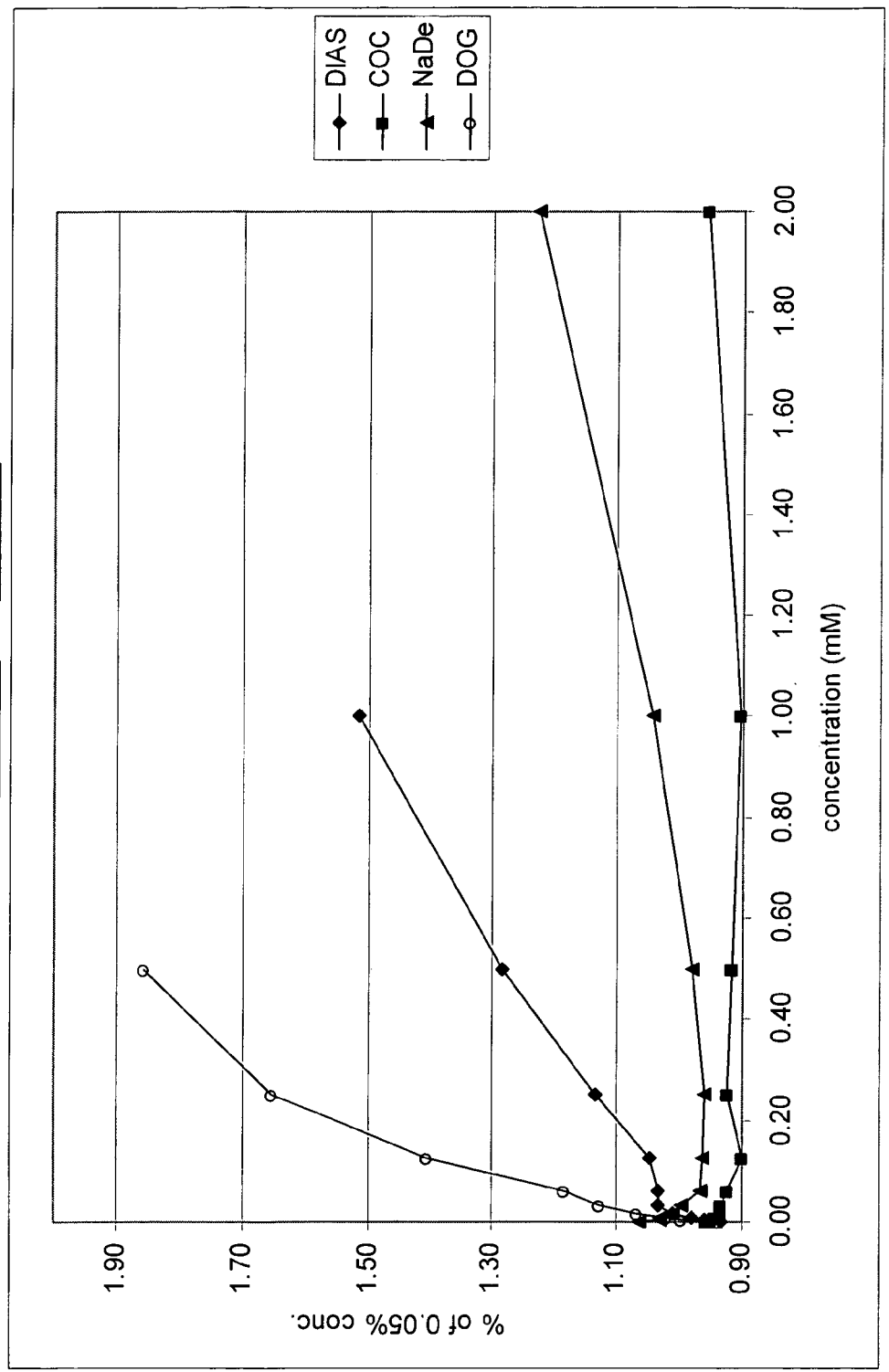
Figure 32M:
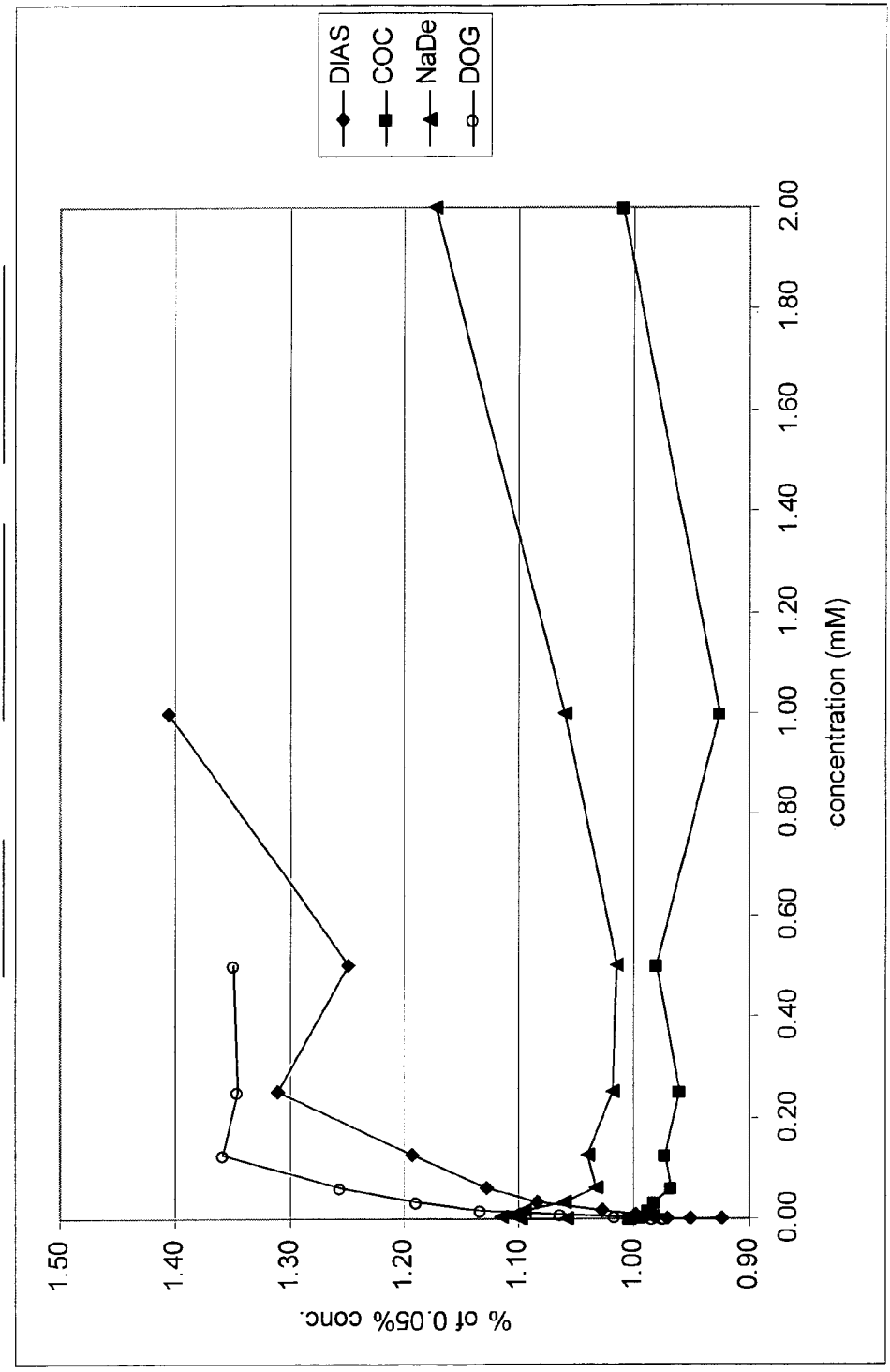

FIG. 29: Fingerprints (fluorescence intensity, relative units) of urine (U), urine spiked with deoxycorticosterone 21-glucoside (U+2) and urine spiked with dehydroisoandrosterone 3-sulfate (U+3) (first bar in each group): 4.1-7F8; (second bar): fmtch-A23-32F33; (third bar) fmtch-T25-32F33; (fourth bar): 4.1-32F33. Triplicate measurements of fluorescence intensity were taken, with standard deviation shown.

FIGS. 30A-30Z, 31A-31Z, and 32A-32N: Plots of individual sensor fluorescent response to analyte concentration (SEQ ID NOs 154-178; 179-203; and 204-217 respectively. 'MNS' is a laboratory code given to sensors during screening. Underlined portion of the sequence structure folds into three-way junction, with or without mismatches, bulges, modifications fT is fluorescent analog of T (or U) and R is rhodamine green analog of T (or U); these are directly constructed sensors, without any need to derivatize them. A '*' is a phoshorothioate analog $(P(S^-)(O)(OR)_2)$ of phosphodiester bond $(P(O^-)(O)(OR)_2)$—these precursors were derivatized with 6-iodoacetoamido fluorescein in order to construct sensors. m is a methylphoshonate $(P(O)(Me)(OR)_2)$ analog of phosphodiester bond. p is a propinyl analog. aT is amino-modifier dT analog. '2NH$_2$— is 2'-amino derivatized analog.~are spacers, usually 18 atom spacer, but could be shorter, spacers (C9, C3, dSpacer, examples not inclusive). NI—nitroindol analog. The y-axis is given as a fraction increase in fluorescence ((F−Fo)/Fo). x-axis is given in analyte concentrations in mM. cor—cortisone, NaDe sodium deoxycholate, Coc—cocaine, DIAS—dehydroisoandrosterone 3-sulfate, DOG—deoxycorticosterone 21-glucoside.

DETAILED DESCRIPTION OF THE PREFERRED EMBODIMENT

The present invention provides a composition comprising an oligonucleotide which comprises consecutive nucleotides having the sequences set forth in SEQ ID NO:1 and SEQ ID NO:2, wherein SEQ ID NO:1 is located 5' to SEQ ID NO:2.

The present invention further provides the instant oligonucleotide, wherein the oligonucleotide folds so that the sequences set forth in SEQ ID NO:1 and SEQ ID NO:1 contained in the oligonucleotide are arranged as set forth in the following structure, wherein SEQ ID NO:1-1 is the left hand sequence and SEQ ID NO:2 is the right hand sequence:

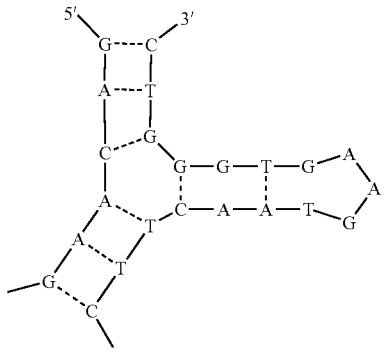

The present invention further provides the instant oligonucleotide, wherein the oligonucleotide comprises consecutive nucleotides having the sequence set forth in SEQ ID NO:152, wherein SEQ ID NO:152 is located 3' to SEQ ID NO:1 and 5' to SEQ ID NO:2.

The present invention also provides composition comprising an oligonucleotide which comprises consecutive nucleotides having the sequences set forth in SEQ ID NO:101 and SEQ ID NO:102, wherein SEQ ID NO:101 is located 5' to SEQ ID NO:102.

The present invention further provides the instant oligonucleotide, wherein the oligonucleotide folds so that the sequences set forth in SEQ ID NO:101 and SEQ ID NO:102 contained in the oligonucleotide are arranged as set forth in the following structure, wherein SEQ ID NO:101 is the left hand sequence and SEQ ID NO:102 is the right hand sequence:

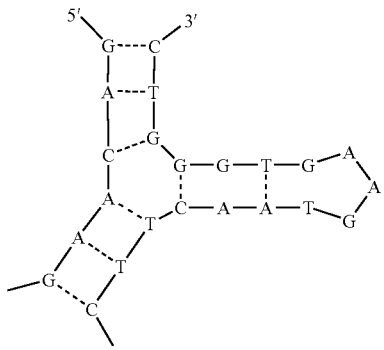

The present invention further provides the instant compositions, wherein the oligonucleotide comprises consecutive nucleotides having the sequence set forth in SEQ ID NO:153, wherein SEQ ID NO:153 is located 3' to SEQ ID NO:101 and 5' to SEQ ID NO:102.

This invention also provides a composition comprising an oligonucleotide which comprises consecutive nucleotides having the sequences set forth in SEQ ID NO:3 and SEQ ID NO:4, wherein SEQ ID NO:3 is located 5' to SEQ ID NO:4.

This invention further provides the instant oligonucleotide, wherein the oligonucleotide folds so that the sequences set forth in SEQ ID NO:3 and SEQ ID NO:4 contained in the oligonucleotide are arranged as set forth in the following structure, wherein SEQ ID NO:1-1 is the left hand sequence and SEQ ID NO:4 is the right hand sequence:

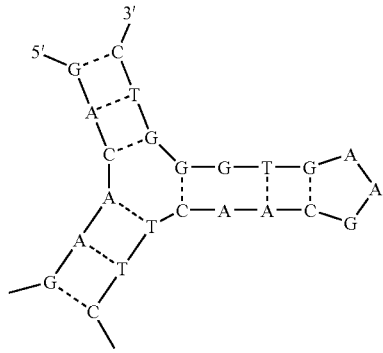

This invention further provides the instant composition, wherein the oligonucleotide comprises consecutive nucleotides having the sequence set forth in SEQ ID NO:152, wherein SEQ ID NO:152 is located 3' to SEQ ID NO:3 and 5' to SEQ ID NO:4.

This invention also provides a composition comprising an oligonucleotide which comprises consecutive nucleotides having the sequences set forth in SEQ ID NO:103 and SEQ ID NO:102, wherein SEQ ID NO:103 is located 5' to SEQ ID NO:102.

This invention further provides the instant oligonucleotide, wherein the oligonucleotide folds so that the sequences set forth in SEQ ID NO:103 and SEQ ID NO:102 contained in the oligonucleotide are arranged as set forth in the following structure, wherein SEQ ID NO:103 is the left hand sequence and SEQ ID NO:102 is the right hand sequence:

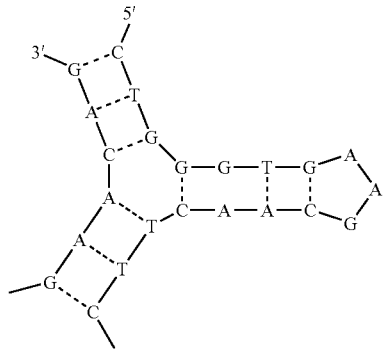

This invention further provides the instant composition, wherein the oligonucleotide comprises consecutive nucleotides having the sequence set forth in SEQ ID NO:153, wherein SEQ ID NO:153 is located 3' to SEQ ID NO:103 and 5' to SEQ ID NO:102.

This invention also provides a composition comprising an oligonucleotide which comprises consecutive nucleotides having the sequences set forth in SEQ ID NO:5 and SEQ ID NO:6, wherein SEQ ID NO:5 is located 5' to SEQ ID NO:6.

This invention further provides the instant oligonucleotide, wherein the oligonucleotide folds so that the sequences set forth in SEQ ID NO:5 and SEQ ID NO:6 contained in the oligonucleotide are arranged as set forth in the following structure, wherein SEQ ID NO:103 is the left hand sequence and SEQ ID NO:102 is the right hand sequence:

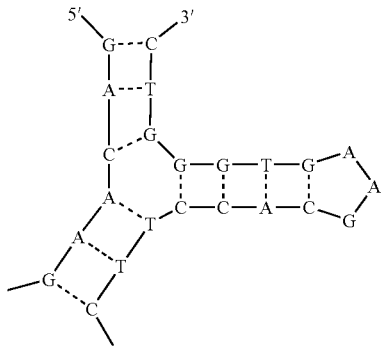

This invention further provides the instant composition, wherein the oligonucleotide comprises consecutive nucleotides having the sequence set forth in SEQ ID NO:152, wherein SEQ ID NO:152 is located 3' to SEQ ID NO:5 and 5' to SEQ ID NO:6.

This invention also provides a composition comprising an oligonucleotide which comprises consecutive nucleotides having the sequences set forth in SEQ ID NO:104 and SEQ ID NO:102, wherein SEQ ID NO:104 is located 5' to SEQ ID NO:102.

This invention further provides the instant oligonucleotide, wherein the oligonucleotide folds so that the sequences set forth in SEQ ID NO:7 and SEQ ID NO:8 contained in the oligonucleotide are arranged as set forth in the following structure, wherein SEQ ID NO:103 is the left hand sequence and SEQ ID NO:102 is the right hand sequence:

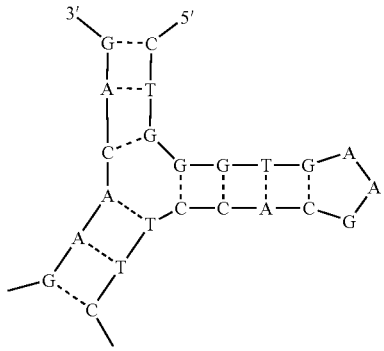

This invention further provides the instant composition, wherein the oligonucleotide comprises consecutive nucleotides having the sequence set forth in SEQ ID NO:153, wherein SEQ ID NO:153 is located 3' to SEQ ID NO:104 and 5' to SEQ ID NO:102.

This invention also provides a composition comprising an oligonucleotide which comprises consecutive nucleotides having the sequences set forth in SEQ ID NO:7 and SEQ ID NO:8, wherein SEQ ID NO:7 is located 5' to SEQ ID NO:8.

This invention further provides the instant oligonucleotide, wherein the oligonucleotide folds so that the sequences set forth in SEQ ID NO:7 and SEQ ID NO:8 contained in the oligonucleotide are arranged as set forth in the following structure, wherein SEQ ID NO:7 is the left hand sequence and SEQ ID NO:8 is the right hand sequence:

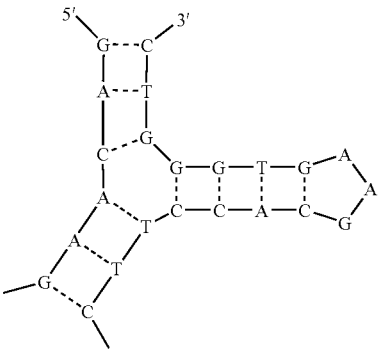

This invention further provides the instant composition, wherein the oligonucleotide comprises consecutive nucleotides having the sequence set forth in SEQ ID NO:152, wherein SEQ ID NO:152 is located 3' to SEQ ID NO:7 and 5' to SEQ ID NO:8.

This invention also provides a composition comprising an oligonucleotide which comprises consecutive nucleotides having the sequences set forth in SEQ ID NO:105 and SEQ ID NO:102, wherein SEQ ID NO:105 is located 5' to SEQ ID NO:102.

This invention further provides the instant osigonucleotide, wherein the oligonucleotide folds so that the sequences set forth in SEQ ID NO:105 and SEQ ID NO:102 contained in the oligonucleotide are arranged as set forth in the following structure, wherein SEQ ID NO:105 is the left hand sequence and SEQ ID NO:102 is the right hand sequence:

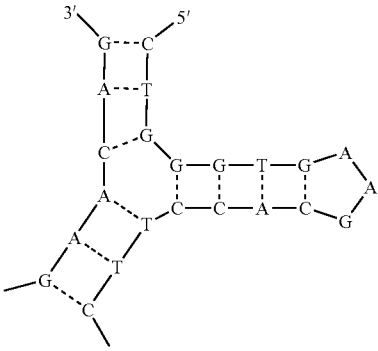

This invention further provides the instant composition, wherein the oligonucleotide comprises consecutive nucleotides having the sequence set forth in SEQ ID NO:153, wherein SEQ ID NO:153 is located 3' to SEQ ID NO:105 and 5' to SEQ ID NO:102.

This invention also provides a composition comprising an oligonucleotide which comprises consecutive nucleotides having the sequences set forth in SEQ ID NO:9 and SEQ ID NO:10, wherein SEQ ID NO:9 is located 5' to SEQ ID NO:10.

This invention further provides the instant oligonucleotide, wherein the oligonucleotide folds so that the sequences set forth in SEQ ID NO:9 and SEQ ID NO:10 contained in the oligonucleotide are arranged as set forth in the following structure, wherein SEQ ID NO:105 is the left hand sequence and SEQ ID NO:102 is the right hand sequence:

This invention further provides the instant composition, wherein the oligonucleotide comprises consecutive nucleotides having the sequence set forth in SEQ ID NO:152, wherein SEQ ID NO:152 is located 3' to SEQ ID NO:9 and 5' to SEQ ID NO:10.

This invention also provides a composition comprising an oligonucleotide which comprises consecutive nucleotides having the sequences set forth in SEQ ID NO:106 and SEQ ID NO:102, wherein SEQ ID NO:106 is located 5' to SEQ ID NO:102.

This invention further provides the instant oligonucleotide, wherein the oligonucleotide folds so that the sequences set forth in SEQ ID NO:106 and SEQ ID NO:102 contained in the oligonucleotide are arranged as set forth in the following structure, wherein SEQ ID NO:106 is the left hand sequence and SEQ ID NO:102 is the right hand sequence:

This invention further provides the instant composition, wherein the oligonucleotide comprises consecutive nucleotides having the sequence set forth in SEQ ID NO:153, wherein SEQ ID NO:153 is located 3' to SEQ ID NO:106 and 5' to SEQ ID NO:102.

This invention also provides a composition comprising an oligonucleotide which comprises consecutive nucleotides having the sequences set forth in SEQ ID NO:11 and SEQ ID NO:12, wherein SEQ ID NO:11 is located 5' to SEQ ID NO:12.

This invention further provides the instant oligonucleotide, wherein the oligonucleotide folds so that the sequences set forth in SEQ ID NO:11 and SEQ ID NO:12 contained in the oligonucleotide are arranged as set forth in the following structure, wherein SEQ ID NO:11 is the left hand sequence and SEQ ID NO:12 is the right hand sequence:

This invention further provides the instant composition, wherein the oligonucleotide comprises consecutive nucleotides having the sequence set forth in SEQ ID NO:152, wherein SEQ ID NO:152 is located 3' to SEQ ID NO:11 and 5' to SEQ ID NO:12.

This invention also provides a composition comprising an oligonucleotide which comprises consecutive nucleotides having the sequences set forth in SEQ ID NO:107 and SEQ ID NO:102, wherein SEQ ID NO:107 is located 5' to SEQ ID NO:102.

This invention further provides the instant composition, wherein the oligonucleotide folds so that the sequences set forth in SEQ ID NO:107 and SEQ ID NO:102 contained in the oligonucleotide are arranged as set forth in the following structure:

This invention further provides the instant oligonucleotide, wherein the oligonucleotide folds so that the squence set forth in SEQ ID NO:107 SEQ ID NO:102 contained in the oligonucleotide are arranged as set forth in the following strucrure, wherein SEQ ID NO:107 is the left hand sequence and SEQ ID NO:102 is the right hand sequence:

This invention also provides a composition comprising an oligonucleotide which comprises consecutive nucleotides having the sequences set forth in SEQ ID NO:13 and SEQ ID NO:14, wherein SEQ ID NO:13 is located 5' to SEQ ID NO:14.

This invention further provides the instant oligonucleotide, wherein the oligonucleotide folds so that the sequences set forth in SEQ ID NO:13 and SEQ ID NO:14 contained in the oligonucleotide are arranged as set forth in the following structure, wherein SEQ ID NO:13 is the left hand sequence and SEQ ID NO:14 is the right hand sequence:

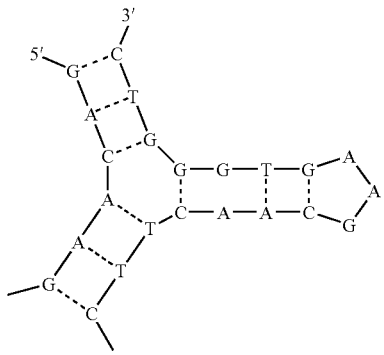

This invention further provides the instant composition, wherein the oligonucleotide comprises consecutive nucleotides having the sequence set forth in SEQ ID NO:152, wherein SEQ ID NO:152 is located 31 to SEQ ID NO:13 and 5' to SEQ ID NO:14.

This invention also provides a composition comprising an oligonucleotide which comprises consecutive nucleotides having the sequences set forth in SEQ ID NO:108 and SEQ ID NO:102, wherein SEQ ID NO:108 is located 5' to SEQ ID NO:102.

This invention further provides the instant oligonucleotide, wherein the oligonucleotide folds so that the sequences set forth in SEQ ID NO:108 and SEQ ID NO:102 contained in the oligonucleotide are arranged as set forth in the following structure, wherein SEQ ID NO:108 is the left hand sequence and SEQ ID NO:102 is the right hand sequence:

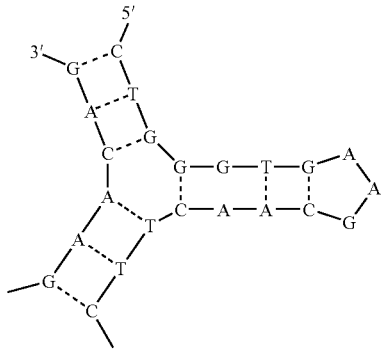

This invention further provides the instant composition, wherein the oligonucleotide comprises consecutive nucleotides having the sequence set forth in SEQ ID NO:153, wherein SEQ ID NO:153 is located 3' to SEQ ID NO:108 and 5' to SEQ ID NO:102.

This invention also provides a composition comprising an oligonucleotide which comprises consecutive nucleotides having the sequences set forth in SEQ ID NO:15 and SEQ ID NO:16, wherein SEQ ID NO:15 is located 5' to SEQ ID NO:16.

This invention further provides the instant oligonucleotide, wherein the oligonucleotide folds so that the sequences set forth in SEQ ID NO:15 and SEQ ID NO:16 contained in the oligonucleotide are arranged as set forth in the following structure, wherein SEQ ID NO:15 is the left hand sequence and SEQ ID NO:16 is the right hand sequence:

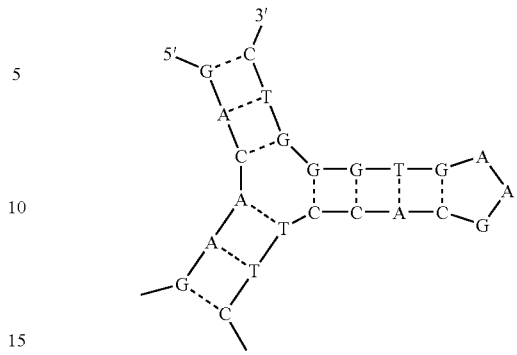

This invention further provides the instant composition, wherein the oligonucleotide comprises consecutive nucleotides having the sequence set forth in SEQ ID NO:152, wherein SEQ ID NO:152 is located 3' to SEQ ID NO:15 and 5' to SEQ ID NO:16.

This invention also provides a composition comprising an oligonucleotide which comprises consecutive nucleotides having the sequences set forth in SEQ ID NO:109 and SEQ ID NO:102, wherein SEQ ID NO:109 is located 5' to SEQ ID NO:102.

This invention further provides the instant oligonucleotide, wherein the oligonucleotide folds so that the sequences set forth in SEQ ID NO:109 and SEQ ID NO:102 contained in the oligonucleotide are arranged as set forth in the following structure, wherein SEQ ID NO:109 is the left hand sequence and SEQ ID NO:102 is the right hand sequence:

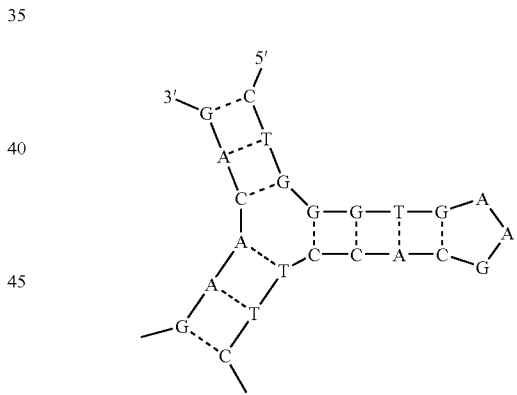

This invention further provides the instant composition, wherein the oligonucleotide comprises consecutive nucleotides having the sequence set forth in SEQ ID NO:153, wherein SEQ ID NO:153 is located 3' to SEQ ID NO:109 and 5' to SEQ ID NO:102.

This invention also provides a composition comprising an oligonucleotide which comprises consecutive nucleotides having the sequences set forth in SEQ ID NO:17 and SEQ ID NO:18, wherein SEQ ID NO:17 is located 5' to SEQ ID NO:18.

This invention further provides the instant oligonucleotide, wherein the oligonucleotide folds so that the sequences set forth in SEQ ID NO:17 and SEQ ID NO:18 contained in the oligonucleotide are arranged as set forth in the following structure, wherein SEQ ID NO:17 is the left hand sequence and SEQ ID NO:18 is the right hand sequence:

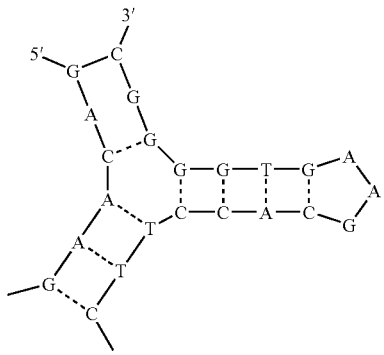

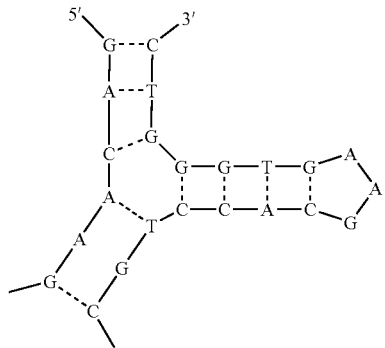

This invention further provides the instant composition, wherein the oligonucleotide comprises consecutive nucleotides having the sequence set forth in SEQ ID NO:152, wherein SEQ ID NO:152 is located 3' to SEQ ID NO:17 and 5' to SEQ ID NO:18.

This invention also provides a composition comprising an oligonucleotide which comprises consecutive nucleotides having the sequences set forth in SEQ ID NO:110 and SEQ ID NO:102, wherein SEQ ID NO:110 is located 5' to SEQ ID NO:102.

This invention further provides the instant oligonucleotide, wherein the oligonucleotide folds so that the sequences set forth in SEQ ID NO:110 and SEQ ID NO:102 contained in the oligonucleotide are arranged as set forth in the following structure, wherein SEQ ID NO:110 is the left hand sequence and SEQ ID NO:102 is the right hand sequence:

This invention further provides the instant composition, wherein the oligonucleotide comprises consecutive nucleotides having the sequence set forth in SEQ ID NO:152, wherein SEQ ID NO:152 is located 3' to SEQ ID NO:19 and 5' to SEQ ID NO:20.

This invention also provides a composition comprising an oligonucleotide which comprises consecutive nucleotides having the sequences set forth in SEQ ID NO:111 and SEQ ID NO:102, wherein SEQ ID NO:111 is located 5' to SEQ ID NO:102.

This invention further provides the instant oligonucleotide, wherein the oligonucleotide folds so that the sequences set forth in SEQ ID NO:111 and SEQ ID NO:102 contained in the oligonucleotide are arranged as set forth in the following structure, wherein SEQ ID NO:111 is the left hand sequence and SEQ ID NO:102 is the right hand sequence:

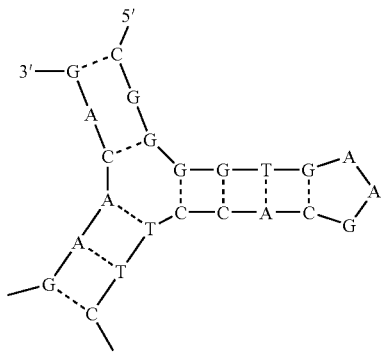

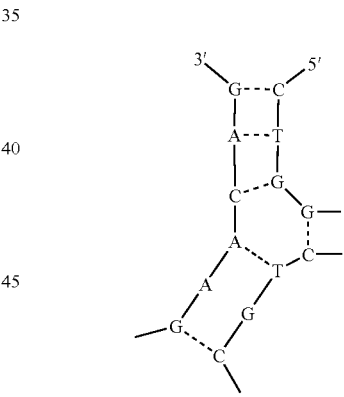

This invention further provides the instant composition, wherein the oligonucleotide comprises consecutive nucleotides having the sequence set forth in SEQ ID NO:153, wherein SEQ ID NO:153 is located 3' to SEQ ID NO:110 and 5' to SEQ ID NO:102.

This invention also provides a composition comprising an oligonucleotide which comprises consecutive nucleotides having the sequences set forth in SEQ ID NO:19 and SEQ ID NO:20, wherein SEQ ID NO:19 is located 5' to SEQ ID NO:20.

This invention further provides the instant oligonucleotide, wherein the oligonucleotide folds so that the sequences set forth in SEQ ID NO:19 and SEQ ID NO:20 contained in the oligonucleotide are arranged as set forth in the following structure, wherein SEQ ID NO:19 is the left hand sequence and SEQ ID NO:20 is the right hand sequence:

This invention further provides the instant composition, wherein the oligonucleotide comprises consecutive nucleotides having the sequence set forth in SEQ ID NO:153, wherein SEQ ID NO:153 is located 3' to SEQ ID NO:111 and 5' to SEQ ID NO:102.

This invention also provides a composition comprising an oligonucleotide which comprises consecutive nucleotides having the sequences set forth in SEQ ID NO:21 and SEQ ID NO:22, wherein SEQ ID NO:21 is located 5' to SEQ ID NO:22.

This invention further provides the instant oligonucleotide, wherein the oligonucleotide folds so that the sequences set forth in SEQ ID NO:21 and SEQ ID NO:22 contained in the oligonucleotide are arranged as set forth in the following structure, wherein SEQ ID NO:1 is the left hand sequence and SEQ ID NO:2 is the right hand sequence:

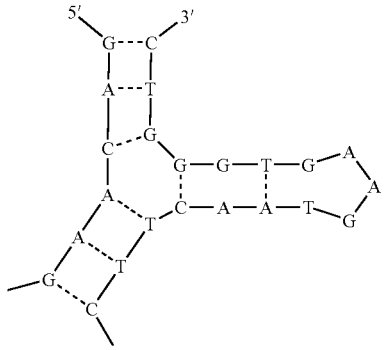

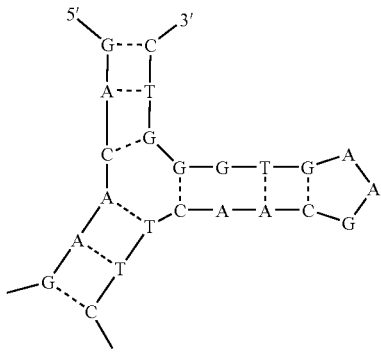

This invention further provides the instant composition, wherein the oligonucleotide comprises consecutive nucleotides having the sequence set forth in SEQ ID NO:152, wherein SEQ ID NO:152 is located 3' to SEQ ID NO:21 and 5' to SEQ ID NO:22.

This invention also provides a composition comprising an oligonucleotide which comprises consecutive nucleotides having the sequences set forth in SEQ ID NO:112 and SEQ ID NO:102, wherein SEQ ID NO:112 is located 5' to SEQ ID NO:102.

This invention further provides the instant oligonucleotide, wherein the oligonucleotide folds so that the sequences set forth in SEQ ID NO:112 and SEQ ID NO:102 contained in the oligonucleotide are arranged as set forth in the following structure, wherein SEQ ID NO:112 is the left hand sequence and SEQ ID NO:102 is the right hand sequence:

This invention further provides the instant composition, wherein the oligonucleotide comprises consecutive nucleotides having the sequence set forth in SEQ ID NO:152, wherein SEQ ID NO:152 is located 3' to SEQ ID NO:23 and 5' to SEQ ID NO:24.

This invention also provides a composition comprising an oligonucleotide which comprises consecutive nucleotides having the sequences set forth in SEQ ID NO:113 and SEQ ID NO:102, wherein SEQ ID NO:113 is located 5' to SEQ ID NO:102.

This invention further provides the instant oligonucleotide, wherein the oligonucleotide folds so that the sequences set forth in SEQ ID NO:113 and SEQ ID NO:102 contained in the oligonucleotide are arranged as set forth in the following structure, wherein SEQ ID NO:113 is the left hand sequence and SEQ ID NO:102 is the right hand sequence:

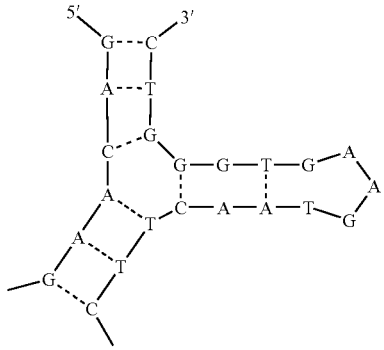

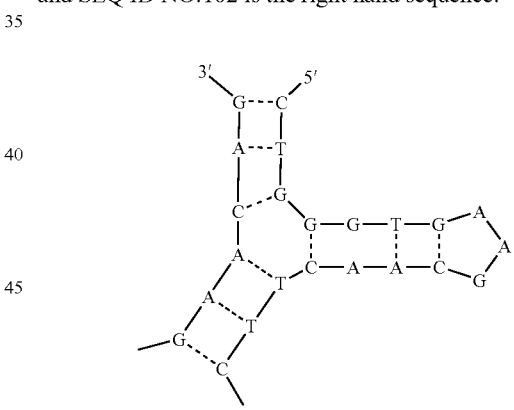

This invention further provides the instant composition, wherein the oligonucleotide comprises consecutive nucleotides having the sequence set forth in SEQ ID NO:153, wherein SEQ ID NO:153 is located 3' to SEQ ID NO:112 and 5' to SEQ ID NO:102.

This invention also provides a composition comprising an oligonucleotide which comprises consecutive nucleotides having the sequences set forth in SEQ ID NO:23 and SEQ ID NO:24, wherein SEQ ID NO:23 is located 5' to SEQ ID NO:24.

This invention further provides the instant oligonucleotide, wherein the oligonucleotide folds so that the sequences set forth in SEQ ID NO:23 and SEQ ID NO:24 contained in the oligonucleotide are arranged as set forth in the following structure, wherein SEQ ID NO:23 is the left hand sequence and SEQ ID NO:24 is the right hand sequence:

This invention further provides the instant composition, wherein the oligonucleotide comprises consecutive nucleotides having the sequence set forth in SEQ ID NO:153, wherein SEQ ID NO:153 is located 3' to SEQ ID NO:113 and 5' to SEQ ID NO:102.

This invention also provides a composition comprising an oligonucleotide which comprises consecutive nucleotides having the sequences set forth in SEQ ID NO:25 and SEQ ID NO:26, wherein SEQ ID NO:3 is located 5' to SEQ ID NO:4.

This invention further provides the instant oligonucleotide, wherein the oligonucleotide folds so that the sequences set forth in SEQ ID NO:25 and SEQ ID NO:26 contained in the oligonucleotide are arranged as set forth in the following structure, wherein SEQ ID NO:25 is the left hand sequence and SEQ ID NO:26 is the right hand sequence:

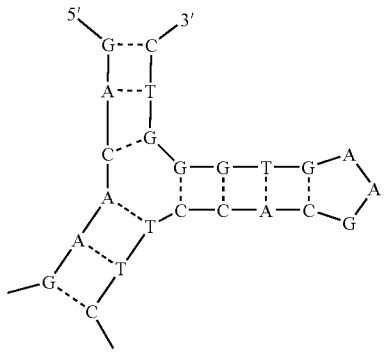

This invention further provides the instant composition, wherein the oligonucleotide comprises consecutive nucleotides having the sequence set forth in SEQ ID NO:152, wherein SEQ ID NO:152 is located 3l to SEQ ID NO:25 and 5' to SEQ ID NO:26.

This invention also provides a composition comprising an oligonucleotide which comprises consecutive nucleotides having the sequences set forth in SEQ ID NO:114 and SEQ ID NO:102, wherein SEQ ID NO:114 is located 5' to SEQ ID NO:102.

This invention further provides the instant oligonucleotide, wherein the oligonucleotide folds so that the sequences set forth in SEQ ID NO:114 and SEQ ID NO:102 contained in the oligonucleotide are arranged as set forth in the following structure, wherein SEQ ID NO:114 is the left hand sequence and SEQ ID NO:102 is the right hand sequence:

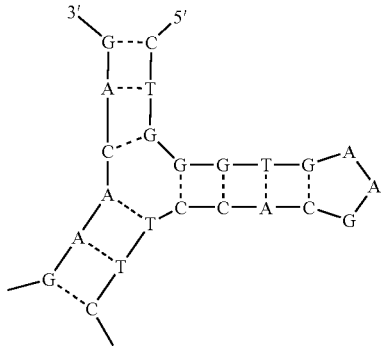

This invention further provides the instant composition, wherein the oligonucleotide comprises consecutive nucleotides having the sequence set forth in SEQ ID NO:153, wherein SEQ ID NO:153 is located 3' to SEQ ID NO:114 and 5' to SEQ ID NO:102.

This invention also provides a composition comprising an oligonucleotide which comprises consecutive nucleotides having the sequences set forth in SEQ ID NO:27 and SEQ ID NO:28, wherein SEQ ID NO:27 is located 5' to SEQ ID NO:28.

This invention further provides the instant oligonucleotide, wherein the oligonucleotide folds so that the sequences set forth in SEQ ID NO:27 and SEQ ID NO:28 contained in the oligonucleotide are arranged as set forth in the following structure, wherein SEQ ID NO:27 is the left hand sequence and SEQ ID NO:28 is the right hand sequence:

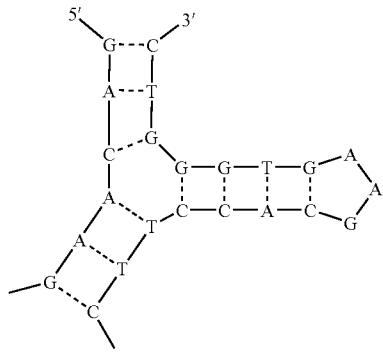

This invention further provides the instant composition, wherein the oligonucleotide comprises consecutive nucleotides having the sequence set forth in SEQ ID NO:152, wherein SEQ ID NO:152 is located 3' to SEQ ID NO:27 and 5' to SEQ ID NO:28.

This invention also provides a composition comprising an oligonucleotide which comprises consecutive nucleotides having the sequences set forth in SEQ ID NO:115 and SEQ ID NO:102, wherein SEQ ID NO:115 is located 5' to SEQ ID NO:102.

This invention further provides the instant oligonucleotide, wherein the oligonucleotide folds so that the sequences set forth in SEQ ID NO:115 and SEQ ID NO:102 contained in the oligonucleotide are arranged as set forth in the following structure, wherein SEQ ID NO:115 is the left hand sequence and SEQ ID NO:102 is the right hand sequence:

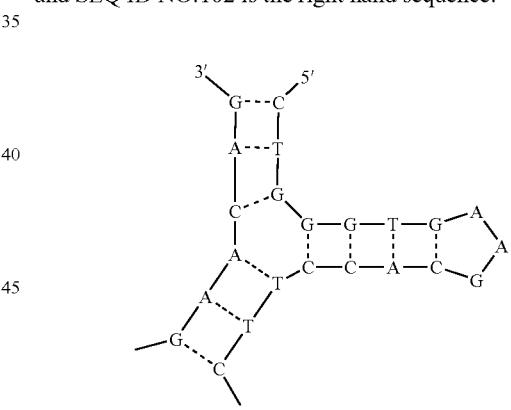

This invention further provides the instant composition, wherein the oligonucleotide comprises consecutive nucleotides having the sequence set forth in SEQ ID NO:153, wherein SEQ ID NO:153 is located 3' to SEQ ID NO:115 and 5' to SEQ ID NO:102.

This invention also provides a composition comprising an oligonucleotide which comprises consecutive nucleotides having the sequences set forth in SEQ ID NO:29 and SEQ ID NO:30, wherein SEQ ID NO:3 is located 5' to SEQ ID NO:4.

This invention further provides the instant oligonucleotide, wherein the oligonucleotide folds so that the sequences set forth in SEQ ID NO:29 and SEQ ID NO:30 contained in the oligonucleotide are arranged as set forth in the following structure, wherein SEQ ID NO:29 is the left hand sequence and SEQ ID NO:304 is the right hand sequence:

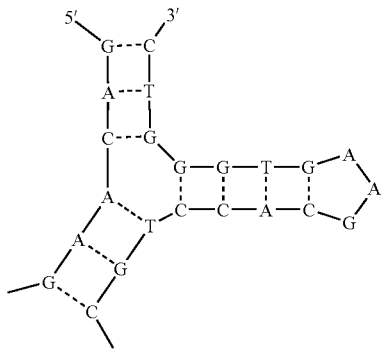

This invention further provides the instant composition, wherein the oligonucleotide comprises consecutive nucleotides having the sequence set forth in SEQ ID NO:152, wherein SEQ ID NO:152 is located 3' to SEQ ID NO:29 and 5' to SEQ ID NO:30.

This invention also provides a composition comprising an oligonucleotide which comprises consecutive nucleotides having the sequences set forth in SEQ ID NO:116 and SEQ ID NO:102, wherein SEQ ID NO:116 is located 5' to SEQ ID NO:102.

This invention further provides the instant oligonucleotide, wherein the oligonucleotide folds so that the sequences set forth in SEQ ID NO:116 and SEQ ID NO:102 contained in the oligonucleotide are arranged as set forth in the following structure, wherein SEQ ID NO:116 is the left hand sequence and SEQ ID NO:102 is the right hand sequence:

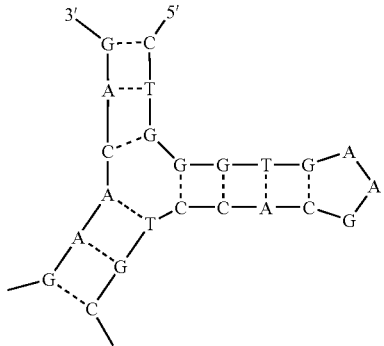

This invention further provides the instant composition, wherein the oligonucleotide comprises consecutive nucleotides having the sequence set forth in SEQ ID NO:153, wherein SEQ ID NO:153 is located 3' to SEQ ID NO:116 and 5' to SEQ ID NO:102.

This invention also provides a composition comprising an oligonucleotide which comprises consecutive nucleotides having the sequences set forth in SEQ ID NO:31 and SEQ ID NO:32, wherein SEQ ID NO:31 is located 5' to SEQ ID NO:32.

This invention further provides the instant oligonucleotide, wherein the oligonucleotide folds so that the sequences set forth in SEQ ID NO:31 and SEQ ID NO:32 contained in the oligonucleotide are arranged as set forth in the following structure, wherein SEQ ID NO:31 is the left hand sequence and SEQ ID NO:32 is the right hand sequence:

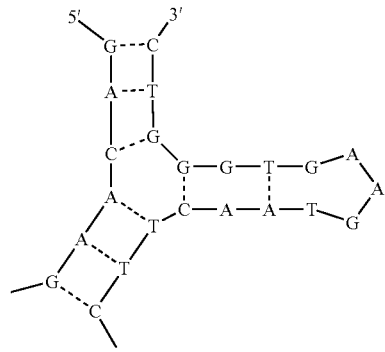

This invention further provides the instant composition, wherein the oligonucleotide comprises consecutive nucleotides having the sequence set forth in SEQ ID NO:152, wherein SEQ ID NO:152 is located 3' to SEQ ID NO:31 and 5' to SEQ ID NO:32.

This invention also provides a composition comprising an oligonucleotide which comprises consecutive nucleotides having the sequences set forth in SEQ ID NO:117 and SEQ ID NO:102, wherein SEQ ID NO:117 is located 5' to SEQ ID NO:102.

This invention further provides the instant oligonucleotide, wherein the oligonucleotide folds so that the sequences set forth in SEQ ID NO:117 and SEQ ID NO:102 contained in the oligonucleotide are arranged as set forth in the following structure, wherein SEQ ID NO:117 is the left hand sequence and SEQ ID NO:102 is the right hand sequence:

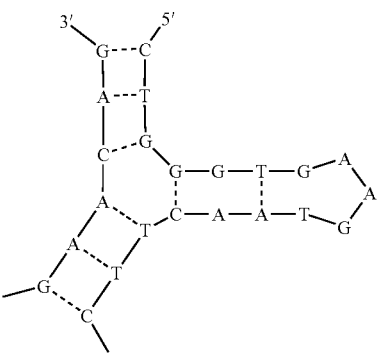

This invention further provides the instant composition, wherein the oligonucleotide comprises consecutive nucleotides having the sequence set forth in SEQ ID NO:153, wherein SEQ ID NO:153 is located 3' to SEQ ID NO:117 and 5' to SEQ ID NO:102.

This invention also provides a composition comprising an oligonucleotide which comprises consecutive nucleotides having the sequences set forth in SEQ ID NO:33 and SEQ ID NO:34, wherein SEQ ID NO:3 is located 5' to SEQ ID NO:4.

This invention further provides the instant oligonucleotide, wherein the oligonucleotide folds so that the sequences set forth in SEQ ID NO:33 and SEQ ID NO:34 contained in the oligonucleotide are arranged as set forth in the following structure, wherein SEQ ID NO:33 is the left hand sequence and SEQ ID NO:34 is the right hand sequence:

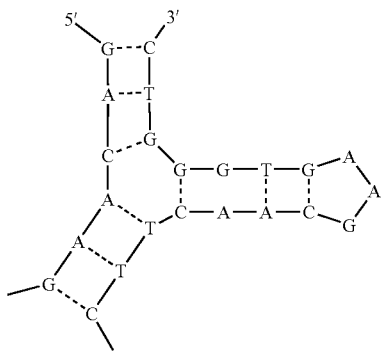

This invention further provides the instant composition, wherein the oligonucleotide comprises consecutive nucleotides having the sequence set forth in SEQ ID NO:152, wherein SEQ ID NO:152 is located 3' to SEQ ID NO:33 and 5' to SEQ ID NO:34.

This invention also provides a composition comprising an oligonucleotide which comprises consecutive nucleotides having the sequences set forth in SEQ ID NO:118 and SEQ ID NO:102, wherein SEQ ID NO:118 is located 5' to SEQ ID NO:102.

This invention further provides the instant oligonucleotide, wherein the oligonucleotide folds so that the sequences set forth in SEQ ID NO:118 and SEQ ID NO:102 contained in the oligonucleotide are arranged as set forth in the following structure, wherein SEQ ID NO:118 is the left hand sequence and SEQ ID NO:102 is the right hand sequence:

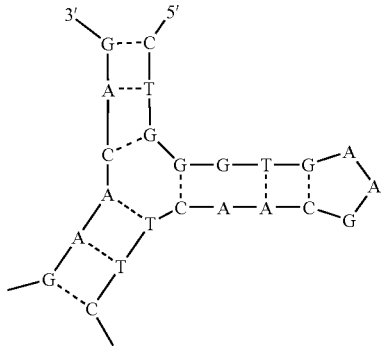

This invention further provides the instant composition, wherein the oligonucleotide comprises consecutive nucleotides having the sequence set forth in SEQ ID NO:153, wherein SEQ ID NO:153 is located 3' to SEQ ID NO:118 and 5' to SEQ ID NO:102.

This invention also provides a composition comprising an oligonucleotide which comprises consecutive nucleotides having the sequences set forth in SEQ ID NO:35 and SEQ ID NO:36, wherein SEQ ID NO:35 is located 5' to SEQ ID NO:36.

This invention further provides the instant oligonucleotide, wherein the oligonucleotide folds so that the sequences set forth in SEQ ID NO:35 and SEQ ID NO:36 contained in the oligonucleotide are arranged as set forth in the following structure, wherein SEQ ID NO:35 is the left hand sequence and SEQ ID NO:36 is the right hand sequence:

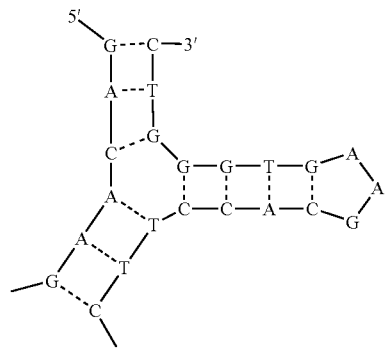

This invention further provides the instant composition, wherein the oligonucleotide comprises consecutive nucleotides having the sequence set forth in SEQ ID NO:152, wherein SEQ ID NO:152 is located 3' to SEQ ID NO:35 and 5' to SEQ ID NO:36.

This invention also provides a composition comprising an oligonucleotide which comprises consecutive nucleotides having the sequences set forth in SEQ ID NO:119 and SEQ ID NO:102, wherein SEQ ID NO:119 is located 5' to SEQ ID NO:102.

This invention further provides the instant oligonucleotide, wherein the oligonucleotide folds so that the sequences set forth in SEQ ID NO:119 and SEQ ID NO:102 contained in the oligonucleotide are arranged as set forth in the following structure, wherein SEQ ID NO:119 is the left hand sequence and SEQ ID NO:102 is the right hand sequence:

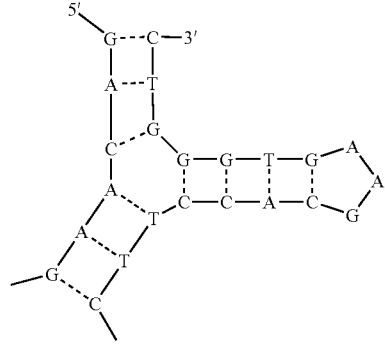

This invention further provides the instant composition, wherein the oligonucleotide comprises consecutive nucleotides having the sequence set forth in SEQ ID NO:153, wherein SEQ ID NO:153 is located 3' to SEQ ID NO:119 and 5' to SEQ ID NO:102.

This invention also provides a composition comprising an oligonucleotide which comprises consecutive nucleotides having the sequences set forth in SEQ ID NO:37 and SEQ ID NO:38, wherein SEQ ID NO:37 is located 5' to SEQ ID NO:38.

This invention further provides the instant oligonucleotide, wherein the oligonucleotide folds so that the sequences set forth in SEQ ID NO:37 and SEQ ID NO:38 contained in the oligonucleotide are arranged as set forth in the following structure, wherein SEQ ID NO:37 is the left hand sequence and SEQ ID NO:38 is the right hand sequence:

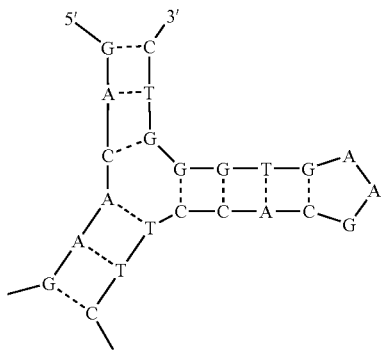

This invention further provides the instant composition, wherein the oligonucleotide comprises consecutive nucleotides having the sequence set forth in SEQ ID NO:152, wherein SEQ ID NO:152 is located 3' to SEQ ID NO:37 and 5' to SEQ ID NO:38.

This invention also provides a composition comprising an oligonucleotide which comprises consecutive nucleotides having the sequences set forth in SEQ ID NO:120 and SEQ ID NO:102, wherein SEQ ID NO:120 is located 5' to SEQ ID NO:102.

This invention further provides the instant oligonucleotide, wherein the oligonucleotide folds so that the sequences set forth in SEQ ID NO:120 and SEQ ID NO:102 contained in the oligonucleotide are arranged as set forth in the following structure, wherein SEQ ID NO:120 is the left hand sequence and SEQ ID NO:102 is the right hand sequence:

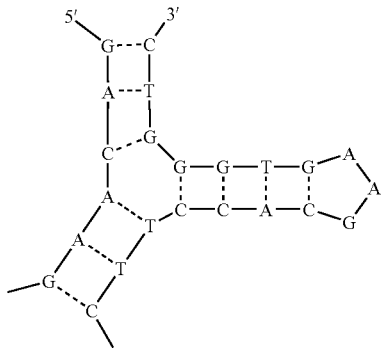

This invention further provides the instant composition, wherein the oligonucleotide comprises consecutive nucleotides having the sequence set forth in SEQ ID NO:153, wherein SEQ ID NO:153 is located 3' to SEQ ID NO:120 and 5' to SEQ ID NO:102.

This invention also provides a composition comprising an oligonucleotide which comprises consecutive nucleotides having the sequences set forth in SEQ ID NO:39 and SEQ ID NO:40, wherein SEQ ID NO:39 is located 5' to SEQ ID NO:40.

This invention further provides the instant oligonucleotide, wherein the oligonucleotide folds so that the sequences set forth in SEQ ID NO:121 and SEQ ID NO:102 contained in the oligonucleotide are arranged as set forth in the following structure, wherein SEQ ID NO:121 is the left hand sequence and SEQ ID NO:102 is the right hand sequence:

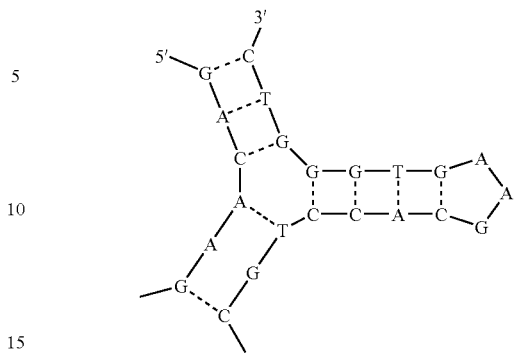

This invention further provides the instant composition, wherein the oligonucleotide comprises consecutive nucleotides having the sequence set forth in SEQ ID NO:152, wherein SEQ ID NO:152 is located 3' to SEQ ID NO:39 and 5' to SEQ ID NO:40.

This invention also provides a composition comprising an oligonucleotide which comprises consecutive nucleotides having the sequences set forth in SEQ ID NO:121 and SEQ ID NO:102, wherein SEQ ID NO:121 is located 5' to SEQ ID NO:102.

This invention further provides the instant oligonucleotide, wherein the oligonucleotide folds so that the sequences set forth in SEQ ID NO:13 and SEQ ID NO:14 contained in the oligonucleotide are arranged as set forth in the following structure, wherein SEQ ID NO:13 is the left hand sequence and SEQ ID NO:14 is the right hand sequence:

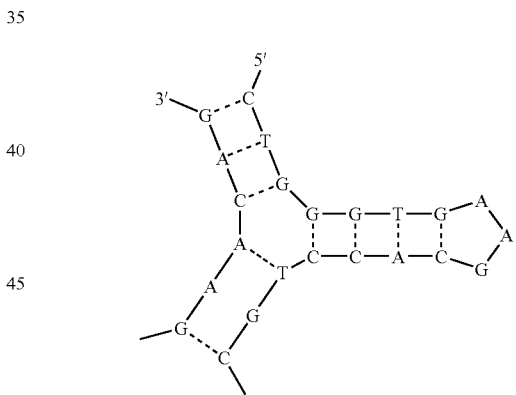

This invention further provides the instant composition, wherein the oligonucleotide comprises consecutive nucleotides having the sequence set forth in SEQ ID NO:153, wherein SEQ ID NO:153 is located 3' to SEQ ID NO:121 and 5' to SEQ ID NO:102.

This invention also provides a composition comprising an oligonucleotide which comprises consecutive nucleotides having the sequences set forth in SEQ ID NO:41 and SEQ ID NO:42, wherein SEQ ID NO:41 is located 5' to SEQ ID NO:42.

This invention further provides the instant oligonucleotide, wherein the oligonucleotide folds so that the sequences set forth in SEQ ID NO:41 and SEQ ID NO:42 contained in the oligonucleotide are arranged as set forth in the following structure, wherein SEQ ID NO:41 is the left hand sequence and SEQ ID NO:42 is the right hand sequence:

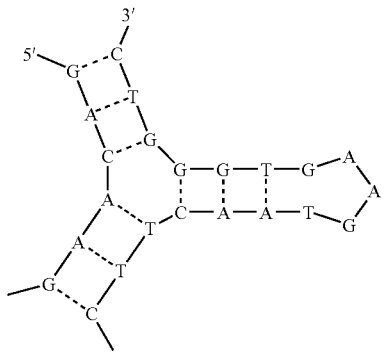

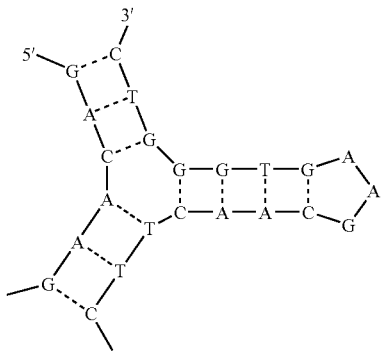

This invention further provides the instant composition, wherein the oligonucleotide comprises consecutive nucleotides having the sequence set forth in SEQ ID NO:152, wherein SEQ ID NO:152 is located 3' to SEQ ID NO:41 and 5' to SEQ ID NO:42.

This invention also provides a composition comprising an oligonucleotide which comprises consecutive nucleotides having the sequences set forth in SEQ ID NO:122 and SEQ ID NO:102, wherein SEQ ID NO:122 is located 5' to SEQ ID NO:102.

This invention further provides the instant oligonucleotide, wherein the oligonucleotide folds so that the sequences set forth in SEQ ID NO:122 and SEQ ID NO:102 contained in the oligonucleotide are arranged as set forth in the following structure, wherein SEQ ID NO:122 is the left hand sequence and SEQ ID NO:102 is the right hand sequence:

This invention further provides the instant composition, wherein the oligonucleotide comprises consecutive nucleotides having the sequence set forth in SEQ ID NO:152, wherein SEQ ID NO:152 is located 3' to SEQ ID NO:43 and 5' to SEQ ID NO:44.

This invention also provides a composition comprising an oligonucleotide which comprises consecutive nucleotides having the sequences set forth in SEQ ID NO:123 and SEQ ID NO:102, wherein SEQ ID NO:123 is located 5' to SEQ ID NO:102.

This invention further provides the instant oligonucleotide, wherein the oligonucleotide folds so that the sequences set forth in SEQ ID NO:123 and SEQ ID NO:102 contained in the oligonucleotide are arranged as set forth in the following structure, wherein SEQ ID NO:123 is the left hand sequence and SEQ ID NO:102 is the right hand sequence:

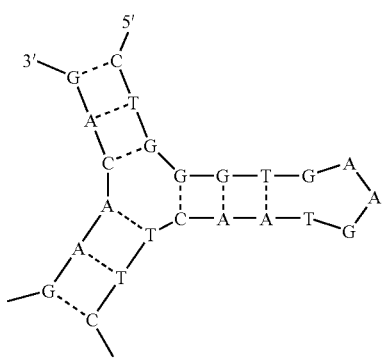

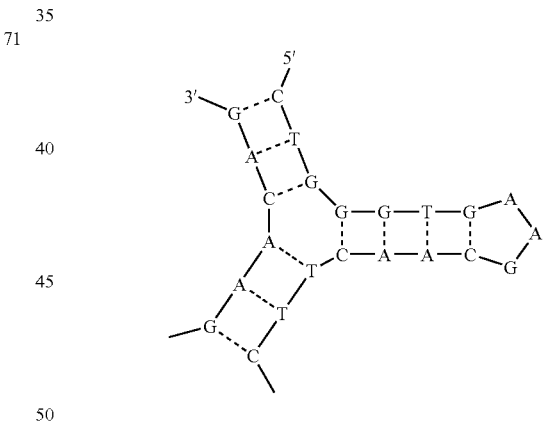

This invention further provides the instant composition, wherein the oligonucleotide comprises consecutive nucleotides having the sequence set forth in SEQ ID NO:153, wherein SEQ ID NO:153 is located 3' to SEQ ID NO:122 and 5' to SEQ ID NO:102.

This invention also provides a composition comprising an oligonucleotide which comprises consecutive nucleotides having the sequences set forth in SEQ ID NO:43 and SEQ ID NO:44, wherein SEQ ID NO:43 is located 5' to SEQ ID NO:44.

This invention further provides the instant oligonucleotide, wherein the oligonucleotide folds so that the sequences set forth in SEQ ID NO:43 and SEQ ID NO:44 contained in the oligonucleotide are arranged as set forth in the following structure, wherein SEQ ID NO:43 is the left hand sequence and SEQ ID NO:44 is the right hand sequence:

This invention further provides the instant composition, wherein the oligonucleotide comprises consecutive nucleotides having the sequence set forth in SEQ ID NO:153, wherein SEQ ID NO:153 is located 3' to SEQ ID NO:123 and 5' to SEQ ID NO:102.

This invention also provides a composition comprising an oligonucleotide which comprises consecutive nucleotides having the sequences set forth in SEQ ID NO:45 and SEQ ID NO:46, wherein SEQ ID NO:45 is located 5' to SEQ ID NO:46.

This invention further provides the instant oligonucleotide, wherein the oligonucleotide folds so that the sequences set forth in SEQ ID NO:119 and SEQ ID NO:102 contained in the oligonucleotide are arranged as set forth in the following structure, wherein SEQ ID NO:45 is the left hand sequence and SEQ ID NO:46 is the right hand sequence:

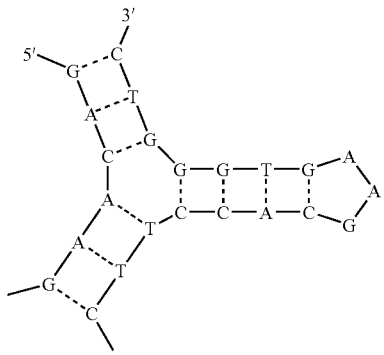

This invention further provides the instant composition, wherein the oligonucleotide comprises consecutive nucleotides having the sequence set forth in SEQ ID NO:152, wherein SEQ ID NO:152 is located 3' to SEQ ID NO:45 and 5' to SEQ ID NO:46.

This invention also provides a composition comprising an oligonucleotide which comprises consecutive nucleotides having the sequences set forth in SEQ ID NO:124 and SEQ ID NO:102, wherein SEQ ID NO:124 is located 5' to SEQ ID NO:102.

This invention further provides the instant oligonucleotide, wherein the oligonucleotide folds so that the sequences set forth in SEQ ID NO:124 and SEQ ID NO:102 contained in the oligonucleotide are arranged as set forth in the following structure, wherein SEQ ID NO:124 is the left hand sequence and SEQ ID NO:102 is the right hand sequence:

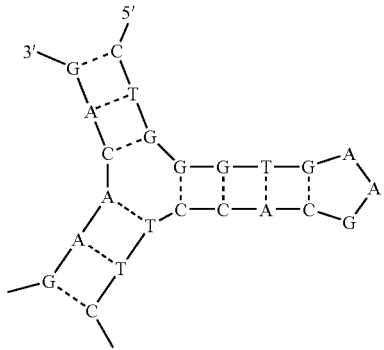

This invention further provides the instant composition, wherein the oligonucleotide comprises consecutive nucleotides having the sequence set forth in SEQ ID NO:153, wherein SEQ ID NO:153 is located 3' to SEQ ID NO:124 and 5' to SEQ ID NO:102.

This invention also provides a composition comprising an oligonucleotide which comprises consecutive nucleotides having the sequences set forth in SEQ ID NO:47 and SEQ ID NO:48, wherein SEQ ID NO:47 is located 5' to SEQ ID NO:48.

This invention further provides the instant oligonucleotide, wherein the oligonucleotide folds so that the sequences set forth in SEQ ID NO:47 and SEQ ID NO:48 contained in the oligonucleotide are arranged as set forth in the following structure, wherein SEQ ID NO:47 is the left hand sequence and SEQ ID NO:48 is the right hand sequence:

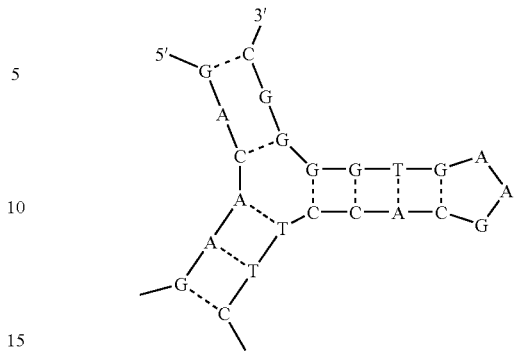

This invention further provides the instant composition, wherein the oligonucleotide comprises consecutive nucleotides having the sequence set forth in SEQ ID NO:152, wherein SEQ ID NO:152 is located 3' to SEQ ID NO:47 and 5' to SEQ ID NO:48.

This invention also provides a composition comprising an oligonucleotide which comprises consecutive nucleotides having the sequences set forth in SEQ ID NO:125 and SEQ ID NO:102, wherein SEQ ID NO:125 is located 5' to SEQ ID NO:102.

This invention further provides the instant oligonucleotide, wherein the oligonucleotide folds so that the sequences set forth in SEQ ID NO:125 and SEQ ID NO:102 contained in the oligonucleotide are arranged as set forth in the following structure, wherein SEQ ID NO:125 is the left hand sequence and SEQ ID NO:102 is the right hand sequence:

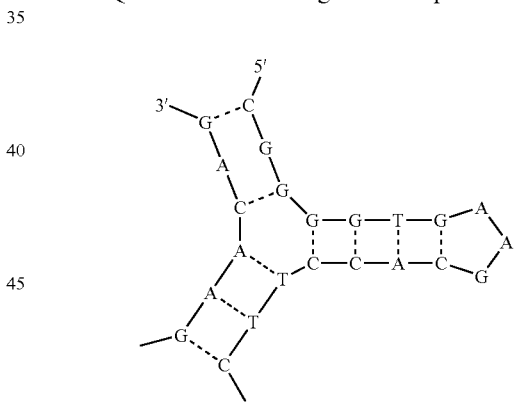

This invention further provides the instant composition, wherein the oligonucleotide comprises consecutive nucleotides having the sequence set forth in SEQ ID NO:153, wherein SEQ ID NO:153 is located 3' to SEQ ID NO:125 and 5' to SEQ ID NO:102.

This invention also provides a composition comprising an oligonucleotide which comprises consecutive nucleotides having the sequences set forth in SEQ ID NO:49 and SEQ ID NO:50, wherein SEQ ID NO:3 is located 5' to SEQ ID NO:4.

This invention further provides the instant oligonucleotide, wherein the oligonucleotide folds so that the sequences set forth in SEQ ID NO:49 and SEQ ID NO:50 contained in the oligonucleotide are arranged as set forth in the following structure, wherein SEQ ID NO:49 is the left hand sequence and SEQ ID NO:50 is the right hand sequence:

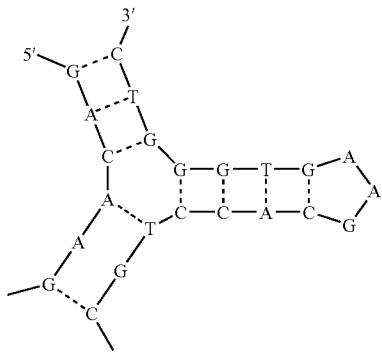

This invention further provides the instant composition, wherein the oligonucleotide comprises consecutive nucleotides having the sequence set forth in SEQ ID NO:152, wherein SEQ ID NO:152 is located 3' to SEQ ID NO:49 and 5' to SEQ ID NO:50.

This invention also provides a composition comprising an oligonucleotide which comprises consecutive nucleotides having the sequences set forth in SEQ ID NO:126 and SEQ ID NO:102, wherein SEQ ID NO:126 is located 5' to SEQ ID NO:102.

This invention further provides the instant oligonucleotide, wherein the oligonucleotide folds so that the sequences set forth in SEQ ID NO:126 and SEQ ID NO:102 contained in the oligonucleotide are arranged as set forth in the following structure, wherein SEQ ID NO:126 is the left hand sequence and SEQ ID NO:102 is the right hand sequence:

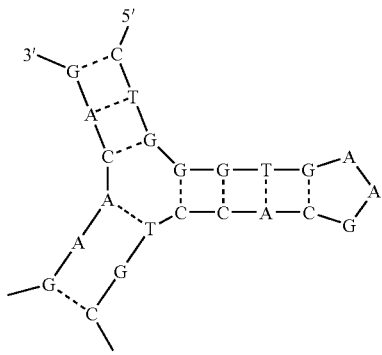

This invention further provides the instant composition, wherein the oligonucleotide comprises consecutive nucleotides having the sequence set forth in SEQ ID NO:153, wherein SEQ ID NO:153 is located 3' to SEQ ID NO:126 and 5' to SEQ ID NO:102.

This invention also provides a composition comprising an oligonucleotide which comprises consecutive nucleotides having the sequences set forth in SEQ ID NO:51 and SEQ ID NO:52, wherein SEQ ID NO:51 is located 5' to SEQ ID NO:52.

This invention further provides the instant oligonucleotide, wherein the oligonucleotide folds so that the sequences set forth in SEQ ID NO:51 and SEQ ID NO:52 contained in the oligonucleotide are arranged as set forth in the following structure, wherein SEQ ID NO:51 is the left hand sequence and SEQ ID NO:52 is the right hand sequence:

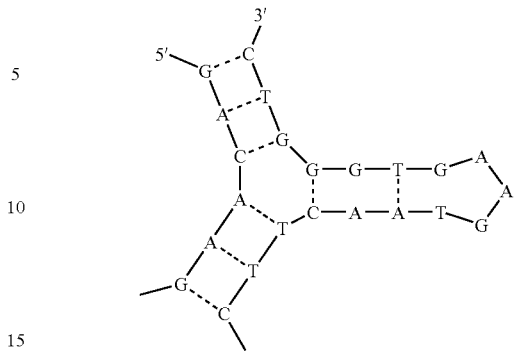

This invention further provides the instant composition, wherein the oligonucleotide comprises consecutive nucleotides having the sequence set forth in SEQ ID NO:152, wherein SEQ ID NO:152 is located 3' to SEQ ID NO:51 and 5' to SEQ ID NO:52.

This invention also provides a composition comprising an oligonucleotide which comprises consecutive nucleotides having the sequences set forth in SEQ ID NO:127 and SEQ ID NO:102, wherein SEQ ID NO:127 is located 5' to SEQ ID NO:102.

This invention further provides the instant oligonucleotide, wherein the oligonucleotide folds so that the sequences set forth in SEQ ID NO:127 and SEQ ID NO:102 contained in the oligonucleotide are arranged as set forth in the following structure, wherein SEQ ID NO:127 is the left hand sequence and SEQ ID NO:102 is the right hand sequence:

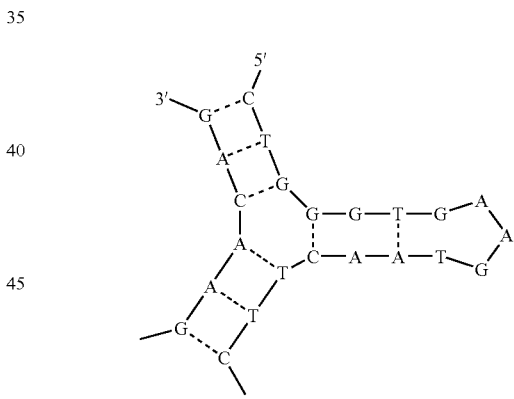

This invention further provides the instant composition, wherein the oligonucleotide comprises consecutive nucleotides having the sequence set forth in SEQ ID NO:153, wherein SEQ ID NO:153 is located 3' to SEQ ID NO:127 and 5' to SEQ ID NO:102.

This invention also provides a composition comprising an oligonucleotide which comprises consecutive nucleotides having the sequences set forth in SEQ ID NO:53 and SEQ ID NO:54, wherein SEQ ID NO:53 is located 5' to SEQ ID NO:54.

This invention further provides the instant oligonucleotide, wherein the oligonucleotide folds so that the sequences set forth in SEQ ID NO:53 and SEQ ID NO:5554 contained in the oligonucleotide are arranged as set forth in the following structure, wherein SEQ ID NO:53 is the left hand sequence and SEQ ID NO:55 is the right hand sequence:

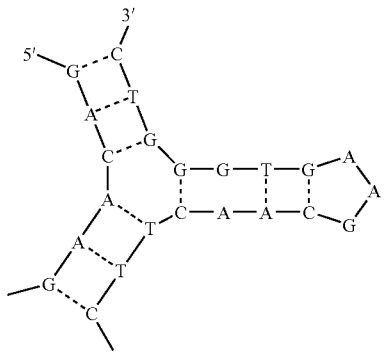

This invention further provides the instant composition, wherein the oligonucleotide comprises consecutive nucleotides having the sequence set forth in SEQ ID NO:152, wherein SEQ ID NO:152 is located 3' to SEQ ID NO:53 and 5' to SEQ ID NO:54.

This invention also provides a composition comprising an oligonucleotide which comprises consecutive nucleotides having the sequences set forth in SEQ ID NO:128 and SEQ ID NO:102, wherein SEQ ID NO:128 is located 5' to SEQ ID NO:102.

This invention further provides the instant oligonucleotide, wherein the oligonucleotide folds so that the sequences set forth in SEQ ID NO:128 and SEQ ID NO:102 contained in the oligonucleotide are arranged as set forth in the following structure, wherein SEQ ID NO:128 is the left hand sequence and SEQ ID NO:102 is the right hand sequence:

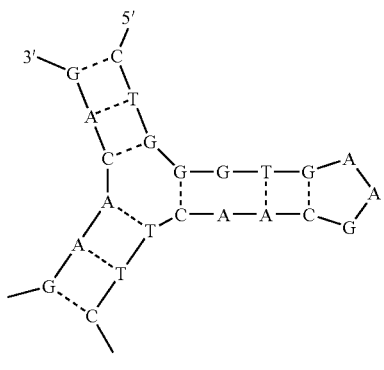

This invention further provides the instant composition, wherein the oligonucleotide comprises consecutive nucleotides having the sequence set forth in SEQ ID NO:153, wherein SEQ ID NO:153 is located 3' to SEQ ID NO:128 and 5' to SEQ ID NO:102.

This invention also provides a composition comprising an oligonucleotide which comprises consecutive nucleotides having the sequences set forth in SEQ ID NO:55 and SEQ ID NO:56, wherein SEQ ID NO:55 is located 5' to SEQ ID NO:56.

This invention further provides the instant oligonucleotide, wherein the oligonucleotide folds so that the sequences set forth in SEQ ID NO:55 and SEQ ID NO:56 contained in the oligonucleotide are arranged as set forth in the following structure, wherein SEQ ID NO:55 is the left hand sequence and SEQ ID NO:56 is the right hand sequence:

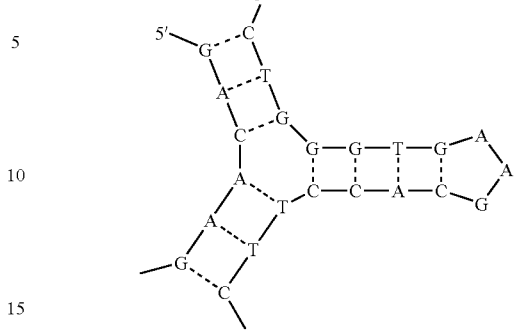

This invention further provides the instant composition, wherein the oligonucleotide comprises consecutive nucleotides having the sequence set forth in SEQ ID NO:152, wherein SEQ ID NO:152 is located 3' to SEQ ID NO:55 and 5' to SEQ ID NO:56.

This invention also provides a composition comprising an oligonucleotide which comprises consecutive nucleotides having the sequences set forth in SEQ ID NO:129 and SEQ ID NO:102, wherein SEQ ID NO:129 is located 5' to SEQ ID NO:102.

This invention further provides the instant oligonucleotide, wherein the oligonucleotide folds so that the sequences set forth in SEQ ID NO:129 and SEQ ID NO:102 contained in the oligonucleotide are arranged as set forth in the following structure, wherein SEQ ID NO:129 is the left hand sequence and SEQ ID NO:102 is the right hand sequence:

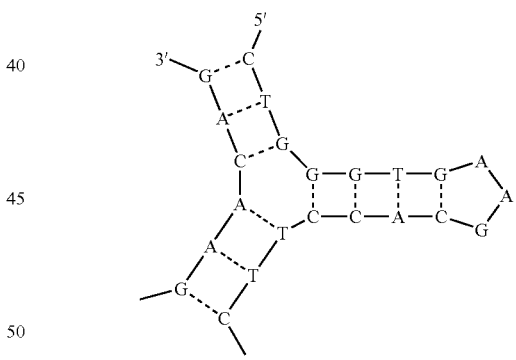

This invention further provides the instant composition, wherein the oligonucleotide comprises consecutive nucleotides having the sequence set forth in SEQ ID NO:153, wherein SEQ ID NO:153 is located 3' to SEQ ID NO:129 and 5' to SEQ ID NO:102.

This invention also provides a composition comprising an oligonucleotide which comprises consecutive nucleotides having the sequences set forth in SEQ ID NO:57 and SEQ ID NO:58, wherein SEQ ID NO:57 is located 5' to SEQ ID NO:58.

This invention further provides the instant oligonucleotide, wherein the oligonucleotide folds so that the sequences set forth in SEQ ID NO:57 and SEQ ID NO:58

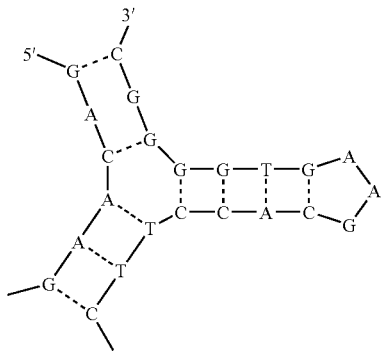

This invention further provides the instant composition, wherein the oligonucleotide comprises consecutive nucleotides having the sequence set forth in SEQ ID NO:152, wherein SEQ ID NO:152 is located 3' to SEQ ID NO:57 and 5' to SEQ ID NO:58.

This invention also provides a composition comprising an oligonucleotide which comprises consecutive nucleotides having the sequences set forth in SEQ ID NO:130 and SEQ ID NO:102, wherein SEQ ID NO:130 is located 5' to SEQ ID NO:102.

This invention further provides the instant oligonucleotide, wherein the oligonucleotide folds so that the sequences set forth in SEQ ID NO:130 and SEQ ID NO:102 contained in the oligonucleotide are arranged as set forth in the following structure, wherein SEQ ID NO:130 is the left hand sequence and SEQ ID NO:102 is the right hand sequence:

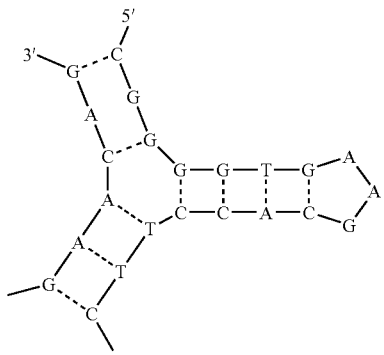

This invention further provides the instant composition, wherein the oligonucleotide comprises consecutive nucleotides having the sequence set forth in SEQ ID NO:153, wherein SEQ ID NO:153 is located 3' to SEQ ID NO:130 and 5' to SEQ ID NO:102.

This invention also provides a composition comprising an oligonucleotide which comprises consecutive nucleotides having the sequences set forth in SEQ ID NO:59 and SEQ ID NO:60, wherein SEQ ID NO:59 is located 5' to SEQ ID NO:60.

This invention further provides the instant oligonucleotide, wherein the oligonucleotide folds so that the sequences set forth in SEQ ID NO:59 and SEQ ID NO:60 contained in the oligonucleotide are arranged as set forth in the following structure, wherein SEQ ID NO:59 is the left hand sequence and SEQ ID NO:60 is the right hand sequence:

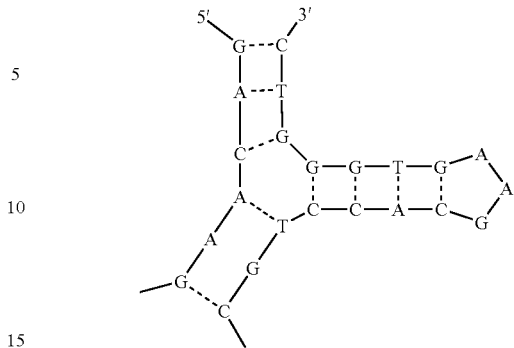

This invention further provides the instant composition, wherein the oligonucleotide comprises consecutive nucleotides having the sequence set forth in SEQ ID NO:152, wherein SEQ ID NO:152 is located 3' to SEQ ID NO:59 and 5' to SEQ ID NO:60.

This invention also provides a composition comprising an oligonucleotide which comprises consecutive nucleotides having the sequences set forth in SEQ ID NO:131 and SEQ ID NO:102, wherein SEQ ID NO:131 is located 5' to SEQ ID NO:102.

This invention further provides the instant oligonucleotide, wherein the oligonucleotide folds so that the sequences set forth in SEQ ID NO:131 and SEQ ID NO:102 contained in the oligonucleotide are arranged as set forth in the following structure, wherein SEQ ID NO:131 is the left hand sequence and SEQ ID NO:102 is the right hand sequence:

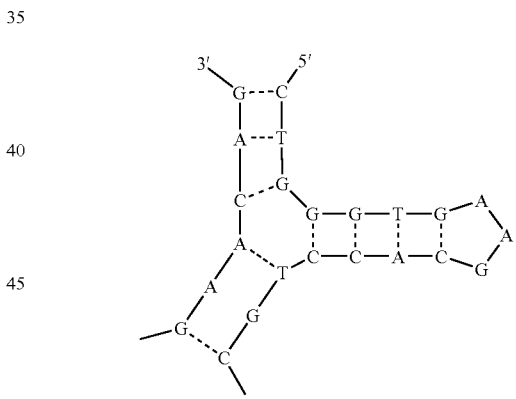

This invention further provides the instant composition, wherein the oligonucleotide comprises consecutive nucleotides having the sequence set forth in SEQ ID NO:153, wherein SEQ ID NO:153 is located 3' to SEQ ID NO:131 and 5' to SEQ ID NO:102.

This invention also provides a composition comprising an oligonucleotide which comprises consecutive nucleotides having the sequences set forth in SEQ ID NO:61 and SEQ ID NO:62, wherein SEQ ID NO:61 is located 5' to SEQ ID NO:62.

This invention further provides the instant oligonucleotide, wherein the oligonucleotide folds so that the sequences set forth in SEQ ID NO:61 and SEQ ID NO:62 contained in the oligonucleotide are arranged as set forth in the following structure, wherein SEQ ID NO:61 is the left hand sequence and SEQ ID NO:62 is the right hand sequence:

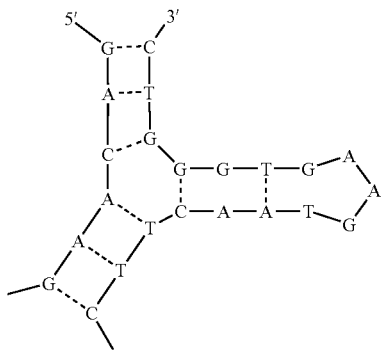

This invention further provides the instant composition, wherein the oligonucleotide comprises consecutive nucleotides having the sequence set forth in SEQ ID NO:152, wherein SEQ ID NO:152 is located 3' to SEQ ID NO:61 and 5' to SEQ ID NO:62.

This invention also provides a composition comprising an oligonucleotide which comprises consecutive nucleotides having the sequences set forth in SEQ ID NO:132 and SEQ ID NO:102, wherein SEQ ID NO:132 is located 5' to SEQ ID NO:102.

This invention further provides the instant oligonucleotide, wherein the oligonucleotide folds so that the sequences set forth in SEQ ID NO:132 and SEQ ID NO:102 contained in the oligonucleotide are arranged as set forth in the following structure, wherein SEQ ID NO:132 is the left hand sequence and SEQ ID NO:102 is the right hand sequence:

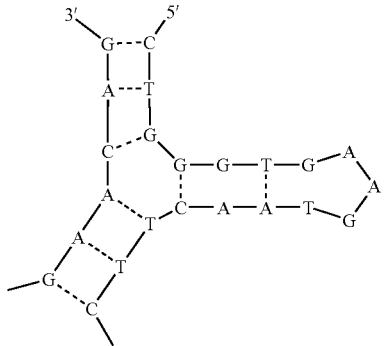

This invention further provides the instant composition, wherein the oligonucleotide comprises consecutive nucleotides having the sequence set forth in SEQ ID NO:153, wherein SEQ ID NO:153 is located 3' to SEQ ID NO:132 and 5' to SEQ ID NO:102.

This invention also provides a composition comprising an oligonucleotide which comprises consecutive nucleotides having the sequences set forth in SEQ ID NO:63 and SEQ ID NO:64, wherein SEQ ID NO:63 is located 5' to SEQ ID NO:64.

This invention further provides the instant oligonucleotide, wherein the oligonucleotide folds so that the sequences set forth in SEQ ID NO:63 and SEQ ID NO:64 contained in the oligonucleotide are arranged as set forth in the following structure, wherein SEQ ID NO:63 is the left hand sequence and SEQ ID NO:642 is the right hand sequence:

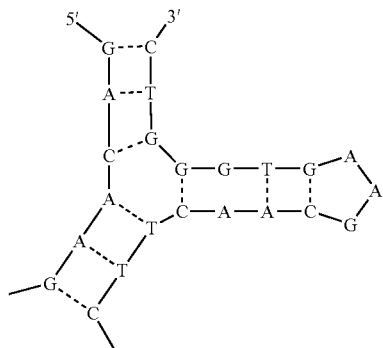

This invention further provides the instant composition, wherein the oligonucleotide comprises consecutive nucleotides having the sequence set forth in SEQ ID NO:152, wherein SEQ ID NO:152 is located 3' to SEQ ID NO:63 and 5' to SEQ ID NO:64.

This invention also provides a composition comprising an oligonucleotide which comprises consecutive nucleotides having the sequences set forth in SEQ ID NO:133 and SEQ ID NO:102, wherein SEQ ID NO:133 is located 5' to SEQ ID NO:102.

This invention further provides the instant oligonucleotide, wherein the oligonucleotide folds so that the sequences set forth in SEQ ID NO:133 and SEQ ID NO:102 contained in the oligonucleotide are arranged as set forth in the following structure, wherein SEQ ID NO:133 is the left hand sequence and SEQ ID NO:102 is the right hand sequence:

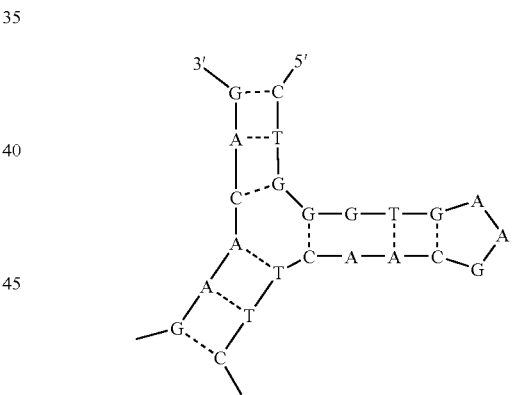

This invention further provides the instant composition, wherein the oligonucleotide comprises consecutive nucleotides having the sequence set forth in SEQ ID NO:153, wherein SEQ ID NO:153 is located 3' to SEQ ID NO:133 and 5' to SEQ ID NO:102.

This invention also provides a composition comprising an oligonucleotide which comprises consecutive nucleotides having the sequences set forth in SEQ ID NO:65 and SEQ ID NO:66, wherein SEQ ID NO:61 is located 5' to SEQ ID NO:62.

This invention further provides the instant oligonucleotide, wherein the oligonucleotide folds so that the sequences set forth in SEQ ID NO:65 and SEQ ID NO:66 contained in the oligonucleotide are arranged as set forth in the following structure, wherein SEQ ID NO:65 is the left hand sequence and SEQ ID NO:66 is the right hand sequence:

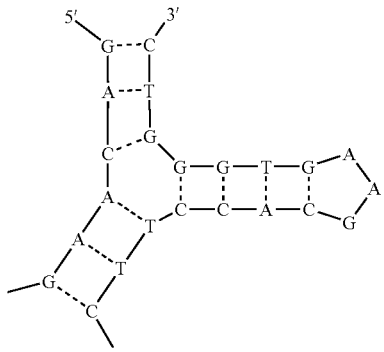

This invention further provides the instant composition, wherein the oligonucleotide comprises consecutive nucleotides having the sequence set forth in SEQ ID NO:152, wherein SEQ ID NO:152 is located 3' to SEQ ID NO:65 and 5' to SEQ ID NO:66.

This invention also provides a composition comprising an oligonucleotide which comprises consecutive nucleotides having the sequences set forth in SEQ ID NO:134 and SEQ ID NO:102, wherein SEQ ID NO:134 is located 5' to SEQ ID NO:102.

This invention further provides the instant oligonucleotide, wherein the oligonucleotide folds so that the sequences set forth in SEQ ID NO:134 and SEQ ID NO:102 contained in the oligonucleotide are arranged as set forth in the following structure, wherein SEQ ID NO:134 is the left hand sequence and SEQ ID NO:102 is the right hand sequence:

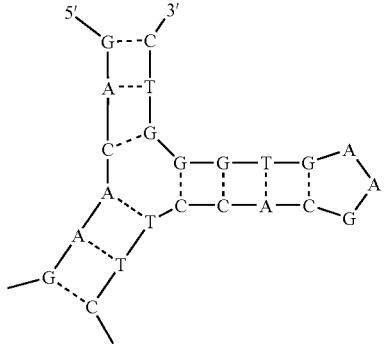

This invention further provides the instant composition, wherein the oligonucleotide comprises consecutive nucleotides having the sequence set forth in SEQ ID NO:153, wherein SEQ ID NO:153 is located 3' to SEQ ID NO:134 and 5' to SEQ ID NO:102.

This invention also provides a composition comprising an oligonucleotide which comprises consecutive nucleotides having the sequences set forth in SEQ ID NO:67 and SEQ ID NO:68, wherein SEQ ID NO:67 is located 5' to SEQ ID NO:68.

This invention further provides the instant oligonucleotide, wherein the oligonucleotide folds so that the sequences set forth in SEQ ID NO:67 and SEQ ID NO:68 contained in the oligonucleotide are arranged as set forth in the following structure, wherein SEQ ID NO:67 is the left hand sequence and SEQ ID NO:68 is the right hand sequence:

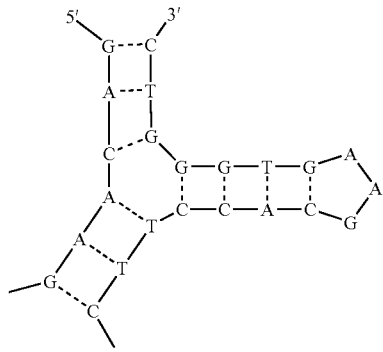

This invention further provides the instant composition, wherein the oligonucleotide comprises consecutive nucleotides having the sequence set forth in SEQ ID NO:152, wherein SEQ ID NO:152 is located 3' to SEQ ID NO:67 and 5' to SEQ ID NO:68.

This invention also provides a composition comprising an oligonucleotide which comprises consecutive nucleotides having the sequences set forth in SEQ ID NO:135 and SEQ ID NO:102, wherein SEQ ID NO:135 is located 5' to SEQ ID NO:102.

This invention further provides the instant oligonucleotide, wherein the oligonucleotide folds so that the sequences set forth in SEQ ID NO:135 and SEQ ID NO:102 contained in the oligonucleotide are arranged as set forth in the following structure, wherein SEQ ID NO:135 is the left hand sequence and SEQ ID NO:102 is the right hand sequence:

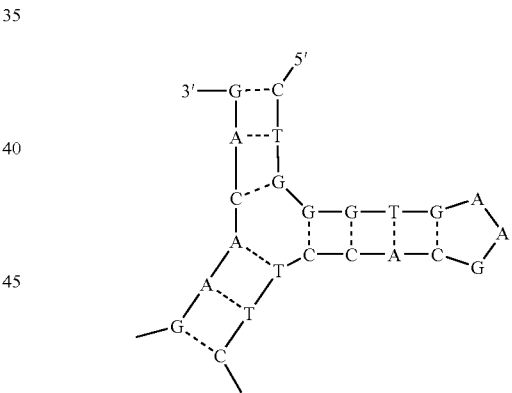

This invention further provides the instant composition, wherein the oligonucleotide comprises consecutive nucleotides having the sequence set forth in SEQ ID NO:153, wherein SEQ ID NO:153 is located 3' to SEQ ID NO:135 and 5' to SEQ ID NO:102.

This invention also provides a composition comprising an oligonucleotide which comprises consecutive nucleotides having the sequences set forth in SEQ ID NO:69 and SEQ ID NO:70, wherein SEQ ID NO:69 is located 5' to SEQ ID NO:70.

This invention further provides the instant oligonucleotide, wherein the oligonucleotide folds so that the sequences set forth in SEQ ID NO:69 and SEQ ID NO:70 contained in the oligonucleotide are arranged as set forth in the following structure, wherein SEQ ID NO:69 is the left hand sequence and SEQ ID NO:70 is the right hand sequence:

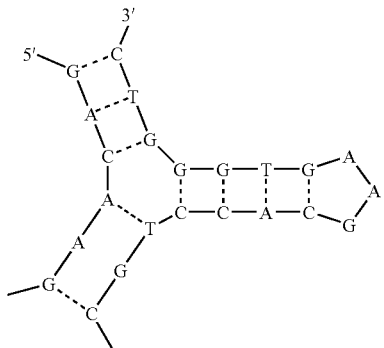

This invention further provides the instant composition, wherein the oligonucleotide comprises consecutive nucleotides having the sequence set forth in SEQ ID NO:152, wherein SEQ ID NO:152 is located 3' to SEQ ID NO:69 and 5' to SEQ ID NO:70.

This invention also provides a composition comprising an oligonucleotide which comprises consecutive nucleotides having the sequences set forth in SEQ ID NO:136 and SEQ ID NO:102, wherein SEQ ID NO:136 is located 5' to SEQ ID NO:102.

This invention further provides the instant oligonucleotide, wherein the oligonucleotide folds so that the sequences set forth in SEQ ID NO:136 and SEQ ID NO:102 contained in the oligonucleotide are arranged as set forth in the following structure, wherein SEQ ID NO:136 is the left hand sequence and SEQ ID NO:102 is the right hand sequence:

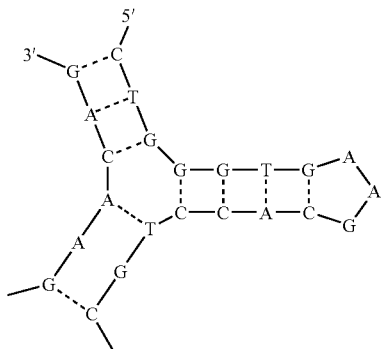

This invention further provides the instant composition, wherein the oligonucleotide comprises consecutive nucleotides having the sequence set forth in SEQ ID NO:153, wherein SEQ ID NO:153 is located 3' to SEQ ID NO:136 and 5' to SEQ ID NO:102.

This invention also provides a composition comprising an oligonucleotide which comprises consecutive nucleotides having the sequences set forth in SEQ ID NO:71 and SEQ ID NO:72, wherein SEQ ID NO:71 is located 5' to SEQ ID NO:72.

This invention further provides the instant oligonucleotide, wherein the oligonucleotide folds so that the sequences set forth in SEQ ID NO:71 and SEQ ID NO:72 contained in the oligonucleotide are arranged as set forth in the following structure, wherein SEQ ID NO:72 is the left hand sequence and SEQ ID NO:72 is the right hand sequence:

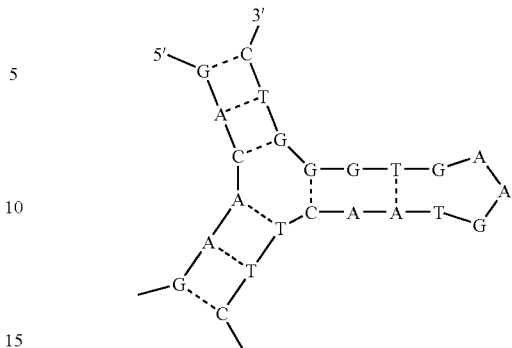

This invention further provides the instant composition, wherein the oligonucleotide comprises consecutive nucleotides having the sequence set forth in SEQ ID NO:152, wherein SEQ ID NO:152 is located 3' to SEQ ID NO:71 and 5' to SEQ ID NO:72.

This invention also provides a composition comprising an oligonucleotide which comprises consecutive nucleotides having the sequences set forth in SEQ ID NO:137 and SEQ ID NO:102, wherein SEQ ID NO:137 is located 5' to SEQ ID NO:102.

This invention further provides the instant oligonucleotide, wherein the oligonucleotide folds so that the sequences set forth in SEQ ID NO:137 and SEQ ID NO:102 contained in the oligonucleotide are arranged as set forth in the following structure, wherein SEQ ID NO:137 is the left hand sequence and SEQ ID NO:102 is the right hand sequence:

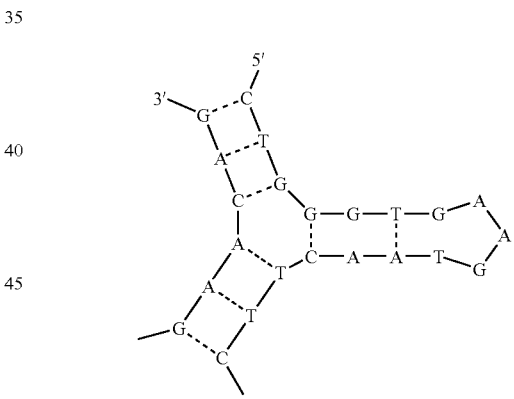

This invention further provides the instant composition, wherein the oligonucleotide comprises consecutive nucleotides having the sequence set forth in SEQ ID NO:153, wherein SEQ ID NO:153 is located 3' to SEQ ID NO:137 and 5' to SEQ ID NO:102.

This invention also provides a composition comprising an oligonucleotide which comprises consecutive nucleotides having the sequences set forth in SEQ ID NO:73 and SEQ ID NO:74, wherein SEQ ID NO:73 is located 5' to SEQ ID NO:74.

This invention further provides the instant oligonucleotide, wherein the oligonucleotide folds so that the sequences set forth in SEQ ID NO:73 and SEQ ID NO:74 contained in the oligonucleotide are arranged as set forth in the following structure, wherein SEQ ID NO:73 is the left hand sequence and SEQ ID NO:74 is the right hand sequence:

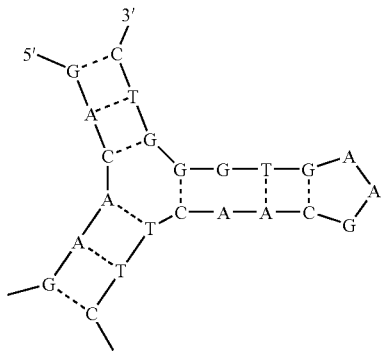

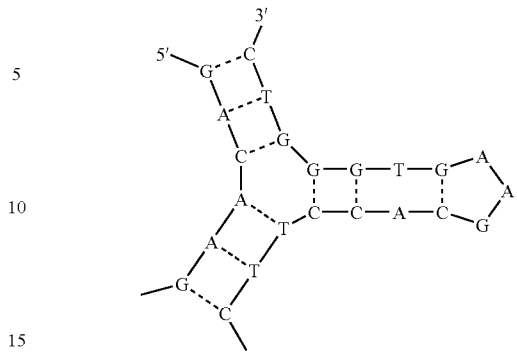

This invention further provides the instant composition, wherein the oligonucleotide comprises consecutive nucleotides having the sequence set forth in SEQ ID NO:152, wherein SEQ ID NO:152 is located 3' to SEQ ID NO:73 and 5' to SEQ ID NO:74.

This invention also provides a composition comprising an oligonucleotide which comprises consecutive nucleotides having the sequences set forth in SEQ ID NO:138 and SEQ ID NO:102, wherein SEQ ID NO:138 is located 5' to SEQ ID NO:102.

This invention further provides the instant oligonucleotide, wherein the oligonucleotide folds so that the sequences set forth in SEQ ID NO:138 and SEQ ID NO:102 contained in the oligonucleotide are arranged as set forth in the following structure, wherein SEQ ID NO:138 is the left hand sequence and SEQ ID NO:102 is the right hand sequence:

This invention further provides the instant composition, wherein the oligonucleotide comprises consecutive nucleotides having the sequence set forth in SEQ ID NO:152, wherein SEQ ID NO:152 is located 3' to SEQ ID NO:75 and 5' to SEQ ID NO:76.

This invention also provides a composition comprising an oligonucleotide which comprises consecutive nucleotides having the sequences set forth in SEQ ID NO:139 and SEQ ID NO:102, wherein SEQ ID NO:139 is located 5' to SEQ ID NO:102.

This invention further provides the instant oligonucleotide, wherein the oligonucleotide folds so that the sequences set forth in SEQ ID NO:139 and SEQ ID NO:102 contained in the oligonucleotide are arranged as set forth in the following structure, wherein SEQ ID NO:139 is the left hand sequence and SEQ ID NO:102 is the right hand sequence:

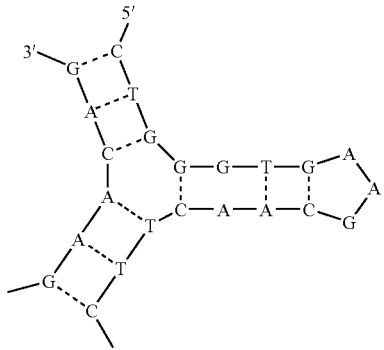

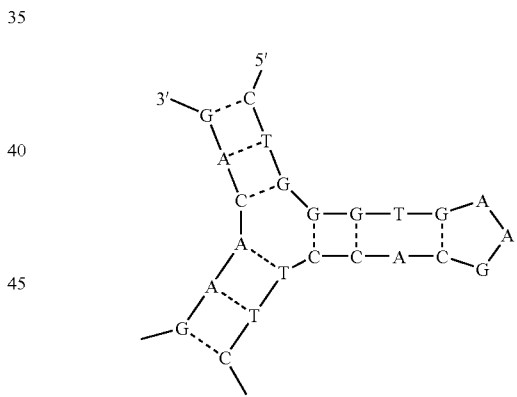

This invention further provides the instant composition, wherein the oligonucleotide comprises consecutive nucleotides having the sequence set forth in SEQ ID NO:153, wherein SEQ ID NO:153 is located 3' to SEQ ID NO:138 and 5' to SEQ ID NO:102.

This invention also provides a composition comprising an oligonucleotide which comprises consecutive nucleotides having the sequences set forth in SEQ ID NO:75 and SEQ ID NO:76, wherein SEQ ID NO:75 is located 5' to SEQ ID NO:76.

This invention further provides the instant oligonucleotide, wherein the oligonucleotide folds so that the sequences set forth in SEQ ID NO:75 and SEQ ID NO:76 contained in the oligonucleotide are arranged as set forth in the following structure, wherein SEQ ID NO:75 is the left hand sequence and SEQ ID NO:76 is the right hand sequence:

This invention further provides the instant composition, wherein the oligonucleotide comprises consecutive nucleotides having the sequence set forth in SEQ ID NO:153, wherein SEQ ID NO:153 is located 3' to SEQ ID NO:139 and 5' to SEQ ID NO:102.

This invention also provides a composition comprising an oligonucleotide which comprises consecutive nucleotides having the sequences set forth in SEQ ID NO:77 and SEQ ID NO:78, wherein SEQ ID NO:77 is located 5' to SEQ ID NO:78.

This invention further provides the instant oligonucleotide, wherein the oligonucleotide folds so that the sequences set forth in SEQ ID NO:77 and SEQ ID NO:78 contained in the oligonucleotide are arranged as set forth in the following structure, wherein SEQ ID NO:77 is the left hand sequence and SEQ ID NO:78 is the right hand sequence:

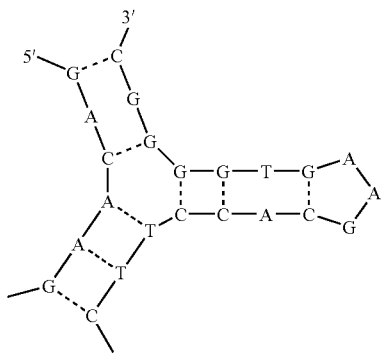

This invention further provides the instant composition, wherein the oligonucleotide comprises consecutive nucleotides having the sequence set forth in SEQ ID NO:152, wherein SEQ ID NO:152 is located 3' to SEQ ID NO:77 and 5' to SEQ ID NO:78.

This invention also provides a composition comprising an oligonucleotide which comprises consecutive nucleotides having the sequences set forth in SEQ ID NO:140 and SEQ ID NO:102, wherein SEQ ID NO:140 is located 5' to SEQ ID NO:102.

This invention further provides the instant oligonucleotide, wherein the oligonucleotide folds so that the sequences set forth in SEQ ID NO:140 and SEQ ID NO:102 contained in the oligonucleotide are arranged as set forth in the following structure, wherein SEQ ID NO:140 is the left hand sequence and SEQ ID NO:102 is the right hand sequence:

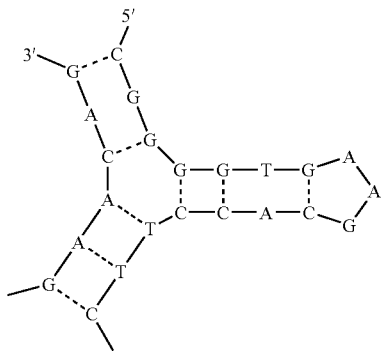

This invention further provides the instant composition, wherein the oligonucleotide comprises consecutive nucleotides having the sequence set forth in SEQ ID NO:153, wherein SEQ ID NO:153 is located 3' to SEQ ID NO:140 and 5' to SEQ ID NO:102.

This invention also provides a composition comprising an oligonucleotide which comprises consecutive nucleotides having the sequences set forth in SEQ ID NO:79 and SEQ ID NO:80, wherein SEQ ID NO:79 is located 5' to SEQ ID NO:80.

This invention further provides the instant oligonucleotide, wherein the oligonucleotide folds so that the sequences set forth in SEQ ID NO:79 and SEQ ID NO:80 contained in the oligonucleotide are arranged as set forth in the following structure, wherein SEQ ID NO:79 is the left hand sequence and SEQ ID NO:80 is the right hand sequence:

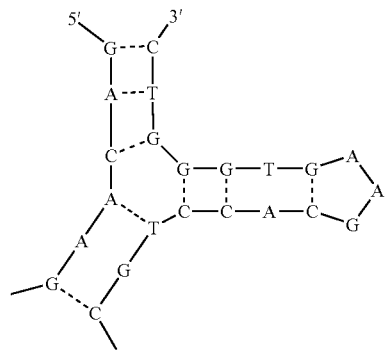

This invention further provides the instant composition, wherein the oligonucleotide comprises consecutive nucleotides having the sequence set forth in SEQ ID NO:152, wherein SEQ ID NO:152 is located 3' to SEQ ID NO:79 and 5' to SEQ ID NO:80.

This invention also provides a composition comprising an oligonucleotide which comprises consecutive nucleotides having the sequences set forth in SEQ ID NO:141 and SEQ ID NO:102, wherein SEQ ID NO:141 is located 5' to SEQ ID NO:102.

This invention further provides the instant oligonucleotide, wherein the oligonucleotide folds so that the sequences set forth in SEQ ID NO:141 and SEQ ID NO:102 contained in the oligonucleotide are arranged as set forth in the following structure, wherein SEQ ID NO:141 is the left hand sequence and SEQ ID NO:102 is the right hand sequence:

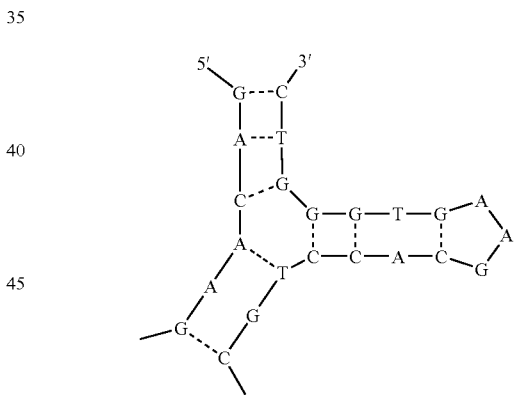

This invention further provides the instant composition, wherein the oligonucleotide comprises consecutive nucleotides having the sequence set forth in SEQ ID NO:153, wherein SEQ ID NO:153 is located 3' to SEQ ID NO:141 and 5' to SEQ ID NO:102.

This invention also provides a composition comprising an oligonucleotide which comprises consecutive nucleotides having the sequences set forth in SEQ ID NO:81 and SEQ ID NO:82, wherein SEQ ID NO:81 is located 5' to SEQ ID NO:82.

This invention further provides the instant oligonucleotide, wherein the oligonucleotide folds so that the sequences set forth in SEQ ID NO:81 and SEQ ID NO:82 contained in the oligonucleotide are arranged as set forth in the following structure, wherein SEQ ID NO:81 is the left hand sequence and SEQ ID NO:82 is the right hand sequence:

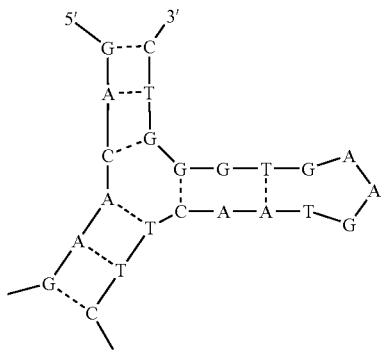

This invention further provides the instant composition, wherein the oligonucleotide comprises consecutive nucleotides having the sequence set forth in SEQ ID NO:152, wherein SEQ ID NO:152 is located 3' to SEQ ID NO:81 and 5' to SEQ ID NO:82.

This invention also provides a composition comprising an oligonucleotide which comprises consecutive nucleotides having the sequences set forth in SEQ ID NO:142 and SEQ ID NO:102, wherein SEQ ID NO:142 is located 5' to SEQ ID NO:102.

This invention further provides the instant oligonucleotide, wherein the oligonucleotide folds so that the sequences set forth in SEQ ID NO:142 and SEQ ID NO:102 contained in the oligonucleotide are arranged as set forth in the following structure, wherein SEQ ID NO:142 is the left hand sequence and SEQ ID NO:102 is the right hand sequence:

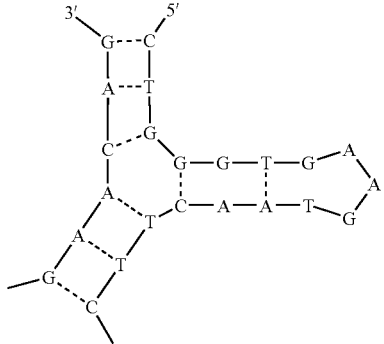

This invention further provides the instant composition, wherein the oligonucleotide comprises consecutive nucleotides having the sequence set forth in SEQ ID NO:153, wherein SEQ ID NO:153 is located 3' to SEQ ID NO:142 and 5' to SEQ ID NO:102.

This invention also provides a composition comprising an oligonucleotide which comprises consecutive nucleotides having the sequences set forth in SEQ ID NO:83 and SEQ ID NO:84, wherein SEQ ID NO:83 is located 5' to SEQ ID NO:84.

This invention further provides the instant oligonucleotide, wherein the oligonucleotide folds so that the sequences set forth in SEQ ID NO:83 and SEQ ID NO:84 contained in the oligonucleotide are arranged as set forth in the following structure, wherein SEQ ID NO:83 is the left hand sequence and SEQ ID NO:84 is the right hand sequence:

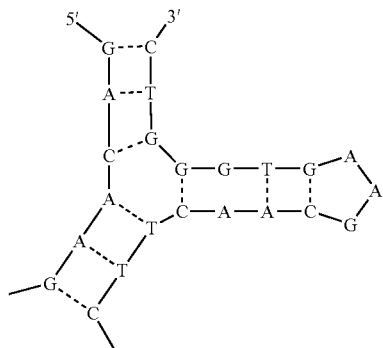

This invention further provides the instant composition, wherein the oligonucleotide comprises consecutive nucleotides having the sequence set forth in SEQ ID NO:152, wherein SEQ ID NO:152 is located 3' to SEQ ID NO:83 and 5' to SEQ ID NO:84.

This invention also provides a composition comprising an oligonucleotide which comprises consecutive nucleotides having the sequences set forth in SEQ ID NO:143 and SEQ ID NO:102, wherein SEQ ID NO:143 is located 5' to SEQ ID NO:102.

This invention further provides the instant oligonucleotide, wherein the oligonucleotide folds so that the sequences set forth in SEQ ID NO:143 and SEQ ID NO:102 contained in the oligonucleotide are arranged as set forth in the following structure, wherein SEQ ID NO:143 is the left hand sequence and SEQ ID NO:102 is the right hand sequence:

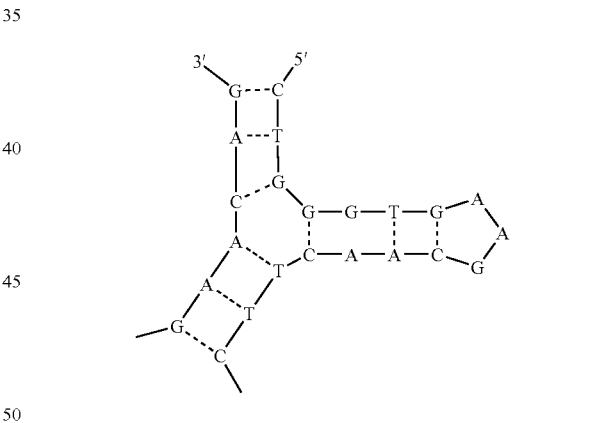

This invention further provides the instant composition, wherein the oligonucleotide comprises consecutive nucleotides having the sequence set forth in SEQ ID NO:153, wherein SEQ ID NO:153 is located 3' to SEQ ID NO:143 and 5' to SEQ ID NO:102.

This invention also provides a composition comprising an oligonucleotide which comprises consecutive nucleotides having the sequences set forth in SEQ ID NO:85 and SEQ ID NO:86, wherein SEQ ID NO:85 is located 5' to SEQ ID NO:86.

This invention further provides the instant oligonucleotide, wherein the oligonucleotide folds so that the sequences set forth in SEQ ID NO:85 and SEQ ID NO:86 contained in the oligonucleotide are arranged as set forth in the following structure, wherein SEQ ID NO:85 is the left hand sequence and SEQ ID NO:86 is the right hand sequence:

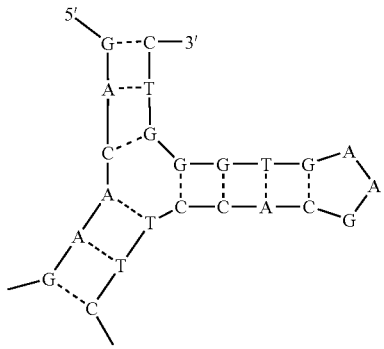

This invention further provides the instant composition, wherein the oligonucleotide comprises consecutive nucleotides having the sequence set forth in SEQ ID NO:152, wherein SEQ ID NO:152 is located 3' to SEQ ID NO:85 and 5' to SEQ ID NO:86.

This invention further provides the instant oligonucleotide, wherein the oligonucleotide folds so that the sequences set forth in SEQ ID NO:144 and SEQ ID NO:102 contained in the oligonucleotide are arranged as set forth in the following structure, wherein SEQ ID NO:144 is the left hand sequence and SEQ ID NO:102 is the right hand sequence:

This invention further provides the instant composition, wherein the oligonucleotide folds so that the sequences set forth in SEQ ID NO:144 and SEQ ID NO:102 contained in the oligonucleotide are arranged as set forth in the following structure:

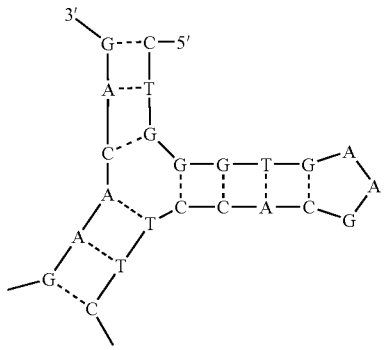

This invention further provides the instant composition, wherein the oligonucleotide comprises consecutive nucleotides having the sequence set forth in SEQ ID NO:153, wherein SEQ ID NO:153 is located 3' to SEQ ID NO:144 and 5' to SEQ ID NO:102.

This invention also provides a composition comprising an oligonucleotide which comprises consecutive nucleotides having the sequences set forth in SEQ ID NO:87 and SEQ ID NO:88, wherein SEQ ID NO:87 is located 5' to SEQ ID NO:88.

This invention further provides the instant oligonucleotide, wherein the oligonucleotide folds so that the sequences set forth in SEQ ID NO:87 and SEQ ID NO:88 contained in the oligonucleotide are arranged as set forth in the following structure, wherein SEQ ID NO:87 is the left hand sequence and SEQ ID NO:88 is the right hand sequence:

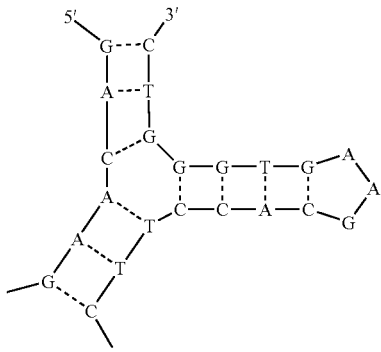

This invention further provides the instant composition, wherein the oligonucleotide comprises consecutive nucleotides having the sequence set forth in SEQ ID NO:152, wherein SEQ ID NO:152 is located 3' to SEQ ID NO:87 and 5' to SEQ ID NO:88.

This invention also provides a composition comprising an oligonucleotide which comprises consecutive nucleotides having the sequences set forth in SEQ ID NO:145 and SEQ ID NO:102, wherein SEQ ID NO:145 is located 5' to SEQ ID NO:102.

This invention further provides the instant oligonucleotide, wherein the oligonucleotide folds so that the sequences set forth in SEQ ID NO:145 and SEQ ID NO:102 contained in the oligonucleotide are arranged as set forth in the following structure, wherein SEQ ID NO:145 is the left hand sequence and SEQ ID NO:102 is the right hand sequence:

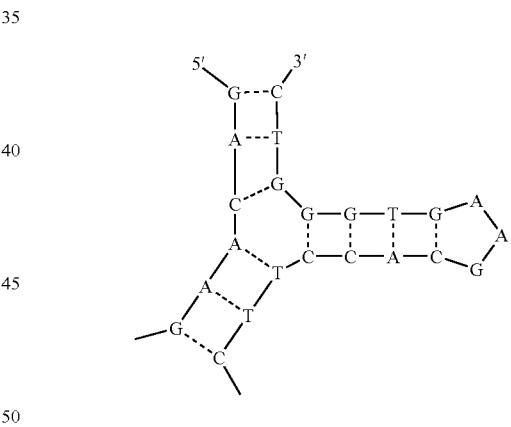

This invention further provides the instant composition, wherein the oligonucleotide comprises consecutive nucleotides having the sequence set forth in SEQ ID NO:153, wherein SEQ ID NO:153 is located 3' to SEQ ID NO:145 and 5' to SEQ ID NO:102.

This invention also provides a composition comprising an oligonucleotide which comprises consecutive nucleotides having the sequences set forth in SEQ ID NO:89 and SEQ ID NO:90, wherein SEQ ID NO:89 is located 5' to SEQ ID NO:90.

This invention further provides the instant oligonucleotide, wherein the oligonucleotide folds so that the sequences set forth in SEQ ID NO:89 and SEQ ID NO:90 contained in the oligonucleotide are arranged as set forth in the following structure, wherein SEQ ID NO:89 is the left hand sequence and SEQ ID NO:90 is the right hand sequence:

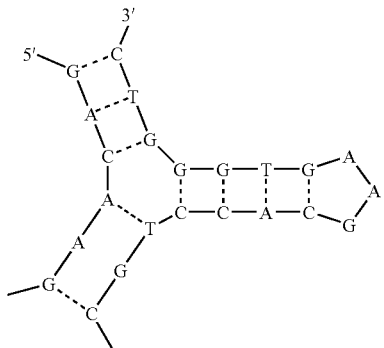

This invention further provides the instant composition, wherein the oligonucleotide comprises consecutive nucleotides having the sequence set forth in SEQ ID NO:152, wherein SEQ ID NO:152 is located 3' to SEQ ID NO:89 and 5' to SEQ ID NO:90.

This invention also provides a composition comprising an oligonucleotide which comprises consecutive nucleotides having the sequences set forth in SEQ ID NO:145 and SEQ ID NO:102, wherein SEQ ID NO:146 is located 5' to SEQ ID NO:102.

This invention further provides the instant oligonucleotide, wherein the oligonucleotide folds so that the sequences set forth in SEQ ID NO:146 and SEQ ID NO:102 contained in the oligonucleotide are arranged as set forth in the following structure, wherein SEQ ID NO:146 is the left hand sequence and SEQ ID NO:102 is the right hand sequence:

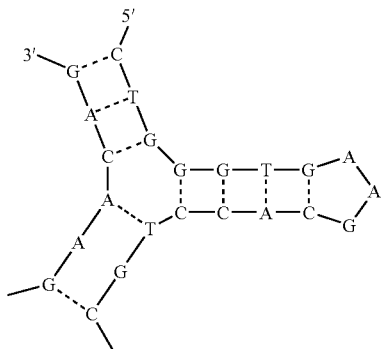

This invention further provides the instant composition, wherein the oligonucleotide comprises consecutive nucleotides having the sequence set forth in SEQ ID NO:153, wherein SEQ ID NO:153 is located 3' to SEQ ID NO:146 and 5' to SEQ ID NO:102.

This invention also provides a composition comprising an oligonucleotide which comprises consecutive nucleotides having the sequences set forth in SEQ ID NO:91 and SEQ ID NO:92, wherein SEQ ID NO:91 is located 5' to SEQ ID NO:92.

This invention further provides the instant oligonucleotide, wherein the oligonucleotide folds so that the sequences set forth in SEQ ID NO:91 and SEQ ID NO:92 contained in the oligonucleotide are arranged as set forth in the following structure, wherein SEQ ID NO:91 is the left hand sequence and SEQ ID NO:92 is the right hand sequence:

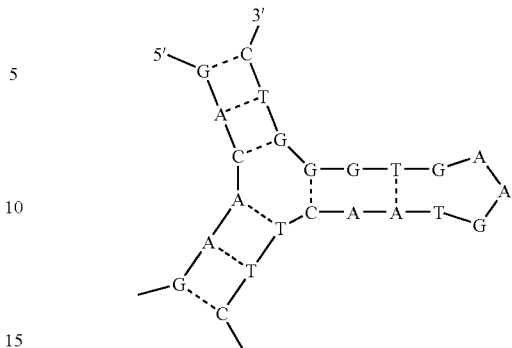

This invention further provides the instant composition, wherein the oligonucleotide comprises consecutive nucleotides having the sequence set forth in SEQ ID NO:152, wherein SEQ ID NO:152 is located 3' to SEQ ID NO:91 and 5' to SEQ ID NO:92.

This invention also provides a composition comprising an oligonucleotide which comprises consecutive nucleotides having the sequences set forth in SEQ ID NO:147 and SEQ ID NO:102, wherein SEQ ID NO:147 is located 5' to SEQ ID NO:102.

This invention further provides the instant oligonucleotide, wherein the oligonucleotide folds so that the sequences set forth in SEQ ID NO:147 and SEQ ID NO:102 contained in the oligonucleotide are arranged as set forth in the following structure, wherein SEQ ID NO:147 is the left hand sequence and SEQ ID NO:102 is the right hand sequence:

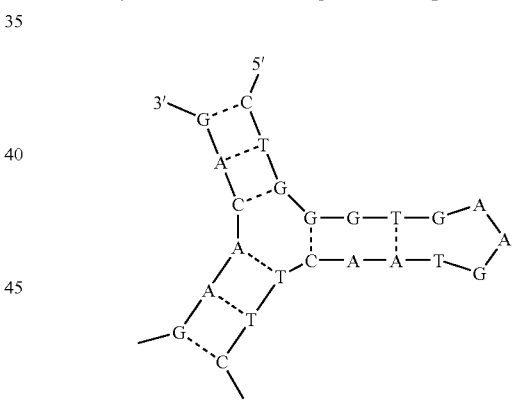

This invention further provides the instant composition, wherein the oligonucleotide comprises consecutive nucleotides having the sequence set forth in SEQ ID NO:153, wherein SEQ ID NO:153 is located 3' to SEQ ID NO:147 and 5' to SEQ ID NO:102.

This invention also provides a composition comprising an oligonucleotide which comprises consecutive nucleotides having the sequences set forth in SEQ ID NO:93 and SEQ ID NO:94, wherein SEQ ID NO:93 is located 5' to SEQ ID NO:94.

This invention further provides the instant oligonucleotide, wherein the oligonucleotide folds so that the sequences set forth in SEQ ID NO:93 and SEQ ID NO:94 contained in the oligonucleotide are arranged as set forth in the following structure, wherein SEQ ID NO:93 is the left hand sequence and SEQ ID NO:94 is the right hand sequence:

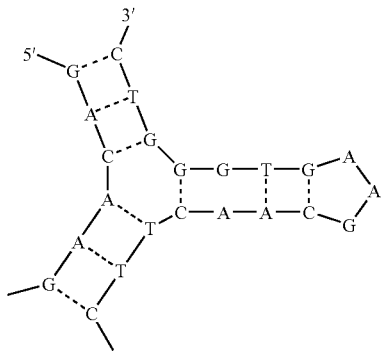

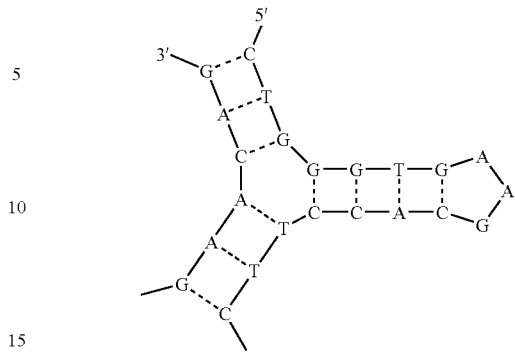

This invention further provides the instant composition, wherein the oligonucleotide comprises consecutive nucleotides having the sequence set forth in SEQ ID NO:152, wherein SEQ ID NO:152 is located 3' to SEQ ID NO:94 and 5' to SEQ ID NO:94.

This invention also provides a composition comprising an oligonucleotide which comprises consecutive nucleotides having the sequences set forth in SEQ ID NO:148 and SEQ ID NO:102, wherein SEQ ID NO:148 is located 5' to SEQ ID NO:102.

This invention further provides the instant oligonucleotide, wherein the oligonucleotide folds so that the sequences set forth in SEQ ID NO:148 and SEQ ID NO:102 contained in the oligonucleotide are arranged as set forth in the following structure, wherein SEQ ID NO:148 is the left hand sequence and SEQ ID NO:102 is the right hand sequence:

This invention further provides the instant composition, wherein the oligonucleotide comprises consecutive nucleotides having the sequence set forth in SEQ ID NO:152, wherein SEQ ID NO:152 is located 3' to SEQ ID NO:95 and 5' to SEQ ID NO:96.

This invention also provides a composition comprising an oligonucleotide which comprises consecutive nucleotides having the sequences set forth in SEQ ID NO:149 and SEQ ID NO:102, wherein SEQ ID NO:149 is located 5' to SEQ ID NO:102.

This invention further provides the instant oligonucleotide, wherein the oligonucleotide folds so that the sequences set forth in SEQ ID NO:149 and SEQ ID NO:102 contained in the oligonucleotide are arranged as set forth in the following structure, wherein SEQ ID NO:149 is the left hand sequence and SEQ ID NO:102 is the right hand sequence:

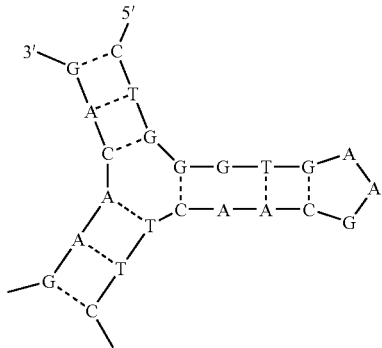

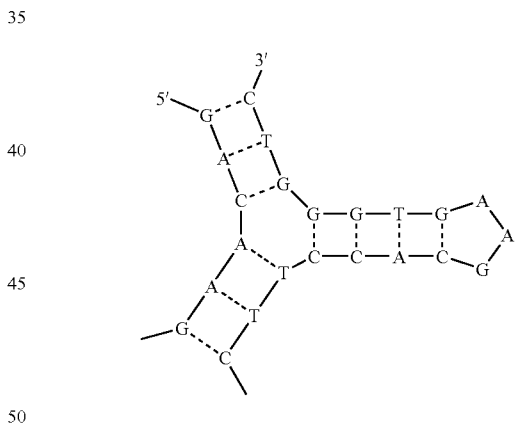

This invention further provides the instant composition, wherein the oligonucleotide comprises consecutive nucleotides having the sequence set forth in SEQ ID NO:153, wherein SEQ ID NO:153 is located 3' to SEQ ID NO:148 and 5' to SEQ ID NO:102.

This invention also provides a composition comprising an oligonucleotide which comprises consecutive nucleotides having the sequences set forth in SEQ ID NO:95 and SEQ ID NO:96, wherein SEQ ID NO:95 is located 5' to SEQ ID NO:96.

This invention further provides the instant oligonucleotide, wherein the oligonucleotide folds so that the sequences set forth in SEQ ID NO:95 and SEQ ID NO:96 contained in the oligonucleotide are arranged as set forth in the following structure, wherein SEQ ID NO:95 is the left hand sequence and SEQ ID NO:96 is the right hand sequence:

This invention further provides the instant composition, wherein the oligonucleotide comprises consecutive nucleotides having the sequence set forth in SEQ ID NO:153, wherein SEQ ID NO:153 is located 3' to SEQ ID NO:149 and 5' to SEQ ID NO:102.

This invention also provides a composition comprising an oligonucleotide which comprises consecutive nucleotides having the sequences set forth in SEQ ID NO:97 and SEQ ID NO:98, wherein SEQ ID NO:97 is located 5' to SEQ ID NO:98.

This invention further provides the instant oligonucleotide, wherein the oligonucleotide folds so that the sequences set forth in SEQ ID NO:97 and SEQ ID NO:98 contained in the oligonucleotide are arranged as set forth in the following structure, wherein SEQ ID NO:97 is the left hand sequence and SEQ ID NO:98 is the right hand sequence:

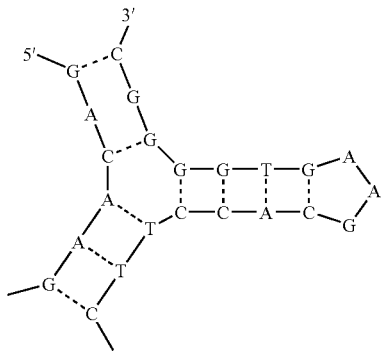

This invention further provides the instant composition, wherein the oligonucleotide comprises consecutive nucleotides having the sequence set forth in SEQ ID NO:152, wherein SEQ ID NO:152 is located 3' to SEQ ID NO:97 and 5' to SEQ ID NO:98.

This invention also provides a composition comprising an oligonucleotide which comprises consecutive nucleotides having the sequences set forth in SEQ ID NO:150 and SEQ ID NO:102, wherein SEQ ID NO:150 is located 5' to SEQ ID NO:102.

This invention further provides the instant oligonucleotide, wherein the oligonucleotide folds so that the sequences set forth in SEQ ID NO:150 and SEQ ID NO:102 contained in the oligonucleotide are arranged as set forth in the following structure, wherein SEQ ID NO:150 is the left hand sequence and SEQ ID NO:102 is the right hand sequence:

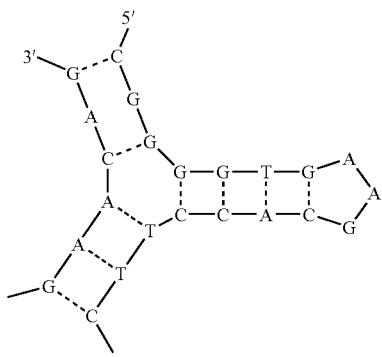

This invention further provides the instant composition, wherein the oligonucleotide comprises consecutive nucleotides having the sequence set forth in SEQ ID NO:153, wherein SEQ ID NO:153 is located 3' to SEQ ID NO:150 and 5' to SEQ ID NO:102.

This invention also provides a composition comprising an oligonucleotide which comprises consecutive nucleotides having the sequences set forth in SEQ ID NO:99 and SEQ ID NO:100, wherein SEQ ID NO:99 is located 5' to SEQ ID NO:100.

This invention further provides the instant oligonucleotide, wherein the oligonucleotide folds so that the sequences set forth in SEQ ID NO:99 and SEQ ID NO:100 contained in the oligonucleotide are arranged as set forth in the following structure, wherein SEQ ID NO:99 is the left hand sequence and SEQ ID NO:100 is the right hand sequence:

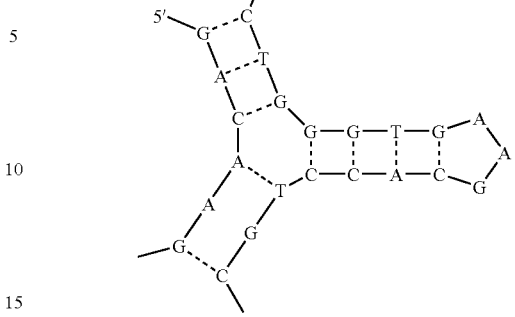

This invention further provides the instant composition, wherein the oligonucleotide comprises consecutive nucleotides having the sequence set forth in SEQ ID NO:152, wherein SEQ ID NO:152 is located 3' to SEQ ID NO:99 and 5' to SEQ ID NO:100.

This invention also provides a composition comprising an oligonucleotide which comprises consecutive nucleotides having the sequences set forth in SEQ ID NO:151 and SEQ ID NO:102, wherein SEQ ID NO:151 is located 5' to SEQ ID NO:102.

This invention further provides the instant oligonucleotide, wherein the oligonucleotide folds so that the sequences set forth in SEQ ID NO:151 and SEQ ID NO:102 contained in the oligonucleotide are arranged as set forth in the following structure, wherein SEQ ID NO:151 is the left hand sequence and SEQ ID NO:102 is the right hand sequence:

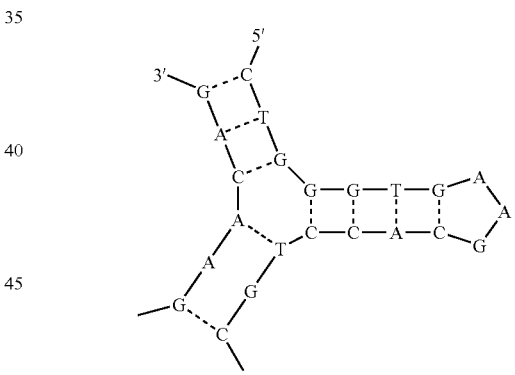

This invention further provides the instant composition, wherein the oligonucleotide comprises consecutive nucleotides having the sequence set forth in SEQ ID NO:153, wherein SEQ ID NO:153 is located 3' to SEQ ID NO:151 and 51 to SEQ ID NO:102.

The present invention further provides the instant oligonucleotides, wherein the oligonucleotide comprises a phosphorothioate group.

The present invention further provides the instant oligonucleotides, wherein the oligonucleotides further comprise a fluorophore attached to a sulfur of the phosphorothioate group.

The present invention further provides the instant oligonucleotides, wherein the fluorophore is chosen from the group consisting of fluorescein, Oregon Green, JOE, HEX, TET Alexa Fluor, Rhodamine Green, eosin, erythroscein, and BODIPY related dye.

The present invention further provides the instant oligonucleotides, wherein the fluorophore is a fluorescein derivative.

The present invention further provides the instant oligonucleotides, wherein the fluorescein derivative comprises a substituent attached to an aromatic carbon of a fluorescein.

The present invention further provides the instant oligonucleotides, wherein the oligonucleotide is 25 to 120 nucleotides in length.

This invention also provides a method of detecting an analyte in a solution comprising:
- (a) providing a composition comprising an oligonucleotide and a fluorescent moiety attached to the oligonucleotide, wherein the oligonucleotide undergoes a conformational change upon contact with the analyte and the fluorescent moiety undergoes a change of fluorescence upon the conformational change;
- (b) quantitating the fluorescence of the fluorescent moiety of the composition in the absence of the analyte;
- (c) subsequently contacting the composition with the solution containing the analyte;
- (d) quantitating the fluorescence of the fluorescent moiety of the composition in contact with the solution containing the analyte; and
- (e) comparing the fluorescence quantitated in step (b) with that quantitated in step (d),
- wherein a change in the fluorescence quantitated in step (d) as compared with the fluorescence quantitated in step (b) indicates that the analyte is present in the solution.

This invention also provides a method of determining whether an amount of an analyte in a first solution is different to that of an amount of the analyte in a second solution comprising:
- (a) providing a composition comprising an oligonucleotide and a fluorescent moiety attached to the oligonucleotide, wherein the oligonucleotide undergoes a conformational change upon contact with the analyte and the fluorescent moiety undergoes a change of fluorescence upon the conformational change;
- (b) contacting the composition with the first solution containing the analyte;
- (c) quantitating the fluorescence of the fluorescent moiety of the composition;
- (d) washing the composition to remove the first solution;
- (e) contacting the composition with the second solution containing the analyte;
- (f) quantitating the fluorescence of the fluorescent moiety of the composition; and
- (g) comparing the fluorescence quantitated in step (f) with that quantitated in step (c),
- wherein a change in the fluorescence quantitated in step (f) as compared with the fluorescence quantitated in step (c) indicates that the amount of the analyte in the first solution is different to the amount of the analyte in the second solution.

This invention also provides a method of quantitating an analyte in a solution comprising:
- (a) providing a composition comprising an oligonucleotide and a fluorescent moiety attached to the oligonucleotide, wherein the oligonucleotide undergoes a conformational change upon contact with the analyte and the fluorescent moiety undergoes a change of fluorescence upon the conformational change;
- (b) providing a predetermined relationship between the fluorescent moiety fluorescence and the analyte concentration;
- (c) contacting the composition with the solution containing the analyte;
- (d) quantitating the fluorescence of the fluorescent moiety of the composition in contact with the solution containing the analyte;
- (e) quantitating the analyte in the solution from the fluorescence quantitated in step (d) and the predetermined relationship provided in step (b).

This invention also provides the instant methods, wherein two or more compositions are present.

This invention also provides a method of determining whether a first solution comprising a first analyte has an analyte composition different to that of a second solution comprising a second analyte comprising:
- (a) providing a first composition comprising a first oligonucleotide and a first fluorescent moiety attached to the first oligonucleotide, and a second composition comprising a second oligonucleotide and a second fluorescent moiety attached to the second oligonucleotide, wherein each of the first and second oligonucleotides undergoes a conformational change upon contact with the first analyte and upon contact with the second analyte, and each of the fluorescent moieties undergoes a change of fluorescence upon the conformational change of the oligonucleotides upon contact with the first analyte and upon contact with the second analyte;
- (b) contacting the first composition and second composition with the first solution containing the first analyte;
- (c) quantitating the fluorescence of each of the fluorescent moieties;
- (d) washing to remove the first solution;
- (e) contacting the first composition and second composition with the second solution containing the second analyte;
- (f) quantitating the fluorescence of each of the fluorescent moieties; and
- (g) comparing the fluorescence quantitated in step (f) with that quantitated in step (c),
- wherein a change in the fluorescence quantitated in step (f) as compared with the fluorescence quantitated in step (c) indicates that the first solution containing the first analyte has an analyte composition different to that of the second solution containing the second analyte.

This invention also provides the instant methods, wherein the oligonucleotide comprises a phosphorothioate group and a fluorescence moiety attached to the sulfur of the phosphorothioate group.

This invention also provides the instant methods, wherein the first solution is a sample derived from a subject and the second solution is a reference solution.

This invention also provides the instant methods, wherein the second solution is a sample derived from a subject and the first solution is a reference solution.

This invention also provides the instant methods, further comprising providing in step (a) a third composition comprising a third oligonucleotide and a fluorescent moiety attached to the third oligonucleotide, wherein the third oligonucleotide undergoes a conformational change upon contact with the first analyte and upon contact with the second analyte, and which fluorescent moiety undergoes a change of fluorescence upon the conformational change.

This invention also provides the instant methods, further comprising providing in step (a) a fourth composition comprising a fourth oligonucleotide and a fluorescent moiety attached to the fourth oligonucleotide, wherein the fourth oligonucleotide undergoes a conformational change upon contact with the first analyte and upon contact with the second analyte, and which fluorescent moiety undergoes a change of fluorescence upon the conformational change.

This invention also provides the instant methods, further comprising providing an xth composition comprising an xtholigonucleotide and a fluorescent moiety attached to the oligonucleotide, wherein x is between 4 and 3000, wherein the xtholigonucleotide undergoes a conformational change upon contact with the first analyte and upon contact with the second analyte, and which fluorescent moiety undergoes a change of fluorescence upon the conformational change.

This invention also provides the instant methods, wherein two or more analytes are present in each solution and each oligonucleotide undergoes a conformational change upon contact with each of the 2 or more analytes.

This invention also provides the instant methods, further comprising providing a predetermined relationship between fluorescence and analyte concentration for each analyte and determining the concentration of each analyte from the predetermined relationship.

This invention also provides the instant methods, wherein the solution is a sample of a bodily fluid obtained from a subject.

This invention also provides the instant methods, wherein the bodily fluid is blood, a blood product, urine, a urine product, saliva, a saliva product, or sweat.

This invention also provides the instant methods, wherein the subject is mammalian.

This invention also provides the instant methods, wherein the subject is human.

This invention also provides the instant methods, wherein the oligonucleotides have any of the following structures:

This invention also provides the instant methods, wherein each analyte is a molecule.

This invention also provides the instant methods, wherein the first and second analyte are molecules having the same molecular structure.

This invention also provides the instant methods, wherein the first and second analyte have a different molecular structure.

This invention also provides the instant methods, wherein the molecule is a steroid or an alkaloid.

This invention also provides the instant methods, wherein the steroid has a cholestane, androstane, or pregnane core.

This invention also provides the instant methods, wherein the steroid is bile acids, 17-keto steroid, 17-hydroxycorticosteroid analog, cortisone, corticosterone or a derivative thereof.

This invention also provides the instant methods, wherein the analyte is brucine, strychnine or a fullerene C60.

This invention also provides the instant methods, wherein the first solution contains more than one analyte.

This invention also provides the instant methods, wherein the second solution contains more than one analyte.

This invention also provides the instant methods, wherein at least one composition is attached to a solid surface.

This invention also provides the instant methods, wherein the solid surface is a microchip, optical fiber, glass, a bead, a multi-well plate, a column, a membrane, or a matrix.

This invention also provides compositions comprising an oligonucleotide comprising consecutive nucleotides containing the sequences set forth in SEQ ID NO:1 and 2, or SEQ ID NO:3 and 4, or SEQ ID NO:5 and 6, or SEQ ID NO:7 and 8, or SEQ ID NO:9 and 10 or SEQ ID NO:13 and 14, or SEQ ID NO:15 and 16, or SEQ ID NO:17 and 18, or SEQ ID NO:19 and 20, or SEQ ID NO:21 and 22, or SEQ ID NO:23 and 24, or SEQ ID NO:25 and 26, or SEQ ID NO:27 and 28, or SEQ ID NO:29 and 30, or SEQ ID NO:31 and 32, or SEQ ID NO:33 and 34, or SEQ ID NO:35 and 36, or SEQ ID NO:37 and 38, or SEQ ID NO:39 and 40, or SEQ ID NO:41 and 42, or SEQ ID NO:43 and 44, or SEQ ID NO:45 and 46, or SEQ ID NO:47 and 48, or SEQ ID NO:49 and 50, or SEQ ID NO:51 and 52, or SEQ ID NO:53 and 54, or SEQ ID NO:55 and 56, or SEQ ID NO:57 and 58, or SEQ ID NO:59 and 60, or SEQ ID NO:61 and 62, or SEQ ID NO:63 and 64, or SEQ ID NO:65 and 66, or SEQ ID NO:67 and 68, or SEQ ID NO:69 and 70, or SEQ ID NO:71 and 72, or SEQ ID NO:73 and 74, or SEQ ID NO:75 and 76, or SEQ ID NO:77 and 78, or SEQ ID NO:79 and 80, or SEQ ID NO:81 and 82, or SEQ ID NO:83 and 84, or SEQ ID NO:85 and 86, or SEQ ID NO:87 and 88, or SEQ ID NO:89 and 90, or SEQ ID NO:91 and 92, or SEQ ID NO:93 and 94, or SEQ ID NO:95 and 96, or SEQ ID NO:97 and 98, or SEQ ID NO:99 and 100, wherein the first mentioned sequence of each pair is located 5' to the second mentioned sequence. This invention also provides compositions comprising an oligonucleotide comprising consecutive nucleotides containing the sequences set forth in SEQ ID NO:102 and 101, or SEQ ID NO:102 and 103, or SEQ ID NO:102 and 104, or SEQ ID NO:102 and 105, or SEQ ID NO:102 and 106, or SEQ ID NO:102 and 107, or SEQ ID NO:102 and 108, or SEQ ID NO:102 and 109, or SEQ ID NO:102 and 110, or SEQ ID NO:102 and 111, or SEQ ID NO:102 and 112, or SEQ ID NO:102 and 113, or SEQ ID NO:102 and 114, or SEQ ID NO:102 and 115, or SEQ ID NO:102 and 116, or SEQ ID NO:102 and 117, or SEQ ID NO:102 and 118, or SEQ ID NO:102 and 119, or SEQ ID NO:102 and 120, or SEQ ID NO:102 and 121, or SEQ ID NO:102 and 122, or SEQ ID NO:102 and 123, or SEQ ID NO:102 and 124, or SEQ ID NO:102 and 125, or SEQ ID NO:102 and 126, or SEQ ID NO:102 and 127, or SEQ ID NO:102 and 128, or SEQ ID NO:102 and 129, or SEQ ID NO:102 and 130, or SEQ ID NO:102 and 131, or SEQ ID NO:102 and 132, or SEQ ID NO:102 and 133, or SEQ ID NO:102 and 134, or SEQ ID NO:102 and 135, or SEQ ID NO:102 and 136, or SEQ ID NO:102 and 137, or SEQ ID NO:102 and 138, or SEQ ID NO:102 and 139, or SEQ ID NO:102 and 140, or SEQ ID NO:102 and 141, or SEQ ID NO:102 and 142, or SEQ ID NO:102 and 143, or SEQ ID NO:102 and 144, or SEQ ID NO:102 and 145, or SEQ ID NO:102 and 146, or SEQ ID NO:102 and 147, or SEQ ID NO:102 and 148, or SEQ ID NO:102 and 149, or SEQ ID NO:102 and 150, or SEQ ID NO:102 and 151, wherein the second mentioned sequence of each pair is located 5' to the first mentioned sequence.

Figure 1:
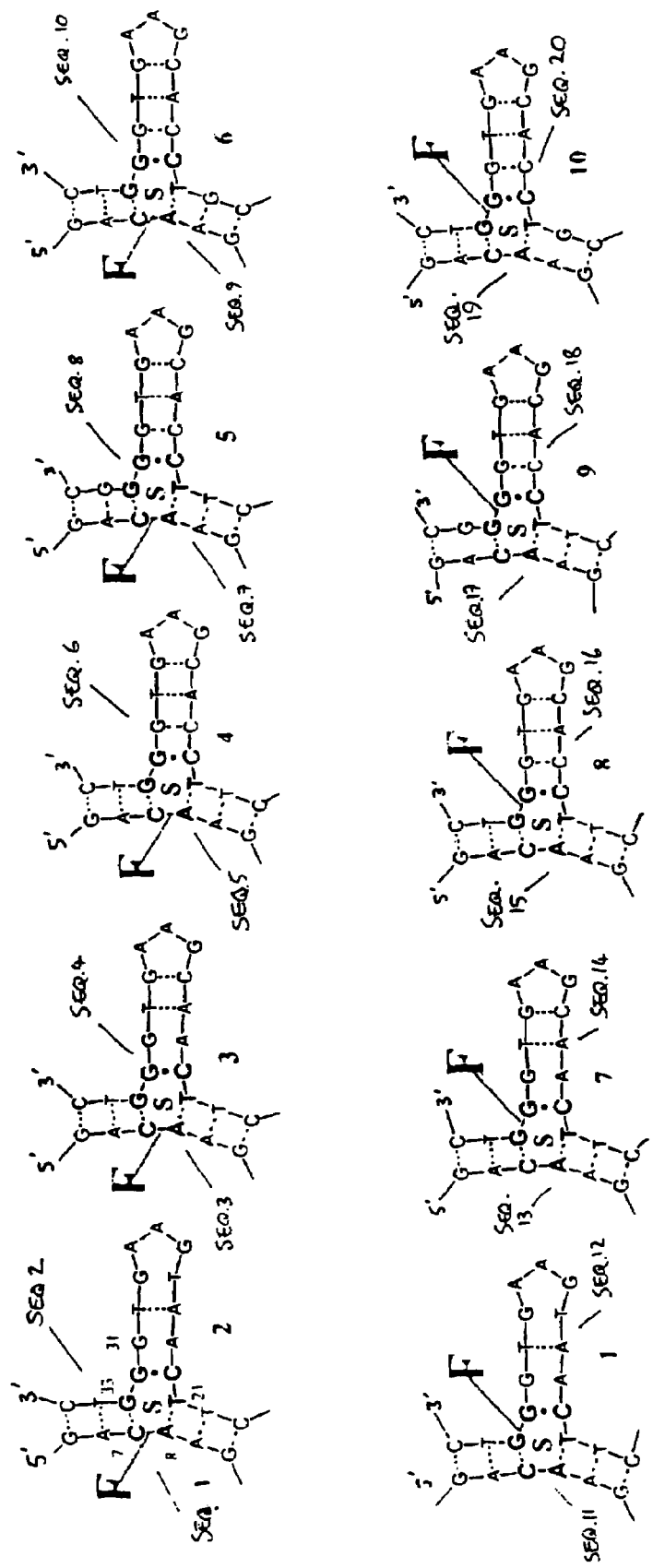
FIG. 1: Oligonucleotide structures 1-10 comprising consecutive nucleotides. Broken lines between bases represent hydrogen bonding. Structures run from 5' top left to 3' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:152. F is a fluorophore, and also represents the position of a phosphorothioate bond.
Figure 2:
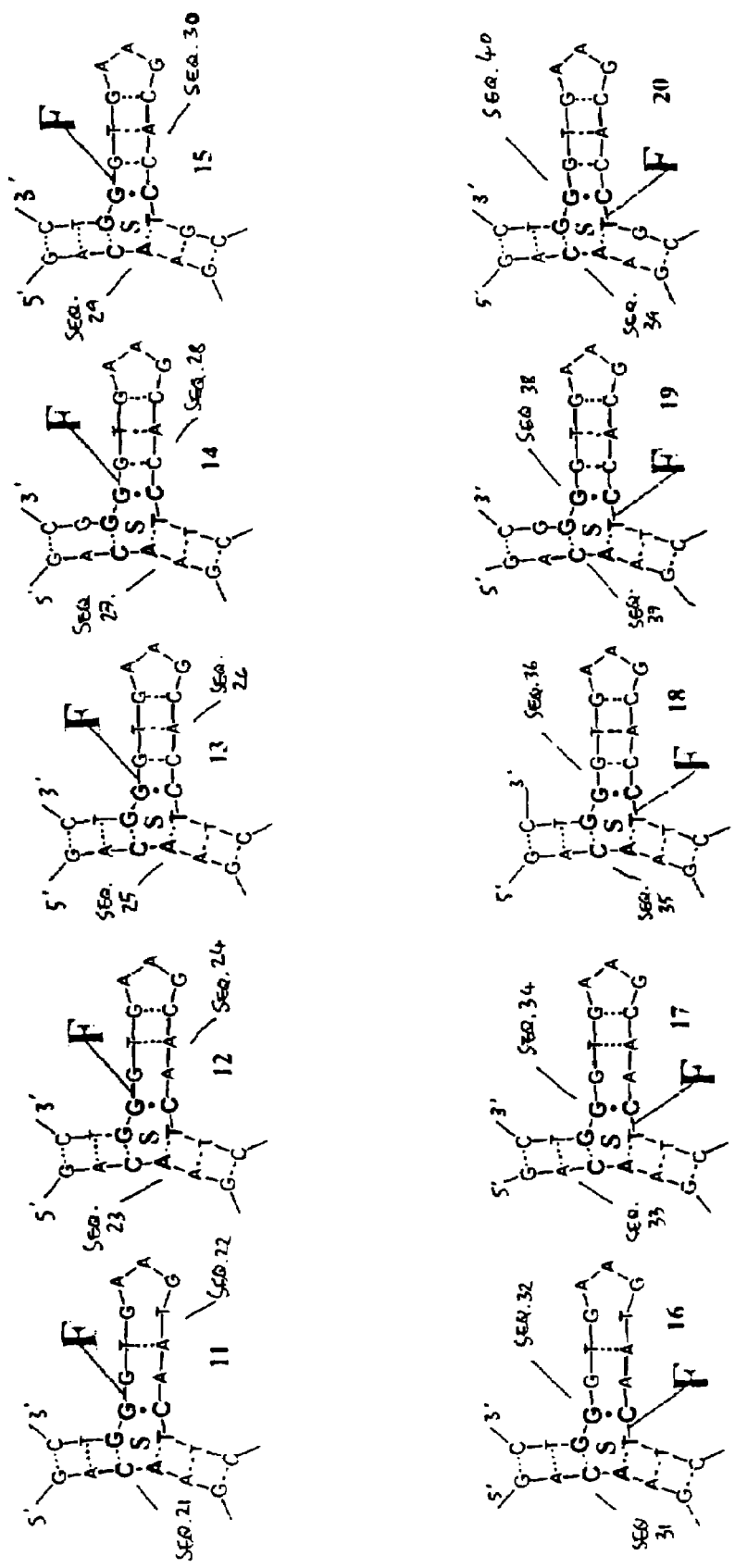
FIG. 2: Oligonucleotide structures 11-20 comprising consecutive nucleotides. Broken lines between bases represent hydrogen bonding. Structures run from 5' top left to 3' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:152. F is a fluorophore, and also represents the position of a phosphorothioate bond.
Figure 3:
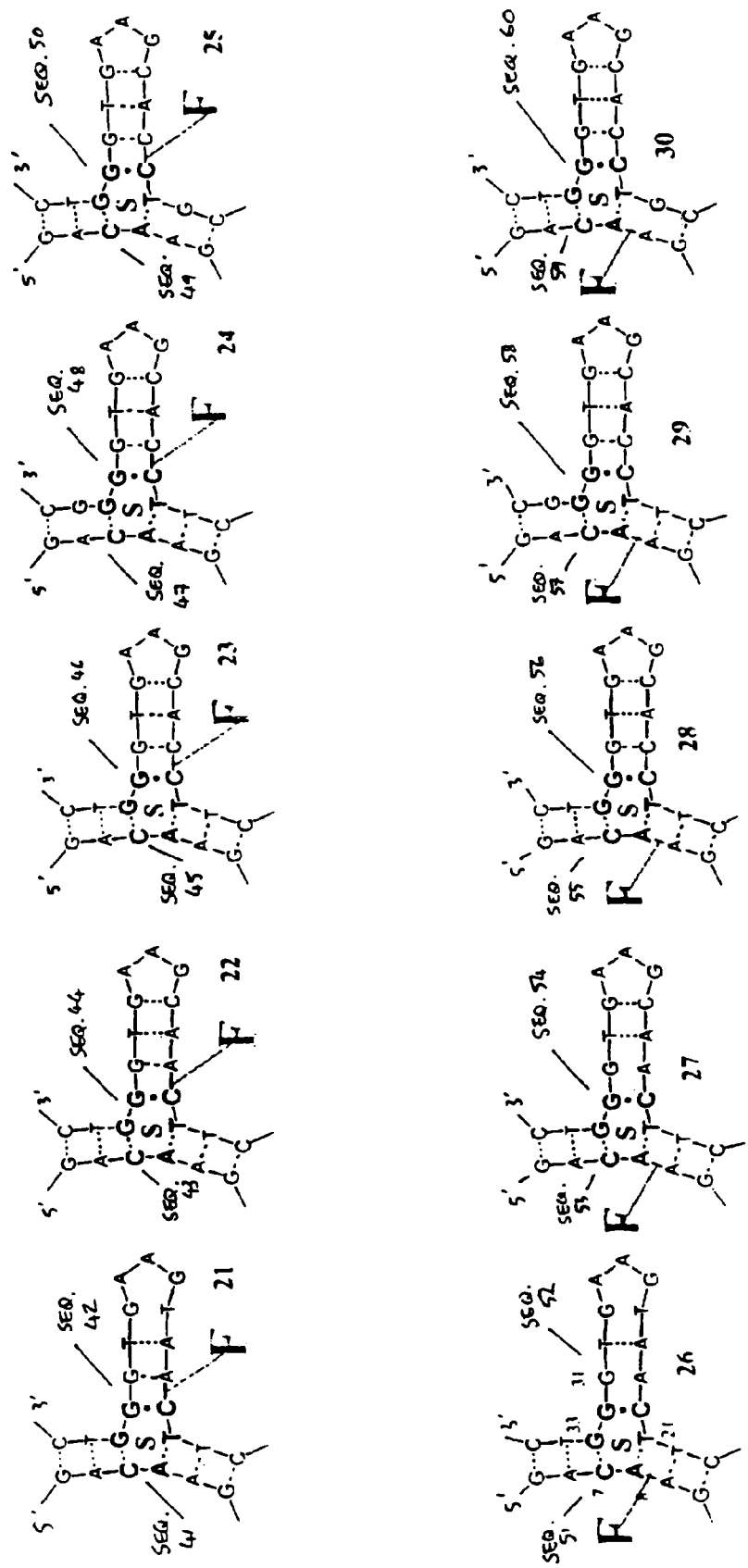
FIG. 3: Oligonucleotide structures 21-30 comprising consecutive nucleotides. Broken lines between bases represent hydrogen bonding. Structures run from 5' top left to 3' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:152. F is a fluorophore, and also represents the position of a phosphorothioate bond.
Figure 4:
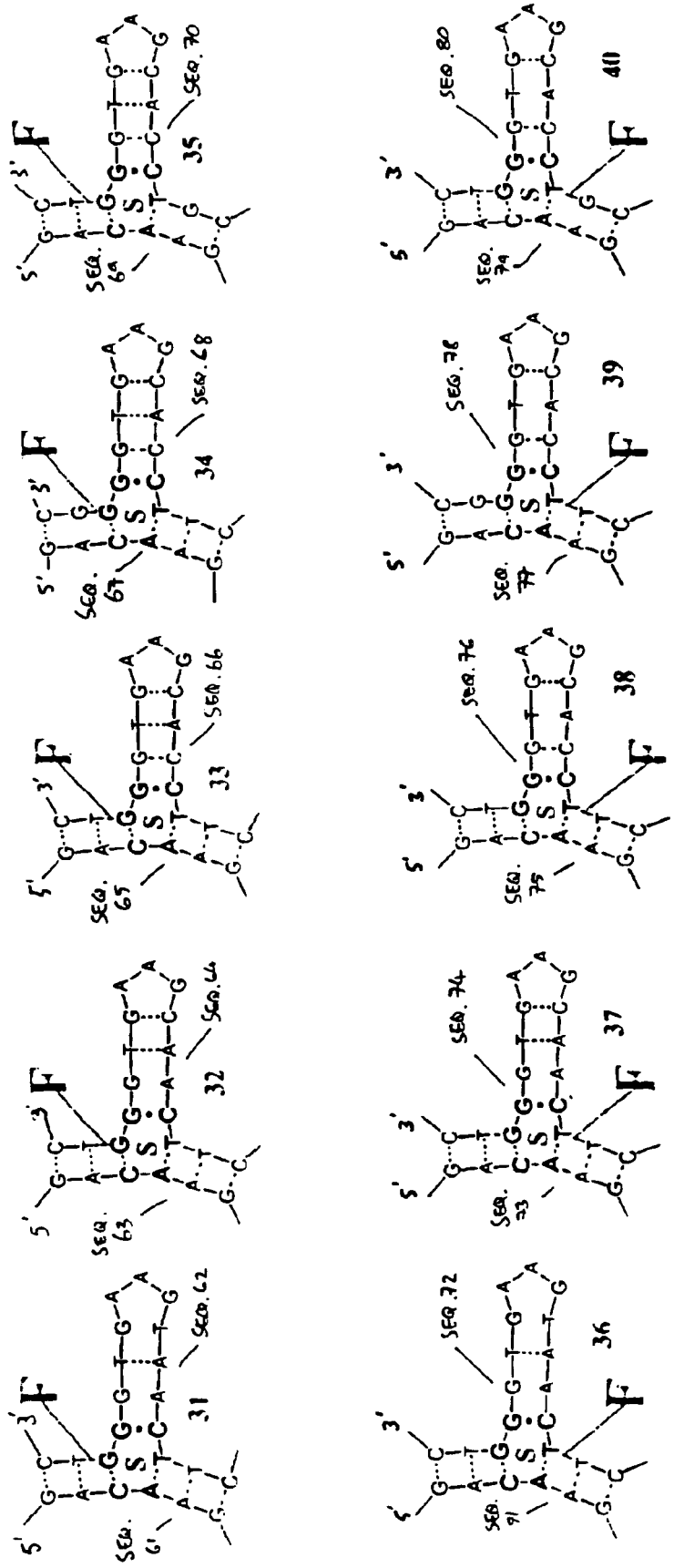
FIG. 4: Oligonucleotide structures 31-40 comprising consecutive nucleotides. Broken lines between bases represent hydrogen bonding. Structures run from 5' top left to 3' top right, and comprise a hydrophobic pocket by which the analyte (S) can be contained. SEQ ID NOs. for sequences are denoted by SEQ. X, wherein X is integer. The 9 of the g-c pair bottom is joined by consecutive nucleotides to the c of the g-c pair bottom left (not shown) e.g. by SEQ ID NO:152. F is a fluorophore, and also represents the position of a phosphorothioate bond.
Figure 5:
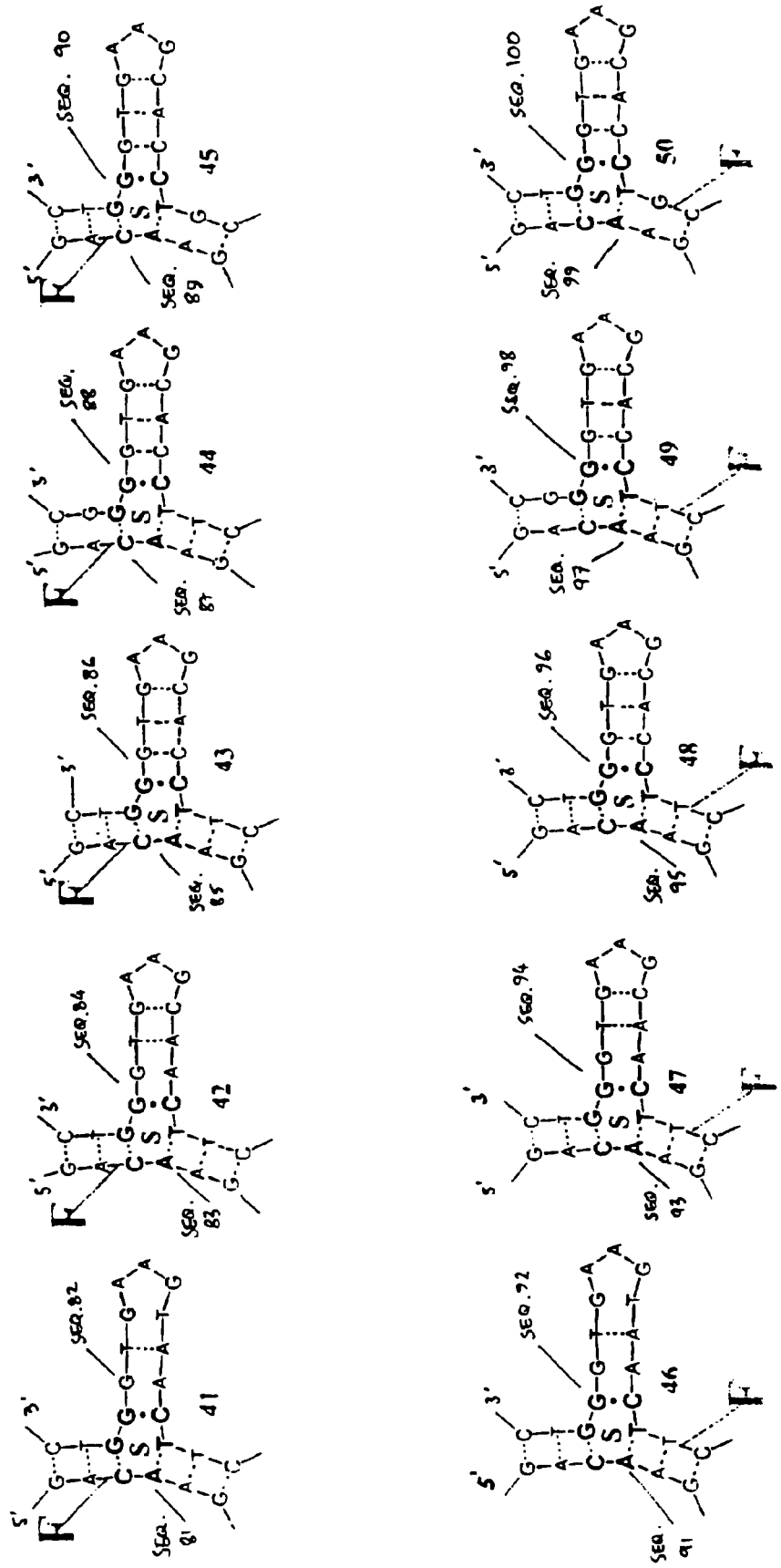
FIG. 5: Oligonucleotide structures 41-50 comprising consecutive nucleotides. Broken lines between bases represent hydrogen bonding. Structures run from 5' top left to 3' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:152. F is a fluorophore, and also represents the position of a phosphorothioate bond.

This invention further provides the instant oligonucleotides, wherein the oligonucleotide folds so that the sequences set forth in SEQ ID NO:1 and 2 contained in the oligonucleotide are arranged as set forth in structure 2 of FIG. 1, so that the sequences set forth in SEQ ID NO:3 and 4 contained in the oligonucleotide are arranged as set forth in structure 3 of FIG. 1, so that the sequences set forth in SEQ ID NO:5 and 6 contained in the oligonucleotide are arranged as set forth in structure 4 of FIG. 1, so that the sequences set forth in SEQ ID NO:7 and 8 contained in the oligonucleotide are arranged as set forth in structure 5 of FIG. 1, so that the sequences set forth in SEQ ID NO:9 and 10 contained in the oligonucleotide are arranged as set forth in structure 6 of FIG. 1, so that the sequences set forth in SEQ ID NO:13 and 14 contained in the oligonucleotide are arranged as set forth in structure 7 of FIG. 1, so that the sequences set forth in SEQ ID NO:15 and 16 contained in the oligonucleotide are arranged as set forth in structure 8 of FIG. 1, so that the sequences set forth in SEQ ID NO:17 and 18 contained in the oligonucleotide are arranged as set forth in structure 9 of FIG. 1, so that the sequences set forth in SEQ ID NO:19 and 20 contained in the oligonucleotide are arranged as set forth in structure 10 of FIG. 1, so that the sequences set forth in SEQ ID NO:21 and 22 contained in the oligonucleotide are arranged as set forth in structure 11 of FIG. 2, so that the sequences set forth in SEQ ID NO:23 and 24 contained in the oligonucleotide are arranged as set forth in structure 12 of FIG. 2, so that the sequences set forth in SEQ ID NO:25 and 26 contained in the oligonucleotide are arranged as set forth in structure 13 of FIG. 2, so that the sequences set forth in SEQ ID NO:27 and 28 contained in the oligonucleotide are arranged as set forth in structure 14 of FIG. 2, so that the sequences set forth in SEQ ID NO:29 and 30 contained in the oligonucleotide are arranged as set forth in structure 15 of FIG. 2, so that the sequences set forth in SEQ ID NO:31 and 32 contained in the oligonucleotide are arranged as set forth in structure 16 of FIG. 2, so that the sequences set forth in SEQ ID NO:33 and 34 contained in the oligonucleotide are arranged as set forth in structure 17 of FIG. 2, so that the sequences set forth in SEQ ID NO:35 and 36 contained in the oligonucleotide are arranged as set forth in structure 18 of FIG. 2, so that the sequences set forth in SEQ ID NO:37 and 38 contained in the oligonucleotide are arranged as set forth in structure 19 of FIG. 2, so that the sequences set forth in SEQ ID NO:39 and 40 contained in the oligonucleotide are arranged as set forth in structure 20 of FIG. 2, so that the sequences set forth in SEQ ID NO:41 and 42 contained in the oligonucleotide are arranged as set forth in structure 21 of FIG. 3, so that the sequences set forth in SEQ ID NO:43 and 44 contained in the oligonucleotide are arranged as set forth in structure 22 of FIG. 3, so that the sequences set forth in SEQ ID NO:45 and 46 contained in the oligonucleotide are arranged as set forth in structure 23 of FIG. 3, so that the sequences set forth in SEQ ID NO:47 and 48 contained in the oligonucleotide are arranged as set forth in structure 24 of FIG. 3, so that the sequences set forth in SEQ ID NO:49 and 50 contained in the oligonucleotide are arranged as set forth in structure 25 of FIG. 3, so that the sequences set forth in SEQ ID NO:51 and 52 contained in the oligonucleotide are arranged as set forth in structure 26 of FIG. 3, so that the sequences set forth in SEQ ID NO:53 and 54 contained in the oligonucleotide are arranged as set forth in structure 27 of FIG. 3, so that the sequences set forth in SEQ ID NO:55 and 56 contained in the oligonucleotide are arranged as set forth in structure 28 of FIG. 3, so that the sequences set forth in SEQ ID NO:57 and 58 contained in the oligonucleotide are arranged as set forth in structure 29 of FIG. 3, so that the sequences set forth in SEQ ID NO:59 and 60 contained in the oligonucleotide are arranged as set forth in structure 30 of FIG. 3, so that the sequences set forth in SEQ ID NO:61 and 62 contained in the oligonucleotide are arranged as set forth in structure 31 of FIG. 4, so that the sequences set forth in SEQ ID NO:63 and 64 contained in the oligonucleotide are arranged as set forth in structure 30 of FIG. 3, so that the sequences set forth in SEQ ID NO:65 and 66 contained in the oligonucleotide are arranged as set forth in structure 33 of FIG. 4, so that the sequences set forth in SEQ ID NO:67 and 68 contained in the oligonucleotide are arranged as set forth in structure 34 of FIG. 4, so that the sequences set forth in SEQ ID NO:69 and 70 contained in the oligonucleotide are arranged as set forth in structure 35 of FIG. 4, so that the sequences set forth in SEQ ID NO:71 and 72 contained in the oligonucleotide are arranged as set forth in structure 36 of FIG. 4, so that the sequences set forth in SEQ ID NO:73 and 74 contained in the oligonucleotide are arranged as set forth in structure 37 of FIG. 4, so that the sequences set forth in SEQ ID NO:75 and 76 contained in the oligonucleotide are arranged as set forth in structure 38 of FIG. 4, so that the sequences set forth in SEQ ID NO:77 and 78 contained in the oligonucleotide are arranged as set forth in structure 39 of FIG. 4, so that the sequences set forth in SEQ ID NO:79 and 80 contained in the oligonucleotide are arranged as set forth in structure 40 of FIG. 4, so that the sequences set forth in SEQ ID NO:81 and 82 contained in the oligonucleotide are arranged as set forth in structure 41 of FIG. 5, so that the sequences set forth in SEQ ID NO:83 and 84 contained in the oligonucleotide are arranged as set forth in structure 42 of FIG. 5, so that the sequences set forth in SEQ ID NO:85 and 86 contained in the oligonucleotide are arranged as set forth in structure 43 of FIG. 5, so that the sequences set forth in SEQ ID NO:87 and 88 contained in the oligonucleotide are arranged as set forth in structure 44 of FIG. 5, so that the sequences set forth in SEQ ID NO:89 and 90 contained in the oligonucleotide are arranged as set forth in structure 45 of FIG. 5, so that the sequences set forth in SEQ ID NO:91 and 92 contained in the oligonucleotide are arranged as set forth in structure 46 of FIG. 5, so that the sequences set forth in SEQ ID NO:93 and 94 contained in the oligonucleotide are arranged as set forth in structure 47 of FIG. 5, so that the sequences set forth in SEQ ID NO:95 and 96 contained in the oligonucleotide are arranged as set forth in structure 48 of FIG. 5, so that the sequences set forth in SEQ ID NO:97 and 98 contained in the oligonucleotide are arranged as set forth in structure 49 of FIG. 5, so that the sequences set forth in SEQ ID NO:99 and 100 contained in the oligonucleotide are arranged as set forth in structure 50 of FIG. 5.

This invention further provides any of the instant oligonucleotides further comprising consecutive nucleotides having the sequence set forth in SEQ ID NO:152, wherein SEQ ID NO:152 is located 3' to the first mentioned sequence of each pair, and located 5' to the second mentioned sequence of each pair. This invention further provides any of the instant oligonucleotides further comprising consecutive nucleotides having the sequence set forth in SEQ ID NO:153, wherein SEQ ID NO:153 is located 5' to the first mentioned sequence of each pair, and located 3' to the second mentioned sequence of each pair.

Figure 6:
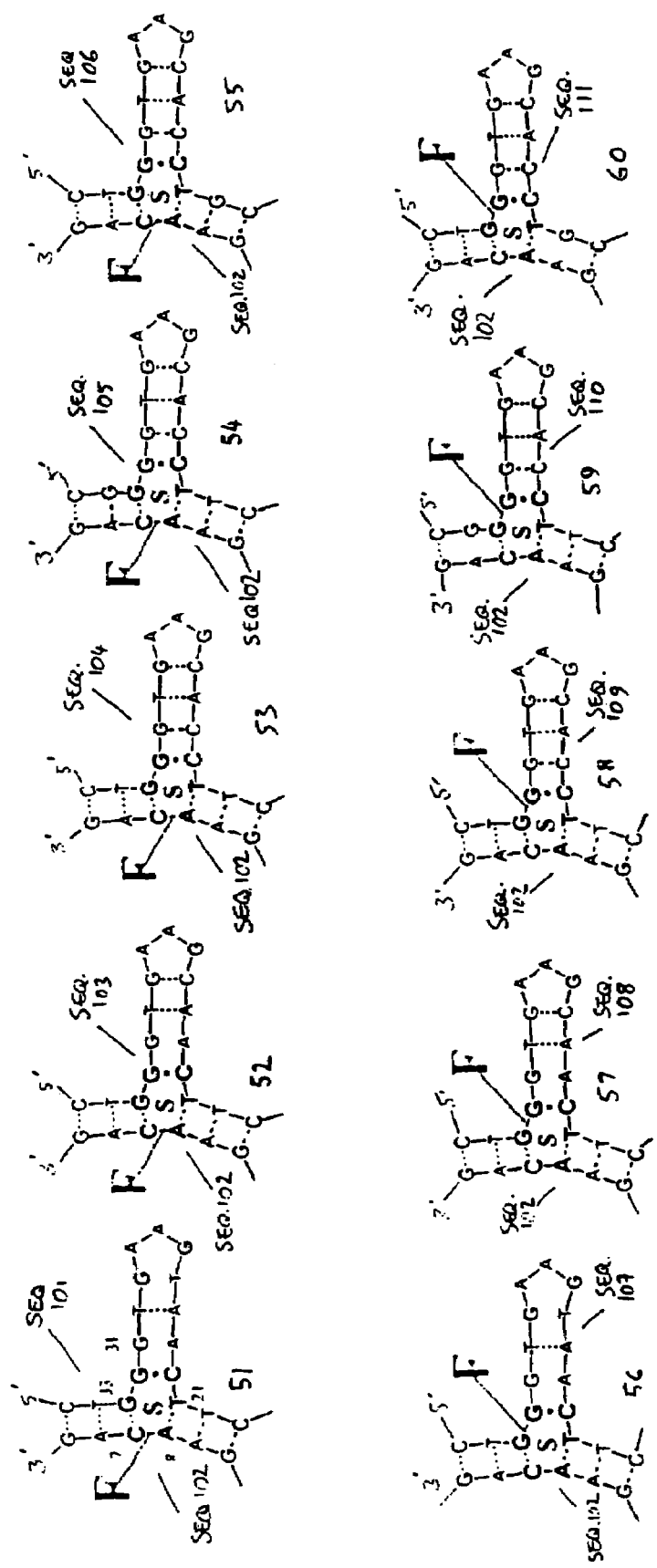
FIG. 6: Oligonucleotide structures 51-60 comprising consecutive nucleotides. Broken lines between bases represent hydrogen bonding. Structures run from 3' top left to 5' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:153. F is a fluorophore, and also represents the position of a phosphorothioate bond.
Figure 7:
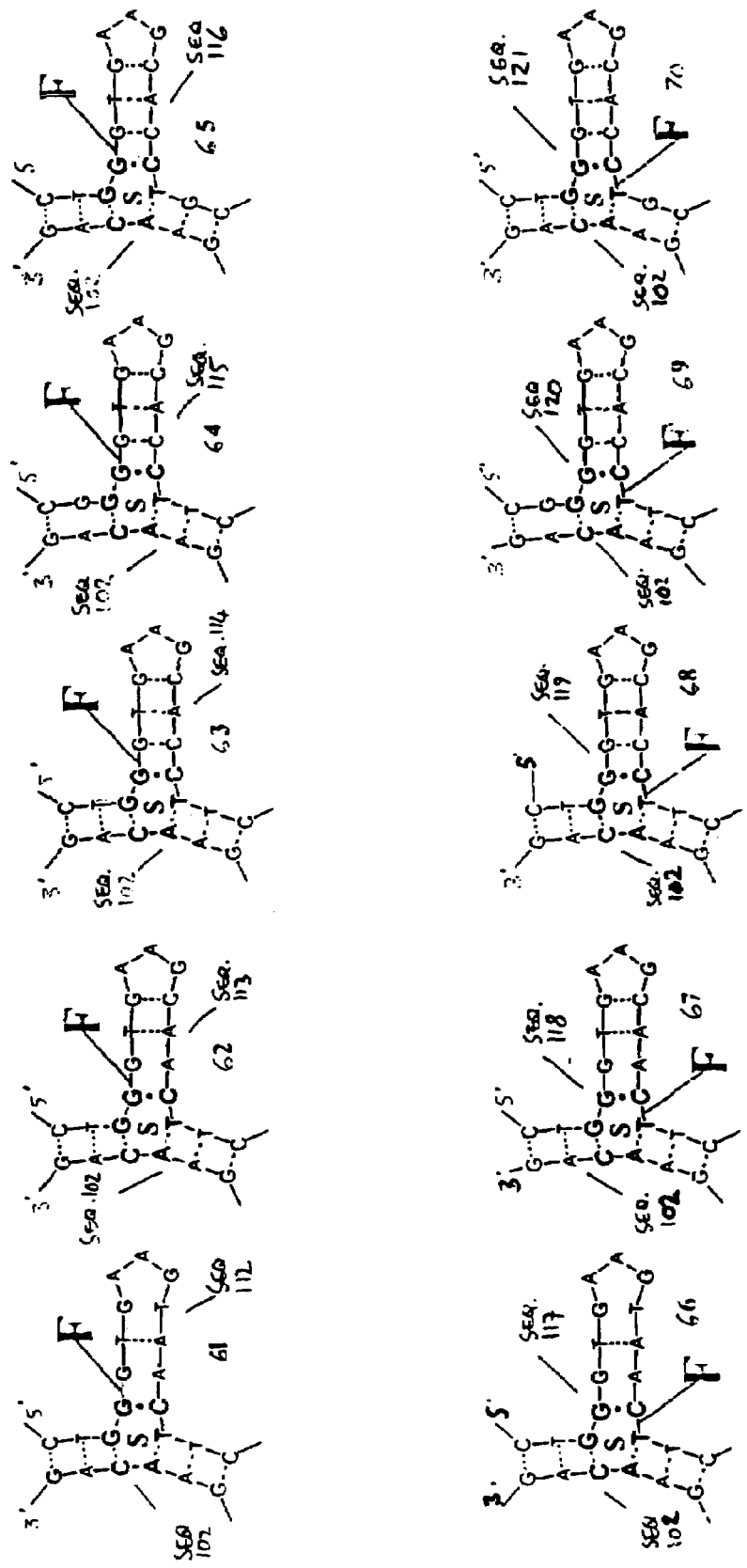
FIG. 7: Oligonucleotide structures 61-70 comprising consecutive nucleotides. Broken lines between bases represent hydrogen bonding. Structures run from 3' top left to 5' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:153. F is a fluorophore, and also represents the position of a phosphorothioate bond.
Figure 8:
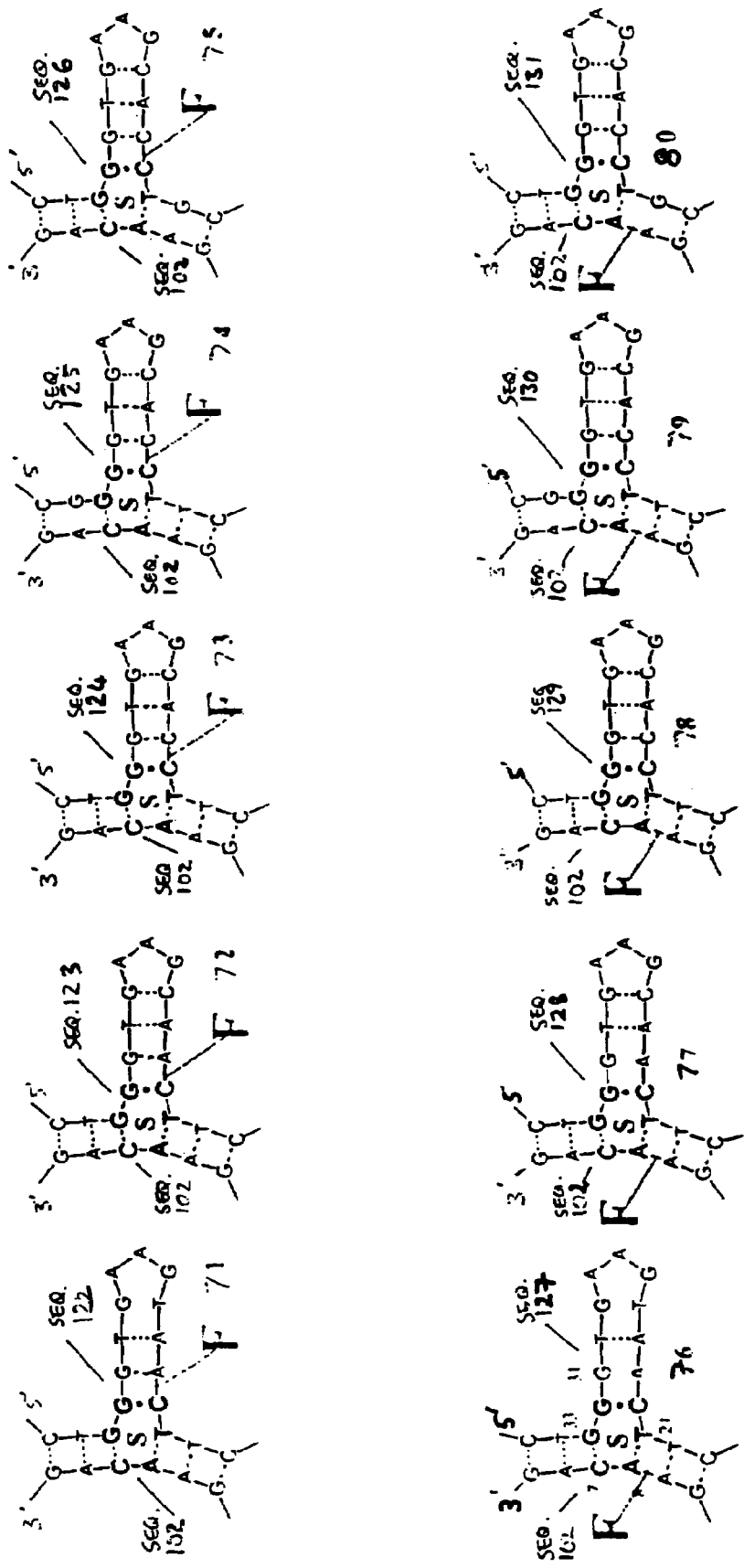
FIG. 8: Oligonucleotide structures 71-80 comprising consecutive nucleotides. Broken lines between bases represent hydrogen bonding. Structures run from 3' top left to 5' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:153. F is a fluorophore, and also represents the position of a phosphorothioate bond.
Figure 9:
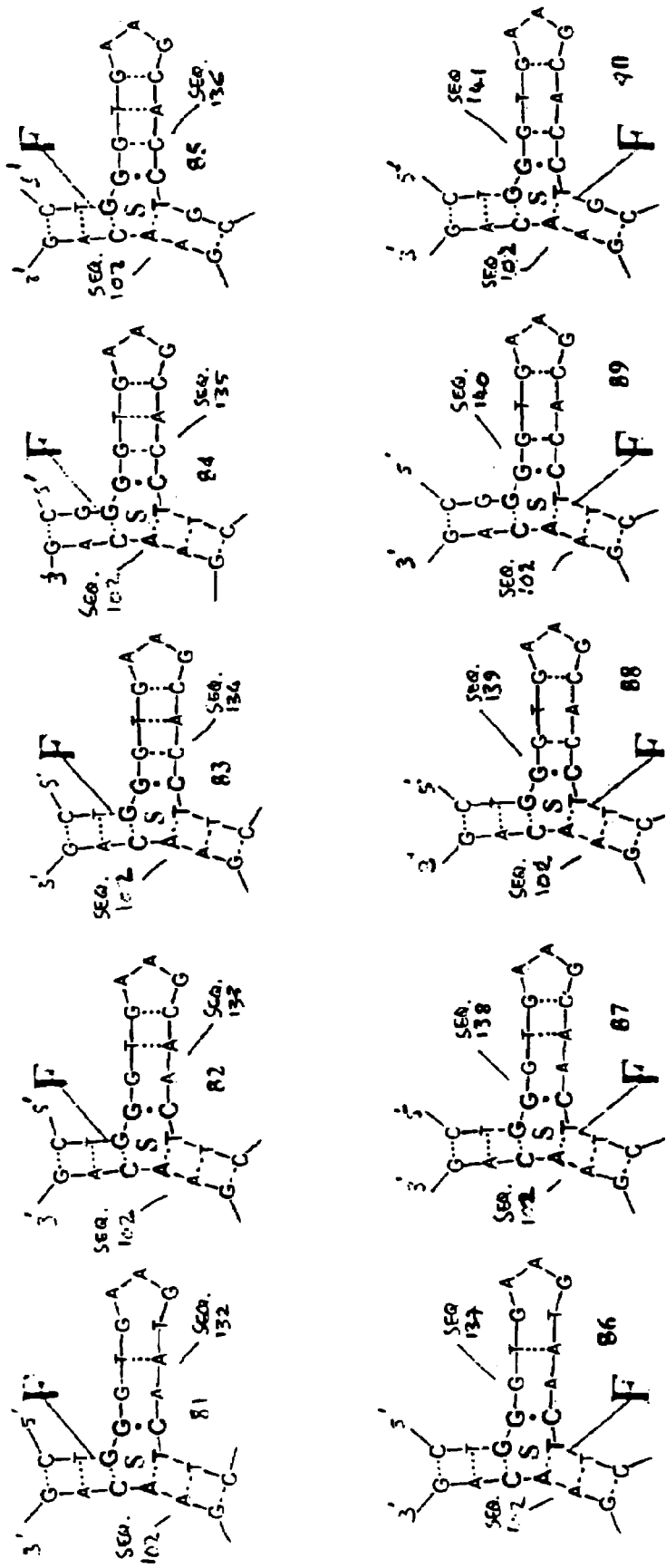
FIG. 9: Oligonucleotide structures 81-90 comprising consecutive nucleotides. Broken lines between bases represent hydrogen bonding. Structures run from 3' top left to 5' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:153. F is a fluorophore, and also represents the position of a phosphorothioate bond.
Figure 10:
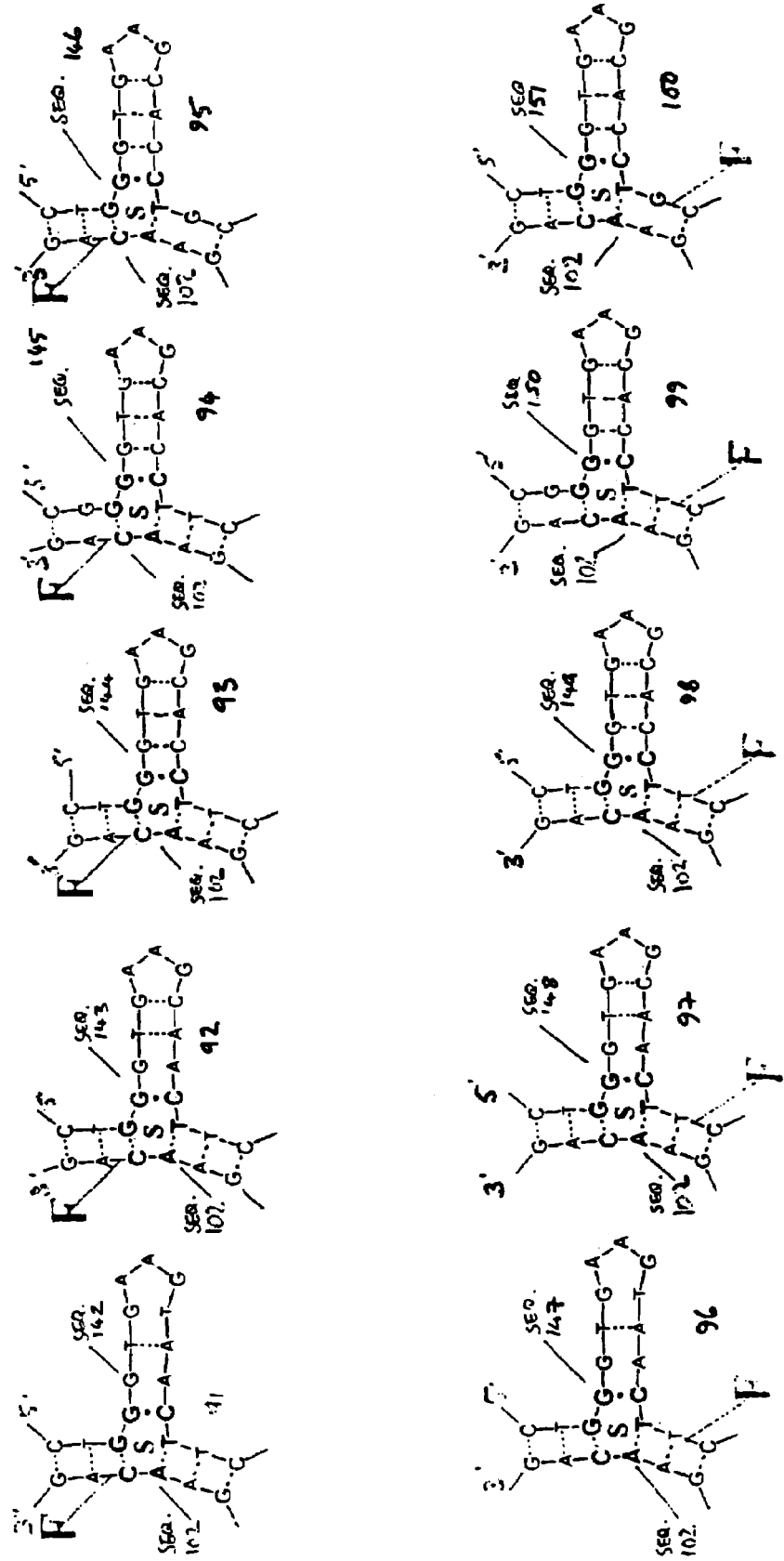
FIG. 10: Oligonucleotide structures 91-100 comprising consecutive nucleotides. Broken lines between bases represent hydrogen bonding. Structures run from 3' top left to 5' top right, and comprise a hydrophobic pocket by which the analyte (S) can be contained. SEQ ID NOs. for sequences are denoted by SEQ. X, wherein X is integer. The g of the g-c pair bottom is joined by consecutive nucleotides to the c of the g-c pair bottom left (not shown) e.g. by SEQ ID NO:153. F is a fluorophore, and also represents the position of a phosphorothioate bond.
Figure 11:
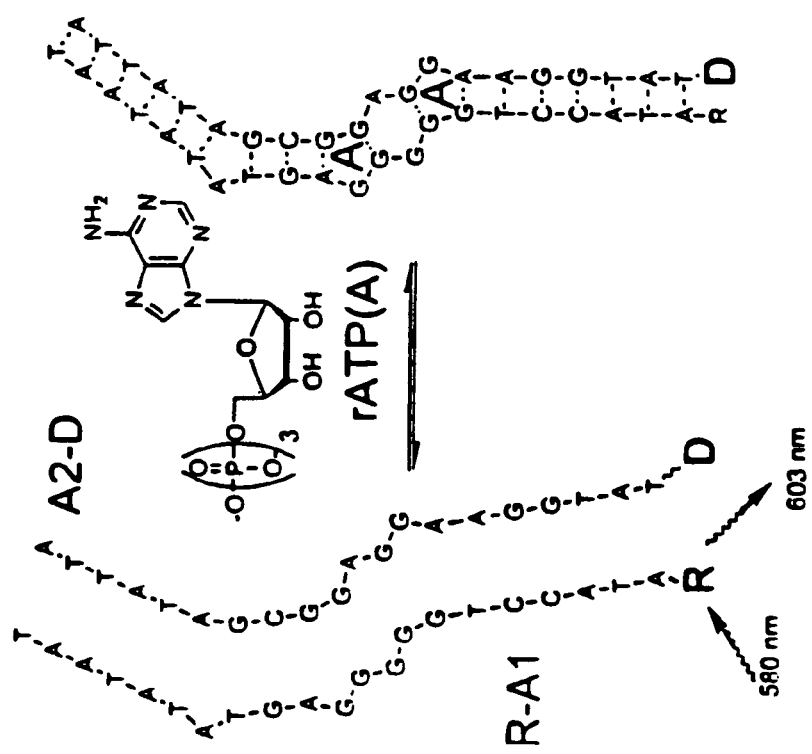
FIG. 11: Self-assembling sensor for cocaine and ATP operating in parallel in solution. Cocaine sensor reports concentration through the quenching of fluorescein, while ATP sensor reports through the quenching of Rhodamine X. From left to right the SEQ ID NOs. for each of the sensors before assembly are SEQ ID NOs. 154, 155, 156, and 157, respectively.
Figure 11:
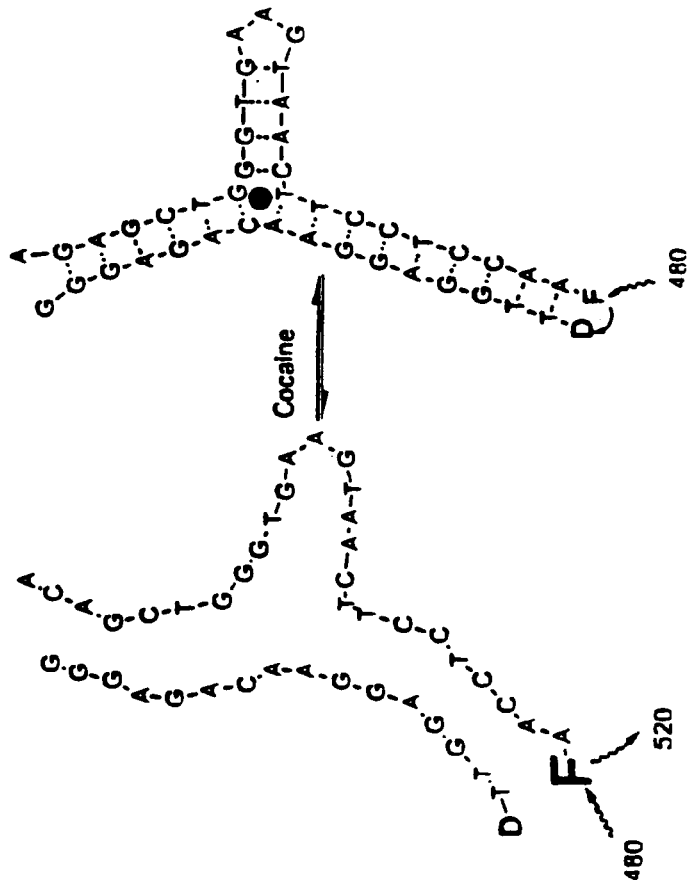
Figure 12:
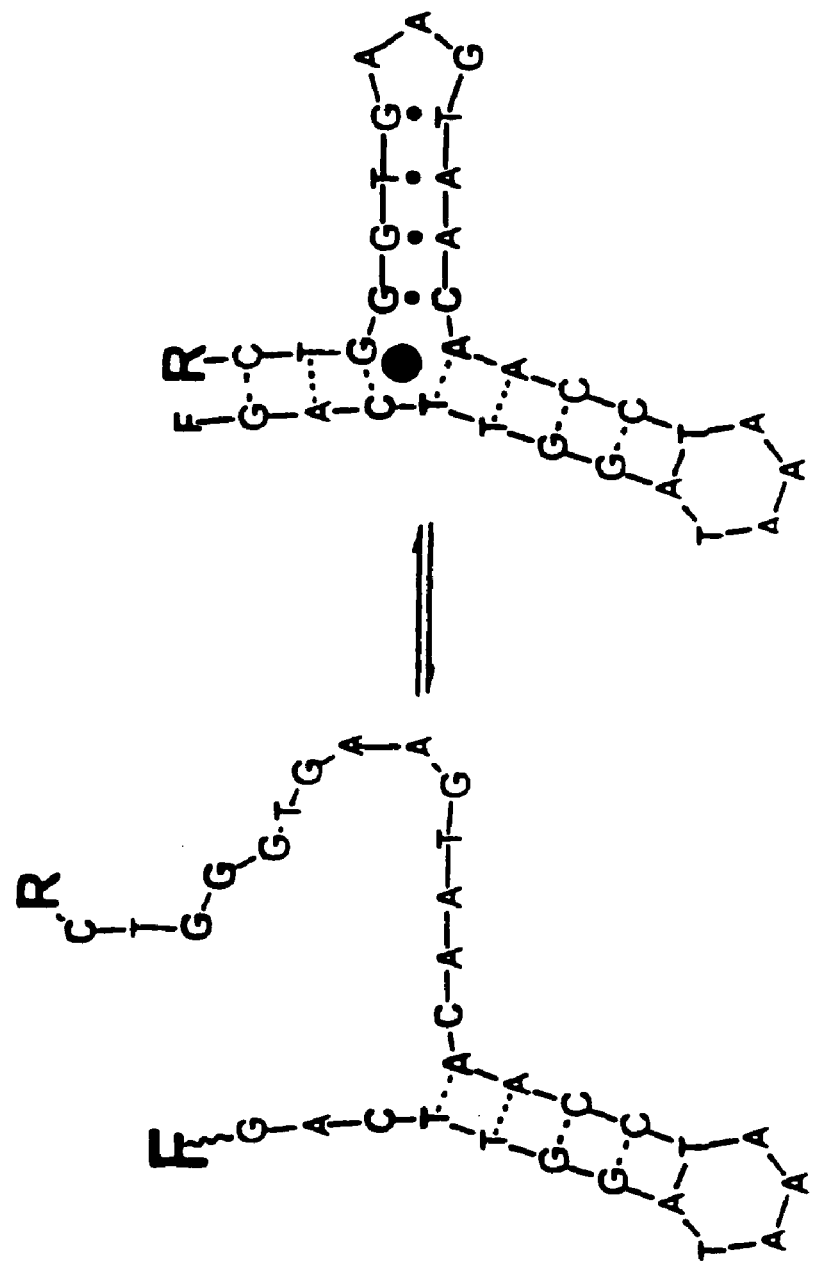
FIG. 12: Cocaine sensors fold around cocaine molecule in solution, and signals this conformational change through fluorescence quenching of fluorescein. (SEQ ID NO. 158).

This invention further provides any of the instant oligonucleotides, further comprising a phosphorothioate bond at the position marked "F" in structures 1-10 of FIG. 1, structures 11 to 20 of FIG. 2, structures 21 to 30 of FIG. 3, structures 31 to 40 of FIG. 4, and structures 41 to 50 of FIG. 5, structures 51 to 60 of FIG. 6, structures 61 to 70 of FIG. 7, structures 71 to 80 of FIG. 8, structures 81 to 90 of FIG. 9, and structures 91 to 100 of FIG. 10. Alternatively, bases in the oligonucleotide sequences can be derivatized with fluorescent moieties. For example, a uridine within the hydrophobic pocket derivatized with a fluorescent group, (9) and (12), showed fluorescence responses in the presence of cocaine and various steroids.

This invention further provides the instant methods wherein the compositions comprising oligonucleotides are non-specific in binding or interacting with analytes. In one embodiment the non specific binding is cross-reactive: i.e. the oligonucleotide composition or "sensor" has more a 20% change in the fluorescence of the fluorescent moiety upon binding or interacting with more than one steroid or alkaloid analyte in the concentration ranges from 1 micromolar to 1000 micromolar (1 millimolar). In an embodiment the oligonucleotide composition or "sensor" has differential cross-reactivity: i.e. a group of two or more oligonucleotide compositions/sensors having different slopes and/or different inflection points of dose-response curves for steroids or alkaloid analytes which cause a change in fluorescence in the concentration from 1 micromolar to 1000 micromolar. In one embodiment the fluorescence change is between 1 and 5%. In another embodiment the fluorescence change is between 5 and 15%. In another embodiment the fluorescence change is between 15 and 25%. In another embodiment the fluorescence change is between 25 and 35%. In another embodiment the fluorescence change is between 35 and 55%. In another embodiment the fluorescence change is between 55 and 75%. In another embodiment the fluorescence change is between 75 and 125%. In another embodiment the fluorescence change is between 125 and 500%. In another embodiment the fluorescence change is between 500 and 1000%. In another embodiment the fluorescence change is greater than 1000%.

Design and Methods

A class of hydrophobic receptors based on DNA can be rationally varied in structure and can fold reliably to yield families of receptors. Some receptors can be adapted to yield molecular scale sensors and an array of these sensors would provide a fingerprint for hydrophobic molecules analogous to identification by olfaction. One can construct families of hydrophobic receptors for steroids and the behavior of arrays of sensors based on these receptors can be studied. This approach can be extended to non-hydrophobic molecules, like oligosaccharides.

Site-specific, random mutagenesis and footprinting studies led that cocaine binds in a hydrophobic pocket defined by unstacked base pairs forming a three-way junction with one stem of the junction containing mismatched base pairs (Kd ~1 µM) Accordingly, (through competitive gel equilibrium filtration) a collection of hydrophobic molecules for the capacity to bind to this junction. Identified were various steroids and large molecules were screened with hydrophobic surfaces as ligands for this receptor (estimated Kd's ranged from mid-nanomolar for brucine, ~1 µM for corticosterone, up to 100 µM for deoxycholic acid).

Figure 13:
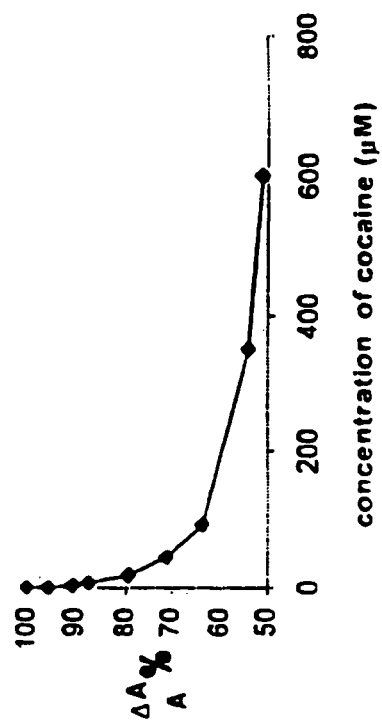
FIG. 13: Release of the hydrophobic dye from cocaine aptamer: Dye is precomplexed to aptamers, and it is released upon addition of cocaine. This process leads to the attenuation of absorbance, and it could be used to signal presence of cocaine in solution. (SEQ ID NO. 159).
Figure 13:
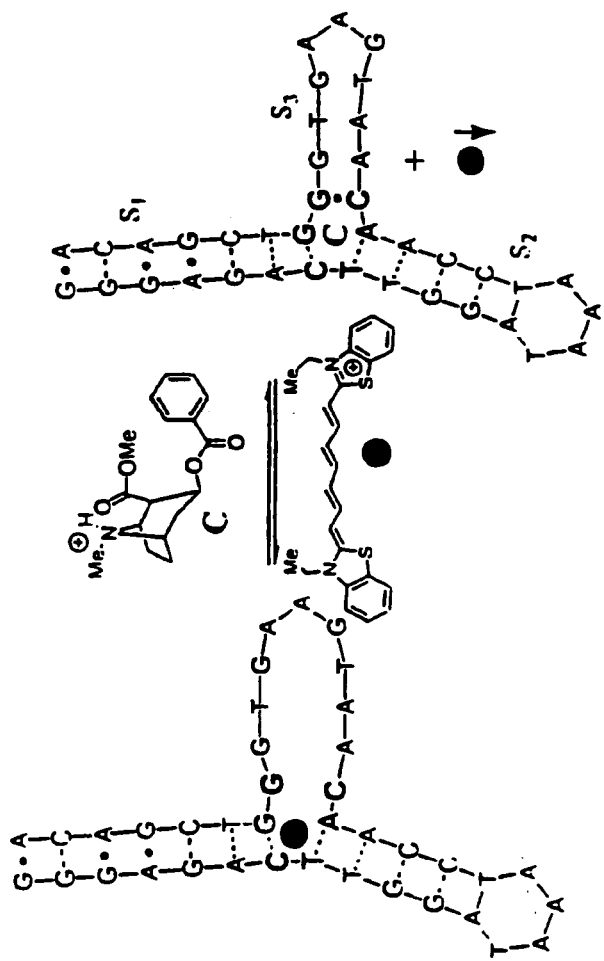

This discovery was turned into the first colorimetric sensor for cocaine in the following manner: It was determined that minimal hydrophobic pocket (other than intercalation binding mode) in DNA is defined by two coaxially stacked stems. A collection of hydrophobic dyes were screened for binding to coaxially stacked stems (including a mismatched junction), and identified a group of indocyanine dyes as binders. Cocaine displaced one dye in particular from the mismatched junction and this was used to construct first visual molecular sensor for cocaine. Similar screening procedure could be used for any other ligand-aptamer couple. (See FIG. 13)

Figure 14:
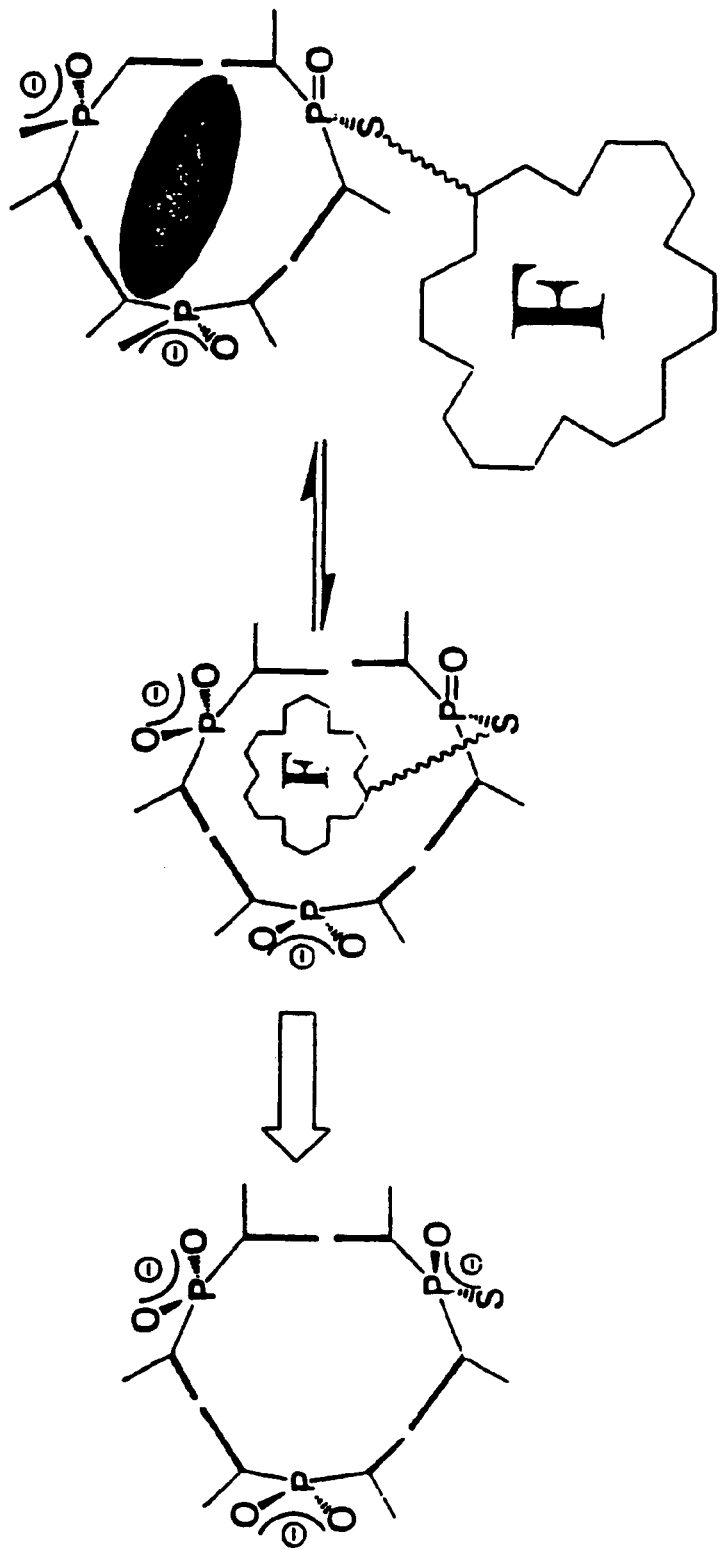
FIG. 14: A schematic representation of the sensors based on three-way junction with a single phosphorothioate, that is derivatized with fluorophore (F). Black ellipsoid represents hydrophobic molecule that upon binding displaces fluorophore, causing an increase in fluorescence (larger font). Only one phosphorothioate isomer is shown.
Figure 15:
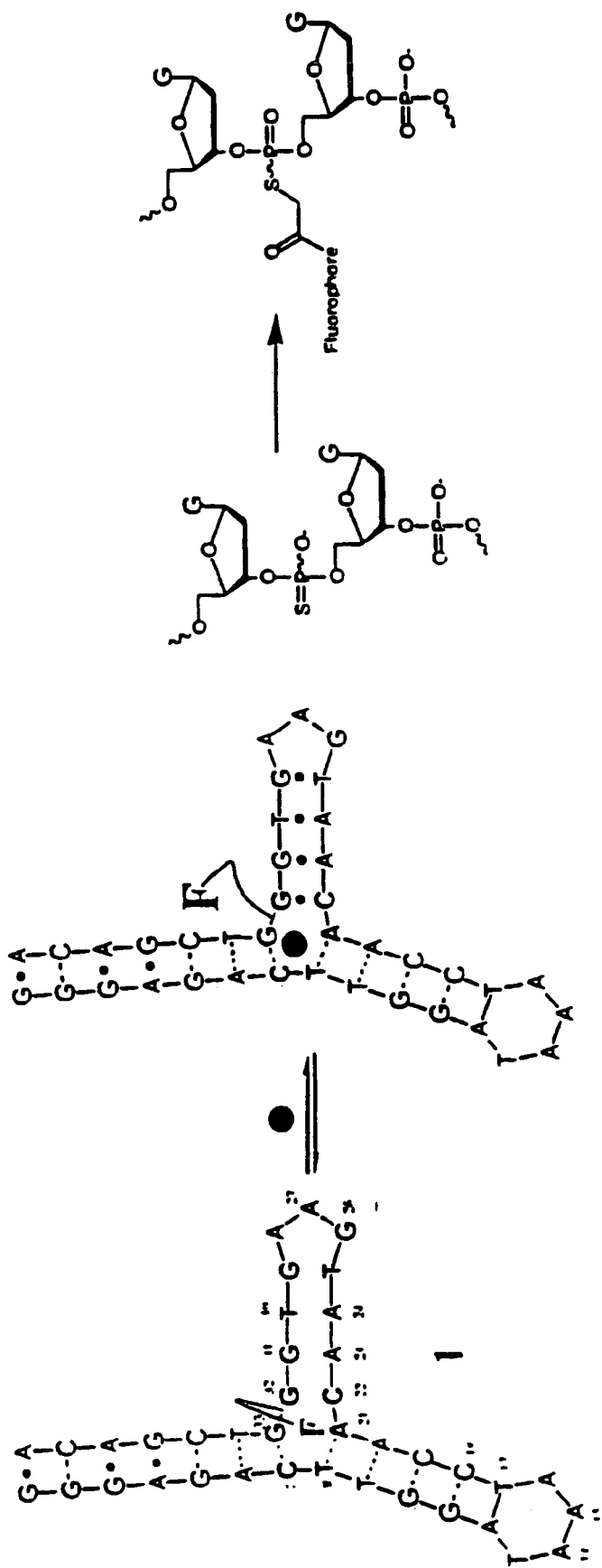
FIG. 15: Molecular sensor based on three-way junction signals binding of hydrophobic molecules (black dot). Phosphorothioate bond is derivatized with thiol-reactive fluorophore. (SEQ ID NO. 160).

Next, we directly introduced of fluorophore into nucleic acid junction. In each junction structure, a single phosphodiester was substituted functionality within junction with a phosphorothioate group (FIGS. 14 and 15). In the next step modified junctions containing this uniquely reactive site were treated with an excess of thiol-reactive fluorophores (either iodoacetamide or bromo acetamide derivatives of fluorophores, and in the case of bimane fluorophores, monobromobimane). A series of receptors capable of transducing binding of hydrophobic molecules into increase (for steroids and cocaine) of fluorescence intensity was constructed. This increase resulted from a change in fluorophore microenvironment, likely leading to the decrease in fluorophore quenching by neighboring guanines. Change in fluorescence could be used to quantitate a known analyte that binds junction. However, the crossreactivity with other hydrophobic molecules rendered these sensors unlikely candidates for a "lock and key" approach to sensors, limiting them to highly controlled environments, like in vitro high-throughput screening for cocaine hydrolase activity. Each molecular sensor is a mixture of two diastereomers at phosphorous, which are separable by affinity chromatography. These diastereomers interact differently with analytes, but the nature of crossreacive arrays makes this additional complexity acceptable. As discussed herein the mixture of diastereomers will be referred to as a single molecular sensor, and the composite response will be used for characterization and selection.

Figure 16:
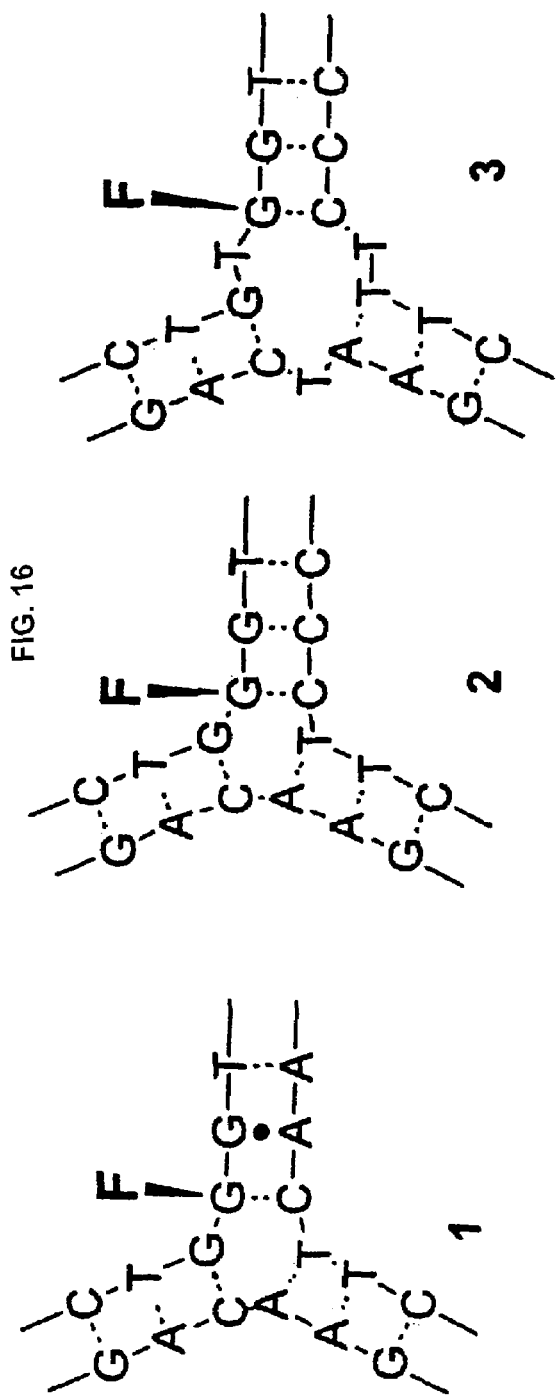
FIG. 16: Cross-reactive array from three three-way junctions detecting cocaine (C, 1 mM), deoxycholic acid (DC, 2 mM) and corticosterone (CS, 120 μM). Bars are responses (increase in fluorescence intensity) from junction 1 (dark gray bars), from junction 2 (black bars) and light from junction 3 (light gray). Experiment was performed in 96-well plates. SEQ ID NOs. for each three-way junction, in a clockwise fashion starting with the leftmost sequence, are SEQ ID NOs. 161, 162, 163 (#1); 161, 164, 163 (#2) and 165, 166 and 167.
Figure 16:

Proof of concept of DNA-based array of cross-reactive hydrophobic DNA receptors: FIG. 16 shows the use of three fluorescent junctions on a fluorescence plate reader to demonstrate, how three molecules, cocaine, deoxycholate and corticosterone could be fingerprinted by this small array. A single molecular sensor will not be able to identify an unknown molecule, but an array of three sensors would be able not only to identify these molecules, but also to report concentration. Importantly, previous research has demonstrated that arrays could be connected to neural networks, and trained to analyze complex mixtures. The limit of sensitivity of an array that consists of only three sensors without redundancy is 2 µM for corticosterone, 10 µM for cholic acid and 25 µM for cocaine. This sensitivity is sufficient for the direct urinalisys of the corticosteroids in urine or bile acids in feces. But, one can expect to improve sensitivity of arrays to nanomolar by a combination of screening of large number of molecular sensors and parallel readouts from multiple redundant sensors. The latter was demonstrated earlier as a viable approach to increase sensitivity. The current sensitivity is sufficient for determination of corticosteroids in urine.

Overall, studies demonstrated versatility of stoichiometric and catalytic sensors based on nucleic acids. However, there is an inadequacy of the existing technologies that use in vitro selection and amplification to isolate aptamers as the first step to obtain fluorescent molecular sensors. Namely, the limited structural motifs (i.e. mostly unstacked bases and base-pairs) result in the inability to produce significant specificity for hydrophobic molecules. This lack of specificity is a general problem in recognition of hydrophobic molecules by both synthetic and biomolecular receptors, and makes them applicable only within certain contexts (e.g. ultra-high throughput screening in controlled environment). The similar problem will exist in the analytical methods based on nucleic acids for determination of oligosaccharides. While moderate selectivity for binding to the targeted disaccharide has been reported, the structural similarity of these molecules will dictate significant cross-reactivity.

The approach according to the present invention is different from the aptamer-based approaches that have been used earlier. Perhaps the most important novel aspect is the realization that one can take advantage of the lack of specificity for hydrophobic molecules, if these receptors are organized in arrays or crossreactive sensors. Thus, instead of isolating specific binders through in vitro selection and amplification of oligonucleotide from libraries in the initial stage, one can construct a series of incrementally different fluorescent oligonucleotide junctions, which can be screened for response to a panel of analytes.

Based on the results, the size of these junctions is especially well suited for characterization of hydrophobic space of steroids, as the steroid core has a molecular volume that approximately corresponds to the size of the cavity in the three-way junction. The steroidal hydrophobic space is actually a complex multidimensional space, as polarity of molecules will not be the sole determinant of interactions with individual hydrophobic molecular sensors, but rather a combination of hydrophobicity, molecular volume, shape of the molecule, its flexibility and the ability of the molecule to induce conformational changes in various receptors (i.e. induced fit). One may expect numerous variations in structures of hydrophobic junctions to give subtle differences in interactions with very similar compounds (e.g. testosterone vs. epitestosterone—hallmark of anabolic abuse in doping), providing one with the opportunity to precisely characterize presence and ratios of closely related compounds. This level of discrimination cannot be expected from polymer- or chemical receptors-based approaches to detect hydrophobic molecules, and is a unique characteristic of the biomimetic system.

Nucleic acid junctions are formed at the intersection of three and more double helixes. The first cocaine-binding aptamers were previously isolated and these structures were characterized through mutagenesis as three-way junctions with mismatched stems (3). The fully matched analog of the aptamer was found to bind cocaine less efficiently, but was able to bind other hydrophobic molecules. The capacity of various nucleic acid junctions to incorporate hydrophobic molecules was reported during early footprinting studies (4) and confirmed by the isolation of anti-steroid aptamers comprised of fully matched three-way junctions (5). The three exposed aromatic surfaces of unstacked base-pairs in three-way junctions form a lipophilic cavity approximately 11 Å in diameter, which is capable of binding a wide range of hydrophobic guest molecules (4). The framework provided by the stems would ensure proper folding regardless of the modifications at the junctions. The ability to vary easily and systematically the structure of these receptors through the introduction of mutations, mismatches and chemical modifications represents an important advantage over other hydrophobic hosts (6), such as cyclodextrines and calixarenes. According to preliminary screening, each junction could interact with multiple guest molecules, and each guest could interact with multiple functions. Thus, this system seemed suitable to test the utility of sensors based on three-way junctions as the basis of arrays capable of generating fingerprints. In this case, the fingerprints would be characteristic for hydrophobic surfaces and the resulting array would be a primitive solution-phase mimic of the olfactory system.

Another consideration was a reporting event (7). Aware of the seminal work of Ueno and colleagues on cyclodextrines (8), the possibility that introduction of a fluorophore into the hydrophobic cavity of the junction would yield a molecular sensor based on the internal displacement of the fluorophore by a guest molecule was tested. The invention provides synthesis of fluorescent-signaling sensors based on three-way junctions and demonstrates that an array of such sensors is capable of fingerprinting hydrophobic molecules in solution.

Synthesis and Characterization of Individual Junctions: Individual oligonucleotides may be custom made. A basic set of unmodified oligonucleotides may consist of approximately 100 junctions. Illustrative examples are given in FIG. 17. Variations in the size and shape of hydrophobic pocket of junctions will be introduced by variations in: (1) base pairs making a junction (e.g., J1-J4); (2) introduction of mismatches within junctions (J5), outside of (J6) of both (J7); and (3) bulges (J11). Another source of variations is the position of phorphorothioate group. Upon functionalization, each of these isomers will give distinct molecular sensor (as demonstrated in preliminary results, where a phosphorothioate group was substituted at all three positions within junctions, and different responses were obtained with each ensuing sensor to cocaine). Accordingly, each junction may be transformed into three to five different phosphorothioate analogs (black dots in FIG. 17 represent position of phosphorothioate).

Specifically, fully matched three-way junctions be individually made with each of the phosphodiester bonds within junction substituted with phosphorothioates, except in the $C_3$ and $D_2$ symmetrical junctions. Three-way junctions with mismatches be made with an additional phosphorothioate substitution at the stem containing mismatches. Synthesis can be performed at 250 nmol scale, which would be expected to yield approximately 20 nmols of a final product. Also, one may use previously reported cyclodextrin-based molecular sensors to expand the coverage of hydrophobic space.

Each phosphorothioate-containing junction may then be coupled to six different fluorescent dyes, which may be used in their commercially available thiol-reactive forms. (Flourescein iodoacetamide, Texas Red bromoacetamide, EDANS iodoacetamide, Bromobimane, DANSYL iodoacetamide, BODIPY 507/545 iodoacetamide). Preferably all molecular sensors in arrays are based on a single fluorophore. Standard coupling procedure may be used (molar ratio of a dye to oligonucleotide 3:1, dye dissolved in DMSO, coupling in TRIS buffer, six hours at room temperature for iodoacetoamides, twelve hours for bromo derivatives). Excess dye may be removed on Sephadex G-25 microspin columns, and so obtained fluorescent junction may be sufficiently pure to proceed with screening. Upon modification, each dye becomes part of the hydrophobic pocket. Thus, this procedure effectively yields over 1000 sensors with incremental variations in structures. One may be able to construct and purify in this way at least 12 sensors per day. Each molecular sensor (12 per day) may be tested in four measurements for reactivity against eight compounds at concentrations of 20 μM in buffer: dehydroisoandrosterone 3-sulfate, testosterone 17-sulfate, epitestosterone 17-sulfate, corticosterone-21-sulfate, glycodeoxycholic acid, amphetamine, naloxane and cocaine. Sensors may be tested in fluorescence plate readers (12 sensors×8 analytes×4 redundancies in one 384-well plate) with excitation and emission filters of appropriate wavelengths. Sensors that respond to any of these analytes may be selected for further testing, and fully characterized for response in spectrofluorimeter. Final cutoff value for selection of sensors for the second phase will be reproducible 2% change in fluorescence to 5 μM solution of any of the analytes. The sensitivity may be further through multiple parallel readouts (through microprinting on nitrocellulose filters one could achieve up to one thousand repeated measurements, leading to the theoretical improvement in the signal to noise ratio of 100).

One may demonstrate synthesis of molecular sensors on surfaces. Junctions showing promise as sensors be custom made with 5' amine and 5' biotin and with a single phosphorothioate substitution. (See FIGS. 18 and 19). The purpose of this derivative is to achieve simple coupling chemistry to beads and surfaces. Oligonucleotides may be incubated with Affigel-10 (NHS-activated carboxy agarose), with Streptavidine Agarose Affinity Gel, with NHS-carboxy plates and with epoxy-derivatized glass slides. Upon the completion of reaction, surfaces may be treated with thiol reactive fluorophores, and upon extensive washing of excess dyes, these surfaces may be tested for the response to analytes. For testing one may use a fluorescence plates reader, except for glass slides, which can be tested with fluorescence scanning microscopy (shared facility at Columbia University Health Sciences Campus). Solid-state synthesis opens a possibility to combinatorial approach to synthesis and characterization of junctions.

One can expect to have at least one hundred unique receptors to proceed to the second phase. Specific chemistry has been already developed and tested on 15 different junctions earlier, and it has worked in each case. Some of the junctions could be less reactive toward derivatization reagents; however, this problem could be circumvented by the prolonged incubation times, increased amounts of fluorophores and changing ionic strength. One may also not be able to use some of the fluorophores with some of the unnatural nucleotides, because of the potential for strong quenching. Furthermore, some fluorophore may have too small a fluorescent response, and may end up being unsuitable for solid-state approaches. One may initially focus efforts on fluorescein and its analogs, fluorescein shows the highest increase in fluorescence upon displacement from the hydrophobic cavity. For example, some junctions, as shown in FIG. 26, showed an increase in fluorescence up to 200%. One may attribute this favorable property of fluorescein to the most efficient short-distance fluorescent quenching by proximal guanidines.

Construction and characterization of crossreactive arrays. From the sensors selected in the phase 1, one may take 96 and integrate them first in 384-well plates and, eventually, in an array based on 1586-well plates. Arrays on 384-well plates would have four readouts, while arrays on 1586-well plates would have 16 readouts for each molecular sensor. While one would expect that 384-well plates will be sufficiently sensitive for initial experiments, 1586-well plates would have several advantages in future applications. First, they would allow characterization of each urine or serum sample with 96 molecular sensors with 16 measurements each, thus increasing sensitivity through redundant readouts. Also, even for the initial experiments, where an increase sensitivity below 1 µM of analytes is unneeded, 1586-well plates would lead to the significant reduction in the amount of sensor used for each fingerprint. In these experiments, which would use smaller number of sensors, one could run multiple urine samples on one plate.

Arrays on Solid Surfaces

In order to better mimic the olfactory system, it is desireable to increase even more number of crossreactive sensors per array, and number of parallel reading per sensor.

For this purpose, one may work to develop microchip and microbeads based methods. This also may allow the use of each array multiple times, and will help integration of arrays with neural networks.

Initial results indicate that nucleic acid junctions operate well in various environments, and that they will be functional on nitrocellulose filters, which is a standard approach developed for applying macromolecules (proteins, oligonucleotides and oligosaccharides) to microarrays. This would be the most direct approach, as it would not need any further covalent modifications to attach oligonucleotides to microchip. One possible drawback is that one could not be certain that this attachment mode would work for all molecular sensors tested in solution, and in some cases the properties of sensor may be significantly changed. On the other hand, the favorable partition between membrane impregnated with hydrophobic receptors and solution may actually increase sensitivity. However, alternative approaches exist for attaching oligonucleotides to microchips, some of which may be developed in the sub-goal 4 of the phase one. For example, one can attach either amine or thiols to 5' end and attach sensors to epoxide slides or gold microchips. The advantage of these two methods would be that one could use lower concentrations of oligonucleotides in synthetic steps. In all three approaches, in order to prevent formation of oligomeric sensors or self-quenching, one could control density of sensors on a spot by diluting sensor with irrelevant oligonucleotide, or unlabeled junctions. Once one selects set of molecular sensors that can operate on microchips, they can test both intra- and inter-chip reproducibility of hydrophobic fingerprints.

Fingerprinting of standard steroids, alkaloids and mixtures: One can first obtain fingerprints of various standard samples of steroids and alkaloids and their mixtures in buffers. One can perform the fingerprinting in urine matrix with standard additions of soluble forms of steroids. Urine matrices will be generated from specimens from healthy persons by removing all steroids by repeated solid phase extraction procedures, and then individually characterize representative constituents of urine.

One can first test arrays for reproducibility fingerprints of steroids that were used to select individual sensors. Next, this test can be expanded to other commercially available steroids. Especially important will be characterization of steroids that are solubilized in the similar way as in urine and bile, like testosterone 17-sulfate, corticosterone-21 sulfate, taurocholic and glycocholic acids, deoxycholic acid and dehydroisoandrosterone 3-sulfate, androstanediol 17-glucuronide and androstanone 3-glucuronide. These experiments will also help determine the smallest size of an array, which will be useful in initial demonstrations. Next, one can characterize calibrating mixtures that are commercially available (e.g. bile acids calibrators from Sigma). Alternatively, one can perform all tests in solution of lyophilized urine fraction of Mw<10,000 (Sigma). Then, one can demonstrate that they can reproducibly detect changes in fingerprints of urine upon addition of one component in excess.

Demonstration of diagnostic applications of hydrophobic fingerprints of urine: As the first demonstration of the methodology, one may validate arrays on 24-h urine samples send for determination of 17-ketosteroids (17-KS) and 17-hydroxycorticosteroids (17-OHCS) by endocrinologists. In this way one would be able to compare whether fingerprints could substitute values obtained through standard methods, and would be able to correlate fingerprints with specific disease states. Namely, these two tests (in combination with ACTH) can be used for diagnosing and differentiating Cushing syndrome (see Table 1).

For

| Differentiating Cushing Syndrome | Cushing Disease | Adrenal Adenoma | Adrenal Cancer |
|---|---|---|---|
| Urinary 17OHCS | High | High | High |
| Urinary 17KS | High | Low | Very High | example, a cortisol-producing adrenal adenoma is suggested if the urinary 17-OHCS is markedly elevated, while 17-KS is decreased or minimally changed. Adrenal carcinoma is suggested if both urinary 17-OHCS and 17-KS are strikingly elevated. As carefully timed urine collection is a prerequisite for all excretory determinations, urinary creatinine level will be measured to determine the accuracy and adequacy of the collection procedure.

In the initial experiments one may use the smallest array that will provide the clean differentiation between soluble model compounds tested above. There is a possibility that during comprehensive screening one may come up with a single sensor which would give immediate readout of a gross abnormality in urine which could be correlated to a specific disease state. This would be significant accomplishment, as it would allow eliminated multi step procedures that are currently used. Importantly it would not diminish interest in the more complex arrays. However, it is most likely that one will have to use array of several sensors to distinguish clearly fingerprints of these three diseases. One of the most important immediate applications of arrays will be the screening for inborn errors of corticosteroid metabolism. For example, congenital adrenal hyperplasia, which occurs in 1:15,000 births, is characterized by overproduction of androgens. A complex multicomponent analytical procedure has been proposed to characterize infants with disorders of adrenal steroid production and excretion. With arrays, one would be able to achieve simple and rapid detection of exact defect, leading to a routine procedure.

With larger arrays one would also be able to pick up fine differences in solubilizing groups and metabolites, which was not possible before, without elaborate and impractical procedures. For example, fractionation of urinary 17-ketosteroids is reported to be an effective test in the evaluation of hirsutism. While plasma and total urinary 17-KS were elevated in only 21% of the patients, elevated concentration of indivudual androsterone, etiocholanolone, and dehydroepiandrosterone were elevated in 81% of the samples as determined by gas chromatography of hydrolysates. With the larger array one should be able to fingerprint this mixture without difficulties.

Sample Analysis

All samples sent for free cortisol, 17-KS and 17-OHCS determination can be handled in following manner: One aliquot (12 mL) may be sent to a service such as LabCorp for 17-OHCS determination; other aliquot (25 mL) may be sent to LabCorp for 17-KS determination, while the third aliquot (15 mL) will be used by to obtain fingerprints.

Fingerprinting be performed by taking 50 µL aliquots of sterile filtered urine (for 386-well plate) and adding them to each well containing buffered solution of individual molecular sensors (5 µL) and by reading the fluorescence at the appropriate excitation and emission wavelength after 10 minutes.

Sensors have been demonstrated to operate well in buffered bodily fluids and that binding to serum proteins does not interfere with fluorescence changes due to presence of cocaine. The procedure would be a single step procedure, as one would not expect solubilizing groups (mostly sulfates and glucuronides) on steroids to influence readout, for as long as they are on the same position. Thus, in a single-step mix and measure procedure one could obtain a reliable readout of steroids in urine. In contrast to standard spectrophotometric methods, one would not expect interference from other small molecules that have no large hydrophobic surfaces.

In the initial stage of the process one may compare fingerprints obtained directly from urine with those obtained after concentration of steroids through solid phase extraction (SPE), followed by enzymatic/chemical hydrolysis and normal phase SPE. While these two methods would give different fingerprints, one can establish equivalency in detecting gross abnormalities.

Results and Discussion

Construction of three-way junction-based sensor: sensors derived from a basic set of five three-way junctions, were screened with various degrees and positions of mismatches in the S3 stem (FIG. 22). They were: cocaine binding MNS 4.1-32F33, its fully matched analog fmtch-32F33, and three junctions with single base-pair mismatches: A23-32F33, A24-32F33 and T25-32F33. All junctions bind various steroids and cocaine with micromolar dissociation constants. This cross-reactivity is to be expected from a receptor with a primary recognition mechanism based on hydrophobic interactions. In addition to junctional mismatches, fluorophore positional isomers of MNS4.1: 4.1-7F8, 4.1-21F22, 4.1-22F23, 4.1-31F32 and the above-mentioned 4.1-32F33 (FIG. 23). In total, nine sensors were screened initially.

Although fluorophores have been introduced stochastically outside of the binding pocket of an anti-ATP aptamer, by the individual substitution of standard bases with fluorescent analogs to yield successfully ATP sensor, (9) this method did not appear particularly suitable for the introduction of fluorophores directly into the hydrophobic pocket. Instead, a two-step method was adapted for the construction of sensors, in which a single phosphorothioate group was introduced in an aptamer, followed by the selective functionalization of this group with a thiol-reactive fluorophore (10) (FIG. 24). This method is especially convenient when rapidly screening various fluorophores as signaling components, at various positions of oligonucleotide-based sensors. The drawback of this method is that the sensors are obtained as mixtures of diastereomers at phosphorous, which interact differently with ligands. Although diastereomers are separable by ligand-affinity chromatography, for array work one may use the mixtures directly. Hereafter, each pair of diastereomers will be referred to as a single sensor.

At first, a sensor was devised based on our cocaine-binding junction MNS4.1. Accordingly, an oligonucleotide was constructed in which a single phosphodiester bond between G32 and G33 at the rim of the putative three-way junction was substituted with a phosphorothioate group. This derivative was coupled with a series of thiol-reactive fluorophores (11). While many fluorophores yielded moderately successful cocaine sensors, focus was put on a fluorescein-modified derivative 4.1-G32FG33, which displayed an unusually strong three-fold increase in fluorescence upon binding of cocaine, with a dynamic range from 50 µM to 5000 µM. The magnitude of the increase in fluorescence compares favorably to all previously reported monofluorophoric aptameric systems, including those that were isolated through in vitro selection (12). The excellent signaling of this monofluorophoric aptamer could be rationalized by the possibility that several proximal guanosines in the non-canonical stem provide a potent quenching of fluorescein (13). Although the affinity of the aptamer for the cocaine diminished with fluorescent labeling, the sensor preserved initial selectivity of the aptamer for cocaine over less hydrophobic cocaine metabolites, benzoyl ecgonine and ecgonine methyl ester, making it a useful tool for the high-throughput screening of cocaine esterases (14).

In order to characterize the affinity of 4.1-G32FG33 for hydrophobic ligands, this junction was screened for binding to three steroids, deoxycorticosterone 21-glucoside (2), dehydroisoandrosterone 3-sulfate (3) and deoxycholic acid (4). These steroids are potential targets for "mix and measure" assays of urine samples. The first two steroids are conjugated members of the 17-ketosteroid (17-KS) and corticosteroid (including 17-hydroxycorticosteroid or 17-OHCS) groups. They have very similar hydrophobic shapes in solution and differ mostly in the position of the solubilizing groups. These steroids are of interest clinically because a change in their ratio indicates a gross abnormality in steroidogenesis and differentiates various forms of Cushing's disease. Current assays are cumbersome, multi-step procedures. The third steroid is a representative bile acid, which is determined in clinical samples to diagnose abnormalities in liver function. The reference values for 17-KS, 17-OHCS and bile acids in urine and bile are well within the sensitivity ranges of our sensors (15). FIG. 22 shows the sensor response to the cocaine and the three steroids. The 4.1-32GsFG33 clearly demonstrates the ability to react differentially with various hydrophobic molecules. Yet, low specificity of responses would typically invalidate such a sensor. Accordingly, eight additional sensors were constructed and, as above, and established that seven of them (all but 4.1-21F22) responded with satisfactory intensity to hydrophobic molecules.

Fingerprints of ligands: For each ligand solution screened, the screening results were organized into a fingerprint for that ligand (FIGS. 27 and 28). The power and advantage of this approach in comparison to the classic sensor approach is clearly demonstrated by the following example: Concentrations were taken of the four ligands that provided a response of similar intensity (50-70%) to the sensor 4.1-32F33 (eighth bar in FIG. 27): 1-500 µM, 2-32 µM, 3-125 µM, and 4-2 mM. Presented with these four samples, a single sensor would not be able to disstinguish them. On the other hand, the array clearly and reproducibly distinguished the solutions of the three steroids from each other and from cocaine (FIG. 29).

FIG. 28 provides the minimal characteristic fingerprints for all tested concentrations of the four ligands. Several comments are in order at this point: Firstly, only four sensors were needed to distinguish these four compounds unambiguously. The remaining four sensors, although functioning well, were redundant for this task. Secondly, with multiple batches of individual sensors, each concentration of each ligand had a unique fingerprint (shape-defined as a ratio of intensities)—and/or intensity. Shapes of fingerprints are not conserved over wide concentration ranges. Importantly, the conservation of fingerprint shape is not a requirement for array-based approaches, where individual arrays are usually incorporated with neural networks and trained to recognize exemplary solutions of interest. Thirdly, molecules widely different in hydrophobic properties are easily recognized with small subsets of sensors in arrays. Specifically, any solution of cocaine can be easily distinguished from any solution of deoxycholic acid or any solution containing two urinary metabolites based on the characteristic ratio of responses by, for example, 4.1-32F33 and fmtch-32F33. However, corticosterone and androsterone derivatives 2 and 3 with very similar hydrophobic shapes are more challenging to distinguish; up to four sensors were needed to remove the ambiguity at all tested concentrations.

Another experiment tested the ability of these sensors to obtain useful fingerprints in complex mixtures. A sample of urine (Sigma, lyophilized human male urine metabolites) was compared to aliquots of the same urine spiked with 200 µM concentrations of 2 or 3. The three solutions were differentiated unambiguously based on their fingerprints obtained through the subset of four sensors (FIG. 29). Most of the other sensors were unresponsive under these conditions; possibly as a result of saturation by steroids present in urine. Importantly, this also demonstrated that a sensor which might have been initially considered redundant (i.e. one of the two sensors with identical response to one ligand) can play a key role in the analysis of complex mixtures (cf. fmtch-A23-32F33 and fmtch-T25-32F33). Clinical urine samples contain large quantities of various steroidal metabolites and these results provide a proof-of-concept for fingerprinting gross deviations from clinical norms.

Without extensive structural studies of the individual sensors it is not possible to rationalize or generalize the behavior of the substituted junctions, but some broad comments are appropriate. For example, assuming 1:1 host-guest binding in all cases, most of the sensors derived from the original 4.1 junction showed the strongest signaling with deoxycorticosterone 2, followed by dehydroisoandrosterone 3 and cocaine 1 and the weakest interactions with deoxycholic acid 4. However, the maximum fluorescence intensity for each ligand and each junction differed, indicating that the maximal absolute fluorescence value may be dependent on the interactions of fluorophores with the side chains as well. On the other hand, all sensors structurally closer to the fmtch junction bound strongly to all steroids, including deoxycholic acid, while they bound poorly to cocaine. The strong sensing of the cholic acids by the fully matched junction could be rationalized with the slightly larger and more symmetric shape of the fully matched junction compared to the mismatched junction and with the less planar structure of cholic acids. The weak interactions of cocaine with the fully-matched junction are consistent with exclusive isolation of a mismatched junction through in vitro selection and amplification on a cocaine affinity column (5). The lack of strong signaling of cholic acid by the mismatched junctions is consistent with the reported isolation of a fully matched junction during in vitro selection and amplification using a cholic acid affinity column (4). That other steroids seem to bind very well to both structures may suggest their different orientations within the two junctions. Of particular mechanistic interest is the observation that samples of corticosterone 2 and androsterone 3 used for demonstration in the FIG. 27 show a proportional response to all five junctions containing an A23-G31 mismatch base pair, but show very different responses to junctions containing a C23-G31 matched pair. This may be indicative of the position of these two steroids in the junctions, whereas it is possible that the junction with proximal mismatch accommodates the central region of the steroids without any interactions with solubilizing polar groups.

Of note are the types of structural variations near the junction, available: First, the positions of mismatches have the most striking influence on the interactions with hydrophobic molecules. The gross shape of the junction is apparently defined through mismatches (and bulges, not used here). Second, the positional isomers of sensors have different shapes and charge distributions within the hydrophobic pockets. For example, 4.1-32F33 and 4.1-22F23 have clearly different relative response to cocaine than with deoxycholic acid, with more negatively charged junction (4.1-22F23) binding cocaine more strongly (FIG. 27). Additional sources of variations are the choice of of fluorophore, the use of modified and unnatural oligonucleotides, the substitution of phosphodiester bonds with analogs, and expansion of the framework to a four-way junction. These additional sources of variations could prove important in the pending full characterization of steroid space. Some points have wide standard deviations, but this issue is resolved in larger arrays based on optical fibers or beads with individual sensor redundancies. This appears to be the strategy used in the mammalian olfactory system, wherein the thousand receptors are expressed in up to one hundred million cells. Such redundancies also have the potential to increase sensitivity and make these large arrays useful in serum analysis. Finally, there is a small inter-batch variability within an individual sensor, consistent with moderate variations in the diastereomeric ratios, leading to the necessity to train individually each array when more challenging analytical applications are desired. It is an intriguing possibility that these hydrophobic fingerprints are intrinsic characteristics of the hydrophobic region of the molecule, similar to IR patterns or NMR spectra. In an effort to standardize them, one may pursue the preparative scale synthesis of sensors with large-scale affinity separation of diastereomers.

This invention provides a composition comprising consecutive nucleotides the sequence of which is set forth in any one of SEQ ID NOs:154-220, wherein the composition comprises a fluorescent dye and wherein the composition undergoes a conformational change upon contact with an analyte and the fluorescent dye undergoes a change of fluorescence upon the conformational change.

This invention further provides the instant composition, wherein the fluorescent dye is chosen from the group consisting of fluorescein, Oregon Green, JOE, HEX, TET Alexa Fluor, Rhodamine Green, eosin, erythroscein, and BODIPY related dye, wherein the fluorescent dye is a fluorescein derivative, and wherein the fluorescein derivative comprises a substituent attached to an aromatic carbon of a fluorescein.

This invention further provides the instant composition, wherein the analyte is chosen from the group consisting of cocaine, cortisone, sodium deoxycholate, dehydroisoandrosterone 3-sulfate, or deoxycorticosterone 21-glucoside.

Materials and Methods

Materials: All oligonucleotides were custom made and HPLC purified by Integrated DNA Technologies Inc. (Coralville, Iowa) or TriLink Biotechnologies (San Diego, Calif.) and used as received. Liophilized human male urine metabolites and steroids were purchased from Sigma. Cocaine was obtained through the National Institute of Drug Abuse.

Instrumental: Initial characterization of fluorescent spectra for MNS4.1-32F33 and fmtch-32F33 were performed on Hitachi Instruments Inc. (San Jose, Calif.) F-2000 Fluorescence Spectrophotometer with Hamamatsu Xenon Lamp. Experiments were performed at the excitation wavelength of 480 nm and emission scan at 500-600 nm. All assays were performed using a Wallac Victor2 1420 Multilabel Counter (PerkinElmer Instruments, Shelton, Conn.) in 96-well plates (F96 Maxisorb, Nunc-immunoplates), using appropriate filters ($\lambda_{em}$=530+/−10 nm, $\lambda_{exc}$=480+/−10 nm).

Synthesis of sensors: Procedures: 5 nmol of aptamer in 20 µL of binding buffer (TRIS 20 mM, pH=7.4, NaCl 140 mM, 6 mM KCl), 40 µL of deionized water and 5 µL of 6-iodoacetamido fluorescein (Molecular Probes, Eugene, Oreg.) in DMSO (1 mg/10 µL) were incubated at room temperature (for mismatched junctions) or at 50° C. (fully matched junctions). After 90 minutes for heated and 180 minutes for room temperature mixtures, reactions were applied to Sephadex G-25 column (1.8 mL) and fluorescent macromolecular fractions (total of 400 µL) isolated. The solutions (mixtures of diastereomers and starting materials) were used directly in assays. In a control reaction without a phosphorothioate group on a three-way junciton only negligible fluorescence was observed in these fractions.

Characterization of sensors with ligands: Solutions of sensors were diluted in binding buffer with 2 mM MgCl$_2$ to achieve response between 300 and 1000 fluorescence units on the plate reader. Then, standard dilutions of ligand concentrations were made in the solution of sensors on 96-well plates. All measurements were performed in triplicates.

Characterization of urine: Urine metabolites were dissolved in 35 mL of water and pH adjusted to 7.4 by addition of 300 uL of 10N NaOH and 1 mL 1M TRIS buffer (pH 7.4). Urine was spiked with deoxycorticosterone 21-glucoside 2 and dehydroisoandresterone 3-sulfate 3 to 200 µM concentration. Samples of urine or spiked urines (25 µL) were diluted with buffer containing sensors (5 µL of sensor solution in 75 µL of binding buffer) followed by reading on the plate reader.

REFERENCES

1) Axel, R. "Molecular logic of smell" Sci. Am. 1995, 273, 154.
2) a) Alberth, K. J.; Lewis, N. S.; Schauer, C. L.; Sotzing, G. A.; Stitzel, S. E. I, Vaid, T. P.; Walt D. R Chem. Rev. 2000, 100, 2595 and references therein. b) Schauer, C. L., Steemers, F. J.; Walt, D. R. J. Am. Chem. Soc. 2001, 123, 9443. c) Lavigne, J. J.; Anslyn, E. V. Angew. Chem. Int. Ed. 2001, 40(17), 3118. d) Rakow, N. A.; Suslick, K. S. Nature (London) 2000, 406(6797), 710.
3) a) Stojanovic, M. N.; Landry, D. W. J. Am. Chem. Soc. 2002, 124, 9678.
4) Lu, M.; Guo, Q.; Mueller, J. E.; Kemper, B.; Studier, F. W.; Seeman, N. C.; Kallenbach, N. R. J. Biol. Chem. 1990, 265, 16778 and references therein.
5) Kato, T.; Yano, K.; Ikebukuro, K.; Karube, I. Nucleic Acids Res. 2000, 28, 1963, and references therein.
6) a) "Molecular Recognition" Gellman, S. (Guest Edt.) Chem. Rev. 1997, 97, special thematic issue; a) Ariga, K.; Terasaka, Y.; Sakai, D.; Tsuji, H.; Kikuchi, J. J. Am. Chem. Soc. 2000, 122, 7835-7836; b) Castellano, R. K.; Craig, S. L.; Nuckolls, C.; Rebek, J. Jr. J. Am. Chem. Soc. 2000, 122, 7876-7882; d) reference 3a. c) Breslow, R., Dong, D. S.; Chem. Rev. 1998, 98, 1997-2011.
7) De Silva, A. P.; Gunaratne, H. Q. N.; Gunnlaugsson, T.; Huxley, A. J. M.; McCoy, C. P.; Rademacher J. T.; Rice, T. E. Chem. Rev. 1997, 97 (15), 1515-1566 and references therein.
8) Ikeda H.; Nakamura, M.; Nobuyuki, I.; Oguma, N.; Nakamura, A.; Ikeda, T.; Toda, F.; Ueno, A. J. Am. Chem. Soc. 1996, 118, 10980-10988 and references therein.
9) The aptamer-based molecular sensors for ATP with fluorophore in the proximity, but outside of the binding site, were reported by: Jhaveri, S. D. et al. J. Am. Chem. Soc. 2000, 122, 2469.
10) Fidanza, J. A.; Ozaki, H.; McLaughlin, L. W. J. Am. Chem. Soc. 1992, 114, 5509.
11) Following derivatives available from Molecular Probes were tested: 6-IAF, IAEDANS, BADAN, 5-TMRIA, mBBR, qBBR, Lucifer Yellow IA, Pyrene IA, PyMPO-maleimid.
12) Jhaveri, S.; Rajendran, M.; Ellington, A. D. Nat. Biotechol. 2000, 18(12) 1293-1297.
13) The distance-dependent quenching influence of guanosine residues has been used as a tool to probe conformation in DNA molecules: Knemeyer, J.-P.; Marne, N.; Sauer, M. Anal. Chem. 2000, 72, 3717-3724 and references therein.
14) Stojanovic, M. N., de Prada, P., Landry, D. W. J. Am. Chem. Soc. 2001, 123, 4938.
15) Elin, R. J. "Reference Intervals and Laboratory Values" in Cecil Textbook of Medicine (Eds. Bennett, J. C. and Plum, F.) 1996, 20th Ed.

What is claimed:

1. A method of detecting an analyte in a solution comprising:
   (a) providing a composition comprising an oligonucleotide and a fluorescent moiety attached to the oligonucleotide, wherein the oligonucleotide undergoes a conformational change upon contact with the analyte, and the fluorescent moiety undergoes a change of fluorescence upon the conformational change, and wherein the oligonucleotide comprises a first series of consecutive nucleotides comprising the sequence set forth in SEQ ID NO:1 and a second series of consecutive nucleotides comprising the sequence set forth in SEQ ID NO:2, wherein the first series of consecutive nucleotides is located at the 5' end of the oligonucleotide and the second series of consecutive nucleotides is located at the 3' end of the oligonucleotide, wherein a 3' portion of the first series of consecutive nucleotides hybridizes with a 5' portion of the second series of consecutive nucleotides, and wherein a 5' portion of the first series of consecutive nucleotides hybridizes with a 3' portion of the second series of consecutive nucleotides of SEQ ID NO:2, and wherein the oligonucleotide is 25 to 120 nucleotides in length;
   (b) quantitating the fluorescence of the fluorescent moiety of the composition in the absence of the analyte;
   (c) subsequently contacting the composition with the solution containing the analyte;
   (d) quantitating the fluorescence of the fluorescent moiety of the composition in contact with the solution containing the analyte; and
   (e) comparing the fluorescence quantitated in step (b) with that quantitated in step (d), wherein a change in the fluorescence quantitated in step (d) as compared with the fluorescence quantitated in step (b) indicates that the analyte is present in the solution.

2. The method of claim 1, wherein two or more compositions are present.

3. The method of claim 1, wherein the oligonucleotide comprises a phosphorothioate group and a fluorescence moiety attached to the sulfur of the phosphorothioate group.

4. The method of claim 1, wherein the solution is a sample of a bodily fluid obtained from a subject.

5. The method of claim 4, wherein the bodily fluid is blood, a blood product, urine, a urine product, saliva, a saliva product, or sweat.

6. The method of claim 4, wherein the subject is a mammal.

7. The method of claim 6, wherein the subject is human.

8. The method of claim 1, wherein the oligonucleotide comprises the following structure:

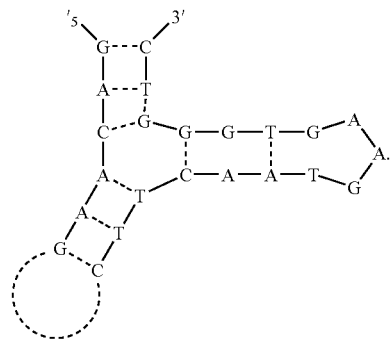

* * * * *

SEQUENCE LISTING

<160> NUMBER OF SEQ ID NOS: 200

<210> SEQ ID NO 1

-continued

```
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 1 gacaag                                                                 6

<210> SEQ ID NO 2
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 2
cttcaatgaa gtgggtc                                                    17

<210> SEQ ID NO 3
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 3 gacaag                                                                 6

<210> SEQ ID NO 4
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 4
cttcaacgaa gtgggtc                                                    17

<210> SEQ ID NO 5
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 5 gacaag                                                                 6

<210> SEQ ID NO 6
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 6
cttccacgaa gtgggtc                                                    17

<210> SEQ ID NO 7
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 7
``` gacaag                                                          6

<210> SEQ ID NO 8
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 8
cttccacgaa gtggggc                                              17

<210> SEQ ID NO 9
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 9 gacaag                                                          6

<210> SEQ ID NO 10
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 10
cgtccacgaa gtgggtc                                              17

<210> SEQ ID NO 11
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 11 gacaag                                                          6

<210> SEQ ID NO 12
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 12
cttcaatgaa gtgggtc                                              17

<210> SEQ ID NO 13
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 13 gacaag                                                          6

<210> SEQ ID NO 14
<211> LENGTH: 17
<212> TYPE: DNA

```
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 14
cttcaacgaa gtgggtc                                                   17

<210> SEQ ID NO 15
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 15 gacaag                                                                6

<210> SEQ ID NO 16
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 16
cttccacgaa gtgggtc                                                   17

<210> SEQ ID NO 17
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 17 gacaag                                                                6

<210> SEQ ID NO 18
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 18
cttccacgaa gtggggc                                                   17

<210> SEQ ID NO 19
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 19 gacaag                                                                6

<210> SEQ ID NO 20
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 20
cgtccacgaa gtgggtc                                                   17
```

```
<210> SEQ ID NO 21
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 21 gacaag                                                                 6

<210> SEQ ID NO 22
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 22
cttcaatgaa gtgggtc                                                    17

<210> SEQ ID NO 23
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 23 gacaag                                                                 6

<210> SEQ ID NO 24
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 24
cttcaacgaa gtgggtc                                                    17

<210> SEQ ID NO 25
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 25 gacaag                                                                 6

<210> SEQ ID NO 26
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 26
cttccacgaa gtgggtc                                                    17

<210> SEQ ID NO 27
<211> LENGTH: 6
<212> TYPE: DNA
<213> ORGANISM: ARTIFICIAL SEQUENCE
<220> FEATURE:
```

<223> OTHER INFORMATION: ARTIFICIAL APTAMER - NO BIOLOGICAL SOURCE

<400> SEQUENCE: 27 gacaag                                                                  6

<210> SEQ ID NO 28
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 28
cttccacgaa gtggggc                                                     17

<210> SEQ ID NO 29
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 29 gacaag                                                                  6

<210> SEQ ID NO 30
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 30
cgtccacgaa gtgggtc                                                     17

<210> SEQ ID NO 31
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 31 gacaag                                                                  6

<210> SEQ ID NO 32
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 32
cttcaatgaa gtgggtc                                                     17

<210> SEQ ID NO 33
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 33 gacaag                                                                  6

```
<210> SEQ ID NO 34
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 34
cttcaacgaa gtgggtc                                                  17

<210> SEQ ID NO 35
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 35 gacaag                                                               6

<210> SEQ ID NO 36
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 36
cttccacgaa gtgggtc                                                  17

<210> SEQ ID NO 37
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 37 gacaag                                                               6

<210> SEQ ID NO 38
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 38
cttccacgaa gtggggc                                                  17

<210> SEQ ID NO 39
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 39 gacaag                                                               6

<210> SEQ ID NO 40
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE
```

```
<400> SEQUENCE: 40
cgtccacgaa gtgggtc                                                 17

<210> SEQ ID NO 41
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 41 gacaag                                                              6

<210> SEQ ID NO 42
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 42
cttcaatgaa gtgggtc                                                 17

<210> SEQ ID NO 43
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 43 gacaag                                                              6

<210> SEQ ID NO 44
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 44
cttcaacgaa gtgggtc                                                 17

<210> SEQ ID NO 45
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 45 gacaag                                                              6

<210> SEQ ID NO 46
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 46
cttccacgaa gtgggtc                                                 17

<210> SEQ ID NO 47
<211> LENGTH: 6
```

```
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 47 gacaag                                                                    6

<210> SEQ ID NO 48
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 48
cttccacgaa gtggggc                                                       17

<210> SEQ ID NO 49
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 49 gacaag                                                                    6

<210> SEQ ID NO 50
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 50
cgtccacgaa gtgggtc                                                       17

<210> SEQ ID NO 51
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 51 gacaag                                                                    6

<210> SEQ ID NO 52
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 52
cttcaatgaa gtgggtc                                                       17

<210> SEQ ID NO 53
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 53
```

```
gacaag                                                              6

<210> SEQ ID NO 54
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 54
cttcaacgaa gtgggtc                                                 17

<210> SEQ ID NO 55
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 55 gacaag                                                              6

<210> SEQ ID NO 56
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 56
cttccacgaa gtgggtc                                                 17

<210> SEQ ID NO 57
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 57 gacaag                                                              6

<210> SEQ ID NO 58
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 58
cttccacgaa gtggggc                                                 17

<210> SEQ ID NO 59
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 59 gacaag                                                              6

<210> SEQ ID NO 60
<211> LENGTH: 17
<212> TYPE: DNA
<213> ORGANISM: ARTIFICIAL SEQUENCE
```

```
<220> FEATURE:
<223> OTHER INFORMATION: ARTIFICIAL APTAMER - NO BIOLOGICAL SOURCE

<400> SEQUENCE: 60
cgtccacgaa gtgggtc                                                  17

<210> SEQ ID NO 61
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 61 gacaag                                                               6

<210> SEQ ID NO 62
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 62
cttcaatgaa gtgggtc                                                  17

<210> SEQ ID NO 63
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 63 gacaag                                                               6

<210> SEQ ID NO 64
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 64
cttcaacgaa gtgggtc                                                  17

<210> SEQ ID NO 65
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 65 gacaag                                                               6

<210> SEQ ID NO 66
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 66
cttccacgaa gtgggtc                                                  17
```

<210> SEQ ID NO 67
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 67 gacaag                                                                    6

<210> SEQ ID NO 68
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 68
cttccacgaa gtgggtc                                                       17

<210> SEQ ID NO 69
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 69 gacaag                                                                    6

<210> SEQ ID NO 70
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 70
cgtccacgaa gtgggtc                                                       17

<210> SEQ ID NO 71
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 71 gacaag                                                                    6

<210> SEQ ID NO 72
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 72
cttcaatgaa gtgggtc                                                       17

<210> SEQ ID NO 73
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

```
<400> SEQUENCE: 73 gacaag                                                                    6

<210> SEQ ID NO 74
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 74
cttcaacgaa gtgggtc                                                       17

<210> SEQ ID NO 75
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 75 gacaag                                                                    6

<210> SEQ ID NO 76
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 76
cttccacgaa gtgggtc                                                       17

<210> SEQ ID NO 77
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 77 gacaag                                                                    6

<210> SEQ ID NO 78
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 78
cttccacgaa gtggggc                                                       17

<210> SEQ ID NO 79
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 79 cacaag                                                                    6

<210> SEQ ID NO 80
```

```
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 80
cgtccacgaa gtgggtc                                                    17

<210> SEQ ID NO 81
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 81 gacaag                                                                 6

<210> SEQ ID NO 82
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 82
cttcaatgaa gtgggtc                                                    17

<210> SEQ ID NO 83
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 83 gacaag                                                                 6

<210> SEQ ID NO 84
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 84
cttcaacgaa gtgggtc                                                    17

<210> SEQ ID NO 85
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 85 gacaag                                                                 6

<210> SEQ ID NO 86
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 86
```

```
cttccacgaa gtgggtc                                                    17

<210> SEQ ID NO 87
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 87 gacaag                                                                6

<210> SEQ ID NO 88
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 88
cttccacgaa gtggggc                                                    17

<210> SEQ ID NO 89
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 89 gacaag                                                                6

<210> SEQ ID NO 90
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 90
cgtccacgaa gtgggtc                                                    17

<210> SEQ ID NO 91
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 91 gacaag                                                                6

<210> SEQ ID NO 92
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 92
cttcaatgaa gtgggtc                                                    17

<210> SEQ ID NO 93
<211> LENGTH: 6
<212> TYPE: DNA
```

```
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 93 gacaag                                                                    6

<210> SEQ ID NO 94
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 94
cttcaacgaa gtgggtc                                                       17

<210> SEQ ID NO 95
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 95 gacaag                                                                    6

<210> SEQ ID NO 96
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 96
cttccacgaa gtgggtc                                                       17

<210> SEQ ID NO 97
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 97 gacaag                                                                    6

<210> SEQ ID NO 98
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 98
cttccacgaa gtggggc                                                       17

<210> SEQ ID NO 99
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 99 gacaag                                                                    6
```

```
<210> SEQ ID NO 100
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 100
cgtccacgaa gtgggtc                                                     17

<210> SEQ ID NO 101
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 101
ctgggtgaag taacttc                                                     17

<210> SEQ ID NO 102
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 102 gaacag                                                                  6

<210> SEQ ID NO 103
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 103
ctgggtgaag caacttc                                                     17

<210> SEQ ID NO 104
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 104
ctgggtgaag caccttc                                                     17

<210> SEQ ID NO 105
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 105
cggggtgaag caccttc                                                     17

<210> SEQ ID NO 106
<211> LENGTH: 17
<212> TYPE: DNA
<213> ORGANISM: ARTIFICIAL SEQUENCE
<220> FEATURE:
```

```
<223> OTHER INFORMATION: ARTIFICIAL APTAMER - NO BIOLOGICAL SOURCE

<400> SEQUENCE: 106
ctgggtgaag cacctgc                                                  17

<210> SEQ ID NO 107
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 107
ctgggtgaag taacttc                                                  17

<210> SEQ ID NO 108
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 108
ctgggtgaag caacttc                                                  17

<210> SEQ ID NO 109
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 109
ctgggtgaag caccttc                                                  17

<210> SEQ ID NO 110
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 110
cggggtgaag caccttc                                                  17

<210> SEQ ID NO 111
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 111
ctgggtgaag cacctgc                                                  17

<210> SEQ ID NO 112
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 112
ctgggtgaag taacttc                                                  17
```

```
<210> SEQ ID NO 113
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 113
ctgggtgaag caacttc                                                      17

<210> SEQ ID NO 114
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 114
ctgggtgaag caccttc                                                      17

<210> SEQ ID NO 115
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 115
cggggtgaag caccttc                                                      17

<210> SEQ ID NO 116
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 116
ctgggtgaag cacctgc                                                      17

<210> SEQ ID NO 117
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 117
ctgggtgaag taacttc                                                      17

<210> SEQ ID NO 118
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 118
ctgggtgaag caacttc                                                      17

<210> SEQ ID NO 119
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE
```

```
<400> SEQUENCE: 119
ctgggtgaag caccttc                                                  17

<210> SEQ ID NO 120
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 120
cggggtgaag caccttc                                                  17

<210> SEQ ID NO 121
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 121
ctgggtgaag cacctgc                                                  17

<210> SEQ ID NO 122
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 122
ctgggtgaag taacttc                                                  17

<210> SEQ ID NO 123
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 123
ctgggtgaag caacttc                                                  17

<210> SEQ ID NO 124
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 124
ctgggtgaag caccttc                                                  17

<210> SEQ ID NO 125
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 125
cggggtgaag caccttc                                                  17

<210> SEQ ID NO 126
<211> LENGTH: 17
```

```
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 126
ctgggtgaag cacctgc                                                  17

<210> SEQ ID NO 127
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 127
ctgggtgaag taacttc                                                  17

<210> SEQ ID NO 128
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 128
ctgggtgaag caacttc                                                  17

<210> SEQ ID NO 129
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 129
ctgggtgaag caccttc                                                  17

<210> SEQ ID NO 130
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 130
cggggtgaag caccttc                                                  17

<210> SEQ ID NO 131
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 131
ctgggtgaag cacctgc                                                  17

<210> SEQ ID NO 132
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 132
```

-continued

```
ctgggtgaag taacttc                                                      17

<210> SEQ ID NO 133
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 133
ctgggtgaag caacttc                                                      17

<210> SEQ ID NO 134
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 134
ctgggtgaag caccttc                                                      17

<210> SEQ ID NO 135
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 135
cggggtgaag caccttc                                                      17

<210> SEQ ID NO 136
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 136
ctgggtgaag cacctgc                                                      17

<210> SEQ ID NO 137
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 137
ctgggtgaag taacttc                                                      17

<210> SEQ ID NO 138
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 138
ctgggtgaag caacttc                                                      17

<210> SEQ ID NO 139
<211> LENGTH: 17
<212> TYPE: DNA
<213> ORGANISM: ARTIFICIAL SEQUENCE
```

-continued

<220> FEATURE:
<223> OTHER INFORMATION: ARTIFICIAL APTAMER - NO BIOLOGICAL SOURCE

<400> SEQUENCE: 139
ctgggtgaag caccttc                                                    17

<210> SEQ ID NO 140
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 140
cggggtgaag caccttc                                                    17

<210> SEQ ID NO 141
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 141
ctgggtgaag cacctgc                                                    17

<210> SEQ ID NO 142
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 142
ctgggtgaag taacttc                                                    17

<210> SEQ ID NO 143
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 143
ctgggtgaag caacttc                                                    17

<210> SEQ ID NO 144
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 144
ctgggtgaag caccttc                                                    17

<210> SEQ ID NO 145
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 145
cggggtgaag caccttc                                                    17

```
<210> SEQ ID NO 146
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 146
ctgggtgaag cacctgc                                              17

<210> SEQ ID NO 147
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 147
ctgggtgaag taacttc                                              17

<210> SEQ ID NO 148
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 148
ctgggtgaag caacttc                                              17

<210> SEQ ID NO 149
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 149
ctgggtgaag caccttc                                              17

<210> SEQ ID NO 150
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 150
cggggtgaag caccttc                                              17

<210> SEQ ID NO 151
<211> LENGTH: 17
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 151
ctgggtgaag cacctgc                                              17

<210> SEQ ID NO 152
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE
```

```
<400> SEQUENCE: 152 ataaat                                                              6

<210> SEQ ID NO 153
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 153 taaata                                                              6

<210> SEQ ID NO 154
<211> LENGTH: 16
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 154
gggagacaag gaggtt                                                  16

<210> SEQ ID NO 155
<211> LENGTH: 27
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 155
aacctccttc aatgaagtgg gtcgaca                                      27

<210> SEQ ID NO 156
<211> LENGTH: 21
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 156
taatatatga gggggtccat a                                            21

<210> SEQ ID NO 157
<211> LENGTH: 20
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 157
tatggaagga ggcgatatta                                              20

<210> SEQ ID NO 158
<211> LENGTH: 30
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 158
gacttggata aatccaacaa tgaagtggtc                                   30

<210> SEQ ID NO 159
```

```
<211> LENGTH: 39
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 159
gggagacttg gataaatcca acaatgaagt gggtcgaca                               39

<210> SEQ ID NO 160
<211> LENGTH: 39
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 160
gggagacttg gataaatcca acaatgaagt gggtcgaca                               39

<210> SEQ ID NO 161
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 161 gacaag                                                                    6

<210> SEQ ID NO 162
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 162 cttcaa                                                                    6

<210> SEQ ID NO 163
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 163 tgggtc                                                                    6

<210> SEQ ID NO 164
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 164 cttccc                                                                    6

<210> SEQ ID NO 165
<211> LENGTH: 7
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 165
```

```
gactaag                                                              7

<210> SEQ ID NO 166
<211> LENGTH: 7
<212> TYPE: DNA
<213> ORGANISM: ARTIFICIAL SEQUENCE
<220> FEATURE:
<223> OTHER INFORMATION: CTTTCCC

<400> SEQUENCE: 166 ctttccc                                                              7

<210> SEQ ID NO 167
<211> LENGTH: 7
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 167 tggtgtc                                                              7

<210> SEQ ID NO 168
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 168 accgta                                                               6

<210> SEQ ID NO 169
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 169 tacgaa                                                               6

<210> SEQ ID NO 170
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 170 ttcggt                                                               6

<210> SEQ ID NO 171
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 171 accata                                                               6

<210> SEQ ID NO 172
<211> LENGTH: 6
<212> TYPE: DNA
```

```
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 172 tatcaa                                                                  6

<210> SEQ ID NO 173
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 173 acaata                                                                  6

<210> SEQ ID NO 174
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 174 tatcca                                                                  6

<210> SEQ ID NO 175
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 175 tggtgt                                                                  6

<210> SEQ ID NO 176
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 176 tataca                                                                  6

<210> SEQ ID NO 177
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 177 tgttgt                                                                  6

<210> SEQ ID NO 178
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 178 acagta                                                                  6
```

```
<210> SEQ ID NO 179
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 179 tacgaa                                                                   6

<210> SEQ ID NO 180
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 180 ttcggt                                                                   6

<210> SEQ ID NO 181
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 181 accata                                                                   6

<210> SEQ ID NO 182
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 182 tatcaa                                                                   6

<210> SEQ ID NO 183
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 183 tggggt                                                                   6

<210> SEQ ID NO 184
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 184 acaata                                                                   6

<210> SEQ ID NO 185
<211> LENGTH: 6
<212> TYPE: DNA
<213> ORGANISM: ARTIFICIAL SEQUENCE
<220> FEATURE:
```

```
<223> OTHER INFORMATION: ARTIFICIAL APTAMER - NO BIOLOGICAL SOURCE

<400> SEQUENCE: 185 tataaa                                                                    6

<210> SEQ ID NO 186
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 186 tgtggt                                                                    6

<210> SEQ ID NO 187
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 187 acctta                                                                    6

<210> SEQ ID NO 188
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 188 taacct                                                                    6

<210> SEQ ID NO 189
<211> LENGTH: 7
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 189 aagtggt                                                                   7

<210> SEQ ID NO 190
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 190 accctt                                                                    6

<210> SEQ ID NO 191
<211> LENGTH: 6
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 191 aagcct                                                                    6
```

```
<210> SEQ ID NO 192
<211> LENGTH: 8
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 192 aggatggt                                                                    8

<210> SEQ ID NO 193
<211> LENGTH: 39
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 193
gggagacaag gataaatcct tccacgaagt gggtcgaca                                  39

<210> SEQ ID NO 194
<211> LENGTH: 4
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 194 acaa                                                                        4

<210> SEQ ID NO 195
<211> LENGTH: 15
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 195
ttcaacgaag tgggt                                                           15

<210> SEQ ID NO 196
<211> LENGTH: 15
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 196
ttccgcgaag ggggt                                                           15

<210> SEQ ID NO 197
<211> LENGTH: 15
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 197
ttccatgaag tgggt                                                           15

<210> SEQ ID NO 198
<211> LENGTH: 15
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE
```

```
<400> SEQUENCE: 198
ttcaatgaag tgggt                                                    15

<210> SEQ ID NO 199
<211> LENGTH: 5
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 199 ttcaa                                                                5

<210> SEQ ID NO 200
<211> LENGTH: 5
<212> TYPE: DNA
<213> ORGANISM: ARTIFICIAL SEQUENCE
<220> FEATURE:
<223> OTHER INFORMATION: ARTIFICIAL APTAMER - NO BIOLOGICAL SOURCE

<400> SEQUENCE: 200 tgggt                                                                5
```